United States Patent [19]
Gallatin et al.

[11] Patent Number: 5,817,515
[45] Date of Patent: Oct. 6, 1998

[54] HUMAN B2 INTEGRIN ALPHA SUBUNIT ANTIBODIES

[75] Inventors: W. Michael Gallatin, Mercer Island; Monica Van der Vieren, Seattle, both of Wash.

[73] Assignee: ICOS Corporation, Bothell, Wash.

[21] Appl. No.: 605,672

[22] Filed: Feb. 22, 1996

Related U.S. Application Data

[63] Continuation-in-part of Ser. No. 362,652, Dec. 21, 1994, which is a continuation-in-part of Ser. No. 286,889, Aug. 5, 1994, Pat. No. 5,470,953, which is a continuation-in-part of Ser. No. 173,497, Dec. 23, 1993, Pat. No. 5,437,958.

[51] Int. Cl.$^6$ .............................. C12N 5/12; C07K 16/28
[52] U.S. Cl. .................................... 435/343.2; 435/70.21; 435/172.02; 435/305; 435/326; 435/332; 435/339; 435/343; 435/343.1; 435/346; 530/387.1; 530/387.9; 530/388.1; 530/388.2; 530/388.22; 530/388.7; 530/388.73; 530/388.75
[58] Field of Search .............................. 435/70.21, 171.2, 435/240.27, 325, 343, 346; 530/387.1, 388.22, 388.75

[56] References Cited

U.S. PATENT DOCUMENTS 4,271,139  6/1981  Hart .
4,568,649  2/1986  Bertoglio-Matte .

OTHER PUBLICATIONS

Van Der Vieren et al Immunity 3: 683–690 (1995).
Paul (Ed.) Fundamental Immunology Raven Press NY 1993 p. 242 only.
Danilenko et al. J. Immunology 155: 35–44 (1995).
Adams, et al., "Experimental graft arteriosclerosis: 1. The Lewis–To–F–344 Allograft Model," *Transplantation*, 53:1115–1119 (1992).
Adams, et al., "Experimental graft arteriosclerosis: II. Immunocytochemical analysis of lesion development," *Transplantation*, 56:794–799 (1993).
Anderson, et al., "Exact definition of species–specific and cross–reactive epitopes of the 65–kilodalton protein of *Mycobacterium leprae* using synthetic peptides," *J. Immunol.* 141:607–613 (1988).
Arfors, et al., "A monoclonal antibody to the membrane glycoprotein complex CD18 inhibits polymorphonuclear leukocyte accumulation and plasma leakage in vivo," *Blood* 69:338–340 (1987).
Arnaout, "Structure and function of the leukocyte adhesion molecules CD11/CD18," *Blood* 75:1037–1050 (1990).
Berman, et al., "Biosynthesis and function of membrane bound and secreted forms of recombinant CD11b/CD18 (Mac–1)," *J.Cell, Biochem* 52:183–195 (1993).
Bochner, et al., "Flow cytometric methods for the analysis of human basophil surface and viability," *J. Immunol.Meth.* 125:265–271 (1989).
Burnett, et al., "The IgA heavy–chain gene family in rabbit: cloning and sequence analysis of 13 Cα genes," *EMBO J.* 8:4041–4047 (1989).

Capecchi, "Altering the genome by homologous recombination," *Science* 244:1288–1292 (1989).
Chang, et al., "A general method for facilitating heterodimeric pairing between two proteins: application to expression of α and β T–cell receptor extracellular segments," *Proc.Natl.Acad.Sci. (USA)*, 91:11408–11412 (1994).
Chisaka, et al., "Developmental defects of the ear, cranial nerves and hindbrain resulting from targeted disruption of the mouse homeobox gene HOX–1.6," *Nature* 355:516–520 (1992).
Cobbold, et al., "Non–lineage, LFA–1 family, and leucocyte common antigens: new and previously defined clusters," *Leukocyte Typing III*, McMichael (ed), Oxford Press, p. 788 (1987).
Collins, et al., "The HL–60 promyelocytic leukemia cell line: proliferation, differentiation, and cellular oncogene expression," *Blood*, 70:1233–1244 (1987).
Corbi, et al., "cDNA cloning and complete primary structure of the α subunit of a leukocyte adhesion glycoprotein, p150,95," *EMBO J.* 6:4023–4028 (1987).
Corbi, et al., "The human leukocyte adhesion glycoprotein Mac–1 (complement receptor type 3, CD116 α subunit," *J.Biol.Chem.* 263:12403–12411 (1988).
Cromartie, et al., "Arthritis in rats after systemic injection of streptococcal cells or cell walls." *J.Exp.Med.* 146:1585–1602 (1977).
Dana, et al., "Deficiency of a surface membrane glycoprotein (Mo1) in man," *J.Clin.Invest.* 73:153–159 (1984).
Danilenko, et al., "Canine leukocyte cell adhesion molecules (LeuCAMS): characterization of the CD11/CD18 family," *Tissue Antigens* 40:13–21 (1992).
Deng, et al., "Location of crossovers during gene targeting with insertion and replacement vectors," *Mol.Cell.Biol.* 13:2134–2140 (1993).
Diamond, et al., "The I domain is a major recognition site on the leukocyte integrin Mac–1 (CD11b/CD18) for four distinct adhesion ligands," *J.Cell, Biol.* 120:1031–1043 (1993).
Fleming, et al., "Structural Analysis of the CD11b gene and phylogenetic analysis of the α–integrin gene family demonstrate remarkable conservation of genomic organization and suggest early diversification during evolution," *J.Immunol.* 150:480–490 (1993).
Frohman, "RACE: Rapid amplification of cDNA ends" in *PCR Protocols: A Guide to Methods and Applications*, Innis, et al. (eds.) Academic press:New York (1990) pp. 28–38.
Greve, et al., "The major human rhinovirus receptor is ICAM–1",*Cell* 56:839 (1989).

(List continued on next page.)

*Primary Examiner*—Lila Feisee
*Assistant Examiner*—Phillip Gambel
*Attorney, Agent, or Firm*—Marshall, O'Toole, Gerstein, Murray & Borun

[57] ABSTRACT

Monoclonal antibodies, and hybridomas that express the antibodies, which are immunospecific for a novel human $\beta_2$ integrin alpha subunit polypeptide are disclosed.

2 Claims, 4 Drawing Sheets

OTHER PUBLICATIONS

Hanenberg, et al., "Macrophage infiltration precedes and is a prerequisite for lymphocytic insulitis in pancreatic islets of prediabetic BB rats," *Diatetologia* 32:126–134 (1989).

Hansel, et al., "Purification of human blood eosinophils by negative selection using immunomagnetic beads," *J.Immunol.Meth.* 122:97–103 (1989).

Hart and Greenwald, "Scintillation proximity assay (SPA)—a new method of immunoassay," *Mol.Immunol.* 12:265–267 (1979).

Hart and Greenwald, "Scintillation proximity assay of antigen–antibody binding kinetics: concise communication," *J.Nuc.Med* 20:1062–1065 (1979).

Hildreth & Orentas, "Involvement of a leukocyte adhesion receptor (LFA–1) in HIV–induced syncytium formation," *Science* 244:1075–1078 (1989).

Huitinga, et al., "Treatment with anti–CR3 antibodies ED7 and ED8 suppresses experimental allergic encephalomyelitis in Lewis rats," *Eur.J.Immunol* 23:709–715 (1993).

Karin and Richards, "Human metallothionein genes —primary structure of the metallothionein–II gene and a related processed protein," *Nature* 299:797–802 (1982).

Ingalls and Golenbock, "CD11c/CD18, A transmembrane signaling receptor for lipopolysaccharide," *J.Exp.Med.*, 181:1473–1479 (1995).

Jutila, et al., "In vivo distribution and characterization of two novel mononuclear phagocyte differentiation antigens in mice," *J.Leukocyte Biol.* 54: 30–39 (1993).

Karin and Richards, "Human metallothionein–II gene and a related processed protein," *Nature* 299:797–802 (1982).

Kishimoto, et al., "Heterologous mutations of the β subunit common to the LFA–1, Mac–1 and p1150,95 glycoproteins cause leukocyte adhesion deficiency," *Cell* 50:193–202 (1987).

Kishimoto, et al., "Cloning of the β subunit of the leukocyte adhesion proteins: homology to an extracellular matrix receptor defines a novel supergene family," *Cell* 48:681–690 (1987).

Kroncke, et al., "Activated macrophages kill pancreatic syngeneic islet cells via arginine–dependent nitric oxide generation," *BBRC* 175:752–758 (1991).

Landis, et al., "A novel LFA–1 activation epitope maps to the I domain," *J.Cell.Biol.* 120:1519–1527 (1993).

Larson, et al., "Primary structure of the leukocyte function–associated molecule–1 α subunit: an integrin with an embodded domain defining a protein superfamily," *J.Cell. Biol.* 108:703–712 (1989).

Larson and Springer, "Structure and function of leukocyte integrins," *Immunol.Rev.* 114:181–217 (1990).

Lawrence, et al., "Purification and characterization of human skin mast cells," *J.Immunol.* 139:3062–2069 (1987).

Letvin, et al., "Conservation of myeloid surface antigens on primary granulocytes," *Blood* 61:408–410 (1983).

Luk, et al., "Biotinylated lipopolysaccharide binds to endotoxin receptor in endothelial and monocytic cells," *Alan. Biochem.* 232:217–224 (1995).

MacMicking, et al., "Altered responses to bacterial infection and endotoxic shock in mice lacking inducible nitric oxide synthase," *Cell* 81:641–650 (1995).

McCabe, "Production of single–stranded DNA by asymmetric PCR," in *PCR Protocols: A Guide to Methods and Applications*, Innis et al. (ed) Academic Press: New York (1990) pp. 76–83.

Merrill, et al., "Microglial cell cytotoxicity of oligodendrocytes is mediated through nitric oxide," *Immunol.* 151:2132 (1993).

Metlay, et al., "The distinct leukocyte integrins of mouse spleen dendritic cells as identified with new hamster monoclonal antibodies," *J.Exp.Med.* 171:1753–1771 (1990).

Michishita, et al., "A novel divalent cation–binding site in the A domain of the β2 integrin CR3 (CD11b/CD18) is essential for ligand binding," *Cell* 72:857–867 (1993).

Moore, et al., "Canine leukocyte integrins: characterization of a CD18 homologue," *Tissue Antigens* 36:211–220 (1990).

Mulligan, et al., "Tissue injury caused by deposition of immune complexes is L–arginine dependent," *Proc.Natl.Acad.Sci.(USA)* 88:6338–6342 (1991).

Nourshargh, et al., "Accumulation of $^{111}$In–neutrophils in rabbit skin in allergic and non–allergic inflammatory reactions in vivo," *J.Immunol.* 142:3193–3198 (1989).

Patarroyo, et al., "Leukocyte–cell adhesion: a molecular process fundamental in leukocyte physiology," *Immunol. Rev.* 114:67–108 (1990).

Price, et al., "In vivo inhibition of neutrophil function in the rabbit using monoclonal antibody to CD18," *J.Immunol.* 139:4174–4177 (1987).

Randi and Hogg, "I domain of $β_2$ integrin lymphocyte function–associated antigen–1 contains a binding site for ligand intercellular adhesion molecule–1," *J.Biol.Chem.* 269:12395–12398 (1994).

Rojiani et al., "In vitro interaction of a polypeptide homologous to human Ro/SS–A antigen (calreticulin) with a highly conserved amino acid sequence in the cytoplasmic domain of integrin α subunits," *Biochemistry* 30:9859–9866 (1991).

Rosenfeld, et al., "Fatty streak initiation in Watanabe heritable hyperlipemic and comparably hypercholesterolemic fat–fed rabbits" *Arteriosclerosis* 7:9–23 (1987).

Rosenfeld, et al., "Fatty streak expansion and maturation in Watanabe heritable hyperlipemic and comparably hypercholesterolemic fat–fed rabbits" *Arteriosclerosis* 7:24–34 (1987).

Sadhu, et al., "LFA–1 Binding site in ICAM–3 contains a conserved motif and non–contiguous amino acids" *Cell Adhesion and Communication*, 2:429–440 (1994).

Sambrook, et al.,(eds), "Immobilization of Bacteriophage λ plaques on nirocellulose filters or nylon membranes" in *Molecular Cloning: a laboratory manual*, Cold Spring Harbor Press:Cold Spring Harbor, NY (1989) p. 2.110.

Sanchez–Madrid, et al., "A human leukocyte differentiation antigen family with distinct α–subunits and a common β–subunit," *J.Exp.Med.* 154:1517 (1981).

Schall, "Biology of the rantes/sis cytokine family" *Cytokine*, 3:165–183 (1991).

Schneiderman, et al., "Expression of 12 rabbit IgA Cα genes as chimeric rabbit–mouse IgA antibodies," *Proc.Natl.Acad. Sci. (USA)* 86:7562–7565 (1989).

Schwab, et al., "Pro–and anti–inflammatory roles of interleukin–1 in recurrence of bacterial cell wall–induced arthritis in rats," *Infection and Immunity* 59:4436–4442 (1991).

Searle, et al., "Regulation, linkage, and sequence of mouse metallothionein I and II genes," *Mol.Cell.Biol.* 4:1221–1230 (1984).

Shaw, et al., "Molecular cloning of the human mucosal lymphocyte integrin $α^E$ subunit," *J.Biol.Chem.* 269:6016–6025 (1994).

Smith, et al., "Cooperative interactions of LFA–1 and Mac–1 with intercellular adhesion molecule–1 in facilitating adherence and transendothelial migration of human neutrophils in vitro," *J.Clin.Invest.* 83:2008–2017 (1989).

Springer, "Adhesion molecules of the immune system," *Nature* 346:425–434 (1990).

Tamura, et al., "Epithelial integrin $\alpha_6\beta_4$: complete primary structure of $\alpha_6$ and variant forms of $\beta_4$," *J.Cell.Biol.* 111:1593–1604 (1990).

Ueda, et al., "Identification of the complement iC3b binding site in the $\beta2$ integrin CR3 (CD11b/CD18)," *Proc.Natl.Acad.Sci. (USA)* 91:10680–10684 (1994).

Varshney, et al., "Structure, organization, and regulation of human metallothionein $I^F$ gene: differential and cell–type–specific expression in response to heavy metals and glucocorticoids," *Mol.Cell.Biol.* 6:26–36 (1986).

Warner, et al., "A rapid Percoll technique for the purification of human basophils," *J.Immunol.Meth.* 106:107–110 (1987).

Wright, "Multiple receptors for endotoxin," *Curr.Opin.Immunol.* 3:83–90 (1991).

Yamada, et al., "Mucosal injury and inflammation in a model of chronic granulomatous colitis in rats," *Gastroenterology* 104:759–771 (1993).

Zhou, et al., "Differential ligand binding specificities of recombinant CD11b/CD8 integrin I–domain" *J.Biol.Chem.* 269: 17076–17079 (1994).

```
αD    TF-GT--VLL  LSVLASYHGF  NLDVEEPTIF  QEDAGGFGQS  VVQFGGSRLV   47
CD11B  MA-LR--VLL  LTALTLCHGF  NLDTENAMTF  QENARGFGQS  VVQLQGSRVV   47
CD11C  MTRTRAALLL  FTALATSLGF  NLDTEELTAF  RVDSAGFGDS  VVQYANSWVV   50

αD    VGAPLEVVAA  NQTGRLYDCA  AATGMCQPIP  LHIRPEAVNM  SLGLTLAAST   97
CD11B  VGAPQEIVAA  NQRGSLYQCD  YSTGSCEPIR  LQVPVEAVNM  SLGLSLAATT   97
CD11C  VGAPQKIIAA  NQIGGLYQCG  YSTGACEPIG  LQVPPEAVNM  SLGLSLASTT  100

αD    NGSRLLACGP  TLHRVCGENS  YSKGSCLLLG  SR-WEIIQTV  PDATPECPHQ  146
CD11B  SPPQLLACGP  TVHQTCSENT  YVKGLCFLFG  SNLRQQPQKF  PEALRGCPQE  147
CD11C  SPSQLLACGP  TVHHECGRNM  YLTGLCFLLG  PT--QLTQRL  PVSRQECPRQ  148

αD    EMDIVFLIDG  SGSIDQNDFN  QMKGFVQAVM  GQFEGTDTLF  ALMQYSNLLK  196
CD11B  DSDIAFLIDG  SGSIIPHDFR  RMKEFVSTVM  EQLKKSKTLF  SLMQYSEEFR  197
CD11C  EQDIVFLIDG  SGSISSRNFA  TMMNFVRAVI  SQFQRPSTQF  SLMQFSNKFQ  198

αD    IHFTFTQFRT  SPSQQSLVDP  IVQLKGLTFT  ATGILTVVTQ  LFHHKNGARK  246
CD11B  IHFTFKEFQN  NPNPRSLVKP  ITQLLGRTHT  ATGIRKVVRE  LFNITNGARK  247
CD11C  THFTFEEFRR  TSNPLSLLAS  VHQLQGFTYT  ATAIQNVVHR  LFHASYGARR  248

αD    SAKKILIVIT  DGQKYKDPLE  YSDVIPQAEK  AGIIRYAIGV  GHAFQGPTAR  296
CD11B  NAFKILVVIT  DGEKFGDPLG  YEDVIPEADR  EGVIRYVIGV  GDAFRSEKSR  297
CD11C  DAIKILIVIT  DGKKEGDSLD  YKDVIPMADA  AGIIRYAIGV  GLAFQNRNSW  298
```

FIGURE 1A

|       |            |            |            |            |            |     |
|-------|------------|------------|------------|------------|------------|-----|
| αD    | QELNTISSAP | PQDHVFKVDN | FAALGSIQKQ | LQEKIYAVEG | TQSRASSSFQ | 346 |
| CD11B | QELNTIASKP | PRDHVFQVNN | FEALKTIQNQ | LREKIFAIEG | TQTGSSSSFE | 347 |
| CD11C | KELNDIASKP | SQEHIFKVED | FDALKDIQNQ | LKEKIFAIEG | TETISSSSFE | 348 |
|       |            |            |            |            |            |     |
| αD    | HEMSQEGFST | ALTMDGLFLG | AVGSFSWSGG | AFLYPPNMSP | TFINMSQENV | 396 |
| CD11B | HEMSQEGFSA | AITSNGPLLS | TVGSYDWAGG | VFLYTSKEKS | TFINMTRVDS | 397 |
| CD11C | LEMAQEGFSA | VFTPDGPVLG | AVGSFTWSGG | AFLYPPNMSP | TFINMSQENV | 398 |
|       |            |            |            |            |            |     |
| αD    | DMRDSYLGYS | TELALWKGVQ | NLVLGAPRYQ | HTGKAVIFTQ | VSRQWRKKAE | 446 |
| CD11B | DMNDAYLGYA | AAIILRNRVQ | SLVLGAPRYQ | HIGLVAMFRQ | NTGMWESNAN | 447 |
| CD11C | DMRDSYLGYS | TELALWKGVQ | SLVLGAPRYQ | HIGKAVIFIQ | VSRQWRMKAE | 448 |
|       |            |            |            |            |            |     |
| αD    | VTGTQIGSYF | GASLCSVDVD | SDGSTDLILI | GAPHYYEQTR | GGQVSVCPLP | 496 |
| CD11B | VKGTQIGAYF | GASLCSVDVD | SNGSTDLVLI | GAPHYYEQTR | GGQVSVCPLP | 497 |
| CD11C | VIGTQIGSYF | GASLCSVDVD | TDGSTDLVLI | GAPHYYEQTR | GGQVSVCPLP | 498 |
|       |            |            |            |            |            |     |
| αD    | RGQRVQWQCD | AVLRGEQGHP | WGRFGAALTV | LGDVNEDKLI | DVAIGAPGEQ | 546 |
| CD11B | RGQRARWQCD | AVLYGEQGQP | WGRFGAALTV | LGDVNGDKLT | DVAIGAPGEE | 547 |
| CD11C | RGWRRWW-CD | AVLYGEQGHP | WGRFGAALTV | LGDVNGDKLT | DVVIGAPGEE | 547 |
|       |            |            |            |            |            |     |
| αD    | ENRGAVYLFH | GASESGISPS | HSQRIASSQL | SPRLQYFGQA | LSGGQDLTQD | 596 |
| CD11B | DNRGAVYLFH | GTSGSGISPS | HSQRIAGSKL | SPRLQYFGQS | LSGGQDLTMD | 597 |
| CD11C | ENRGAVYLFH | GVLGPSISPS | HSQRIAGSQL | SSRLQYFGQA | LSGGQDLTQD | 597 |

FIGURE 1B

```
αD    GLMDLAVGAR GQVLLLRSLP VLKVGVAMRF SPVEVAKAVY RCWEEKPSAL       646
CD11B GLVDLTVGAQ GHVLLLRSQP VLRVKAIMEF NPREVARNVF ECNDQVVKGK       647
CD11C GLVDLAVGAR GQVLLLRTRP VLWVGVSMQF IPAEIPRSAF ECREQVVSEQ       647

αD    EAGDATVCLT IQKSSLDQL- -GDIQSSVRF DLALDPGRLT SRAIFNETKN       694
CD11B EAGEVRVCLH VQKSTRDRLR EGQIQSVVTY DLALDSGRPH SRAVFNETKN       697
CD11C TLVQSNICLY IDKRSKNLLG SRDLQSSVTL DLALAPGRLS PRAIFQETKN       697

αD    PTLTTRKTLG LGIHCETLKL LLPDCVEDVV SPIILHLNFS LVREPIPSPQ       744
CD11B STRRQTQVLG LTQTCETLKL QLPNCIEDPV SPIVLRLNFS LVGTPLSAFG       747
CD11C RSLSRVRVLG LKAHCENFNL LLPSCVEDSV IPIILRLNFT LVGKPLLAFR       747

αD    NLRPVLAVGS QDLFTASLPF EKNCGQDGLC EGDLGVTLSF SGLQTLTVGS       794
CD11B NLRPVLAEDA QRLFTALFPF EKNCGNDNIC QDDLSITFSF MSLDCLVVGG       797
CD11C NLRPMLAALA QRYFTASLPF EKNCGADHIC QDNLGISFSF PGLKSLLVGS       797

αD    SLELNVIVTV WNAGEDSYGT VVSLYYPAGL SHRRVSGAQK QPHQSALRLA       844
CD11B PREFNVTVTV RNDGEDSYRT QVTFFFPLDL SYRKVSTLQN QRSQRSWRLA       847
CD11C NLELNAEVMV WNDGEDSYGT TITFSHPAGL SYRYVAEGQK QGQLRSLHLT       847

αD    CETVPTED-- EGLRSSRCSV NHPIFHEGSN GTFIVTFDVS Y---KATLG        888
CD11B CESASSTEVS GALKSTSCSI NHPIFPENSE ----VTFNIT FDVDSKASLG        893
CD11C CCSA-PVGSQ GTW-STSCRI NHLIFRGGAQ ----ITFLAT FDVSPKAVGL        891
```

FIGURE 1C

|       |                |               |               |               |               | |
|-------|----------------|---------------|---------------|---------------|---------------|------|
| αD    | DRMLMRASAS | SENNKASSSK | ATFQLELPVK | YAVYTMISRQ | EESTKYFNFA | 938 |
| CD11B | NKLLLKANVT | SENNMPRTNK | TEFQLELPVK | YAVYMVVTSH | GVSTKYLNFT | 943 |
| CD11c | DRLLLIANVS | SENNIPRTSK | TIFQLELPVK | YAVYIVVSSH | EQFTKYLNFS | 941 |
|       |                |               |               |               |               | |
| αD    | TS-DEKKMKE | AEHRYRVNNL | SQRDLAISIN | FWVPVLLNGV | AVWDVVMEAP | 987 |
| CD11B | AS-ENTS-RV | MQHQYQVSNL | GQRSLPISLV | FLVPVRLNQT | VIWDRPQVTF | 991 |
| CD11c | ESEEKES-HV | AMHRYQVNNL | GQRDLPVSIN | FWVPVELNQE | AVWMDVEVSH | 990 |
|       |                |               |               |               |               | |
| αD    | SQSLP--CVS | ERKPPQHSDF | LTQISRSPML | DCSIADCLQF | RCDVPSFSVQ | 1035 |
| CD11B | SENLSSTCHT | KERLPSHSDF | LAELRKAPVV | NCSIAVCQRI | QCDIPFFGIQ | 1041 |
| CD11c | PQNPSLRCSS | EKIAPPASDF | LAHIQKNPVL | DCSIAGCLRF | RCDVPSFSVQ | 1040 |
|       |                |               |               |               |               | |
| αD    | EELDFTLKGN | LSFGWVRETL | QKKVLVVSVA | EITFDTSVYS | QLPGQEAFMR | 1085 |
| CD11B | EEFNATLKGN | LSFDWYIKTS | HNHLLIVSTA | EILFNDSVFT | LLPGQGAFVR | 1091 |
| CD11c | EELDFTLKGN | LSFGWVRQIL | QKKVSVSVA | EIIFDTSVYS | QLPGQEAFMR | 1090 |
|       |                |               |               |               |               | |
| αD    | AQMEMVLEED | EVYNAIPIIM | GSSVGALLLL | ALITATLYKL | GFFKRHYKEM | 1135 |
| CD11B | SQTETKVEPF | EVPNPLPLIV | GSSVGGLLLL | ALITAALYKL | GFFKRQYKDM | 1141 |
| CD11c | AQTITVLEKY | KVHNPIPLIV | GSSIGGLLLL | ALITAVLYKV | GFFKRQYKEM | 1140 |
|       |                |               |               |               |               | |
| αD    | LEDKPED--- | ----TATFS | GDDFSCVAPN | VPLS | | 1161 |
| CD11B | M---SEG--- | -----GP--P | GAE-----PQ | ---- | | 1153 |
| CD11c | M---EEANGQ | IAPENGT--Q | TPS-----PP | SEK | | 1163 |

FIGURE 1D

HUMAN B2 INTEGRIN ALPHA SUBUNIT ANTIBODIES

This application is a continuation-in-part of U.S. application Ser. No. 08/362,652, filed Dec. 21, 1994, which is pending, which is a continuation-in-part of U.S. application Ser. No. 08/286,889, filed Aug. 5, 1994, which issued as U.S. Pat. No. 5,470,953 on Nov. 28, 1995, which in turn is a continuation-in-part of U.S. application Ser. No. 08/173,497, filed Dec. 23, 1993, which issued as U.S. Pat. No. 5,437,958 on Aug. 1, 1995.

FIELD OF THE INVENTION

The present invention relates to the cloning and expression of polynucleotides encoding a novel human $\beta_2$ integrin $\alpha$ subunit, designated $\alpha_d$, which is structurally related to the known human $\beta_2$ integrin $\alpha$ subunits, CD11a, CD11b and CD11c. The present invention also relates to polynucleotides isolated from other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an $\alpha$ subunit in noncovalent association with a $\beta$ subunit. To date, at least fourteen $\alpha$ subunits and eight $\beta$ subunits have been identified [reviewed in Springer, Nature 346:425–434 (1990)]. The $\beta$ subunits are generally capable of association with more than one $\alpha$ subunit and the heterodimers sharing a common $\beta$ subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct $\alpha$ subunits, CD11a, CD11b or CD11c. The isolation of a cDNA encoding human CD18 is described in Kishimoto, et al., Cell 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in Leukocyte Typing III, McMichael (ed), Oxford Press, p.788 (1987)]. The human $\beta_2$ integrin $\alpha$ subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., J. Cell Biol. 108:703–712(1989); CD11b, Corbi, et al., J.Biol.Chem. 263:12403–12411 (1988) and CD11c, Corbi, et al. EMBO J. 6:4023–4028 (1987)]. Putative homologs of the human $\beta_2$ integrin $\alpha$ and $\beta$ chains, defined by approximate similarity in molecular weight, have been variously identified in other species including monkeys and other primates [Letvin, et al., Blood 61:408–410 (1983)], mice [Sanchez-Madrid, et al., J.Exp.Med. 154:1517 (1981)], and dogs [Moore, et al., Tissue Antigens 36:211–220 (1990)].

The absolute molecular weights of presumed homologs from other species have been shown to vary significantly [see, e.g., Danilenko et al., Tissue Antigens 40:13–21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., EMBO J. 8:4041–4047 (1989) and Schneiderman, et al., Proc.Natl.Acad.Sci.(USA) 86:7561–7565 (1989)]. Similarly, in humans, at least six variants of the metallothionine protein have been previously identified [Karin and Richards, Nature 299:797–802 (1982) and Varshney, et al., Mol.Cell.Biol. 6:26–37, (1986)], whereas in the mouse, only two such variants are in evidence [Searle, et al., Mol.Cell.Biol. 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct $\alpha$ subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth $\alpha$-like canine subunit also capable of association with the $\beta_2$ subunit, but having a unique molecular weight and restricted in expression to a subset of differentiated tissue macrophages.

Antibodies generated by immunization of hamsters with murine dendritic cells resulted in two anti-integrin antibodies [Metlay, et al., J.Exp.Med. 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11.8H2 antibody and the murine N418 antibody could represent a variant species (e.g., a glycosylation or splice variant) of a previously identified canine or murine $\alpha$ subunit. Alternatively, these antigens may represent unique canine and murine integrin $\alpha$ subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, Blood 75:1037–1050 (1990)]. Expression of the $\alpha$ chains, however, is variable with regard to the state of activation and differentiation of the individual cell types [See review, Larson and Springer, Immunol.Rev. 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/CD18, CD11b/CD18 and CD11c/CD18 actively participate in natural killer (NK) cell binding to lymphoma and adenocarcinoma cells [Patarroyo, et al., *Immunol.Rev.* 114:67–108 (1990)], granulocyte accumulation [Nourshargh, et al., *J.Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J.Immunol.* 139:4174–4177 (1987) and Smith, et al., *J. Clin. Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counter-receptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha$ subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly de- glycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including immobilized ligand binding assays, solution binding assays, scintillation proximity assays, di-hybrid screening assays, and the like.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor Of $\alpha_d$ binding.

Another type of assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

Yet another method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo. Presently preferred antibodies of the invention are secreted by hybridomas designated 169A, 169B, 170D, 170F, 170E, 170X, 170H, 188A, 188B, 188C, 188E, 188F, 188G, 188I, 188J, 188K, 188L, 188M, 188N, 188P, 188R, 188T, 195A, 195C, 195D, 195E, 195H, 197A-1, 197A-2, 197A-3, 197A-4, 199A, 199H, and 199M.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J.Leukocyte Biol.* 54:30–39 (1993). In rats, Adams, et al., [*Transplantation* 53:1115–1119(1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterology* 104:759–771 (1993)] describe an induced inflammatory bowel disease, chronic granulomatous colitis, in rats following injections of streptococcal peptidoglycan-polysaccharide polymers. Cromartie, et al., [*J.Exp.Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur. J.Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport.

The invention also comprehends methods for treatment of disease states in which $\alpha_d$ binding, or localized accumulation of cells which express $\alpha_d$, is implicated, wherein a patient suffering from said disease state is provided an amount of a pharmaceutical composition of the invention sufficient to modulate levels of $\alpha_d$ binding or to modulate accumulation of cell types which express $\alpha_d$. The method of treatment of the invention is applicable to disease states such as, but not limited to, Type I diabetes, atherosclerosis, multiple sclerosis, asthma, psoriasis, lung inflammation, acute respiratory distress syndrome and rheumatoid arthritis.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$, antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule ICAM-R, an ICAM-R mutant protein, and complement fact iC3b. Example 13 describes scintillation proximity screening assays to identify inhibitors or enhancers (i.e., modulators) of $\alpha_d$ ligand/anti-ligand binding interactions. Example 14 addresses construction of expression plasmids which encode soluble forms of $\alpha_d$, and binding analyses of the expression products. Example 15 relates to production of $\alpha_d$-specific polyclonal sera and monoclonal antibodies. Example 16 describes analysis of $\alpha_d$ tissue distribution, expression of $\alpha_d$ on peripheral blood leukocytes, and $\alpha_d$ expression in inflammatory and non-inflammatory synovium using anti-$\alpha_d$ polyclonal serum. Example 17 describes isolation of rat cDNA sequences which show homology to human $\alpha_d$ gene sequences. Example 18 relates to construction of full length rat $\alpha_d$ expression plasmids, rat $\alpha_d$ I domain expression plasmids, including I domain/IgG fusion proteins, and production of monoclonal antibodies to full length and I domain fusion proteins. Example 19 addresses isolation of mouse cDNA sequences which show homology to human $\alpha_d$ gene sequences. Example 20 describes isolation of additional mouse $\alpha_d$ cDNA clones used to confirm sequence analysis. Example 21 relates to in situ hybridization analysis of various mouse tissues to determine tissue and cell specific expression of the putative mouse homolog to human $\alpha_d$. Example 22 describes generation of expression constructs which encode the putative mouse homolog of human $\alpha_d$. Example 23 addresses design of a "knock-out" mouse wherein the gene encoding the putative mouse homolog of human $\alpha_d$ is disrupted. Example 24 describes isolation of rabbit cDNA clones which show homology to human $\alpha_d$ encoding sequences. Example 25 describes animal models of human disease states wherein modulation of $\alpha_d$ is assayed for therapeutic capabilities. Example 26 describes expression of $\alpha_d$ in animal model disease states.

Example 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically 1×10⁶ cells) were incubated with undiluted hybridoma supernatant or a purified mouse IgG-negative control antibody (10 μg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 μg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$. Because the monoclonal antibody Ca11.8H2 specific for the canine α subunit did not cross react with a human homolog, isolation of canine $\alpha_{TM1}$ DNA was deemed a necessary prerequisite to isolate a counterpart human gene if one existed.

Example 2

Affinity Purification Of Canine $\alpha_{TM1}$ For N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with 1/15 volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., J.Cell.Biol. 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

| | |
|---|---|
| 5'-TTYAAYYTGGAYGTNGARGARCCNATGG-TNTTYCA-3' | (SEQ ID NO: 6) |
| 5'-TTCAACCTGGACGTGGAGGAGCCCATGG-TGTTCCAA-3' | (SEQ ID NO: 7) |
| 5'-TTCAACCTGGACGTNGAASANCCCATGG-TCTTCCAA-3' | (SEQ ID NO: 8) |

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

| | |
|---|---|
| 5'-TTYAAYYTNGAYGTNGARGARCC-3' | (SEQ ID NO: 9) |
| 5'-TTYAAYYTGGACGTNGAAGA-3' | (SEQ ID NO: 10) |
| 5'-TGRAANACCATNGGYTC-3' | (SEQ ID NO: 11) |
| 5'-TTGGAAGACCATNGGYTC-3' | (SEQ ID NO: 12) |

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

| | |
|---|---|
| 5'-ATTAACCCTCACTAAAG-3' | (SEQ ID NO: 13) |
| 5'-AATACGACTCACTATAG-3' | (SEQ ID NO: 14) |

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 μg/ml ethidium bromide. DNA was transferred to a Hybond (Amersham, Arlington Heights, Ill.) membrane by wicking overnight in 10× SSPE. After transfer, the immobilized DNA was denatured with 0.5M NaOH with 0.6M NaCl, neutralized with 1.0M Tris-HCl, pH 8.0, in 1.5M NaCl, and washed with 2× SSPE before UV crosslinking with a Stratalinker (Stratagene) crosslinking apparatus. The membrane was incubated in prehybridization buffer (5× SSPE, 4× Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 μCi γP$^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1× SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

Example 3
Large Scale Affinity Purification Of Canine $\alpha_{TM1}$ For Internal Sequencing In order to provide additional amino acid sequence for primer design, canine $\alpha^{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 μl were collected and neutralized with 100 μl 1M Tris buffer, pH 8.0. Aliquots of 15 μl were removed from each fraction and boiled in an equal volume of 2× Laemmli sample buffer with 1/15 volume 1M dithiothreitol (DTT). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 μg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 μl 8M urea, 0.4M NH$_4$HCO$_3$. The fragments were reduced in 5 μl 45 mM dithiothreitol (DTT) and subsequently incubated at 50° C. for 15 minutes. The solution was then cooled to room temperature and the fragments alkylated by adding 5 μl 100 mM iodoacetamide (Sigma, St. Louis, Mo.). Following a 15 minute incubation at room temperature, the sample was diluted with 187 μl Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 μl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

| | |
|---|---|
| VFQEXGAGFGQ | (SEQ ID NO: 15) |
| LYDXVAATGLXQPI | (SEQ ID NO: 16) |
| PLEYXDVIPQAE | (SEQ ID NO: 17) |
| FQEGFSXVLX | (SEQ ID NO: 18) |
| TSPTFIXMSQENVD | (SEQ ID NO: 19) |
| LVVGAPLEVVAVXQTGR | (SEQ ID NO: 20) |
| LDXKPXDTA | (SEQ ID NO: 21) |

Primer Design

One internal amino acid sequence (set out in SEQ ID NO: 22) obtained was then used to design a fully degenerate oligonucleotide primer, designated p4(R) as set out in SEQ ID NO: 23.

| | |
|---|---|
| FGEQFSE | (SEQ ID NO: 22) |
| 5'-RAANCCYTCYTGRAAACTYTC-3' | (SEQ ID NO: 23) |

Example 4

PCR Cloning Of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A+ RNA was then selected on Dynal Oligo dT Dynabeads (Dynal, Oslo, Norway). Five aliquots of 100 μg total RNA were combined and diluted with an equal volume of 2× binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A+ mRNA with 2 mM EDTA, pH 7.5. Double-stranded cDNA was then generated using the eluted poly A+ mRNA and the Boehringer Mannheim cDNA Synthesis Kit according to the manufacturer's suggested protocol.

B. Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded CDNA, 500 ng of each primer, 200 μM dNTPs and 1.5 units Taq polymerase (Boehringer Mannheim) in Taq buffer (Boehringer Mannheim) with magnesium. The resulting products (1 μl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR™II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha^{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×10⁶ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved α subunit amino acid motif GFFKR [Tamura, et al., supra] were also unsuccessful.

Example 5

Cloning Of A Putative Human Homolog Of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

| | |
|---|---|
| 5'-GTNTFYCARGARGAYGG-3' | (SEQ ID NO: 25) |

The PCR product was purified using the Qiagen (Chatsworth, Ga.) Quick Spin kit and the manufacturer's suggested protocol. The purified DNA (200 ng) was labeled with 200 μCi α³²PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2× SSC/0.1% SDS at 37° C. and twice in 2× SSC/0.1% SDS at 50° C. Final stringency washes were 1× SSC/0.1% SDS, twice at 65° C. (1× SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1× SSC/0.1% SDS at 65° C. and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics Of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], $\alpha_E$ [Shaw, et al., *J.Biol.Chem.* 269:6016–6025 (1994)] and in VLA-1 and VLA-2, [Tamura, et al., supra]. The I domain in other integrins has been shown to participate in ICAM binding [Landis, et al., *J.Cell.Biol.* 120:1519–1527 (1993); Diamond, et al., *J. Cell.Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of α subunits in $\beta_2$ integrins are typically distinct from one another within the same species, while individual α subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all α integrins [Rojiani, et al., *Biochemistry* 30: 9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

Isolation of additional human $\alpha_d$ cDNA clones for sequence verification

In order to confirm the DNA sequence encoding human $\alpha_d$, additional human cDNAs were isolated by hybridization from a human splenic oligo dt-primed cDNA library (Invitrogen) in pcDNA/Amp (described in Example 5) which was size selected by agarose gel electrophoresis for cDNA greater than 3 kb in length. The probe for hybridization was derived from a 5' region of $\alpha_d$ as described below. Hybridization conditions were the same as described above for the isolation of the initial human $\alpha_d$ clone, except that following hybridization, filters were washed twice in 2× SSC/0.1% SDS at room temperature and once in 2× SSC/0.1% SDS at 42° C. Filters were exposed to Kodak X-Omat AR film overnight.

The 5' $\alpha_d$ hybridization probe was generated by PCR from the 19A2 clone using primers CD11c 5' For (SEQ ID NO: 94) and CD11c 5' Rev (SEQ ID NO: 95) under the following conditions. Samples were held at 94° C. for four minutes and subjected to 30 cycles of the temperature step sequence i) 94° C., for 15 seconds; ii) 5° C., for 30 seconds; and iii) 72° C., for 1 minute in a Perkin-Elmer 9600 thermocycler.

CD11c 5'For: (5')CTGGTCTGGAGGTGCC-
TTCCTG(3')                                    (SEQ ID NO: 94)

CD11c 5'Rev: (5')CCTGAGCAGGAGCACC-
TGGCC(3')                                     (SEQ ID NO: 95)

The amplification product was purified using the BioRad (Hercules, Calif.) Prep-A-Gene kit according to manufacturer's suggested protocol. The resulting 5' $\alpha_d$ probe was approximately 720 bases long, corresponding to the region from nucleotide 1121 to nucleotide 1839 in SEQ ID NO: 1. The purified DNA (approximately 50 ng) was labeled with $^{32}$P-dCTP using a Boehringer Mannheim (Indianapolis, Ind.) Random Prime Labeling kit according to manufacturer's suggested protocol. Unincorporated isotope was removed using Centrisep Spin Columns (Princeton Separations, Adelphia, N.J.) according to manufacturer's suggested protocol. Labeled probe was added to the filters in a prehybridization solution containing 45% formamide and incubation allowed to proceed overnight at 50° C. Following incubation, the filters were washed as described above.

Thirteen colonies gave signals on duplicate lifts. Positive colonies were picked from master plates, diluted in LBM and carbenicillin (100 μg/ml) and plated at varying dilutions onto Hybond (Amersham) filters. Duplicate filters were hybridized with the same solution from the primary hybridization and following hybridization, the filters were washed at a final stringency of 2× SSC/0.1% SDS at 42° C. and exposed to film.

Ten of the originally identified thirteen positive colonies were confirmed in the secondary screen. Of these ten clones, two (designated A7.Q and A8.Q) were sequenced and determined to encode human $\alpha_d$. Clone A7.Q was found to be approximately 2.5 kb in length, including a 5' leader, part of a coding region, and an additional 60 bases of 5' untranslated sequence. The incomplete coding region was determined to have resulted from an aberrantly spliced intron region at corresponding nucleotide 2152 of SEQ ID NO: 1. Clone A8.Q was determined to be approximately 4 kb in length, spanning the entire $\alpha_d$ coding region and also including an intron sequence at corresponding base 305 of SEQ ID NO: 1. In comparison to the originally isolated $\alpha_d$ clone (SEQ ID NO: 1), one difference was observed in that both A7.Q and A8.Q clones were determined to have a three base CAG codon insertion occurring at base 1495. Sequences for clones A7.Q AND A8.Q are set out in SEQ ID NOs: 96 and 97, respectively, and a composite human sequence derived from clones A7.Q and A8.Q, and its corresponding deduced amino acid sequence, are set out in SEQ ID NOs: 98 and 99, respectively.

Example 6
Northern Analysis of Human $\alpha_d$ Expression in Tissues

In order to determine the relative level of expression and tissue specificity of $\alpha_d$, Northern analysis was performed using fragments from clone 19A2 as probes. Approximately 10 μg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10× SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2× SSC/0.1% SDS at room temperature, 2× SSC/0.1% SDS at 42° C., 2× SSC/0.1% SDS at 50° C., 1× SSC/0.1% SDS at 50° C., 0.5× SSC/0.1% SDS at 50° C. and 0.1× SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA+ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO: 1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

Example 7
Transient Expression of Human $\alpha_d$ Constructs

A. Generation of expression constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is 6 underlined and the EcoRI site is double underlined.

| | |
|---|---|
| 5'-CCACTGTCAGGATGCCCGTG-3' | (SEQ ID NO: 26) |
| 5'-AGTTACGAATTCGCCACCATGGCTC-TACGGGTGCTTCTTCTG-3' | (SEQ ID NO: 27) |
| 5'-AGTTACGAATTCGCCACCATGACTCG-GACTGTGCTTCTFCTG-3' | (SEQ ID NO: 28) |
| 5'-AGTTACGAATTCGCCACCATGACC-TTCGGCACTGTG-3' | (SEQ ID NO: 29) |

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

B. Transfection of COS Cells

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/10% FBS/pen-strep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA, FACS, and immunoprecipitation as described in Examples 8, 9, and 10.

Example 8
ELISA Analysis of COS Transfectants

In order to determine if the COS cells co-transfected with CD18 expression plasmid pRC.CD18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

Example 9
FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$ constructs with the CD18 construct produced a positive population that showed a 4- to 7-fold increase in fluorescence intensity over background.

Example 10
Biotin-Labeled Immunoprecipitation of Human $\alpha_d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the αβ heterodimer complex characteristic of integrins.

Transfected cells (1–3×10⁸ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM $Ca^{++}$, 2 mM $Mg^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 μl (25 μg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 μg anti-CD18 antibody (TS1.18) for 2 hours at 4° C. Antibody/antigen complexes were isolated from supernatants by incubation with 100 μl/sample rabbit anti-mouse/Protein A-sepharose preparation described above. Beads were washed 4 times with 10 mM HEPES, 0.2M NaCl, and 1% Triton-X 100. Washed beads were pelleted and boiled for 10 minutes in 20 μl 2× Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

Example 11
Stable Transfection of Human $\alpha_d$ in Chinese Hamster Ovary Cells To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC1.CD18 encoding human CD18 into dihydrofolate reductase (DHFR)$^-$ Chinese hamster ovary (CHO) cells. The plasmid pDC1.CD18 encodes a DHFR$^+$ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

Example 12
Human $\alpha_d$ binds to ICAM-R in a CD18-dependent fashion

In view of reports that demonstrate interactions between the leukocyte integrins and intercellular adhesion molecules (ICAMs) which mediate cell-cell contact [Hynes, Cell 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 μg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD18 co-transfectants consistently showed a 3–5 fold increase in binding to ICAM-R/IgG1 wells over BSA coated wells. The specificity and CD18-dependence of this binding was demonstrated by the inhibitory effects of anti-CD18 antibody TS1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 μl binding buffer (RPMI and 1% BSA) with or without 10 μg/ml anti-CD18 antibody. After a 20 minute incubation at room temperature, the cells were washed in binding buffer and soluble ICAM-1/IgG1 or ICAM-R/IgG1 fusion protein was added to a final concentration of 5 μg/ml. Binding was allowed to proceed for 30 minute at 37° C., after which the cells were washed three times and resuspended in 100 μl binding buffer containing FITC-conjugated sheep anti-human IgG1 at a 1:100 dilution. After a 30 minute incubation, samples were washed three times and suspended in 200 μl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

The FACS adhesion assay described above was used to test the binding of an ICAM-R mutant E37A/Ig to CHO cells expressing $\alpha_d$/CD18. E37A/Ig has been shown to obviate binding to an LFA-1/Ig chimera [Sadhu, et al., *Cell Adhesion and Communication* 2:429–440 (1994)]. The mutant protein was expressed in a soluble form from stably transfected CHO cell line and purified over a ProsepA column as described by Sadhu, et al., supra.

E37A/Ig binding with the $\alpha_d$/CD18 transfectants was not detected in repeated assays. The mean fluorescence intensity (MFI) of the E37A/Ig chimera detected by FITC-conjugated anti-human antibody was identical to the MFI of the detecting antibody alone, indicating there was no detectable signal above background using the E37A/Ig mutant protein in the assay. Similarly, in an ELISA, carried out as described in Example 14, the E37A/Ig mutant did not appear to bind immobilized $\alpha_d$/CD18.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11b I domain has recently been identified as the site of iC3b interaction [Ueda, et al., *Proc.Natl.Acad.Sci.(USA)* 91:10680–10684 (1994)]. The region of iC3b binding is highly conserved in CD11b, CD11c, and $\alpha_d$, suggesting an $\alpha_d$/iC3b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., *J. Clin. Invest.* 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

Example 13
Screening by Scintillation Proximity Assay

Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol.Immunol.* 12:265–267 (1979), and Hart and Greenwald, *J.Nuc.Med.* 20:1062–1065 (1979), each of which is incorporated herein by reference.

Briefly, one member of the $\alpha_d$ ligand/anti-ligand pair is bound to a solid support either directly or indirectly. Indirect capture would involve a monoclonal antibody, directly bound to the support, which recognizes a specific epitope at the C-terminus of the soluble integrin β chain protein. This epitope would be either the hemagglutinin protein or the mycobacterial IIIE9 epitope [Anderson, et al., *J.Immunol.* 141:607–613 (1988). A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

The soluble recombinant $\alpha_d$/CD18 leucine zipper construct (see Example 14) is used in a scintillation proximity assay to screen for modulators of CAM binding by the following method. The recombinant integrin is immobilized with a nonblocking anti-α subunit or anti-β subunit antibody previously coated on a scintillant-embedded plate. Chemical library compounds and a specific biotinylated CAM/Ig chimera are added to the plate simultaneously. Binding of the CAM/Ig chimera is detected by labeled strepavidin. In the assay, ICAM-1/Ig and ICAM-3/Ig are biotinylated with NHS-Sulfo-biotin LC (long chain, Pierce) according to manufacturer's suggested protocol. Labeled proteins are still reactive with CAM specific antibodies and can be shown to react with immobilized LFA-1 by ELISA, with detection by Strepavidin-HRP and subsequent development with OPD.

Alternatively, the recombinant leucine zipper protein is purified, or partially purified and coated directly on the scintillant embedded plate. Unlabelled CAM/Ig chimera and chemical library compounds are added simultaneously. Bound CAM/Ig is detected with $^{125}$I-labeled anti-human Ig.

As yet another alternative, purified CAM/Ig protein is immobilized on the scintillant plate. Chemical library compounds and concentrated supernatant from cells expressing recombinant leucine zipper integrin are added to the plate. Binding of the recombinant integrin is detected with a labeled, non-blocking α or β subunit antibody.

Example 14
Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

5'-TTGCTGACTGCCTGCAGTTC-3'         (SEQ ID NO: 30)

5'-GTTCTGACGCGTAATGGCATTGTAGACC-
        TCGTCTTC-3'                    (SEQ ID NO: 31)

The PCR amplification product was digested with AatII and MluI and ligated to the HindIII/AatII fragment. The resulting product was ligated into HindIII/MluI-digested plasmid pDC1.s.

This construct is co-expressed with soluble CD18 in stably transfected CHO cells, and expression is detected by autoradiographic visualization of immunoprecipitated CD18 complexes derived from $^{35}$S-methionine labeled cells. The construct is also co-expressed with CD18 in 293 cells [Berman, et al., *J. Cell.Biochem.* 52:183–195 (1993)].

Soluble full-length $\alpha_d$ construct

Alternative $\alpha_d$ expression constructs are also contemplated by the invention. In order to facilitate expression and purification of an intact $\alpha_d$/CD18 heterodimer, soluble $\alpha_d$ and CD18 expression plasmids will be constructed to include a "leucine zipper" fusion sequence which should stabilize the heterodimer during purification [Chang, et al., *Proc.Natl.Acad. Sci.(USA)*, 91: 11408–11412 (1994)]. Briefly, DNA encoding the acidic and basic amino acid strands of the zipper have been generated by primer annealing using oligonucleotides described in Chang, et al. The DNA sequences have been further modified to include additional Mlu1 and Xba1 restriction sites at the 5' and 3' ends, respectively, of the DNA to facilitate subcloning into $\alpha_d$ or CD18 expression constructs previously described. In addition, sequences representing either hemagglutinin protein or a polyhistidine sequence have been added, as well as a stop codon inserted after the Xba1 site. The hemagglutinin or polyhistidine sequences are incorporated to facilitate affinity purification of the expressed protein. Sequences encoding the basic strand of the zipper are incorporated on the plasmid vector expressing CD18; the acidic strand is inserted on the a chain construct. Upon expression of the modified $\alpha_d$ and CD18 proteins in a host cell, it is presumed that interaction between the acidic and basic strands of the zipper structure will stabilize the heterodimer and permit isolation of the intact $\alpha_d$/CD18 molecule by affinity purification as described above.

Plasmids were constructed for expression of soluble $\alpha_d$ and CD18 with acidic and basic "leucine zipper" sequences and transfected into COS cells by the DEAE/Dextran method described in Example 7. The resulting protein was referred to as $\alpha$d/CD18LZ. Hemagglutinin and polyhistidine tags were not incorporated into $\alpha_d$/CD18LZ. Transfected cells were grown for 14 days in reduced serum (2%) conditions. Supernatants harvested every five days from transfected cells were assayed for protein production by ELISA as described in Example 8. Briefly, the $\alpha_d$/CD18LZ heterodimer was immobilized on plates coated with anti-$\alpha_d$ monoclonal antibody 169B (see Example 15). The $\alpha_d$/CD18LZ complex was detected by addition of a biotinylated anti-CD18 monoclonal antibody, TS1/18.1 (see Example 8), followed by addition of strepavidin/horse radish peroxidase (HRP) conjugate and o-phenyldiamine (OPD). Protein was clearly detectable in the supernatants.

Binding Assays Using Soluble Full Length $\alpha_d$ Expression Products

Functional binding assays using the soluble full length $\alpha_d$/CD18LZ heterodimer described above were performed by immobilizing the heterodimer on plates coated with monoclonal antibody 169B or a non-blocking anti-CD18 monoclonal antibody (see Example 15). Wells were blocked with fish skin gelatin to prevent non-specific binding before addition of CAM/Ig chimeras (see Example 12) at a starting concentration of 10 µg/ml. Binding of the chimeras to $\alpha_d$/CD18 was detected with a goat-anti-human Ig HRP conjugate (Jackson Labs) and subsequent development with OPD.

VCAM-1/Ig was observed to bind to captured $\alpha_d$/CD18LZ at a 3–5 fold higher level than to captured CD11a/CD18. ICAM-1/Ig and ICAM-2/Ig bound soluble CD11a/CD18 heterodimer approximately 15 and 10 fold above background, respectively, but did not bind $\alpha_d$/CD18. VCAM-1 binding was reduced approximately 50% in the presence of the VCAM-1 specific antibodies 130K and 130P used in combination.

The binding assay was also performed with the ICAM/Ig protein immobilized on 96-well plates followed by addition of recombinant soluble integrin in cellular supernatant. Binding of the soluble integrins were detected with an unlabeled non-blocking $\alpha$ or $\beta$ subunit specific murine antibody, followed by incubation with HRP-conjugated goat anti-mouse antibody and development with OPD.

Results indicated that a non-blocking antibody detected $\alpha_d$/CD18LZ binding to ICAM-R/Ig 10 fold greater than binding detected in control well containing no antibody. Soluble $\alpha_d$/CD18 binding was not detected with immobilized ICAM-1/Ig, however binding was detected between $\alpha_d$/CD18 and immobilized CD11b/CD18 and CD11a/CD18 15 and 5 fold, respectively, greater than background binding.

Because previous studies have demonstrated that CD11b and CD11c bind lipopolysaccharide (LPS) [Wright, *Curr.Opin.Immunol.* 3:83–90 (1991); Ingalls and Golenbock, *J.Exp.Med.* 181:1473–1479 (1995)], LPS binding to $\alpha_d$/CD18 was also assessed using flow cytometry and plate-based assays. Results indicated that FITC-labelled LPS isolated from S.Minnesota and S.typhosa (both obtained from Sigma) at 20 µg/ml were able to weakly bind $\alpha_d$/CD18 transfected CHO cells. No binding was observed with un-transfected control CHO cells. In ELISA format assays, biotinylated LPS [Luk, et al., *Alan. Biochem.* 232:217–224 (1995)] at 0.5–3.0 µg bound immobilized $\alpha_d$/CD18LZ with a signal four fold greater that the capture antibody and blocking reagent alone. Apparent binding of LPS to CD11a/CD18 was discounted by subtracting from each experimental value background binding to anti-CD11a antibody TS2/4.

In order to identify other ligands for $\alpha_d$/CD18, the recombinant $\alpha_d$/CD18LZ protein is used in a two tier study. Binding of various cell types to immobilized protein is used to determine which cells express $\alpha_d$ ligands on the cell surface. Antibody inhibition is then used to determine if the observed cell binding results from interaction with known surface adhesion molecules. If no inhibition results, co-immunoprecipitation with $\alpha_d$/CD18LZ bound to proteins from lysates of cells which will bind $\alpha_d$ is used to attempt to identify the ligand.

Soluble Human $\alpha_d$ I Domain Expression Constructs

It has previously been reported that the I domain in CD11a can be expressed as an independent structural unit that maintains ligand binding capabilities and antibody recognition [Randi and Hogg, *J.Biol. Chem.* 269:12395–12398 (1994); Zhout, et al., *J.Biol.Chem.* 269:17075–17079 (1994); Michishita, et al., *Cell* 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

> 5'-ACGTATGCAGGATCCCATCAAGAGATGG-
> ACATCGCT-3' (SEQ ID NO: 32)
>
> 5'-ACTGCATGTCTCGAGGCTGAAGCCTTCTT-
> GGGACATC-3' (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Pharmacia) and the I domain fragment sequenced.

The fusion protein is then expressed in COS, CHO or *E. coli* cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein (I$\alpha_d$/IgG4) in TBS were incubated with ICAM-1/IgG, ICAM-R/IgG, VCAM-1/IgG, or an irrelevant IgG1 myeloma protein immobilized on Immulon IV RIA/EIA plates. CD11a I domain/IgG chimeric protein and human IgG4/kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The I$\alpha_d$/IgG4 protein did not bind to fish skin gelatin or bovine serum albumin blocking agents, human IgG1, or ICAM-1/IgG. A two to three fold increase in binding signal over background was detected in ICAM-R/IgG protein coated wells using 1–5 µg/ml concentrations of I$\alpha_d$/IgG4 protein. The signal in VCAM-1/IgG protein coated wells was 7–10 fold higher than background. In previous assays, $\alpha_d$/CD18 transfected CHO cells did not bind VCAM-1/IgG protein, suggesting that VCAM-1 binding may be characteristic of isolated I domain amino acid sequences.

Additional $\alpha_d$ I domain constructs

Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS1 or the prokaryotic expression vector pGEX-4T-3 (Pharmacia) and the I domain sequenced. The fusion proteins are then be expressed in COS, CHO, or *E.coli* cells transformed or transfected with an appropriate expression construct. Protein are purified on a ProSepA column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS1 by PCR using primers which individually incorporate a 5' AatII restriction site (SEQ ID NO: 89) and a 3' Xba1 restriction site (SEQ ID NO: 90).

> 5'-CGCTGTGACGTCAGAGTTGAGTCCAAAT-
> ATGG-3' (SEQ ID NO: 89)
>
> 5'-GGTGACACTATAGAATAGGGC-3' (SEQ ID NO: 90)

Plasmid pATM.D12 is digested with AatII and Xba1, and the appropriately digested and purified IgG4 PCR product ligated into the linear vector.

Example 15

Production of Human $\alpha_d$-Specific Antibodies

A. Production of Monoclonal Antibodies

1. Transiently transfected cells from Example 7 were washed three times in Dulbecco's phosphate buffered saline (D-PBS) and injected at 5×10⁶ cells/mouse into Balb/c mice with 50 µg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

2. As an alternative for production of monoclonal antibodies, soluble $\alpha_d$ I domain/IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d$/CD18 complexes expressed on CHO transfectants.

Mouse 1908 received three initial immunizations of $\alpha_d$/CD18 transfected CHO cells and two subsequent boosts with soluble $\alpha_d$/CD18 heterodimer. Two final immunizations included 50 µg/mouse $\alpha_d$ I domain/IgG4 fusion protein. The fusion produced 270 IgG-producing wells. Supernatant from 45 wells showed at least 7-fold higher binding to I$\alpha_d$/IgG4 fusion protein than to human IgG4 by ELISA. None of the supernatants reacted to $\alpha_d$/CD18 transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d$/CD18 transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

3. As another alternative to monoclonal antibody production, CD18 complexes were immunoprecipitated from human spleen lysates with the anti-CD18 monoclonal antibody 23F2G after preclearance of CD11a/CD18 (using monoclonal antibody TS2/4) and CD11b/CD18 (using monoclonal antibody Mo-1). Five Balb/c mice, ten to twelve weeks old, were immunized by subcutaneous injection with approximately 30 µg of resulting protein in complete Freund's adjuvant on day 0, followed by two boosts of 30 ug immunogen/mouse on days 28 and 43 in incomplete Freund's adjuvant. Test sera were drawn ten days following the final boost and reactivity was assessed by using 1:500 dilution of each serum to detect 1 µg/lane immunogen in a Western blot. Sera from three mice detected bands of approximately 95 and 150 kD; no signal was seen in lanes treated with a 1:50 dilution of preimmune sera. The 150 kD band was presumed to represent $\alpha_d$ in an in vivo glycosylation state. In addition, all post immune sera immunoprecipitated protein from lysates of biotinylated $\alpha_d$/CD18 CHO cells that migrated at appropriate molecular weights on SDS-PAGE to represent the heterodimer. From these results, mouse #2212 was selected and was further immunized by intraperitoneal injection on day 64 with 30 µg immunogen in PBS. The mouse was sacrificed four days later, and the spleen was sterilely removed.

A single-cell suspension was formed by grinding the spleen between the frosted ends of two glass microscope slides submerged in serum-free RPMI 1640 supplemented with 2 mM L-glutamine, 1 mM sodium pyruvate, 100 units/ml penicillin, and 100 µg/ml streptomycin (RPMI) (Gibco, Canada). The cell suspension was filtered through a sterile 70-mesh Nitex cell strainer (Becton Dickinson, Parsippany, N.J.), and the filtrate washed twice by centrifugation at 200×g for 5 minutes. The resulting pellet was resuspended in 20 ml serum-free RPMI. Thymocytes taken from three naive Balb/c mice were prepared in a similar manner.

Prior to fusion, NS-1 myeloma cells, kept in log phase in RPMI with 10% Fetalclone serum (FBS) (Hyclone Laboratories, Inc., Logan, Utah) for three days prior to fusion, were pelleted by centrifugation at 200×g for 5 minutes, washed twice as described in the foregoing paragraph, and counted. Approximately $2 \times 10^8$ spleen cells were combined with $4 \times 10^7$ NS-1 cells, and the resulting mixture pelleted by centrifugation at 200×g. The supernatant was discarded. The cell pellet dislodged by tapping the tube and 2 ml of 50% PEG 1500 in 75 mM Hepes (pH 8.0, 37° C.) (Boehringer Mannheim) was added over the course of one minute with stirring. An additional 14 ml of serum-free RPMI was subsequently added over the next seven minutes, followed by immediate addition of 16 ml RPMI. The resulting mixture was centrifuged at 200×g for 10 minutes and the supernatant was discarded. The pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5 \times 10^6$ thymocytes/ml, and dispensed into ten 96-well flat bottom tissue culture plates (Corning, United Kingdom) at 200 µl/well. Cells were fed on days 2, 4, and 6 days post-fusion by aspirating approximately 100 µl from each well with an 18 G needle (Becton Dickinson), and adding 100 µl/well plating medium described above, except containing 10 units/ml IL-6 and lacking thymocytes.

On day 7–10 post-fusion, supernatant from each well was screened by antibody capture ELISA, testing for the presence of mouse IgG. Immulon 4 plates (Dynatech, Cambridge, Mass.) were coated with 50 µl/well goat anti-mouse IgA, IgG, or IgM (Organon Teknika) diluted 1:5000 in 50 mM carbonate buffer, pH 9.6, at 4° C. Plates were washed 3× with PBS containing 0.5% Tween 20 (PBST) and 50 µl culture supernatant from each well was added. After incubation at 37° C. for 30 minutes, wells were washed with PBST as above, and 50 µl of horseradish peroxidase conjugated goat anti-mouse IgG(fc) (Jackson ImmunoResearch, West Grove, Pa.) diluted 1:3500 in PBST was added to each well. Plates were incubated as above, washed 4× with PBST and 100 µl substrate, consisting of 1 mg/ml o-phenylene diamine (Sigma) and 0.1 µl/ml 30% $H_2O_2$ in 100 mM Citrate, pH 4.5, was added. The color reaction was stopped after five minutes with addition of 50 µl 15% $H_2SO_4$. Absorbance at 490 nm was determined for each well using a plate reader (Dynatech).

Hybridomas were further characterized as follows. Supernatants from IgG-producing cultures were analyzed by flow cytometry for reactivity to $\alpha_d$/CD18-transformed CHO cells but not to JY cells (a B-cell line positive for LFA-1, but not other $\beta_2$ integrins as observed in previous in-house staining experiments). Briefly, $5 \times 10^5$ $\alpha_d$/CD18-transformed CHO or $\alpha_d$/CD18$^-$ JY cells were suspended in 50 µl RPMI containing 2% FBS and 10 mM $NaN_3$ (FACS buffer). Individual cell suspensions were added to 50 µl IgG positive hybridoma culture supernatant in wells of 96-well round bottomed plates (Corning). After a 30 minute incubation on ice, cells were washed twice by pelleting in a clinical centrifuge, supernatant from each well was discarded, and pellets resuspended in 200–300 µl FACS buffer. The last wash was replaced with 50 µl/well of a 1:100 dilution of a F(ab')$_2$ fragment of sheep anti-mouse IgG (H+L)-FITC conjugate (Sigma, St. Louis, Mo.) prepared in FACS Buffer. After incubation as described above, cells were washed twice with Dulbecco's PBS (D-PBS) supplemented with 10 mM $NaN_3$, and finally resuspended in D-PBS containing 1% paraformaldehyde. Samples were then transferred to polystyrene tubes for flow cytometric analysis (FACS) with a Becton Dickinson FACsan analyzer.

The fusion yielded four cultures deemed positive by both criteria. When the secondary screen was repeated on expanded supernatants approximately four days later, three of the four cultures remained positive. The three wells, designated 169A, 169B, 169D were cloned two to three times, successively, by doubling dilution in RPMI, 15% FBS, 100 mM sodium hypoxanthine, 16 mM thymidine, and 10 units/ml IL-6. Wells of clone plates were scored visually after four days and the number of colonies in the least dense wells were recorded. Selected wells of the each cloning were assayed by FACS after 7–10 days. Activity was found in two of the cultures, 169A and 169B. In the final cloning, positive wells containing single colonies were expanded in RPMI with 11% FBS. Antibody from clonal supernatants of 169A and 169B were isotyped using IsoStrip kit (Boehringer Mannheim) according to manufacturer instructions and found to be of the IgG1 isotype.

Immunoprecipitation of $\alpha_d$/CD18 complexes from CHO transfectants and PMA-stimulated HL60 cells was used as a tertiary screen for specificity. Hybridomas 169A and 169B precipitated appropriate bands from CHO lines, and a single α chain species of 150–160 kD from HL60 cells as determined by SDS-PAGE. Hybridomas 169A and 169B were deposited May 31, 1995 with the American Type Culture Collection, 12301 Parklawn Drive, Rockville, Md. 20852 and assigned Accession Numbers HB11907 and HB11906, respectively.

In order to more fully characterize binding properties of 169A and 169B, the ability of each antibody to inhibit binding of the other or the anti-CD18 antibody TS1/18.1 to soluble $\alpha_d$/CD18 was tested. Soluble full length $\alpha_d$/CD18 was immobilized by each unlabeled antibody separately in a 96-well plate format, and biotinylated antibodies were used to detect protein bound by the same or different unlabeled antibodies. Binding was detected using a goat anti-mouse Ig/HRP conjugate followed by addition of OPD substrate. Results indicated that antibody 169A was able to block binding of biotinylated 169A and TS1/18.1, while the antibody 169B blocked binding only of itself.

4. Another mouse (#2214), immunized by the same protocol as mouse #2212, was selected and further immunized by a pre-fusion boost on day 70 with 30 μg purified $\alpha_d$ from spleen lysates in PBS. The mouse was sacrificed four days later, and the spleen was sterilely removed.

The fusion and cloning of positive cells were carried out as described above. The fusion produced five anti-$\alpha_d$ monoclonal hybridomas designated 170D, 170F, 170E, 170X, and 170H which were isotyped as IgG$_1$ using the IsoStrip kit (Boehringer Mannheim) according to the manufacturer's instructions.

5. Still another mouse, #2211, immunized by the same initial protocol as mouse #2212 and mouse #2214, was selected and further immunized on day 88 with 30 μg immunogen and a pre-fusion boost of 30 μg immunogen on day 203. The mouse was sacrificed four days later, and the spleen was removed and fusion carried out as described above. Hybridoma supernatant was screened by antibody capture ELISA and by flow cytometry as detailed in the above paragraphs.

Fifteen positive hybridomas were identified, designated 188A, 188B, 188C, 188E, 188F, 188G, 188I, 188J, 188K, 188L, 188M, 188N, 188P, 188R and 188T, and isotyped in an ELISA assay. Briefly, Immulon 4 plates (Dynatech, Cambridge, Mass.) were coated at 4° C. with 50 μl/well goat anti-mouse IgA,G,M (Organon Teknika) diluted 1:5000 in 50 mM carbonate buffer, pH 9.6. Plates were blocked for 30 minutes at 37° C. with 1% BSA in PBS, washed three times with PBS/0.05% Tween 20 (PBST) and 50 μl culture supernatant (diluted 1:10 in PBST) added. After incubation and washing as above, 50 μl of horseradish peroxidase conjugated rabbit anti-mouse IgG$_1$, G$_{2a}$, or G$_3$ (Zymed, San Francisco, Calif.), diluted 1:1000 in PBST with 1% normal goat serum, was added. Plates were incubated as above, washed four times with PBST, after which 100 μl substrate, consisting of 1 mg/ml o-phenylene diamine (Sigma) and 0.1 μl/ml 30% H$_2$O$_2$ in 100 mM citrate, pH 4.5, was added. The color reaction was stopped in 5 minutes with the addition of 50 μl of 15% H$_2$SO$_4$. A$_{490}$ was read on a plate reader (Dynatech) and all fifteen antibodies were determined to be IgG1.

The excess spleen cells from mouse #2211 were frozen in a cryovial and stored in liquid nitrogen. The cryovial was thawed quickly by placing into a 37° C. water bath, and moving it in a circular motion just until contents were melted. Cells were transferred to a 15 ml centrifuge tube where warm RPMI containing 11% FBS was added slowly 1 ml at a time, allowing three to five minutes between additions. Another 5 ml warm RPMI was added and after a five minute wait, the tube was centrifuged at 200×g for five minutes and supernatant aspirated. Cells were resuspended in RPMI and a fusion carried out as described above. Hybridoma supernatant was screened by antibody capture and flow cytometry as described above.

The fusion yielded five clones designated 195A, 195C, 195D, 195E and 195H. The clones were isotyped by the ELISA procedure as described above; monoclonal antibodies 195A, 195C, 195D and 195E were determined to be IgG$_1$ and 195H was determined to be IgG$_{2a}$.

6. In order to identify antibodies capable of inhibiting functional $\alpha_d$ binding, soluble $\alpha_d$/CD18LZ (see Example 14) is used for immunization. The protein is isolated on an affinity chromatography resin from supernatant of transiently transfected COS cells and the resin-bound $\alpha_d$ used as an immunogen. A selected mouse is immunized as described above and given a final boost two weeks after the initial immunization. Immunization by this technique prevents possible changes in protein conformation often associated with detergent lysis of cells. Additional mice are immunized with recombinant protein, also resin-bound, but were not initially immunized with protein purified from cell lysate.

Hybridomas, prepared as described above, which result from the immunization are screened by ELISA on the recombinant protein immobilized from a cell supernatant using the Fab fragment of a non-blocking antibody. Alternatively, flow cytometry is used to assay for reactivity to JY cells previously transfected with $\alpha_d$ cDNA.

7. As another alternative, monoclonal antibodies are generated as follows. Affinity purified $\alpha_d$/CD18 heterodimeric protein from detergent lysates of stably transfected CHO cells is used with 50 μg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

8. As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

9. As another alternative, CD18 complexes from detergent lysates of PMA stimulated HL60 cells are enriched by preclearance as described above. Other β2 integrins are cleared on the same columns. Immunization with the resulting complexes, hybridoma production, and screening protocols are performed as described supra.

B. Production of Polyclonal Sera

Purified $\alpha_d$ I domain/IgG4 chimera (Example 14) was used to generate polyclonal anti-serum in rabbits. The $\alpha_d$ I domain/IgG4 antigen was injected at 100 μg/rabbit initially in complete Freund's adjuvant, followed by three boosts with the same amount of protein in incomplete Freund's adjuvant. Test bleeds were assayed after the third and fourth injections. Rabbit immunoglobulin (Ig) was purified from the serum on a protein A-sepharose column and precleared of anti-human IgG reactivity on a human IgG/Affigel 10 column. Reactivity by ELISA to the I domain chimera, but not to human IgG, was used to confirm complete preclearance.

The precleared polyclonal sera was used to immunoprecipitate protein from detergent lysates of surface-biotinylated CHO cells previously transfected with $\alpha_d$ and CD18 expression vectors. Immunoprecipitation was carried out by the method previously described in Example 10. The precleared sera recognized a protein complex of the same molecular weight as that precipitated by anti-CD18 monoclonal antibody TS1.18. In addition, the sera recognized a single band of appropriate size in a Western blot of CD18 complexes from $\alpha_d$/CD18 transfected CHO cells. Affinity purified integrins CD11a/CD18, CD11b/CD18, and VLA4 from human spleen were not recognized by the rabbit polyclonal sera. The sera failed to react with $\alpha_d$-transfected CHO cells in solution, as determined by flow cytometry. It was therefore concluded that the polyclonal rabbit sera was only capable of recognizing denatured $\alpha_d$ I domain/IgG4 proteins.

In an attempt to produce polyclonal antisera against $\alpha_d$/CD18, a mouse was immunized 3 times with $\alpha_d$ transfected CHO cells (D6.CHO, $\alpha_d$/CD18) with adjuvant peptide and once with purified $\alpha_d$/CD18 heterodimer. A final boost included only $\alpha_d$/CD18 heterodimer. Approximately 100 μl immunized serum was precleared by addition of approximately $10^8$ LFA-1-transfected CHO cells for 2 hours at 4° C. The resulting serum was assayed for $\alpha_d$ reactivity at dilutions of 1/5000, 1/10000, 1/20000 and 1/40000 on normal human spleen. The polyclonal antibody was reactive at a dilution of 1/20000, while a 1/40000 dilution stained very weakly.

Example 16
Analysis of $\alpha_d$ distribution

Tissue distribution of $\alpha_d$/CD18 was determined using polyclonal anti-serum generated as described in Example 15.

Purified rabbit polyclonal antibody was used at concentrations ranging between 120 ng/ml and 60 μg/ml for immunocytochemical analysis of frozen human spleen sections. Sections of 6 micron thickness were layered onto Superfrost Plus Slides (VWR) and stored at -70° C. Prior to use, slides were removed from -70° C. and placed at 55° C. for 5 minutes. Sections were then fixed in cold acetone for 2 minutes and air dried. Sections were blocked in a solution containing 1% BSA, 30% normal human sera and 5% normal rabbit sera for 30 minutes at room temperature. Primary antibody was applied to each section for 1 hour at room temperature. Unbound antibody was removed by washing the slides 3 times in TBS buffer for 5 minutes per wash. Next, a rabbit anti-mouse IgG link antibody was applied to each section in the same TBS buffer. A mouse alkaline phosphatase anti-alkaline phosphatase (APAAP) antibody, incubated for 30 minutes at room temperature, was used to detect the second antibody. Slides were then washed 3 times in TBS buffer. Fast Blue substrate (Vector Labs) was applied and color development stopped by immersion in water. Slides were counterstained in Nuclear Fast Red (Sigma) and rinsed in water before mounting with Aqua Mount (Baxter). Staining was detected in the splenic red pulp with this reagent, but not with an irrelevant rabbit polyclonal Ig preparation or the unpurified preimmune serum from the same animal.

Once mouse serum was determined to have specific $\alpha_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with $\alpha_d$ polyclonal sera, and monoclonal antibodies to CD11a, CD11b, CD11c, and CD18 revealed the following results. The pattern observed with $\alpha_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to $\alpha_d$ polyclonal sera, nor did labeling in the red pulp give the same pattern of staining as $\alpha_d$ polyclonal sera.

Therefore, the labeling pattern seen with $\alpha_d$ polyclonal serum was unique compared to that seen using antibodies to the other $\beta_2$ integrins (CD11a, CD11b, CD11c, and CD18), and suggests that the in vivo distribution of $\alpha_d$ in man is distinct from that of other $\beta_2$ integrins.

Characterization of Human $\alpha_d$ Expression With Monoclonal Antibodies

Antibodies secreted by hybridomas 169A and 169B were used to analyze human $\alpha_d$ expression in frozen tissue sections by immunocytochemistry and on cell lines and peripheral blood leukocytes by flow cytometry. Hybridoma supernatants used in both sets of experiments were undiluted.

Tissue Staining

All stains were carried out as described above, except for liver sections which were stained in the following manner. After acetone fixation, sections were quenched in 1% $H_2O_2$ and 1% sodium azide in TBS for 15 minutes at room temperature. After primary antibody staining, a rabbit anti-mouse antibody directly conjugated to peroxidase was applied for 30 minutes at room temperature. Slides were washed 3 times in TBS buffer. A swine anti-rabbit antibody, directly conjugated to peroxidase, was incubated for 30 minutes at room temperature to detect the second antibody. Slides were then washed 3 times in TBS buffer and AEC substrate (Vector Labs) was applied and to allow color development. Slides were counterstained with Hematoxylin Gill's No. 2 (Sigma), and subsequently rinsed in water before dehydration and mounting.

In spleen sections, the majority of expression was localized to the splenic red pulp on cells identified by morphology as granulocytes and macrophages. A large number of granulocytes were stained, while only a subset of macrophages gave signal. A small number of follicular dendritic cells in the white pulp also were weakly stained by the $\alpha_d$ antibodies. CD11a and CD18 staining was detected throughout the red and white pulp. CD11c staining was more pronounced in large cells presumed to be macrophages in the splenic white pulp and in the marginal zone surrounding the white pulp; diffuse staining in the red pulp was also noted. CD11b appeared to have distribution overlapping with but not identical to $\alpha_d$ in the red pulp, with no white pulp involvement.

Integrin expression in normal and (rheumatoid) arthritic synovial tissue was compared. Minimal staining with all anti-integrin antibodies (including antibodies specifically immunoreactive with CD11a, CD11b, CD11c, CD18, as well as $\alpha_d$) was noted in normal tissue, with a widespread distribution on resident cells, presumably macrophages. In the inflamed synovium, expression of all integrins was more localized to cells clustered around lymphatic vessels. While $\alpha_d$ and CD11b expression patterns were similar, CD11c did not appear to be as strongly expressed and was restricted to a subset of leukocytes.

In the dog, CD11b, but not $\alpha_d$, expression was observed on liver macrophages, or Kuppfer cells. Staining of normal human liver sections (as previously described for staining of dog liver section, supra) confirmed the conservation of this staining pattern in humans. In addition, CD11c was detected at low levels. In sections from a hepatitis patient, all leukointegrin staining was higher than observed on normal liver, while $\alpha_d$ expression was detected on macrophages and granulocytes in these samples.

Minimal staining of normal human colon sections was observed with anti-$\alpha_d$ antibodies; faint smooth muscle staining and leukocyte staining was observed. All leukointegrins were detected at higher levels in sections from patients with Crohn's disease.

Normal lung showed a limited number of weakly $\alpha_d$-positive cells; these were determined by morphology to be macrophages and neutrophils. In lung tissue from a patent with emphysema, $\alpha_d$ staining was observed on neutrophils and on macrophages containing hemosiderin, an iron-containing pigment, indicating red cell engulfment by these cells.

Sections of normal brain and plaque lesions from patients with multiple sclerosis (MS) were examined for integrin expression. In normal brain, $\alpha_d$ staining was less intense than that of CD11a, CD11b, and CD11c, and restricted to cells typed as microglial cells by morphology and CD68 staining. CD11b positive cells were located surrounding vessels and throughout the tissue. CD11c$^+$ cells appeared to be located within vessels, whereas $\alpha_d^+$ cells surrounded the vessels. In MS tissue sections, $\alpha_d$ expression was found on both microglial cells and on a non-macrophage leukocyte subset; $\alpha_d^+$ cells were located within plaque lesions, as well as throughout the cortex. The $\alpha_d$ signal was equivalent in intensity to CD11c, but lower than that of CD11b.

Both thoracic aorta and abdominal aorta sections from PDAY (Pathobiological Determinants of Atherosclerosis in Youth, LSU Medical Center) tissue samples were analyzed with anti-leukointegrin and anti-CAM antibodies. The lesions examined were consistent with aortic fatty streaks which consisted of subintimal aggregates of large foam cells (mostly macrophages with ingested lipid) and infiltrates of smaller leukocytes. Single label studies with monoclonal antibodies specific for $\alpha_d$ and the other $\beta_2$ integrin $\alpha$ chains (CD11a, CD11b, and CD11c), plus a macrophage marker (CD68) revealed that the majority of lipid-laden macrophages expressed a moderate level of $\alpha_d$ and CD18, while expressing CD11a and CD11c at weak or weak to moderate levels, respectively. CD11b was faintly expressed, and then by only a subset of macrophages.

Double label studies were conducted to determine the relative localization of $\alpha_d$ and ICAM-R antigens in the aortic sections. Since foam cells in these sections stained with the antibody Ham 56, specific for a macrophage marker, but not with antibodies to smooth muscle actin, it was determined that the foam cells were not derived from subintimal smooth muscle cells. CD68 positive macrophages expressing $\alpha_d$ were surrounded by and interspersed with small ICAM-R positive leukocytes. There appeared to be a limited number of small leukocytes which were CD68 negative but stained with both $\alpha_d$ and ICAM-R antibodies.

Distribution of $\alpha_d$ in normal tissues appeared to be on resident leukocytes in a pattern overlapping with but not identical to that of CD11b and CD11c, two other leukointegrin $\alpha$ chains which have previously been characterized as having restricted leukocyte distribution. Cellular morphology indicated that $\alpha_d$ staining is largely confined to macrophages and granulocytes, with limited lymphocyte staining. Generally, tissue inflammation appeared to increase the number and types of leukocytes observed in a particular tissue, along with increased staining of leukointegrins, including $\alpha_d$. Since the cellular and spatial distribution of the leukointegrins was not identical in pathologic tissues, it was inferred that distinct functions and ligands exist for each family member, including $\alpha_d$, in specific contexts.

Interestingly, $\alpha_d$ expression in early atherosclerotic lesions appeared to be more pronounced than that of CD11a, CD11b, and CD11c, suggesting that $\alpha_d$ may play a central role in the establishment of these lesions. The apposed distribution of $\alpha_d$ and ICAM-R positive cells, supported by evidence suggesting an interaction between $\alpha_d$ and ICAM-R, suggests that $\alpha_d$ may be involved in leukocyte recruitment or activation at early stages in these lesions.

Cell Line and Peripheral Blood Leukocyte Staining

The antibodies 169A and 169B stained a promyeolmonocytic cell line, HL60, by FACS. Surface expression of $\alpha_d$ in these cells is negatively affected by PMA stimulation, which is reported to induce differentiation along a macrophage pathway, but is unaffected by DMSO, which induces granulocyte differentiation [Collins, et al., Blood 70:1233–1244 (1987)]. The FACS profiles of 169A and 169B were antithetical with PMA stimulation to those observed with anti-CD11b and anti-CD11c monoclonal antibodies. A monocyte cell line, THP-1, also exhibited weak staining with 169A and 169B. In addition, a subset of cells in the lymphocyte and monocyte gates of peripheral blood leukocytes appeared to be weakly positive by FACS. A subset of peripheral blood monocytes stained weakly with 169A and 169B, while B lymphocytes were found to have no surface expression of $\alpha_d$. The CD8$^+$ subset of T lymphocytes was $\alpha_d^+$. In addition, antibodies 169A and 169B failed to detect antigen on the B cell lines, JY, Ramos, a basophilic line, KU812, and T cell lines, Jurkat, SKW, and Molt 16.

In light of the results with HL60 cells, granulocytes were isolated from peripheral blood by ficoll/hypaque gradient centrifugation and subsequent red blood cells lysis. All preparations were found to be>90% PMNs by visualization of nuclear morphology in acetic acid. Separate populations were stimulated for 30 minutes with 50 ng/ml PMA or $10^{-8}$M formyl peptide (fMLP) to release potential intracellular integrin stores. Unstimulated populations exhibited low, but significant expression of 169A and 169B antigens over an IgG1 control, with a detectable increase observed upon stimulation. On PMNs, levels of $\alpha_d$ and CD11c surface expression were more similar than that observed on HL60 cells. The antibody 169B was used subsequently to precipitate a heterodimeric molecule from a detergent lysate of biotinylated PMNs with subunit sizes of approximately 150 and 95 kD appropriate to $\alpha_d$ and CD18, respectively.

The presence of $\alpha_d$ on PMNs could not be anticipated from the information known about canine $\alpha_d$ expression. Canine neutrophils, unlike their human counterparts, express the T helper cell marker CD4, and also integrin VLA-4, and therefore may have different ligands and functions in the dog than in the human.

Staining of PBL subgroups

The present study was undertaken to determine the distribution of this $\beta_2$ integrin in human peripheral blood leukocytes. In addition, the cell surface density of $\alpha_d$ relative to other $\beta_2$ integrins was compared. Finally, the acute regulation of $\alpha_d$ expression in purified human eosinophils was also evaluated.

Human peripheral blood leukocytes were separated by density gradient centrifugation into a mononuclear cell fraction (containing monocytes, lymphocytes, and basophils) and granulocytes (neutrophils and eosinophils) [Warner, et al., *J. Immunol.Meth.* 105:107–110 (1987)]. For some experiments, eosinophils were purified using CD16 immunomagnetic selection to purities greater than 95% [Hansel, et al., *J.Immunol.Meth.* 122:97–103 (1989)]. Skin mast cells were enzymatically dispersed from human skin and enriched as previously described [Lawrence, et al., *J.Immunol.* 139:3062–3069 (1987)].

Cells were labelled with appropriate dilutions of monoclonal antibody specific for either CD11a (MHM24), CD11b (H5A4), CD11c (BU-15), or $\alpha_d$ (169A). A murine control IgG$_1$ was also employed. Cells were washed and then incubated with phycoerythrin-conjugated goat-anti-mouse IgG. In some experiments, cells were incubated with excess murine IgG and FITC-labelled murine monoclonal antibody or goat polyclonal antibody specific for a particular cell (e.g., CD3, CD4, or CD8 for T-cells; CD16+ lymphocytes for NK cells; anti-IgE for basophils [Bochner, et al., *J.Immunol.Meth.* 125:265–271 (1989)]. The samples were then examined by flow cytometry (Coulter EPICS Profile) using appropriate gating to identify cell subsets.

For studies with human eosinophils in which acute upregulation of $\alpha_d$ expression was examined, cells were stimulated for 15 minutes at 37° C. with phorbol ester (10 ng/ml), RANTES (100 ng/ml) [Schall, *Cytokine* 3:165–183 (1991)], or IL-5 (10 ng/ml) prior to labeling with the various monoclonal antibodies as described above.

Results showed that $\alpha_d$ was present on all peripheral blood eosinophils, basophils, neutrophils, monocytes, and NK cells. A small subset (approximately 30%) of CD8+ lymphocytes was also found to express $\alpha_d$. Skin mast cells and CD4+ lymphocytes did not express $\alpha_d$. In general, CD11a and CD11b are present at a higher density on leukocytes then $\alpha_d$, the latter being expressed at relatively low levels similar to CD11c. Among leukocytes, monocytes and CD8+ cells have the highest density of $\alpha_d$, while eosinophils have the lowest level of $\alpha_d$ expression. Expression on neutrophils, basophils, and NK cells was intermediate.

Stimulation of peripheral eosinophils with the CC chemokine RANTES caused no change in the expression of any of the $\beta_2$ integrins. Treatment with phorbol ester, however, produced a two to three fold increase in expression of both CD11b and $\alpha_d$, but did not effect expression of CD11a or CD11c. IL-5 treatment resulted in the selective upregulation of CD11b expression without affecting levels of the other integrin subunits.

Combined, these results indicate that in peripheral blood leukocytes, $\alpha_d$ is generally expressed at a level comparable to CD11c. Highest levels are found on monocytes and a subset of CD8+ lymphocytes. Human skin mast cells do not express $\alpha_d$. Purified eosinophils appear to have pre-formed intracytoplasmic storage pools of CD11b and $\alpha_d$. However, the differential upregulation shown by IL-5 versus PMA suggests that these storage pools are separate from each other.

Staining patterns for peripheral blood leukocyte (PBL) subgroups were also determined by flow cytometry using a combination of gating and surface markers, as described above, in an attempt to more precisely define the 169 A/B negative lymphocyte group. PBL were isolated on Ficoll as previously described and stained separately with 169A, 169B and monoclonal antibodies to CD14 (monocyte/macrophage marker), CD20 (B cell), CD56 (NK cell), T cell receptor $\alpha/\beta$ (T cell), CD16 (neutrophils, NKs), and $\alpha$4 (a negative marker for neutrophils). Gates were defined by size and marker distribution.

Results indicated that cells in the CD14+ monocyte gate exhibited low levels of 169A and 169B staining. A bimodal expression pattern observed in earlier experiments in the lymphocyte gate was resolved by increasing forward scatter. The mixed TCR+/CD20+ population appeared to have low, but homogenous levels of 169A/B expression, whereas a population mapped at slightly higher side scatter (cellular complexity), which stained 50% positive for CD56, appeared to have a distinctly 169A/B negative population. The negative population was also not recognized by TCR, CD20, CD14, or CD16 antibodies.

Synovial Distribution of $\alpha_d$

In order to determine cellular distribution of $\alpha_d$, other $\beta_2$ integrins and their counterreceptors in inflammatory and non-inflammatory synovium, monoclonal antibodies to the various $\beta_2$ integrin and immunoglobulin supergene families were used in immunohistological studies. Protein expression was determined in normal, osteoarthritic and rheumatoid synovial tissue samples.

Results indicated that the synovial lining cell layer expressed high levels of VCAM-1, CD11b/CD18 and $\alpha_d$/CD18. In these cells, CD11c/CD18 expression is restricted and CD11a/CD18 is generally not detected. In rheumatoid arthritis synovitis, expression of $\beta_2$ integrins in the synovial cell layer increases in proportion to the degree of hyperplasia. The ratio of cells which express CD11c increases significantly, approaching that of CD11b and $\alpha_d$, but there is no increase in CD11a expression.

In the sublining areas of the tissue, aggregates and diffuse infiltrates of CD3/CD11a/ICAM-R+ lymphocytes are interspersed among CD68/CD11b/$\alpha_d$+ macrophages. A significant number of aggregates demonstrate intense $\alpha_d$ staining, particularly in T cell rich areas.

The synovial endothelium variably expressed ICAM-1 and ICAM-2 with minimal evidence of ICAM-R expression.

Combined, these results indicate that synovial macrophages and macrophage-like synovial cells constitutively express high levels of the $\beta_2$ integrins CD11b and $\alpha_d$. In synovitis, there is an expansion of this subset of cells in both the lining and sublining areas, along with an apparent increase in expression of CD11c. Specific populations of rheumatoid synovial T lymphocytes, in addition to expressing CD11a and ICAM-R, also express high levels of $\alpha_d$, the latter molecule having been shown above to be expressed at low levels by peripheral blood lymphocytes.

Example 17

Isolation of Rat cDNA Clones

In view of the existence of both canine and human $\alpha_d$ subunits, attempts were made to isolate homologous genes in other species, including rat (this example) and mouse (Example 17, infra).

A partial sequence of a rat cDNA showing homology to the human $\alpha_d$ gene was obtained from a rat splenic $\lambda$gt10 library (Clontech). The library was plated at $2\times10^4$ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2× SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 17, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

| | |
|---|---|
| 5'-TATAGACTGCTGGGTAGTCCCCAC-3' | (SEQ ID NO: 34) |
| 5'-TGAAGATTGGGGGTAAATAACAGA-3' | (SEQ ID NO: 35) |

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Cloning of the 5' end of Rat $\alpha_d$

A 5' cDNA fragment for the rat $\alpha_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).

| | |
|---|---|
| 5'-CCAAAGCTGGCTGCATCCTCTC-3' | (SEQ ID NO: 59) |
| 5'-GGCCTTGCAGCTGGACAATG-3' | (SEQ ID NO: 58) |

Oligo 741.11#2R encompasses base pairs 131–152 in SEQ ID NO: 36, in the reverse orientation and 741.2#1R encompasses bases pairs 696–715 in SEQ ID NO: 36, also in the reverse orientation. A primary PCR was carried out using the 3'-most oligo, 741.2#1R. A second PCR followed using oligo 741.11#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 μl LBM containing 1 μl of a 50 mg/ml carbenicillin stock solution and 1 μl M13 K07 phage culture in individual wells in a round bottom 96 well tissue culture plate. The mixture was incubated at 37° C. for 30 minutes to one hour. Following the initial incubation period, 100 μl of LBM (containing 1 μl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond nylon filters. The filters were denatured, neutralized and cross linked by standard protocols. The filters were prehybridized in 20 mls of prehybridization buffer (5× SSPE; 5× Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86–105 (SEQ ID NO: 36) in the forward and reverse orientation respectively, were labeled as follows.

| | |
|---|---|
| 5'-CCTGTCATGGGTCTAACCTG-3' | (SEQ ID NO: 56) |
| 5'-AGGTTAGACCCATGACAGG-3' | (SEQ ID NO: 57) |

Approximately 65 ng oligo DNA in 12 μl dH$_2$O was heated to 65° C. for two minutes. Three μl of 10 mCi/ml γ-$^{32}$P-ATP were added to the tube along with 4 μl 5× Kinase Buffer (Gibco) and 1 μl T4 DNA Kinase (Gibco). The mixture was incubated at 37° C. for 30 minutes. Following incubation, 16 μl of each labeled oligo probe were added to the prehybridization buffer and filters and hybridization was continued overnight at 42° C. The filters were washed three times in 5× SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat α subunits in β$_2$ integrins. However sequence comparisons to reported human β$_2$ integrin α subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

Example 18

Production and Characterization of Rodent $\alpha_d$-Specific Antibodies

A. Antibodies against Rat $\alpha_d$ I domain/Hu IgG4 Fusion Proteins

In view of the fact that the I domain of human β$_2$ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469–493 and base pairs 1101–1125 (in the reverse orientation), respectively, in SEQ ID NO: 54. The oligos were used in a standard PCR reaction to generate a rat $\alpha_d$ DNA fragment containing the I domain spanning base pairs 459–1125 in SEQ ID NO: 54. The PCR product was ligated into vector pCRTAII (Invitrogen) according to manufacturer's suggested protocol. A positive colony was selected and expanded for DNA purification using a Qiagen (Chatswoth, Ga.) Midi Prep kit according to manufacturer's protocol. The DNA was digested with XhoI and BglII in a standard restriction enzyme digest and a 600 base pair band was gel purified which was subsequently ligated into pDCS1/HuIgG4 expression vector. A positive colony was selected, expanded and DNA purified with a Quiagen Maxi Prep Kit.

COS cells were plated at half confluence on 100 mm culture dishes and grown overnight at 37° C. in 7% $CO_2$. Cells were rinsed once with 5 ml DMEM. To 5 ml DMEM, 50 µl DEAE-Dextran, 2 µl chloroquine and 15 µg rat $\alpha_d$ I domain/HuIgG4 DNA described above was added. The mixture was added to the COS cells and incubated at 37° C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37° C. in 7% $CO_2$. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a Prosep-A column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55M diethanolamine, pH 8.5, and 15 column volumes 50 mM citric acid, pH 5.0. Protein was eluted with 50 mM citric acid, pH 3.0. Protein was neutralized with 1.0M Tris, pH 8.0, and dialyzed in sterile PBS.

The rat $\alpha_d$ I domain protein was analyzed as described in Example 14. The detected protein migrated in the same manner as observed with human I domain protein.

B. Production of Monoclonal Antibodies to Rat $\alpha_d$ I Domain/HuIgG4 Fusion Proteins Mice were individually immunized with 50 µg purified rat $\alpha_d$ I domain/HuIgG4 fusion protein previously emulsified in an equal volume of Freunds Complete Adjuvant (FCA) (Sigma). Approximately 200 µl of the antigen/adjuvant preparation was injected at 4 sites in the back and flanks of each of the mice. Two weeks later the mice were boosted with an injection of 100 µl rat $\alpha_d$ I domain/HuIgG4 antigen (50 µg/mouse) previously emulsified in an equal volume of Freunds Incomplete Adjuvant (FIA). After two additional weeks, the mice were boosted with 50 µg antigen in 200 µl PBS injected intravenously.

To evaluate serum titers in the immunized mice, retro-orbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon 4 plates (Dynatech, Cambridge, Mass.) were coated at 4° C. with 50 µl/well goat anti-mouse IgA, IgG or IgM (Organon Teknika) diluted 1:5000 in 50 mM carbonate buffer, pH 9.6. Plates were washed 3× with PBS containing 0.05% Tween 20 (PBST) and 50 µl culture supernatant was added. After incubation at 37° C. for 30 minutes, and washing as described above, 50 µl horseradish peroxidase-conjugated goat anti-mouse IgG9 (Fc) (Jackson ImmunoResearch, West Grove, Pa.) diluted 1:3500 in PBST was added. Plates were incubated as described above and washed 4× with PBST. Immediately thereafter, 100 µl substrate, containing 1 mg/ml o-phenylene diamine (Sigma) and 0.1 µl/ml 30% $H_2O_2$ in 100 mM citrate, pH4.5, was added. The color reaction was stopped after 5 minutes with the addition of 50 µl 15% $H_2SO_4$. Absorbance at 490 nm was read on a Dynatech plate reader.

Supernatant from antibody-containing wells was also analyzed by ELISA with immobilized rat $\alpha_d$ I domain/HuIgG4 fusion protein. An ELISA with HuIgG4 antibody coated plates served as a control for reactivity against the IgG fusion partner. Positive wells were selected for further screening by BIP on rat splenocyte lysates using techniques described below.

C. Production of Polyclonal Sera To Rat $\alpha_d$ I domain/HuIgG4 Fusion Protein Two rabbits were prebled prior to immunization with 100 µg purified rat $\alpha_d$ I domain/HuIgG4 fusion protein in complete Freund's adjuvant. Injections were repeated at the same dose every three weeks in incomplete Freunds adjuvant (IFA). After three injections the rabbits were test bled and the collected sera used in a standard immunoprecipitation on rat splenocyte lysates. It was determined that sera from both rabbits were immunoreactive with rat $\alpha_d$. The rabbits were boosted again with 100 ug antigen in IFA, and the collected sera assayed for increased immunoreactivity with rat $\alpha_d$ by immunoprecipitation. The animals were given a final boost and 10 days later, bled out and sera collected.

Rat $\alpha_d$ Histology

Rabbit polyclonal sera generated against rat $\alpha_d$ "I" domain was used in immunohistochemical staining of rat tissue sections by the technique described in Example. 16. The staining pattern detected on frozen and on parafin embedded rat spleen sections was essentially identical to that observed with the antibodies against human $\alpha_d$, with staining individual cells throughout the red pulp. The staining pattern differed from that observed with monoclonal antibodies against rat CD11a, CD11b and CD18. In addition, a positive staining pattern was seen in the thymus on individual cells throughout the cortex. Neither of these tissue gave any signal when stained with the rabbit preimmune sera.

D. Analysis of Antibody Specificity

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000×g to pellet the insoluble material. Supernatant was collected into a new tube and stored at between 4° C. and −20° C.

One ml cell lysate was precleared by incubation with 200 μl of a protein A sepharose slurry (Zymed) overnight at 4° C. Precleared lysate was aliquoted into Eppendorf tubes at 50 μl/tube for each antibody to be tested. Twenty-five μl of polyclonal serum or 100 to 500 μl of monoclonal antibody supernatant were added to the precleared lysates and the resulting mixture incubated for 2 hours at 4° C. with rotation. One hundred μl rabbit anti-mouse IgG (Jackson) bound to protein A sepharose beads in a PBS slurry was then added and incubation continued for 30 minutes at room temperature with rotation. Beads were pelleted with gentle centrifugation, and washed three times with cold Wash Buffer (10 mM HEPES; 0.2M NaCl; 1% Trition X-100). Supernatant was removed by aspiration, and 20 μl 2× SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

E. Production of Monoclonal Antibodies To Full Length Rat $\alpha_d$ Protein

Purification of Rat $\alpha_d$ Protein

Rat $\alpha_d$ was purified from rat splenocytes to prepare an immunogen for generating anti-rat $\alpha_d$ monoclonal antibodies. Spleens from approximately 50 normal female Lewis rats, 12–20 weeks of age, were collected and a single cell suspension was made from the tissue by forcing it through a fine wire screen. Red blood cells were removed by lysis in buffer containing 150 mM $NH_4Cl$, 10 mM $KHCO_3$, 0.1 mM EDTA, pH 7.4, and remaining leukocytes were washed two times with phosphate buffered saline (PBS). The splenocytes were pelleted by centrifugation and lysed in buffer containing 50 mM Tris, 150 mM NaCl, 2 mM CaCl2, 2 mM MgCl2, 10 mM PMSF, leupeptin, pepstatin and 1% Triton X-100. Splenocyte lysis was carried out on ice for 30 minutes with one ml of lysis buffer per $5\times10^8$ splenocytes. Insoluble material was removed by centrifugation.

CD11a, CD11b and CD11c were removed from the spleen lysate by immunoprecipitation as follows. A 750 μl volume of a Protein A-Sepharose slurry was incubated with 2 mg rabbit anti-mouse immunoglobulin at 4° C. for 30 minutes. The rabbit anti-mouse-Protein A-Sepharose was washed three times with lysis buffer and suspended in a final volume of 1.5 ml of lysis buffer. Approximately 200 μg each of rat $\beta_2$ integrin specific monoclonal antibodies, 515F (specific for rat CD11a), OX-42 (specific for rat CD11b) and 100 g (specific for rat CD11c) were each added to 50 ml of the rat spleen lysate. Following a 30 minute incubation at 4° C., 500 μl of the rabbit anti-mouse-Protein A-Sepharose was added to the spleen lysates and mixed with end-over-end rotation for 30 minutes at 4° C. The lysate was centrifuged at 2500×g for 10 minutes to pellet the CD11a, CD11b, and CD11c bound to the rabbit anti-mouse-Protein A-Sepharose, and the supernatant transferred to a clean 50 ml centrifuge tube. Immunoprecipitation with the antibodies 515F, OX-42, and 100 g was repeated two additional times to insure complete removal of CD11a, CD11b, and CD11c.

$\beta_2$ integrins remaining in the lysate were isolated using affinity purification. Approximately 250 μl of a slurry of anti-rat CD18 monoclonal antibody 20C5B conjugated to CNBr-Sepharose was added to the lysates and mixed with end-over-end rotation for 30 minutes at 4° C. Antibody/antigen complexes were pelleted by centrifugation at 2500×g for ten minutes and the pellet washed three times with lysis buffer before being stored at 4° C.

Immunization of Armenian Hamsters

Armenian hamsters, six to eight weeks old, were initially immunized with approximately 50 μg of a recombinant protein consisting of the I domain of rat $\alpha_d$ fused to the human $IgG_4$ heavy chain emulsified in complete Freund's adjuvant. Primary immunization was followed by subsequent immunizations with rat $\alpha_d$ I domain/$HuIgG_4$ emulsified in incomplete Freund's adjuvant on Days 14, 33, and 95. Two separate fusions, designated 197 and 199, were subsequently performed.

Four days prior to fusion 197 (day 306), one hamster was administered a combination of rat $\alpha_d$ protein purified from splenocytes and CHO cells transfected with rat $\alpha_d$. The fusion boost was given three days prior to the fusion (day 307) with purified rat $\alpha_d$ protein and $\alpha_d$ transfected CHO cells. Rat $\alpha_d$ transfected CHO cells were prepared as described below.

A gene segment encoding full length rat $\alpha_d$ protein was inserted into the pDC1 vector and transfected by electroporation into CHO cells together with a human CD18-pRC construct. Transfected cells were grown in the presence of hypoxanthine to select for cells successfully transfected with the pRC construct and in the presence of g418 to select for cells transfected with the pDC1 construct. After 3 weeks, the cells were stained with the rat $\alpha_d$ specific rabbit polyclonal sera and sorted by FACS. A small percentage of the cells which expressed the highest levels of surface $\alpha_d$ (approximately 3% of the total population) were collected and further expanded. FACS selection was repeated several times to provide a population cells with high levels of $\alpha_d$ surface expression.

The $\alpha_d$ transfected cells were also characterized by flow cytometry using a rat $\alpha_d$ specific polyclonal sera and a human CD18 specific monoclonal antibody, TS1.18.1. Results confirmed that the transfected CHO cells expressed high levels of both rat $\alpha_d$ and human CD18.

Finally, $\alpha_d$ and CD18 expression in the cells was evaluated by immunoprecipitation. A rat $\alpha_d$ specific rabbit polyclonal sera was found to immunoprecipitate proteins with two distinct molecular weights: the higher molecular weight protein(s) being approximately 170 kD, and the lower molecular weight protein(s) 95 kD. These findings were consistent with expression of a rat $\alpha_d$/human CD18 heterodimeric complex on the surface of the transfected CHO cells.

On the day of the fusion, the spleen was removed and a single-cell suspension was formed by grinding the tissue between frosted ends of two glass microscope slides submerged in serum free RPM1 1640 supplemented with 2 mM L-glutamine, 1 mM sodium pyruvate, 100 units/ml penicillin, and 100 µg/ml streptomycin (RPM1) (Gibco, Canada). The cell suspension was filtered through sterile 70-mesh Nitex cell strainer (Becton Dickinson, Parsippany, N.J.), and washed twice by centrifuging at 200×g for five minutes and resuspending the pellet in 20 ml serum free RPMI. Thymocytes taken from three naive Balb/c mice were prepared in a similar manner. NS-1 myeloma cells, kept in log phase in RPM1 with 10% Fetaclone serum (FBS) (Hyclone Laboratories, Inc. Logan, Utah) for three days prior to fusion, were centrifuged at 200×g for five minutes, and the pellet was washed twice as previously described.

Approximately $1.15 \times 10^8$ spleen cells were combined with $5.8 \times 10^7$ NS-1 cells, centrifuged and the supernatant removed by aspiration. The cell pellet was dislodged by tapping the tube and seven ml of 37° C. PEG 1500 (50% in 75 mM Hepes, pH 8.0) (Boehringer Mannheim) was added with stirring over the course of one minute, followed by adding 14 ml of serum free RPM1 over seven minutes. An additional eight ml RPMI was added and the cells were centrifuged at 200×g for 10 minutes. The supernatant was removed and the pellet resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5 \times 10^6$ thymocytes/ml. The suspension was dispensed into ten 96-well flat bottom tissue culture plates (Corning, United Kingdom) at 200 µl/well and the cells were fed on days 4, 5, 6, and 7 days post fusion by aspirating approximately 100 µl from each well with an 18 G needle (Becton Dickinson) and adding 100 µl plating medium described above except lacking thymocytes.

On day 10, supernatants from the fusion wells were screened by flow cytometry for reactivity to rat $\alpha_d$/human CD18 transfected CHO cells. Approximately $5 \times 10^5$ rat $\alpha_d$ transfected CHO cells were suspended in 50 µl RPMI containing 2.0% FBS and 0.05% sodium azide and added to approximately 100 µl of hybridoma culture supernatant in 96-well, round-bottomed plates. Positive controls for staining included rabbit anti-$\alpha_d$ polyclonal sera and TS1/18 (anti-human CD18). Cells were incubated for 30 minutes on ice, washed three times in FACS buffer (RPM1, 2.0% FBS, 0.05% NaAzide), and incubated for 30 minutes on ice with a FITC-conjugated goat anti-hamster antibody (Jackson ImmunolResearch Labs) at a final dilution of 1:200 in FACS buffer. Cells were washed three times in FACS buffer and resuspended in 200 ml of FACS buffer. Samples were analyzed with a Becton Dickinson FACscan analyzer. To insure that positive clone wells were specific for rat $\alpha_d$, the screen was repeated with non-transfected CHO cells. Wells which met the criteria of reacting with rat $\alpha_d$ CHO transfectants and not the untransfected CHO cells were cloned.

Following primary screening, cells from positive wells were cloned initially by doubling dilution and subsequently by limiting dilution in RPM1, 15% FBS 100 mM sodium hypoxanthine, 16 mM thymidine, and 10 units/ml IL-6. In the limiting dilution step, the percentage of wells showing growth was determined and clonality was predicted using a Poisson distribution analysis. Wells showing growth were analyzed by FACS after 10–12 days. After final cloning, positive wells were expanded in RPMI and 11% FBS. Cloning yielded one culture deemed positive by these criteria, from which four separate subclones designated 197A-1, 197A-2, 197A-3, and 197A-4 were expanded.

Prior to fusion 199, a second hamster was boosted on day 307 with $2.3 \times 10^6$ rat $\alpha_d$ transfected CHO cells. Two final immunizations were administered four days prior to the fusion (day 334) and again three days prior to the fusion (day 335). The boost on day 334 consisted of $2 \times 10^6$ rat $\alpha_d$ transfected CHO cells and 200 µl of purified rat $\alpha_d$ bound to Sepharose (described previously) administered by intraperitoneal injection. The day 335 boost consisted of $5 \times 10^6$ rat $\alpha_d$ transfected CHO cells, also administered by intraperitoneal injection. The fusion and screening protocols for fusion 199 were identical to fusion 197, and three hybridomas, designated 199A, 199H, and 199M, with supernatant reactive with rat $\alpha_d$ were identified and cloned. Hybridoma 199M was deposited on Mar. 1, 1996, with the American Type Culture Collection, 12301 Parklawn Drive, Rockville. Md. 20852, and assigned Accession Number HB 12058.

Characterization of Monoclonal Antibodies to Rat $\alpha_d$

In order to characterize the anti-rat $\alpha_d$ antibodies, biotin labeled spleens lysates were prepared as described in Example 18, section D, above. Lysates were precleared prior to use in immunoprecipitations. Initially, 50 µg/ml of normal murine immunoglobulin was added to the lysate and the resulting solution mixed with end-over-end rotation for 30 minutes at 4° C. A 75 µl slurry of a protein A-Sepharose coated with rabbit anti-mouse immunoglobulin was added and mixing was continued with end-over-end rotation for 30 minutes. The rabbit anti-mouse coated protein A beads were pelleted by centrifugation at 15,000 rpm in a table-top microfuge for five minutes at 4° C. and the supernatant collected. The pelleted material was discarded.

For each cloned hybridoma, approximately 300 µl of supernatant was placed into a Eppendorf microfuge tube, to which was added 30 µl 10% Triton X-100, 30 µl of a 100× stock solution of pepstatin, leupeptin and aprotinin, 100 µg PMSF crystals, and 50 µl of precleared biotinylated rat spleen lysate. Samples were vortexed gently and placed onto an end-over-end rotator at 4° C. for 30 minutes. A control sample was prepared by adding 10 mg/ml of a rabbit anti-rat $\alpha_d$ specific polyclonal antibody to 50 µl of rat spleen lysate.

Following a 30 minute incubation, 75 µl of protein A-Sepharose beads in a PBS slurry was added to each sample and incubated with end-over-end rotation at 4° C. for 30 minutes. The protein A-coupled beads were pelleted by centrifugation at 15,000 rpm in a table-top microfuge for 5 minutes at 4° C. and the supernatant was collected. The pelleted beads were washed sequentially with a series of 1 ml detergent washes as follows: buffer #1 containing 10 mM Tris, 400 mM NaCl, 1.0% Triton X-100, pH 8.0; buffer #2 containing 10 mM Tris, 400 mM NaCl, 0.5% Triton X-100, pH 8.0; buffer #3 containing 10 mM Tris, 400 mM NaCl, 1.0% Triton X-100, 0.1% deoxycholate, pH 8.0; and buffer #4 containing 10 mM Tris, 400 mM NaCl, 0.5M $LiCl_2$, pH 8.0. A final washed was carried out with wash buffer #1. Beads were vortexed gently between each wash and pelleted using a tabletop microfuge. Supernatants were removed by transfer pipette, and after the final wash, all remaining buffer was removed from the beads by Hamilton syringe. A 50 µl aliquot of SDS sample buffer containing Bromphenol Blue and Pyronin Y dyes and β-mercaptoethanol at a final concentration of 10% was added to each pellet. The mixture was vortexed vigorously for 1–2 minutes and incubated at room temperature for 5–10 minutes. Samples were centrifuged for 5 minutes at 15,000 rpm in a table-top microfuge at 4° C. and released protein was collected and transferred to a new microfuge tube. Aliquots from each sample were boiled for four minutes in a water bath before loading onto 7.5% SDS-PAGE gels. Following separation by PAGE, proteins were transferred to nitrocellulose filters for one hour at 200 mAmps, and the filters were blocked in a solution of 3.0%

BSA/TBS-T overnight at 4° C. A solution of 0.1% BSA-TBS-T containing a 1:6000 dilution of streptavidin-OPD was added to each filter and incubation allowed to continue for one hour at room temperature. The filters were washed five times for ten minutes each in TBS-T, and developed using Amersham's ECL kit according to the manufacturer's suggested protocol.

Clone 199M was found to immunoprecipitate a heterodimeric protein. The larger protein subunit had an approximate molecular weight of 170–175 kD which was consistent with the size of the protein immunoprecipitated by the rabbit anti-rat $\alpha_d$ polyclonal control. A second protein was also precipitated with an approximate molecular weight of 95 kD, consistent with the weight of CD18.

Example 19
Isolation of Mouse cDNA Clones

Isolation of a mouse $\alpha_d$ homolog was attempted.

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9-10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

| 5'-GTCCAAGCTGTCATGGGCCAG-3' | (SEQ ID NO: 38) |
| 5'-GTCCAGCAGACTGAAGAGCACGG-3' | (SEQ ID NO: 39) |

The PCR products were purified using the Qiagen Quick Spin kit according to manufacturer's suggested protocol, and approximately 180 ng DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2× SSC/0.1% at room temperature, once in 2× SSC/0.1% SDS at 37° C., and once in 2× SSC/0.1% SDS at 42° C. Filters were exposed on Kodak X-Omat AR film at –80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at –80° C. with an intensifying screen.

Twelve plaques giving positive signals were transferred into low Mg$^{++}$ phage diluent containing 10 mM Tris-HCl and 1 mM MgCl$_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript SK$^-$ (Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse.1 primers set out in SEQ ID NOS: 40 and 41, respectively.

| 5'-TGTAAAACGACGGCCAGT-3' | (SEQ ID NO: 40) |
| 5'-GGAAACAGCTATGACCATG-3' | (SEQ ID NO: 41) |

Sequencing was performed as described in Example 4.

Of the six clones, only two, designated 10.3-1 and 10.5-2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT$^-$ and random-primed) in lambda Zap II (Stratagene) was plated at 2.5×10$^4$ phage/15 cm LBM plate. Plaques were lifted on Hybond nylon transfer membranes (Amersham), denatured with 0.5M NaOH/1.5M NaCl, neutralized with 0.5M Tris Base/1.5M NaCl/11.6 HCl, and washed in 2× SSC. The DNA was cross-linked to filters by ultraviolet irradiation.

Approximately 500,000 plaques were screened using probes 10.3-1 and 10.5-2 previously labeled as described supra. Probes were added to a prehybridization solution and incubated overnight at 50° C. The filters were washed twice in 2× SSC/0.1% SDS at room temperature, once in 2× SSC/0.1% SDS at 37° C., and once in 2× SSC/0.1% SDS at 42° C. Filters were exposed on Kodak X-Omat AR film for 24 hours at –80° C. with an intensifying screen. Fourteen plaques giving positive signals on duplicate lifts were subjected to a secondary screen identical to that for the initial screen except for additional final high stringency washes in 2× SSC/0.1% SDS at 50° C., in 0.5× SSC/0.1% SDS at 50° C., and at 55° C. in 0.2× SSC/0.1% SDS. The filters were exposed on Kodak X-Omat AR film at –80° C. for 13 hours with an intensifying screen.

Eighteen positive plaques were transferred into low Mg$^{++}$ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse.1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b.

The second clone A1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A1160) not present in the overlapping region of clone B3800. This insertion occurs at a probable exon-intron boundary [Fleming, et al., *J.Immunol.* 150:480–490 (1993)] and was removed before subsequent ligation of clones A1160 and B3800.

Rapid Amplification of 5' cDNA End of the Putative Mouse $\alpha_d$ Clone

RACE PCR [Frohman, "RACE: Rapid Amplification of cDNA Ends," in *PCR Protocols: A Guide to Methods and Applications*, Innis, et al. (eds.) pp. 28–38, Academic Press:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.

5'-GGACATGTTCACTGCCTCTAGG-3'   (SEQ ID NO: 42)

5'-GGCGGACAGTCAGACGACTGTCCTG-3'   (SEQ ID NO: 43)

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

5'-CTGGTTCGGCCCACCTCTGAAGGTTCCA-GAATCGATAG-3'   (SEQ ID NO: 44)

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases I to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 16, supra, mouse and rat cytoplasmic domains show greater than 60% identity.

Example 20

Isolation of additional mouse αd cDNA clones for sequence verification

In order to verify the nucleic and amino acids sequences describe in Example 19 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed CDNA library in lambda ZAP II (Strategene). The library was plated at $5\times10^5$ phage per 15 cm LBM plate. Plaques were lifted on Hybond nylon membranes (Amersham), and the membranes were denatured (0.5M NaOH/1.5M NaCl), neutralized (0.5M Tris Base/1.5M NaCl/11.6M HCl) and washed (2× SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thermocycler).

The 3' probe was approximately 900 bases long and spanned a region from nucleotides 2752 to 3651 (in SEQ ID NO: 1) (5'→3') and was produced with primers 11.b-1/2FOR11 and 11.b-1/2REV2 as shown in SEQ ID NOS: 69 and 74, respectively. This probe was used in a first set of lifts.

The 5' probe was approximately 800 bases long and spanned a region from nucleotides 149 to 946 (in SEQ ID NO: 1) (5'→3') and was produced with primers 11.b-1/2FOR1 and 11.a-1/1REV1 as shown in SEQ ID NOS: 50 and 85, respectively). This probe was used in a second set of lifts.

In a third set of lifts, both probes described above were used together on the same plates.

Approximately 500,000 plaques were screened using the two probes from above which were labeled in the same way as described in Example 17. Labeled probes were added to a prehybridization solution, containing 45% formamide, and incubated overnight at 50° C. Filters were washed twice in 2×SSC/0.1% SDS at room temperature (22° C.). A final wash was carried out in 2× SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2× SSC/0.1% SDS at 65° C. Autoradiography was performed as described above for 2.5 hours.

Thirteen plaques (designated MS2P1 through MS2P13) giving positive signals were transferred into low $Mg^{++}$ phage diluent. Insert size was determined by PCR amplification (Perkin-Elmer 9600 thermocycler) using T3 and T7 primers which anneal to Bluescript phagemid in ZAP II (sequence previously described) under the same conditions shown above. Band sizes ranged from 500 bases to 4Kb. Phagemids were isolated, prepared, and sequenced with M13 and M13 reverse.1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

| Primer | Sequence | SEQ ID |
|---|---|---|
| 11.b-1/2FOR1 | 5'-GCAGCCAGCTTCGGACAGAC-3' | (SEQ ID NO: 50) |
| 11.a-1/1FOR2 | 5'-CCGCCTGCCACTGGCGTGTGC-3' | (SEQ ID NO: 60) |
| 11.a-1/1FOR3 | 5'-CCCAGATGAAGGACTTCGTCAA-3' | (SEQ ID NO: 61) |
| 11.b-1/2FOR4 | 5'-GCTGGGATCATTCGCTATGC-3' | (SEQ ID NO: 62) |
| 11.b-1/2FOR5 | 5'-CAATGGATGGACCAGTTCTGG-3' | (SEQ ID NO: 63) |
| 11.b-1/2FOR6 | 5'-CAGATCGGCTCCTACTTTGG-3' | (SEQ ID NO: 64) |
| 11.b-1/2FOR7 | 5'-CATGGAGCCTCGAGACAGG-3' | (SEQ ID NO: 65) |
| 11.b-1/2FOR8 | 5'-CCACTGTCCTCGAAGCTGGAG-3' | (SEQ ID NO: 66) |
| 11.b-1/2FOR9 | 5'-CTTCGTCCTGTGCTGGCTGTGGGCTC-3 | (SEQ ID NO: 67) |
| 11.b-1/2FOR10 | 5'-CGCCTGGCATGTGAGGCTGAG-3' | (SEQ ID NO: 68) |
| 11.b-1/2FOR11 | 5'-CCGTGATCAGTAGGCAGGAAG-3' | (SEQ ID NO: 69) |
| 11.b-1/2FOR12 | 5-GTCACAGAGGGAACCTCC-3' | (SEQ ID NO: 70) |
| 11.b-1/2FOR13 | 5'-GCTCCTGAGTGAGGCTGAAATCA-3' | (SEQ ID NO: 71) |
| 11.b-1/2FOR14 | 5'-GAGATGCTGGATCTACCATCTGC-3' | (SEQ ID NO: 72) |
| 11.b-1/2FOR15 | 5'-CTGAGCTGGGAGATTTTTATGG-3' | (SEQ ID NO: 73) |
| 11.b-1/2REV2 | 5'-GTGGATCAGCACTGAAATCTG-3' | (SEQ ID NO: 74) |
| 11.b-1/2REV3 | 5'-CGTTTGAAGAAGCCAAGCTTG-3' | (SEQ ID NO: 75) |
| 11.b-1/2REV4 | 5'-CACAGCGGAGGTGCAGGCAG-3' | (SEQ ID NO: 76) |
| 11.b-1/2REV5 | 5'-CTCACTGCTTGCGCTGGC-3' | (SEQ ID NO: 77) |
| 11.b-1/2REV6 | 5'-CGGTAAGATAGCTCTGCTGG-3' | (SEQ ID NO: 78) |
| 11.b-1/2REV7 | 5'-GAGCCCACAGCCAGCACAGG-3' | (SEQ ID NO: 79) |
| 11.b-1/2REV8 | 5'-GATCCAACGCCAGATCATACC-3' | (SEQ ID NO: 80) |
| 11.b-1/2REV9 | 5'-CACGGCCAGGTCCACCAGGC-3' | (SEQ ID NO: 81) |
| 11.b-1/2REV10 | 5'-CACGTCCCCTAGCACTGTCAG-3' | (SEQ ID NO: 82) |
| 11.b-1/2REV11 | 5'-CCATGTCCACAGAACAGAGAG-3' | (SEQ ID NO: 51) |
| 11.b-1/2REV12 | 5'-TTGACGAAGTCCTFCATCTGGG-3' | (SEQ ID NO: 83) |
| 11.b-1/2REV13 | 5'-GAACTGCAAGCTGGAGCCCAG-3' | (SEQ ID NO: 84) |
| 11.a-1/1REV1 | 5'-CTGGATGCTGCGAAGTGCTAC-3' | (SEQ ID NO: 85) |
| 11.a-1/1REV2 | 5'-GCCTTGGAGCTGGACGATGGC-3' | (SEQ ID NO: 86) |

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

Example 21

In situ hybridizations in Mouse

Tissue distribution was then determined for mouse $\alpha_d$ in order to provide a comparison to that in humans, described in Example 6.

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 μm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2× SSC, rinsed twice in 2× SSC, dehydrated with the ethanol gradient described supra and air dried for 30 minutes. Hybridization was carried out overnight (12–16 hours) at 55° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1× Denhardt's solution, 100 mM dithiothreitol (DTD) and 5 mM EDTA. After hybridization, sections were washed for 1 hour at room temperature in 4× SSC/10 mM DTT, 40 minutes at 60° C. in 50% formamide/2× SSC/10 mM DTT, 30 minutes at room temperature in 2× SSC, and 30 minutes at room temperature in 0.1× SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

Example 22
Generation of Mouse Expression Constructs

In order to construct an expression plasmid including mouse cDNA sequences exhibiting homology to human $\alpha_d$, inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

5'-AGTTACGGATCCGGCACCATGACCTTCG-
   GCACTGTGATCCTCCTGTGTG-3'     (SEQ ID NO: 47)

5'-GCTGGACGATGGCATCCAC-3'       (SEQ ID NO: 48)

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

5'-GTAGAGTTACGGATCCGGCACCAT-3'   (SEQ ID NO: 49)

Primers "mAD.5'.2" and "3' end frag" were used together in PCR with the product from the first amplification as template. A resulting secondary PCR product was subcloned into plasmid pCRtmII (Invitrogen) according to manufacturer's suggested protocol and transformed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/EcoRI fragment. Ligation was allowed to proceed for 14 hours at 14° C. Vector pcDNA.3 (Invitrogen), digested with BamHI and NotI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11. b-1/2REV11 (SEQ ID NOS: 50 and 51, respectively). These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

Example 23
Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., *Mol.Cell.Biol.* 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a λFIXII genomic library. Primary screening resulted in 14 positive plaques, seven of which were confirmed by secondary screening. Liquid lysates were obtained from two of the plaques giving the strongest signal and the λ DNA was isolated by conventional methods. Restriction mapping and Southern analysis confirmed the authenticity of one clone, designated 14-1, and the insert DNA was isolated by digestion with NotI. This fragment was cloned into Bluescript SKII$^+$.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14-1. A 12 kb fragment was identified as a possible candidate and this fragment was subcloned into pBluescript SKII$^+$ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the λFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5' to nucleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript SKII+. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5'-most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo') gene is inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., *Nature* 355:516–520 (1992)].

Example 24
Cloning of Rabbit $\alpha_d$—Construction and Screening of the Rabbit cDNA Library Identification of human $\alpha_d$ homologs in rats and mice led to the investigation of the existence of a rabbit homolog which would be useful in rabbit models of human disease states described infra.

Poly A+ RNA was prepared from a whole rabbit spleen using an Invitrogen FastTrack kit (San Diego, Calif.) according to manufacturer's suggested protocol and reagents supplied with the kit. From 1.65 g tissue, 73 μg poly A+ RNA were isolated. The rabbit spleen RNA was used to construct a ZAP Express cDNA library using a kit from Stratagene (La Jolla, Calif.). Resulting cDNA was directionally cloned into EcoRI and XhoI sites in the lambda arms of a pBK-CMV phagemid vector. Gigapack II Gold (Stratagene) was used to package the lambda arms into phage particles. The resulting library titer was estimated to be approximately $8 \times 10^5$ particles, with an average insert size of 1.2 kb.

The library was amplified once by plating for confluent plaque growth and cell lysate was collected. The amplified library was plated at approximately 30,000 plaque forming units (pfu) per 150 mm plate with *E. coli* and the resulting mixture incubated for 12–16 hrs at 37° C. to allow plaque formation. Phage DNA was transferred onto Hybond N+ nylon membranes (Amersham, Arlington Heights, Ill.). The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex G-50 column to remove unincorporated nucleotides. The hybridization solution was composed of 5× SSPE, 5× Denhardts, 1% SDS, 40% Formamide and the labeled probes at $1 \times 10^6$ dpm/ml. Hybridization was carried out at 42° C. for 16–18 hours. Filters were washed extensively in 2× SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5' end of human $\alpha_d$. Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Clone #7 was completely sequenced by the primer walking method. The nucleotide and deduced amino acid sequences for clone #7 are set out in SEQ ID NOs: 100 and 101, respectively.

The predicted N terminal amino acid sequence for rabbit $\alpha_d$ as determined from clones #2 and #7 indicated a protein with 73% identity with human $\alpha_d$, 65% identity with mouse $\alpha_d$, and 58% identity with mouse CD11b, human CD11b, and human CD11c. The nucleic acid sequence for clone #2 is set out in SEQ ID NO: 92; the predicted amino acid sequence is set out in SEQ ID NO: 93

Isolation of a full length rabbit $\alpha_d$ cDNA was attempted using labeled rabbit clone #7 and rescreening the cDNA library from which the fragment was derived. Twenty-five additional clones were identified with one, designated clone 49, determined to be the largest. Clone 49 was completely sequenced using the nested deletions technique. The nucleotide and amino acid sequences for clone 49 are set out in SEQ ID NOs: 102 and 103, respectively. Since clones #7 and #49 did not overlap, oligonucleotides were designed to be used as primers in a PCR with first strand rabbit spleen cDNA to isolate the missing sequence.

The relationship of the putative amino acid sequence of these two partial clones with that of other leukointegrins is described in Table 1.

TABLE 1

Percent identity of $\beta_2$ integrin family members on the amino acid level.

|  | Human $\alpha_d$ | Rabbit #7 | Rabbit #49 |
|---|---|---|---|
| Human $\alpha_d$ | 100 | 74 | 80 |
| Mouse $\alpha_d$ | 70 | 67 | 74 |
| Rat $\alpha_d$ | 70 | 66 | 73 |
| Mouse CD11a | random* | 28 | 28 |
| Mouse CD11b | 55 | 59 | 53 |
| Human CD11a | 36 | 28 | 28 |
| Human CD11b | 60 | 58 | 55 |
| Human CD11c | 66 | 59 | 62 |

*If <25% identity, it is just random alignment and not significant.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

Example 25
Animal Models For Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes, $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J.Leukocyte Biol.* 54:30–39 (1993)]. SK39-positive macrophages have also been reported at sites of both acute and chronic inflammation. Furthermore, monocytes recruited to thioglycolateinflamed peritoneal cavities also express the SK39 antigen. Collectively, these findings suggest that, if SK39⁺ cells are also $a_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell-cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i) blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

A. Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

B. Atherosclerosis in Rabbits Fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cell-rich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of $\alpha_d$ monoclonal antibodies or small molecule inhibitors, to demonstrate that $a_d^+$ macrophages are involved in the disease process. Additional studies would demonstrate that monoclonal antibodies to $\alpha_d$ or small molecule inhibitors are capable of reversing vessel damage detected in rabbits fed an atherogenic diet.

C. Insulin-dependent Diabetes

BB rats spontaneously develop insulin-dependent diabetes at 70–150 days of age. Using immunohistochemistry, MHC class II⁺, ED1⁺ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population fails to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

D. Inflammatory Bowel Disease (Crohn's Disease, Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IEBD [Yamada, et al., *Gastroenterology* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis anemia and granulomatous hepatitis. The extraintestinal manifestations of the disease make the model attractive for studying Crohn's colitis in that a significant number of patients with active Crohn's disease suffer from arthritic joint disease and hepatobillary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

E. Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J.Exp.Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

F. Multiple Sclerosis

Although pathogenesis of multiple sclerosis (MS) remains unclear, it is generally accepted that the disease is mediated by CD4$^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur.J.Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

G. Immune Complex Alveolitis

Alveolar macrophages located in the alveolar ducts, airways, connective tissue, and pleural spaces of the lung represent the lung's first line of defense against inhaled environmental agents. In response to stimulation by agents, including bacterial-derived LPS, IFN-$\gamma$ and immune complexes, alveolar macrophages release a variety of potent inflammatory mediators, including highly reactive oxygen radicals and nitrogen intermediates. While superoxide anions, hydrogen peroxide and nitric oxide (NO.) have important functions in eradicating pathogens and lysing tumor targets, these agents can have injurious effects on normal tissues.

In a rat model of immune complex alveolitis, NO. release from alveolar macrophages has been shown to mediate much of the lung damage [Mulligan, et al., *Proc.Natl.Acad.Sci.* (*USA*) 88:638–6342 (1991)]. NO. has also been implicated as a mediator in other immune complex mediated injuries including dermal vasculitis [Mulligan, et al., supra] and could potentially play a role in diseases such as glomerulonephritis.

NO. mediated tissue damage is not limited to inflammation involving immune complexes. For example, microglial cell stimulated, by agents such as PMA, LPS or IFN-$\gamma$, produce NO. at levels capable of killing oligodendrocytes [Merrill, et al., *Immunol.* 151:2132 (1993)]. Pancreatic islet cells have also been found to be sensitive to NO., and macrophage release of this mediator has been implicated in the tissue damage which leads to diabetes [Kroncke, et al., *BBRC* 175:752–758 (1991)]. More recently, it was conclusively demonstrated that NO·release plays a role in endotoxic shock [MacMicking, et al., *Cell* 81:641–650 (1995)]. When administered lipopolysaccharide (LPS), normal wild-type mice experience a severe, progressive decline in arterial pressure resulting in death. Mice deficient in inducible nitric oxide, however, experience a much less severe decline in arterial pressure in response to LPS, and all survive the treatment.

In vitro assays indicate that blockage of $\alpha_d$ is effective at blocking some aspects of macrophage (or leukocyte which express $\alpha_d$, in general) activation, including NO·release. Alveolar macrophages stimulated with IFN-γ in the presence of anti-$\alpha_d$ polyclonal anti-serum (generated in rabbits against a rat $\alpha_d$ I domain polypeptide) were found to produce significantly less nitrite/nitrate-breakdown products of NO. than macrophages treated with control anti-serum. This finding indicates that monoclonal antibodies to $\alpha_d$, particularly to the I-domain, may be potent anti-inflammatory agents with potential uses in MS, diabetes, lung inflammation and endotoxic shock. Furthermore, in contrast to CD18, which effects the function of a wide variety of leukocyte types, the limited distribution of $\alpha_d$ may make this a more attractive target than CD18 for preventing macrophage (or leukocyte which express $\alpha_d$, in general) activation.

Rat IgG immune complex-induced alveolitis is a widely used experimental model important in understanding acute lung injury. The injury is elicited by instilling anti-bovine serum albumin (BSA) antibodies into lungs via tracheal cannulation, followed by an intravenous injection of BSA. The formation of immune complexes in the microvasculature of the lung leads to complement activation and the recruitment of neutrophils into the lung. Presumably, formation of immune complexes in the lung following extravasation of leukocytes from the blood and subsequent leukocyte movement across lung epithelium. The subsequent release of mediators, including radicals, TNF-α and nitric oxide (NO.), from activated endothelial cells, neutrophils and macrophages which participate in progression of the disease. Pathologic features of the disease include increased vascular permeability leading to edema and the presence of large numbers of erythrocytes and PMNs present in the alveolar spaces.

Polyclonal anti-serum specific for the I domain of $\alpha_d$ was tested in a rat model of immune complex-induced alveolitis. The anti-$\alpha_d$ polyclonal serum was administered via tracheal cannulation at the same time anti-BSA was introduced into the lungs. Lung injury was subsequently elicited by intravenous administration of BSA along with a trace amount of $^{125}$I-labeled BSA (approximately 800,000 cpm) to quantitate edema resulting from lung injury. Lung injury was allowed to proceed for four hours and damage was assessed using a lung permeability value, is defined as the ratio of $^{125}$I-labeled BSA in the lung compared to the amount of label present in the 1.0 ml of blood. Typically lung permeability values for positive control rates range between 0.6 and 0.8, while negative controls (rats not receiving BSA) have permeability index values in the range of 0.1–0.2.

Initial studies indicated that treatment with anti-$\alpha_d$ polyclonal anti-serum reduced lung permeability values by greater that 50%, representing a dramatic moderation of lung injury. Historically, treatments with anti-CD18 have reduced permeability values by 60%. These findings indicate that $\alpha_d$ may be the most important $\beta_2$ integrin during acute lung injury, however it cannot be precisely determined if the effect of the anti-sera prohibits leukocyte extravasation from the blood, or movement across lung epithelia.

As additional proof that $\alpha_d$ moderates lung injury, TNF-alpha levels in the bronchoalveolar lavage fluid were evaluated. Treatment with the anti-$\alpha_d$ anti-serum was found to reduce TNF-alpha levels approximately four-fold. TNF-alpha has long been viewed as an important mediator in acute lung inflammation, and responsible for the recruitment of inflammatory cells into sites of inflammation, cell activation and tissue damage. Presumably, anti-$\alpha_d$ anti-serum blocks activation of resident alveolar macrophages during the formation of immune complex alveolitis, and thereby moderates the release of TNF-α and NO., and reduces subsequent tissue damage caused by these agents and the recruitment of neutrophils.

Example 26
Expression of $\alpha_d$ in Preclinical Models

In order to assess differential expression of $\alpha_d$ in various disease states, tissue sections from animal disease models were stained with anti-$\alpha_d$ polyclonal serum produced as described above (see Example 18). Tissue from normal and diseased rats was sectioned at 6 μm thickness and air dried on Superfrost Plus (VWR Scientific) slides at room temperature overnight. After drying, sections were stored at −70° C. until use. Prior to use, slides were removed from −70° C. and placed at 50° C. for approximately 5 minutes. Sections were fixed in cold (4° C.) acetone (Stephens Scientific) for 10 minutes at room temperature and allowed to dry at room temperature. Each section was blocked with 150 μl of a solution containing 30% normal rat serum (Harlan Bioproducts), 5% normal goat serum (Vector Laboratories) and 1% bovine serum (BSA) (Sigma Chemical Company) in 1× TBS for 30 minutes at room temperature, after which the solution was gently blotted from the sections. Rabbit polyclonal serum, at a protein concentration of 34 μg/ml, and preimmune serum from the same rabbit, at a protein concentration of 38.5 μg/ml, were diluted in the blocking solution and 100 μl separately applied to each tissue section for 30 minutes 37° C. The serum solution was blotted from the sections and unbound antibody removed by washing three times in 1× TBS for 5 minutes. Excess TBS was removed by blotting following the final wash. Biotinylated goat anti-rabbit antibody from a Elite Rabbit IgG Vectastain ABC kit (Vector) was prepared according to manufacturer's suggested protocol and 100 μl of the resulting solution was applied to each section for 15 minutes at 37° C. Slides were washed two times in 1× TBS for five minutes in each wash, after which 100 μl of streptavidin-gold conjugate (Goldmark Biologicals), diluted 1:100 in 5% normal rat serum and 1% BSA, was applied to each section for one hour at room temperature. Slides were washed three times with TBS for five minutes each wash, and 100 μl of 1% glutaraldehyde (Sigma) in TBS buffer was applied for five minutes at room temperature. Slides were again washed three times in TBS for five minutes each wash, and five times in sterile deionized water for three minutes each wash. Excess liquid was blotted from each slide and two drops each of silver enhancing and initiating solution (Goldmark Biologicals) were applied to each section. The reaction was allowed to proceed for 20–30 minutes at room temperature, after which the sections were rinsed thoroughly in sterile deionized water, air dried overnight at room temperature and mounted with Cytoseal 60 (VWR). As controls, tissue sections were labeled with monoclonal antibodies recognizing CD11a, CD11b, CD11c and CD18 in the same experiments by identical protocols.

Labeling with $\alpha_d$ polyclonal sera and monoclonal antibodies to CD11a, CD11b, CD11c, and CD18 revealed a staining pattern for $\alpha_d$ different from than observed for the other α subunits.

In normal lung tissue, $\alpha_d$ expression was detected on respiratory epithelium of the bronchi (but not the epithelium in the alveolar spaces) and on individual cells which appear to be alveolar macrophages within the airspaces. The signal observed with the polyclonal serum was significantly higher than the background signal level with the pre-immune serum control. In pulmonary granuloma tissue, 24 and 96 hours after administration of glycan, a different signal was detected with the $\alpha_d$ staining respiratory epithelium throughout the alveolar area and a stronger signal detected on what appear to be alveolar marcophages throughout the airways. In the lung tissue from animals which had presumably recovered from the disease (sacrificed 16 days after administration of glycan), no signal was observed with the $\alpha_d$ antibody. Very little background was observed with the pre-immunization serum in each of these tissues.

Using rat lung tissue from an antigen-induced asthma model, a very strong signal was detected with $\alpha_d$ antibody in the respiratory epithelium of both the bronchi and the alveolar spaces. The signal was significantly higher than the background signal level in the pre-immunization serum control.

Numerous modifications and variations in the invention as set forth in the above illustrative examples are expected to occur to those skilled in the art. Consequently only such limitations as appear in the appended claims should be placed on the invention.

---

What is claimed is:

1. A hybridoma designated 199M (A.T.C.C. Deposit No: HB 12058).

2. A monoclonal antibody secreted by the hybridoma of claim 1.

* * * * *

UNITED STATES PATENT AND TRADEMARK OFFICE
CERTIFICATE OF CORRECTION

PATENT NO. : 5,817,515

DATED : October 6, 1998

INVENTOR(S) : Gallatin et al.

It is certified that error appears in the above-identified patent and that said Letters Patent is hereby corrected as shown below:

Title page,
Pg. 2, col. 1: Please insert --Hynes, et al., "Integrins: Versatility, Modulation, and Signaling in Cell Adhesion," Cell 69:11-25 (1992)--.

Pg. 2, col. 1, Larson, et al.: Please delete "embodded", and insert --embedded--.

Pg. 2, col. 1, Lawrence, et al.: Please delete "139:3062-2069", and insert --139:3062-3069--.

Pg. 2, col. 2, Sambrook, et al.: Please delete "nirocellulose", and insert --nitrocellulose--.

Pg. 3, col. 2, Zhou, et al.: Please delete "CD11b/CD8", and insert --CD11b/CD18--.

Col. 4, line 64: Please delete "Of", and insert --of--.

Col. 6, line 5: Please delete "CDNA", and insert --cDNA--.

Col. 6, line 24: Please delete "Kapecchi", and insert --Capecchi--.

Col. 11, line 25: Please delete "50°", and insert ---50°C--.

Col. 13, line 50: Please delete "CDNA", and insert --cDNA--

UNITED STATES PATENT AND TRADEMARK OFFICE
CERTIFICATE OF CORRECTION

PATENT NO. : 5,817,515

DATED : October 6, 1998

INVENTOR(S) : Gallatin et al.

It is certified that error appears in the above-identified patent and that said Letters Patent is hereby corrected as shown below:

Col. 14, line 34: Please delete "5'GTNTFYCARGARGAYGG-3'", and insert --5'-GTNTTYCARGARGAYGG-3'--.

Col. 15, line 53: Please delete "a", and insert --α--.

Col. 17, line 10: Please delete "AND", and insert --and--.

Col. 18, line 41: After "...is", please delete "6".

Col. 18, lines 49-50: Please delete "5' AGTTACGAATTCGCCACCATGACTCGGACTGTGCTTCTFCTG-3'", and insert --5' AGTTACGAATTCGCCACCATGACTCGGACTGTGCTTCTTCTG-3'--.

Col. 24, line 59: Please delete "in", and insert --is--.

Col. 25, line 41: Please delete "a", and insert --α--.

Col. 25, line 51: Please delete "αd/CD18LZ", and insert --$\alpha_d$/CD18LZ--.

Col. 26, line 44: Please delete "that", and insert --than--.

Col. 28, line 10: After "...are than", please delete "be".

Col. 35, line 26: Please delete "patent", and insert --patient--.

Col. 37, line 53: Please delete "effect", and insert --affect--.

Col. 40, line 8: Please delete "mis", and insert --mls--.

UNITED STATES PATENT AND TRADEMARK OFFICE
CERTIFICATE OF CORRECTION

PATENT NO. : 5,817,515

DATED : October 6, 1998

INVENTOR(S) : Gallatin et al.

It is certified that error appears in the above-identified patent and that said Letters Patent is hereby corrected as shown below:

Col. 43, line 10: Please delete "minute", and insert - -minutes- -.

Col. 43, line 55: Please delete "CaCl2", and insert - -$CaCl_2$- -.

Col. 43, line 55: Please delete "MgCl2", and insert - -$MgCl_2$- -.

Col. 46, line 30: Please delete "a", and insert - -an- -.

Col. 46, line 51: Please delete "washed", and insert - -wash- -

Col. 49, line 49: Please delete "I", and insert - -1- -.

Col. 50, line 9: Please delete "αd", and insert - -$\alpha_d$- -.

Col. 50, line 12: Please delete "describe", and insert - -described- -.

Col. 50, line 17: Please delete "CDNA", and insert - -cDNA- -.

Col. 52, lines 15-16: Please delete "11.b-1/REV12 5'-TTGACGAAGTCCTFCA-TCTGGG-3'", and insert --11.B-1/2 REV12 5'-TTGACGAAGTCCTTCA-TCTGGG-3'- -.

Col. 58, line 16: After "...is also", please delete "be".

UNITED STATES PATENT AND TRADEMARK OFFICE
CERTIFICATE OF CORRECTION

PATENT NO. : 5,817,515

DATED : October 6, 1998

INVENTOR(S) : Gallatin et al.

It is certified that error appears in the above-identified patent and that said Letters Patent is hereby corrected as shown below:

Col. 58, line 25: Please delete "simmer", and insert - -similar- -.

Col. 59, line 27: Please delete "IEBD", and insert - -IBD- -.

Signed and Sealed this

Twelfth Day of December, 2000

Attest:

Q. TODD DICKINSON

*Attesting Officer*    *Director of Patents and Trademarks*

SEQUENCE LISTING ( 1 ) GENERAL INFORMATION:

( i i i ) NUMBER OF SEQUENCES: 103

( 2 ) INFORMATION FOR SEQ ID NO:1:

( i ) SEQUENCE CHARACTERISTICS:
        ( A ) LENGTH: 3726 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
    1               5                  10                  15

GGA TTC AAC CTG GAT GTG GAG GAG CCT ACG ATC TTC CAG GAG GAT GCA       95
Gly Phe Asn Leu Asp Val Glu Glu Pro Thr Ile Phe Gln Glu Asp Ala
            20                  25                  30

GGC GGC TTT GGG CAG AGC GTG GTG CAG TTC GGT GGA TCT CGA CTC GTG      143
Gly Gly Phe Gly Gln Ser Val Val Gln Phe Gly Gly Ser Arg Leu Val
        35                  40                  45

GTG GGA GCA CCC CTG GAG GTG GTG GCG GCC AAC CAG ACG GGA CGG CTG      191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC      239
Tyr Asp Cys Ala Ala Ala Thr Gly Met Cys Gln Pro Ile Pro Leu His
        65                  70                  75

ATC CGC CCT GAG GCC GTG AAC ATG TCC TTG GGC CTG ACC CTG GCA GCC      287
Ile Arg Pro Glu Ala Val Asn Met Ser Leu Gly Leu Thr Leu Ala Ala
 80              85                  90                  95

TCC ACC AAC GGC TCC CGG CTC CTG GCC TGT GGC CCG ACC CTG CAC AGA      335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC      383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT      431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC      479
Pro His Gln Glu Met Asp Ile Val Phe Leu Ile Asp Gly Ser Gly Ser
        145                 150                 155
```

| | | | | | | | | | | | | | | | | |
|---|---|---|---|---|---|---|---|---|---|---|---|---|---|---|---|---|
| ATT | GAC | CAA | AAT | GAC | TTT | AAC | CAG | ATG | AAG | GGC | TTT | GTC | CAA | GCT | GTC | 527 |
| Ile | Asp | Gln | Asn | Asp | Phe | Asn | Gln | Met | Lys | Gly | Phe | Val | Gln | Ala | Val | |
| 160 | | | | | 165 | | | | 170 | | | | | | 175 | |
| ATG | GGC | CAG | TTT | GAG | GGC | ACT | GAC | ACC | CTG | TTT | GCA | CTG | ATG | CAG | TAC | 575 |
| Met | Gly | Gln | Phe | Glu | Gly | Thr | Asp | Thr | Leu | Phe | Ala | Leu | Met | Gln | Tyr | |
| | | | | 180 | | | | | 185 | | | | | 190 | | |
| TCA | AAC | CTC | CTG | AAG | ATC | CAC | TTC | ACC | TTC | ACC | CAA | TTC | CGG | ACC | AGC | 623 |
| Ser | Asn | Leu | Leu | Lys | Ile | His | Phe | Thr | Phe | Thr | Gln | Phe | Arg | Thr | Ser | |
| | | | 195 | | | | | 200 | | | | | 205 | | | |
| CCG | AGC | CAG | CAG | AGC | CTG | GTG | GAT | CCC | ATC | GTC | CAA | CTG | AAA | GGC | CTG | 671 |
| Pro | Ser | Gln | Gln | Ser | Leu | Val | Asp | Pro | Ile | Val | Gln | Leu | Lys | Gly | Leu | |
| | | 210 | | | | | 215 | | | | 220 | | | | | |
| ACG | TTC | ACG | GCC | ACG | GGC | ATC | CTG | ACA | GTG | GTG | ACA | CAG | CTA | TTT | CAT | 719 |
| Thr | Phe | Thr | Ala | Thr | Gly | Ile | Leu | Thr | Val | Val | Thr | Gln | Leu | Phe | His | |
| | 225 | | | | | 230 | | | | | 235 | | | | | |
| CAT | AAG | AAT | GGG | GCC | CGA | AAA | AGT | GCC | AAG | AAG | ATC | CTC | ATT | GTC | ATC | 767 |
| His | Lys | Asn | Gly | Ala | Arg | Lys | Ser | Ala | Lys | Lys | Ile | Leu | Ile | Val | Ile | |
| 240 | | | | | 245 | | | | 250 | | | | | | 255 | |
| ACA | GAT | GGG | CAG | AAG | TAC | AAA | GAC | CCC | CTG | GAA | TAC | AGT | GAT | GTC | ATC | 815 |
| Thr | Asp | Gly | Gln | Lys | Tyr | Lys | Asp | Pro | Leu | Glu | Tyr | Ser | Asp | Val | Ile | |
| | | | | 260 | | | | | 265 | | | | | 270 | | |
| CCC | CAG | GCA | GAG | AAG | GCT | GGC | ATC | ATC | CGC | TAC | GCT | ATC | GGG | GTG | GGA | 863 |
| Pro | Gln | Ala | Glu | Lys | Ala | Gly | Ile | Ile | Arg | Tyr | Ala | Ile | Gly | Val | Gly | |
| | | | 275 | | | | | 280 | | | | | 285 | | | |
| CAC | GCT | TTC | CAG | GGA | CCC | ACT | GCC | AGG | CAG | GAG | CTG | AAT | ACC | ATC | AGC | 911 |
| His | Ala | Phe | Gln | Gly | Pro | Thr | Ala | Arg | Gln | Glu | Leu | Asn | Thr | Ile | Ser | |
| | | 290 | | | | | 295 | | | | | 300 | | | | |
| TCA | GCG | CCT | CCG | CAG | GAC | CAC | GTG | TTC | AAG | GTG | GAC | AAC | TTT | GCA | GCC | 959 |
| Ser | Ala | Pro | Pro | Gln | Asp | His | Val | Phe | Lys | Val | Asp | Asn | Phe | Ala | Ala | |
| | 305 | | | | | 310 | | | | | 315 | | | | | |
| CTT | GGC | AGC | ATC | CAG | AAG | CAG | CTG | CAG | GAG | AAG | ATC | TAT | GCA | GTT | GAG | 1007 |
| Leu | Gly | Ser | Ile | Gln | Lys | Gln | Leu | Gln | Glu | Lys | Ile | Tyr | Ala | Val | Glu | |
| 320 | | | | | 325 | | | | | 330 | | | | | 335 | |
| GGA | ACC | CAG | TCC | AGG | GCA | AGC | AGC | TCC | TTC | CAG | CAC | GAG | ATG | TCC | CAA | 1055 |
| Gly | Thr | Gln | Ser | Arg | Ala | Ser | Ser | Ser | Phe | Gln | His | Glu | Met | Ser | Gln | |
| | | | | 340 | | | | | 345 | | | | | 350 | | |
| GAA | GGC | TTC | AGC | ACA | GCC | CTC | ACA | ATG | GAT | GGC | CTC | TTC | CTG | GGG | GCT | 1103 |
| Glu | Gly | Phe | Ser | Thr | Ala | Leu | Thr | Met | Asp | Gly | Leu | Phe | Leu | Gly | Ala | |
| | | | 355 | | | | | 360 | | | | | 365 | | | |
| GTG | GGG | AGC | TTT | AGC | TGG | TCT | GGA | GGT | GCC | TTC | CTG | TAT | CCC | CCA | AAT | 1151 |
| Val | Gly | Ser | Phe | Ser | Trp | Ser | Gly | Gly | Ala | Phe | Leu | Tyr | Pro | Pro | Asn | |
| | | 370 | | | | | 375 | | | | | 380 | | | | |
| ATG | AGC | CCC | ACC | TTC | ATC | AAC | ATG | TCT | CAG | GAG | AAT | GTG | GAC | ATG | AGG | 1199 |
| Met | Ser | Pro | Thr | Phe | Ile | Asn | Met | Ser | Gln | Glu | Asn | Val | Asp | Met | Arg | |
| | 385 | | | | | 390 | | | | | 395 | | | | | |
| GAC | TCT | TAC | CTG | GGT | TAC | TCC | ACC | GAG | CTA | GCC | CTG | TGG | AAG | GGG | GTA | 1247 |
| Asp | Ser | Tyr | Leu | Gly | Tyr | Ser | Thr | Glu | Leu | Ala | Leu | Trp | Lys | Gly | Val | |
| 400 | | | | | 405 | | | | | 410 | | | | | 415 | |
| CAG | AAC | CTG | GTC | CTG | GGG | GCC | CCC | CGC | TAC | CAG | CAT | ACC | GGG | AAG | GCT | 1295 |
| Gln | Asn | Leu | Val | Leu | Gly | Ala | Pro | Arg | Tyr | Gln | His | Thr | Gly | Lys | Ala | |
| | | | | 420 | | | | | 425 | | | | | 430 | | |
| GTC | ATC | TTC | ACC | CAG | GTG | TCC | AGG | CAA | TGG | AGG | AAG | AAG | GCC | GAA | GTC | 1343 |
| Val | Ile | Phe | Thr | Gln | Val | Ser | Arg | Gln | Trp | Arg | Lys | Lys | Ala | Glu | Val | |
| | | | 435 | | | | | 440 | | | | | 445 | | | |
| ACA | GGG | ACG | CAG | ATC | GGC | TCC | TAC | TTC | GGG | GCC | TCC | CTC | TGC | TCC | GTG | 1391 |
| Thr | Gly | Thr | Gln | Ile | Gly | Ser | Tyr | Phe | Gly | Ala | Ser | Leu | Cys | Ser | Val | |
| | | | 450 | | | | | 455 | | | | | 460 | | | |
| GAT | GTG | GAC | AGC | GAT | GGC | AGC | ACC | GAC | CTG | ATC | CTC | ATT | GGG | GCC | CCC | 1439 |
| Asp | Val | Asp | Ser | Asp | Gly | Ser | Thr | Asp | Leu | Ile | Leu | Ile | Gly | Ala | Pro | |
| | 465 | | | | | 470 | | | | | 475 | | | | | |

| | | | | | | | | | | | | | | | | |
|---|---|---|---|---|---|---|---|---|---|---|---|---|---|---|---|---|
| CAT | TAC | TAT | GAG | CAG | ACC | CGA | GGG | GGC | CAG | GTG | TCC | GTG | TGT | CCC | TTG | 1487 |
| His | Tyr | Tyr | Glu | Gln | Thr | Arg | Gly | Gly | Gln | Val | Ser | Val | Cys | Pro | Leu | |
| 480 | | | | | 485 | | | | | 490 | | | | | 495 | |
| CCT | AGG | GGG | CAG | AGG | GTG | CAG | TGG | CAG | TGT | GAC | GCT | GTT | CTC | CGT | GGT | 1535 |
| Pro | Arg | Gly | Gln | Arg | Val | Gln | Trp | Gln | Cys | Asp | Ala | Val | Leu | Arg | Gly | |
| | | | 500 | | | | | 505 | | | | | 510 | | | |
| GAG | CAG | GGC | CAC | CCC | TGG | GGC | CGC | TTT | GGG | GCA | GCC | CTG | ACA | GTG | TTG | 1583 |
| Glu | Gln | Gly | His | Pro | Trp | Gly | Arg | Phe | Gly | Ala | Ala | Leu | Thr | Val | Leu | |
| | | | 515 | | | | | 520 | | | | | 525 | | | |
| GGG | GAT | GTG | AAT | GAG | GAC | AAG | CTG | ATA | GAC | GTG | GCC | ATT | GGG | GCC | CCG | 1631 |
| Gly | Asp | Val | Asn | Glu | Asp | Lys | Leu | Ile | Asp | Val | Ala | Ile | Gly | Ala | Pro | |
| | | 530 | | | | | 535 | | | | | 540 | | | | |
| GGA | GAG | CAG | GAG | AAC | CGG | GGT | GCT | GTC | TAC | CTG | TTT | CAC | GGA | GCC | TCA | 1679 |
| Gly | Glu | Gln | Glu | Asn | Arg | Gly | Ala | Val | Tyr | Leu | Phe | His | Gly | Ala | Ser | |
| 545 | | | | | 550 | | | | | 555 | | | | | | |
| GAA | TCC | GGC | ATC | AGC | CCC | TCC | CAC | AGC | CAG | CGG | ATT | GCC | AGC | TCC | CAG | 1727 |
| Glu | Ser | Gly | Ile | Ser | Pro | Ser | His | Ser | Gln | Arg | Ile | Ala | Ser | Ser | Gln | |
| 560 | | | | | 565 | | | | | 570 | | | | | 575 | |
| CTC | TCC | CCC | AGG | CTG | CAG | TAT | TTT | GGG | CAG | GCG | CTG | AGT | GGG | GGT | CAG | 1775 |
| Leu | Ser | Pro | Arg | Leu | Gln | Tyr | Phe | Gly | Gln | Ala | Leu | Ser | Gly | Gly | Gln | |
| | | | | 580 | | | | | 585 | | | | | 590 | | |
| GAC | CTC | ACC | CAG | GAT | GGA | CTG | ATG | GAC | CTG | GCC | GTG | GGG | GCC | CGG | GGC | 1823 |
| Asp | Leu | Thr | Gln | Asp | Gly | Leu | Met | Asp | Leu | Ala | Val | Gly | Ala | Arg | Gly | |
| | | | 595 | | | | | 600 | | | | | 605 | | | |
| CAG | GTG | CTC | CTG | CTC | AGG | AGT | CTG | CCG | GTG | CTG | AAA | GTG | GGG | GTG | GCC | 1871 |
| Gln | Val | Leu | Leu | Leu | Arg | Ser | Leu | Pro | Val | Leu | Lys | Val | Gly | Val | Ala | |
| | | 610 | | | | | 615 | | | | | 620 | | | | |
| ATG | AGA | TTC | AGC | CCT | GTG | GAG | GTG | GCC | AAG | GCT | GTG | TAC | CGG | TGC | TGG | 1919 |
| Met | Arg | Phe | Ser | Pro | Val | Glu | Val | Ala | Lys | Ala | Val | Tyr | Arg | Cys | Trp | |
| | 625 | | | | | 630 | | | | | 635 | | | | | |
| GAA | GAG | AAG | CCC | AGT | GCC | CTG | GAA | GCT | GGG | GAC | GCC | ACC | GTC | TGT | CTC | 1967 |
| Glu | Glu | Lys | Pro | Ser | Ala | Leu | Glu | Ala | Gly | Asp | Ala | Thr | Val | Cys | Leu | |
| 640 | | | | | 645 | | | | | 650 | | | | | 655 | |
| ACC | ATC | CAG | AAA | AGC | TCA | CTG | GAC | CAG | CTA | GGT | GAC | ATC | CAA | AGC | TCT | 2015 |
| Thr | Ile | Gln | Lys | Ser | Ser | Leu | Asp | Gln | Leu | Gly | Asp | Ile | Gln | Ser | Ser | |
| | | | | 660 | | | | | 665 | | | | | 670 | | |
| GTC | AGG | TTT | GAT | CTG | GCA | CTG | GAC | CCA | GGT | CGT | CTG | ACT | TCT | CGT | GCC | 2063 |
| Val | Arg | Phe | Asp | Leu | Ala | Leu | Asp | Pro | Gly | Arg | Leu | Thr | Ser | Arg | Ala | |
| | | | 675 | | | | | 680 | | | | | 685 | | | |
| ATT | TTC | AAT | GAA | ACC | AAG | AAC | CCC | ACT | TTG | ACT | CGA | AGA | AAA | ACC | CTG | 2111 |
| Ile | Phe | Asn | Glu | Thr | Lys | Asn | Pro | Thr | Leu | Thr | Arg | Arg | Lys | Thr | Leu | |
| | | 690 | | | | | 695 | | | | | 700 | | | | |
| GGA | CTG | GGG | ATT | CAC | TGT | GAA | ACC | CTG | AAG | CTG | CTT | TTG | CCA | GAT | TGT | 2159 |
| Gly | Leu | Gly | Ile | His | Cys | Glu | Thr | Leu | Lys | Leu | Leu | Leu | Pro | Asp | Cys | |
| | | 705 | | | | | 710 | | | | | 715 | | | | |
| GTG | GAG | GAT | GTG | GTG | AGC | CCC | ATC | ATT | CTG | CAC | CTC | AAC | TTC | TCA | CTG | 2207 |
| Val | Glu | Asp | Val | Val | Ser | Pro | Ile | Ile | Leu | His | Leu | Asn | Phe | Ser | Leu | |
| 720 | | | | | 725 | | | | | 730 | | | | | 735 | |
| GTG | AGA | GAG | CCC | ATC | CCC | TCC | CCC | CAG | AAC | CTG | CGT | CCT | GTG | CTG | GCC | 2255 |
| Val | Arg | Glu | Pro | Ile | Pro | Ser | Pro | Gln | Asn | Leu | Arg | Pro | Val | Leu | Ala | |
| | | | | 740 | | | | | 745 | | | | | 750 | | |
| GTG | GGC | TCA | CAA | GAC | CTC | TTC | ACT | GCT | TCT | CTC | CCC | TTC | GAG | AAG | AAC | 2303 |
| Val | Gly | Ser | Gln | Asp | Leu | Phe | Thr | Ala | Ser | Leu | Pro | Phe | Glu | Lys | Asn | |
| | | | | 755 | | | | | 760 | | | | | 765 | | |
| TGT | GGG | CAA | GAT | GGC | CTC | TGT | GAA | GGG | GAC | CTG | GGT | GTC | ACC | CTC | AGC | 2351 |
| Cys | Gly | Gln | Asp | Gly | Leu | Cys | Glu | Gly | Asp | Leu | Gly | Val | Thr | Leu | Ser | |
| | | | 770 | | | | | 775 | | | | | 780 | | | |
| TTC | TCA | GGC | CTG | CAG | ACC | CTG | ACC | GTG | GGG | AGC | TCC | CTG | GAG | CTC | AAC | 2399 |
| Phe | Ser | Gly | Leu | Gln | Thr | Leu | Thr | Val | Gly | Ser | Ser | Leu | Glu | Leu | Asn | |
| 785 | | | | | 790 | | | | | 795 | | | | | | |

| | |
|---|---|
| GTG ATT GTG ACT GTG TGG AAC GCA GGT GAG GAT TCC TAC GGA ACC GTG<br>Val Ile Val Thr Val Trp Asn Ala Gly Glu Asp Ser Tyr Gly Thr Val<br>800                           805                       810                       815 | 2447 |
| GTC AGC CTC TAC TAT CCA GCA GGG CTG TCG CAC CGA CGG GTG TCA GGA<br>Val Ser Leu Tyr Tyr Pro Ala Gly Leu Ser His Arg Arg Val Ser Gly<br>                         820                                825                       830 | 2495 |
| GCC CAG AAG CAG CCC CAT CAG AGT GCC CTG CGC CTG GCA TGT GAG ACA<br>Ala Gln Lys Gln Pro His Gln Ser Ala Leu Arg Leu Ala Cys Glu Thr<br>                 835                                840                       845 | 2543 |
| GTG CCC ACT GAG GAT GAG GGC CTA AGA AGC AGC CGC TGC AGT GTC AAC<br>Val Pro Thr Glu Asp Glu Gly Leu Arg Ser Ser Arg Cys Ser Val Asn<br>850                                     855                       860 | 2591 |
| CAC CCC ATC TTC CAT GAG GGC TCT AAC GGC ACC TTC ATA GTC ACA TTC<br>His Pro Ile Phe His Glu Gly Ser Asn Gly Thr Phe Ile Val Thr Phe<br>865                           870                                875 | 2639 |
| GAT GTC TCC TAC AAG GCC ACC CTG GGA GAC AGG ATG CTT ATG AGG GCC<br>Asp Val Ser Tyr Lys Ala Thr Leu Gly Asp Arg Met Leu Met Arg Ala<br>880                           885                       890                       895 | 2687 |
| AGT GCA AGC AGT GAG AAC AAT AAG GCT TCA AGC AGC AAG GCC ACC TTC<br>Ser Ala Ser Ser Glu Asn Asn Lys Ala Ser Ser Ser Lys Ala Thr Phe<br>                         900                                905                       910 | 2735 |
| CAG CTG GAG CTC CCG GTG AAG TAT GCA GTC TAC ACC ATG ATC AGC AGG<br>Gln Leu Glu Leu Pro Val Lys Tyr Ala Val Tyr Thr Met Ile Ser Arg<br>                 915                                920                       925 | 2783 |
| CAG GAA GAA TCC ACC AAG TAC TTC AAC TTT GCA ACC TCC GAT GAG AAG<br>Gln Glu Glu Ser Thr Lys Tyr Phe Asn Phe Ala Thr Ser Asp Glu Lys<br>                 930                                935                       940 | 2831 |
| AAA ATG AAA GAG GCT GAG CAT CGA TAC CGT GTG AAT AAC CTC AGC CAG<br>Lys Met Lys Glu Ala Glu His Arg Tyr Arg Val Asn Asn Leu Ser Gln<br>945                           950                                955 | 2879 |
| CGA GAT CTG GCC ATC AGC ATT AAC TTC TGG GTT CCT GTC CTG CTG AAC<br>Arg Asp Leu Ala Ile Ser Ile Asn Phe Trp Val Pro Val Leu Leu Asn<br>960                           965                       970                       975 | 2927 |
| GGG GTG GCT GTG TGG GAT GTG GTC ATG GAG GCC CCA TCT CAG AGT CTC<br>Gly Val Ala Val Trp Asp Val Val Met Glu Ala Pro Ser Gln Ser Leu<br>                         980                                985                       990 | 2975 |
| CCC TGT GTT TCA GAG AGA AAA CCT CCC CAG CAT TCT GAC TTC CTG ACC<br>Pro Cys Val Ser Glu Arg Lys Pro Pro Gln His Ser Asp Phe Leu Thr<br>                 995                               1000                     1005 | 3023 |
| CAG ATT TCA AGA AGT CCC ATG CTG GAC TGC TCC ATT GCT GAC TGC CTG<br>Gln Ile Ser Arg Ser Pro Met Leu Asp Cys Ser Ile Ala Asp Cys Leu<br>                 1010                             1015                     1020 | 3071 |
| CAG TTC CGC TGT GAC GTC CCC TCC TTC AGC GTC CAG GAG GAG CTG GAT<br>Gln Phe Arg Cys Asp Val Pro Ser Phe Ser Val Gln Glu Glu Leu Asp<br>               1025                             1030                     1035 | 3119 |
| TTC ACC CTG AAG GGC AAT CTC AGT TTC GGC TGG GTC CGC GAG ACA TTG<br>Phe Thr Leu Lys Gly Asn Leu Ser Phe Gly Trp Val Arg Glu Thr Leu<br>1040                       1045                          1050                     1055 | 3167 |
| CAG AAG AAG GTG TTG GTC GTG AGT GTG GCT GAA ATT ACG TTC GAC ACA<br>Gln Lys Lys Val Leu Val Val Ser Val Ala Glu Ile Thr Phe Asp Thr<br>                         1060                             1065                     1070 | 3215 |
| TCC GTG TAC TCC CAG CTT CCA GGA CAG GAG GCA TTT ATG AGA GCT CAG<br>Ser Val Tyr Ser Gln Leu Pro Gly Gln Glu Ala Phe Met Arg Ala Gln<br>                 1075                             1080                     1085 | 3263 |
| ATG GAG ATG GTG CTA GAA GAA GAC GAG GTC TAC AAT GCC ATT CCC ATC<br>Met Glu Met Val Leu Glu Glu Asp Glu Val Tyr Asn Ala Ile Pro Ile<br>1090                       1095                          1100 | 3311 |
| ATC ATG GGC AGC TCT GTG GGG GCT CTG CTA CTG CTG GCG CTC ATC ACA<br>Ile Met Gly Ser Ser Val Gly Ala Leu Leu Leu Leu Ala Leu Ile Thr<br>1105                       1110                          1115 | 3359 |

```
GCC ACA CTG TAC AAG CTT GGC TTC TTC AAA CGC CAC TAC AAG GAA ATG         3407
Ala Thr Leu Tyr Lys Leu Gly Phe Phe Lys Arg His Tyr Lys Glu Met
1120                1125                1130                1135

CTG GAG GAC AAG CCT GAA GAC ACT GCC ACA TTC AGT GGG GAC GAT TTC         3455
Leu Glu Asp Lys Pro Glu Asp Thr Ala Thr Phe Ser Gly Asp Asp Phe
                1140                1145                1150

AGC TGT GTG GCC CCA AAT GTG CCT TTG TCC TAATAATCCA CTTTCCTGTT           3505
Ser Cys Val Ala Pro Asn Val Pro Leu Ser
                1155                1160

TATCTCTACC ACTGTGGGCT GGACTTGCTT GCAACCATAA ATCAACTTAC ATGGAAACAA       3565

CTTCTGCATA GATCTGCACT GGCCTAAGCA ACCTACCAGG TGCTAAGCAC CTTCTCGGAG       3625

AGATAGAGAT TGTAATGTTT TTACATATCT GTCCATCTTT TTCAGCAATG ACCCACTTTT       3685

TACAGAAGCA GGCATGGTGC CAGCATAAAT TTTCATATGC T                           3726
```

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr Phe Gly Thr Val Leu Leu Leu Ser Val Leu Ala Ser Tyr His Gly
 1               5                   10                  15

Phe Asn Leu Asp Val Glu Glu Pro Thr Ile Phe Gln Glu Asp Ala Gly
            20                  25                  30

Gly Phe Gly Gln Ser Val Val Gln Phe Gly Gly Ser Arg Leu Val Val
        35                  40                  45

Gly Ala Pro Leu Glu Val Val Ala Ala Asn Gln Thr Gly Arg Leu Tyr
    50                  55                  60

Asp Cys Ala Ala Ala Thr Gly Met Cys Gln Pro Ile Pro Leu His Ile
65                  70                  75                  80

Arg Pro Glu Ala Val Asn Met Ser Leu Gly Leu Thr Leu Ala Ala Ser
                85                  90                  95

Thr Asn Gly Ser Arg Leu Leu Ala Cys Gly Pro Thr Leu His Arg Val
            100                 105                 110

Cys Gly Glu Asn Ser Tyr Ser Lys Gly Ser Cys Leu Leu Leu Gly Ser
        115                 120                 125

Arg Trp Glu Ile Ile Gln Thr Val Pro Asp Ala Thr Pro Glu Cys Pro
    130                 135                 140

His Gln Glu Met Asp Ile Val Phe Leu Ile Asp Gly Ser Gly Ser Ile
145                 150                 155                 160

Asp Gln Asn Asp Phe Asn Gln Met Lys Gly Phe Val Gln Ala Val Met
                165                 170                 175

Gly Gln Phe Glu Gly Thr Asp Thr Leu Phe Ala Leu Met Gln Tyr Ser
            180                 185                 190

Asn Leu Leu Lys Ile His Phe Thr Phe Thr Gln Phe Arg Thr Ser Pro
        195                 200                 205

Ser Gln Gln Ser Leu Val Asp Pro Ile Val Gln Leu Lys Gly Leu Thr
    210                 215                 220

Phe Thr Ala Thr Gly Ile Leu Thr Val Val Thr Gln Leu Phe His His
225                 230                 235                 240

Lys Asn Gly Ala Arg Lys Ser Ala Lys Lys Ile Leu Ile Val Ile Thr
                245                 250                 255
```

```
Asp Gly Gln Lys Tyr Lys Asp Pro Leu Glu Tyr Ser Asp Val Ile Pro
            260                 265                 270
Gln Ala Glu Lys Ala Gly Ile Ile Arg Tyr Ala Ile Gly Val Gly His
            275                 280                 285
Ala Phe Gln Gly Pro Thr Ala Arg Gln Glu Leu Asn Thr Ile Ser Ser
            290                 295                 300
Ala Pro Pro Gln Asp His Val Phe Lys Val Asp Asn Phe Ala Ala Leu
305                 310                 315                 320
Gly Ser Ile Gln Lys Gln Leu Gln Glu Lys Ile Tyr Ala Val Glu Gly
                325                 330                 335
Thr Gln Ser Arg Ala Ser Ser Ser Phe Gln His Glu Met Ser Gln Glu
            340                 345                 350
Gly Phe Ser Thr Ala Leu Thr Met Asp Gly Leu Phe Leu Gly Ala Val
            355                 360                 365
Gly Ser Phe Ser Trp Ser Gly Gly Ala Phe Leu Tyr Pro Pro Asn Met
            370                 375                 380
Ser Pro Thr Phe Ile Asn Met Ser Gln Glu Asn Val Asp Met Arg Asp
385                 390                 395                 400
Ser Tyr Leu Gly Tyr Ser Thr Glu Leu Ala Leu Trp Lys Gly Val Gln
                405                 410                 415
Asn Leu Val Leu Gly Ala Pro Arg Tyr Gln His Thr Gly Lys Ala Val
            420                 425                 430
Ile Phe Thr Gln Val Ser Arg Gln Trp Arg Lys Lys Ala Glu Val Thr
            435                 440                 445
Gly Thr Gln Ile Gly Ser Tyr Phe Gly Ala Ser Leu Cys Ser Val Asp
            450                 455                 460
Val Asp Ser Asp Gly Ser Thr Asp Leu Ile Leu Ile Gly Ala Pro His
465                 470                 475                 480
Tyr Tyr Glu Gln Thr Arg Gly Gly Gln Val Ser Val Cys Pro Leu Pro
                485                 490                 495
Arg Gly Gln Arg Val Gln Trp Gln Cys Asp Ala Val Leu Arg Gly Glu
            500                 505                 510
Gln Gly His Pro Trp Gly Arg Phe Gly Ala Ala Leu Thr Val Leu Gly
            515                 520                 525
Asp Val Asn Glu Asp Lys Leu Ile Asp Val Ala Ile Gly Ala Pro Gly
            530                 535                 540
Glu Gln Glu Asn Arg Gly Ala Val Tyr Leu Phe His Gly Ala Ser Glu
545                 550                 555                 560
Ser Gly Ile Ser Pro Ser His Ser Gln Arg Ile Ala Ser Ser Gln Leu
                565                 570                 575
Ser Pro Arg Leu Gln Tyr Phe Gly Gln Ala Leu Ser Gly Gly Gln Asp
            580                 585                 590
Leu Thr Gln Asp Gly Leu Met Asp Leu Ala Val Gly Ala Arg Gly Gln
            595                 600                 605
Val Leu Leu Leu Arg Ser Leu Pro Val Leu Lys Val Gly Val Ala Met
            610                 615                 620
Arg Phe Ser Pro Val Glu Val Ala Lys Ala Val Tyr Arg Cys Trp Glu
625                 630                 635                 640
Glu Lys Pro Ser Ala Leu Glu Ala Gly Asp Ala Thr Val Cys Leu Thr
                645                 650                 655
Ile Gln Lys Ser Ser Leu Asp Gln Leu Gly Asp Ile Gln Ser Ser Val
            660                 665                 670
Arg Phe Asp Leu Ala Leu Asp Pro Gly Arg Leu Thr Ser Arg Ala Ile
```

|     |     |     | 675 |     |     |     | 680 |     |     |     | 685 |     |     |
| --- | --- | --- | --- | --- | --- | --- | --- | --- | --- | --- | --- | --- | --- |
| Phe | Asn | Glu | Thr | Lys | Asn | Pro | Thr | Leu | Thr | Arg | Arg | Lys | Thr | Leu | Gly |
|     |     | 690 |     |     |     |     | 695 |     |     |     |     | 700 |     |     |     |
| Leu | Gly | Ile | His | Cys | Glu | Thr | Leu | Lys | Leu | Leu | Leu | Pro | Asp | Cys | Val |
| 705 |     |     |     |     | 710 |     |     |     |     | 715 |     |     |     |     | 720 |
| Glu | Asp | Val | Val | Ser | Pro | Ile | Ile | Leu | His | Leu | Asn | Phe | Ser | Leu | Val |
|     |     |     |     | 725 |     |     |     |     | 730 |     |     |     |     | 735 |     |
| Arg | Glu | Pro | Ile | Pro | Ser | Pro | Gln | Asn | Leu | Arg | Pro | Val | Leu | Ala | Val |
|     |     |     | 740 |     |     |     |     | 745 |     |     |     |     | 750 |     |     |
| Gly | Ser | Gln | Asp | Leu | Phe | Thr | Ala | Ser | Leu | Pro | Phe | Glu | Lys | Asn | Cys |
|     |     | 755 |     |     |     |     | 760 |     |     |     |     | 765 |     |     |     |
| Gly | Gln | Asp | Gly | Leu | Cys | Glu | Gly | Asp | Leu | Gly | Val | Thr | Leu | Ser | Phe |
|     | 770 |     |     |     |     | 775 |     |     |     |     | 780 |     |     |     |     |
| Ser | Gly | Leu | Gln | Thr | Leu | Thr | Val | Gly | Ser | Ser | Leu | Glu | Leu | Asn | Val |
| 785 |     |     |     |     | 790 |     |     |     |     | 795 |     |     |     |     | 800 |
| Ile | Val | Thr | Val | Trp | Asn | Ala | Gly | Glu | Asp | Ser | Tyr | Gly | Thr | Val | Val |
|     |     |     |     | 805 |     |     |     |     | 810 |     |     |     |     | 815 |     |
| Ser | Leu | Tyr | Tyr | Pro | Ala | Gly | Leu | Ser | His | Arg | Arg | Val | Ser | Gly | Ala |
|     |     |     | 820 |     |     |     |     | 825 |     |     |     |     | 830 |     |     |
| Gln | Lys | Gln | Pro | His | Gln | Ser | Ala | Leu | Arg | Leu | Ala | Cys | Glu | Thr | Val |
|     |     | 835 |     |     |     |     | 840 |     |     |     |     | 845 |     |     |     |
| Pro | Thr | Glu | Asp | Glu | Gly | Leu | Arg | Ser | Ser | Arg | Cys | Ser | Val | Asn | His |
| 850 |     |     |     |     | 855 |     |     |     |     | 860 |     |     |     |     |     |
| Pro | Ile | Phe | His | Glu | Gly | Ser | Asn | Gly | Thr | Phe | Ile | Val | Thr | Phe | Asp |
| 865 |     |     |     |     | 870 |     |     |     |     | 875 |     |     |     |     | 880 |
| Val | Ser | Tyr | Lys | Ala | Thr | Leu | Gly | Asp | Arg | Met | Leu | Met | Arg | Ala | Ser |
|     |     |     |     | 885 |     |     |     |     | 890 |     |     |     |     | 895 |     |
| Ala | Ser | Ser | Glu | Asn | Asn | Lys | Ala | Ser | Ser | Lys | Ala | Thr | Phe | Gln |
|     |     |     | 900 |     |     |     |     | 905 |     |     |     |     | 910 |     |
| Leu | Glu | Leu | Pro | Val | Lys | Tyr | Ala | Val | Tyr | Thr | Met | Ile | Ser | Arg | Gln |
|     |     | 915 |     |     |     |     | 920 |     |     |     |     | 925 |     |     |     |
| Glu | Glu | Ser | Thr | Lys | Tyr | Phe | Asn | Phe | Ala | Thr | Ser | Asp | Glu | Lys | Lys |
|     |     | 930 |     |     |     |     | 935 |     |     |     |     | 940 |     |     |     |
| Met | Lys | Glu | Ala | Glu | His | Arg | Tyr | Arg | Val | Asn | Asn | Leu | Ser | Gln | Arg |
| 945 |     |     |     |     | 950 |     |     |     |     | 955 |     |     |     |     | 960 |
| Asp | Leu | Ala | Ile | Ser | Ile | Asn | Phe | Trp | Val | Pro | Val | Leu | Leu | Asn | Gly |
|     |     |     |     | 965 |     |     |     |     | 970 |     |     |     |     | 975 |     |
| Val | Ala | Val | Trp | Asp | Val | Val | Met | Glu | Ala | Pro | Ser | Gln | Ser | Leu | Pro |
|     |     |     | 980 |     |     |     |     | 985 |     |     |     |     | 990 |     |     |
| Cys | Val | Ser | Glu | Arg | Lys | Pro | Pro | Gln | His | Ser | Asp | Phe | Leu | Thr | Gln |
|     |     | 995 |     |     |     |     | 1000 |     |     |     |     | 1005 |     |     |     |
| Ile | Ser | Arg | Ser | Pro | Met | Leu | Asp | Cys | Ser | Ile | Ala | Asp | Cys | Leu | Gln |
|     |     | 1010 |     |     |     |     | 1015 |     |     |     |     | 1020 |     |     |     |
| Phe | Arg | Cys | Asp | Val | Pro | Ser | Phe | Ser | Val | Gln | Glu | Glu | Leu | Asp | Phe |
| 1025 |     |     |     |     | 1030 |     |     |     |     | 1035 |     |     |     |     | 1040 |
| Thr | Leu | Lys | Gly | Asn | Leu | Ser | Phe | Gly | Trp | Val | Arg | Glu | Thr | Leu | Gln |
|     |     |     |     | 1045 |     |     |     |     | 1050 |     |     |     |     | 1055 |     |
| Lys | Lys | Val | Leu | Val | Val | Ser | Val | Ala | Glu | Ile | Thr | Phe | Asp | Thr | Ser |
|     |     |     |     | 1060 |     |     |     |     | 1065 |     |     |     |     | 1070 |     |
| Val | Tyr | Ser | Gln | Leu | Pro | Gly | Gln | Glu | Ala | Phe | Met | Arg | Ala | Gln | Met |
|     |     |     | 1075 |     |     |     |     | 1080 |     |     |     |     | 1085 |     |     |
| Glu | Met | Val | Leu | Glu | Glu | Asp | Glu | Val | Tyr | Asn | Ala | Ile | Pro | Ile | Ile |
|     |     |     | 1090 |     |     |     |     | 1095 |     |     |     |     | 1100 |     |     |

```
Met  Gly  Ser  Ser  Val  Gly  Ala  Leu  Leu  Leu  Leu  Ala  Leu  Ile  Thr  Ala
1105                1110                1115                          1120

Thr  Leu  Tyr  Lys  Leu  Gly  Phe  Phe  Lys  Arg  His  Tyr  Lys  Glu  Met  Leu
               1125                     1130                     1135

Glu  Asp  Lys  Pro  Glu  Asp  Thr  Ala  Thr  Phe  Ser  Gly  Asp  Asp  Phe  Ser
               1140                1145                     1150

Cys  Val  Ala  Pro  Asn  Val  Pro  Lys  Ser
          1155                1160
```

( 2 ) INFORMATION FOR SEQ ID NO:3:

( i ) SEQUENCE CHARACTERISTICS:
        ( A ) LENGTH: 1153 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met  Ala  Leu  Arg  Val  Leu  Leu  Leu  Thr  Ala  Leu  Thr  Leu  Cys  His  Gly
1                   5                        10                       15

Phe  Asn  Leu  Asp  Thr  Glu  Asn  Ala  Met  Thr  Phe  Gln  Glu  Asn  Ala  Arg
               20                  25                       30

Gly  Phe  Gly  Gln  Ser  Val  Val  Gln  Leu  Gln  Gly  Ser  Arg  Val  Val  Val
          35                      40                       45

Gly  Ala  Pro  Gln  Glu  Ile  Val  Ala  Asn  Gln  Arg  Gly  Ser  Leu  Tyr
          50                  55                       60

Gln  Cys  Asp  Tyr  Ser  Thr  Gly  Ser  Cys  Glu  Pro  Ile  Arg  Leu  Gln  Val
65                       70                  75                            80

Pro  Val  Glu  Ala  Val  Asn  Met  Ser  Leu  Gly  Leu  Ser  Leu  Ala  Ala  Thr
               85                       90                            95

Thr  Ser  Pro  Pro  Gln  Leu  Leu  Ala  Cys  Gly  Pro  Thr  Val  His  Gln  Thr
               100                      105                      110

Cys  Ser  Glu  Asn  Thr  Tyr  Val  Lys  Gly  Leu  Cys  Phe  Leu  Phe  Gly  Ser
               115                      120                      125

Asn  Leu  Arg  Gln  Gln  Pro  Gln  Lys  Phe  Pro  Glu  Ala  Leu  Arg  Gly  Cys
130                       135                      140

Pro  Gln  Glu  Asp  Ser  Asp  Ile  Ala  Phe  Leu  Ile  Asp  Gly  Ser  Gly  Ser
145                       150                      155                      160

Ile  Ile  Pro  His  Asp  Phe  Arg  Arg  Met  Lys  Glu  Phe  Val  Ser  Thr  Val
                    165                      170                      175

Met  Glu  Gln  Leu  Lys  Lys  Ser  Lys  Thr  Leu  Phe  Ser  Leu  Met  Gln  Tyr
                    180                      185                      190

Ser  Glu  Glu  Phe  Arg  Ile  His  Phe  Thr  Phe  Lys  Glu  Phe  Gln  Asn  Asn
          195                      200                      205

Pro  Asn  Pro  Arg  Ser  Leu  Val  Lys  Pro  Ile  Thr  Gln  Leu  Leu  Gly  Arg
     210                      215                      220

Thr  His  Thr  Ala  Thr  Gly  Ile  Arg  Lys  Val  Val  Arg  Glu  Leu  Phe  Asn
225                           230                      235                      240

Ile  Thr  Asn  Gly  Ala  Arg  Lys  Asn  Ala  Phe  Lys  Ile  Leu  Val  Val  Ile
                    245                      250                      255

Thr  Asp  Gly  Glu  Lys  Phe  Gly  Asp  Pro  Leu  Gly  Tyr  Glu  Asp  Val  Ile
               260                      265                      270

Pro  Glu  Ala  Asp  Arg  Glu  Gly  Val  Ile  Arg  Tyr  Val  Ile  Gly  Val  Gly
               275                      280                      285

Asp  Ala  Phe  Arg  Ser  Glu  Lys  Ser  Arg  Gln  Glu  Leu  Asn  Thr  Ile  Ala
```

|     |     |     |     |     | 290 |     |     |     | 295 |     |     |     | 300 |     |
| --- | --- | --- | --- | --- | --- | --- | --- | --- | --- | --- | --- | --- | --- | --- |
| Ser 305 | Lys | Pro | Pro | Arg | Asp 310 | His | Val | Phe | Gln 315 | Val | Asn | Asn | Phe | Glu Ala 320 |
| Leu | Lys | Thr | Ile | Gln 325 | Asn | Gln | Leu | Arg | Glu 330 | Lys | Ile | Phe | Ala | Ile Glu 335 |
| Gly | Thr | Gln | Thr 340 | Gly | Ser | Ser | Ser | Phe 345 | Glu | His | Glu | Met 350 | Ser | Gln |
| Glu | Gly | Phe 355 | Ser | Ala | Ala | Ile | Thr 360 | Ser | Asn | Gly | Pro 365 | Leu | Leu | Ser Thr |
| Val | Gly 370 | Ser | Tyr | Asp | Trp | Ala 375 | Gly | Gly | Val | Phe | Leu 380 | Tyr | Thr | Ser Lys |
| Glu 385 | Lys | Ser | Thr | Phe | Ile 390 | Asn | Met | Thr | Arg | Val 395 | Asp | Ser | Asp | Met Asn 400 |
| Asp | Ala | Tyr | Leu | Gly 405 | Tyr | Ala | Ala | Ala | Ile 410 | Ile | Leu | Arg | Asn | Arg Val 415 |
| Gln | Ser | Leu | Val 420 | Leu | Gly | Ala | Pro | Arg 425 | Tyr | Gln | His | Ile 430 | Gly | Leu Val |
| Ala | Met | Phe 435 | Arg | Gln | Asn | Thr | Gly 440 | Met | Trp | Glu | Ser | Asn 445 | Ala | Asn Val |
| Lys | Gly 450 | Thr | Gln | Ile | Gly | Ala 455 | Tyr | Phe | Gly | Ala | Ser 460 | Leu | Cys | Ser Val |
| Asp 465 | Val | Asp | Ser | Asn | Gly 470 | Ser | Thr | Asp | Leu | Val 475 | Leu | Ile | Gly | Ala Pro 480 |
| His | Tyr | Tyr | Glu | Gln 485 | Thr | Arg | Gly | Gly | Gln 490 | Val | Ser | Val | Cys | Pro Leu 495 |
| Pro | Arg | Gly | Gln 500 | Arg | Ala | Arg | Trp | Gln 505 | Cys | Asp | Ala | Val | Leu 510 | Tyr Gly |
| Glu | Gln | Gly | Gln 515 | Pro | Trp | Gly | Arg 520 | Phe | Gly | Ala | Ala | Leu 525 | Thr | Val Leu |
| Gly | Asp 530 | Val | Asn | Gly | Asp | Lys 535 | Leu | Thr | Asp | Val | Ala 540 | Ile | Gly | Ala Pro |
| Gly 545 | Glu | Glu | Asp | Asn | Arg 550 | Gly | Ala | Val | Tyr | Leu 555 | Phe | His | Gly | Thr Ser 560 |
| Gly | Ser | Gly | Ile | Ser 565 | Pro | Ser | His | Ser | Gln 570 | Arg | Ile | Ala | Gly | Ser Lys 575 |
| Leu | Ser | Pro | Arg 580 | Leu | Gln | Tyr | Phe | Gly 585 | Gln | Ser | Leu | Ser | Gly 590 | Gly Gln |
| Asp | Leu | Thr 595 | Met | Asp | Gly | Leu | Val 600 | Asp | Leu | Thr | Val | Gly 605 | Ala | Gln Gly |
| His | Val 610 | Leu | Leu | Leu | Arg | Ser 615 | Gln | Pro | Val | Leu | Arg 620 | Val | Lys | Ala Ile |
| Met 625 | Glu | Phe | Asn | Pro | Arg 630 | Glu | Val | Ala | Arg | Asn 635 | Val | Phe | Glu | Cys Asn 640 |
| Asp | Gln | Val | Val | Lys 645 | Gly | Lys | Glu | Ala | Gly 650 | Glu | Val | Arg | Val | Cys Leu 655 |
| His | Val | Gln | Lys 660 | Ser | Thr | Arg | Asp | Arg 665 | Leu | Arg | Glu | Gly | Gln 670 | Ile Gln |
| Ser | Val | Val 675 | Thr | Tyr | Asp | Leu | Ala 680 | Leu | Asp | Ser | Gly | Arg 685 | Pro | His Ser |
| Arg | Ala 690 | Val | Phe | Asn | Glu | Thr 695 | Lys | Asn | Ser | Thr | Arg 700 | Arg | Gln | Thr Gln |
| Val 705 | Leu | Gly | Leu | Thr | Gln 710 | Thr | Cys | Glu | Thr | Leu 715 | Lys | Leu | Gln | Leu Pro 720 |

-continued

```
Asn  Cys  Ile  Glu  Asp  Pro  Val  Ser  Pro  Ile  Val  Leu  Arg  Leu  Asn  Phe
               725                730                          735

Ser  Leu  Val  Gly  Thr  Pro  Leu  Ser  Ala  Phe  Gly  Asn  Leu  Arg  Pro  Val
          740                745                          750

Leu  Ala  Glu  Asp  Ala  Gln  Arg  Leu  Phe  Thr  Ala  Leu  Phe  Pro  Phe  Glu
     755                     760                     765

Lys  Asn  Cys  Gly  Asn  Asp  Ile  Cys  Gln  Asp  Leu  Ser  Ile  Thr
770                775                     780

Phe  Ser  Phe  Met  Ser  Leu  Asp  Cys  Leu  Val  Val  Gly  Gly  Pro  Arg  Glu
785                790                     795                          800

Phe  Asn  Val  Thr  Val  Thr  Val  Arg  Asn  Asp  Gly  Glu  Asp  Ser  Tyr  Arg
               805                810                          815

Thr  Gln  Val  Thr  Phe  Phe  Pro  Leu  Asp  Leu  Ser  Tyr  Arg  Lys  Val
               820                825                     830

Ser  Thr  Leu  Gln  Asn  Gln  Arg  Ser  Gln  Arg  Ser  Trp  Arg  Leu  Ala  Cys
          835                     840                840 845

Glu  Ser  Ala  Ser  Ser  Thr  Glu  Val  Ser  Gly  Ala  Leu  Lys  Ser  Thr  Ser
850                     855                     860

Cys  Ser  Ile  Asn  His  Pro  Ile  Phe  Pro  Glu  Asn  Ser  Glu  Val  Thr  Phe
865                870                     875                          880

Asn  Ile  Thr  Phe  Asp  Val  Asp  Ser  Lys  Ala  Ser  Leu  Gly  Asn  Lys  Leu
               885                     890                          895

Leu  Leu  Lys  Ala  Asn  Val  Thr  Ser  Glu  Asn  Asn  Met  Pro  Arg  Thr  Asn
               900                     905                          910

Lys  Thr  Glu  Phe  Gln  Leu  Glu  Leu  Pro  Val  Lys  Tyr  Ala  Val  Tyr  Met
               915                     920                     925

Val  Val  Thr  Ser  His  Gly  Val  Ser  Thr  Lys  Tyr  Leu  Asn  Phe  Thr  Ala
     930                     935                     940

Ser  Glu  Asn  Thr  Ser  Arg  Val  Met  Gln  His  Gln  Tyr  Gln  Val  Ser  Asn
945                     950                     955                          960

Leu  Gly  Gln  Arg  Ser  Leu  Pro  Ile  Ser  Leu  Val  Phe  Leu  Val  Pro  Val
                    965                     970                          975

Arg  Leu  Asn  Gln  Thr  Val  Ile  Trp  Asp  Arg  Pro  Gln  Val  Thr  Phe  Ser
               980                     985                     990

Glu  Asn  Leu  Ser  Ser  Thr  Cys  His  Thr  Lys  Glu  Arg  Leu  Pro  Ser  His
               995                     1000                    1005

Ser  Asp  Phe  Leu  Ala  Glu  Leu  Arg  Lys  Ala  Pro  Val  Val  Asn  Cys  Ser
          1010                    1015                    1020

Ile  Ala  Val  Cys  Gln  Arg  Ile  Gln  Cys  Asp  Ile  Pro  Phe  Phe  Gly  Ile
1025                    1030                    1035                         1040

Gln  Glu  Glu  Phe  Asn  Ala  Thr  Leu  Lys  Gly  Asn  Leu  Ser  Phe  Asp  Trp
                    1045                    1050                         1055

Tyr  Ile  Lys  Thr  Ser  His  Asn  His  Leu  Leu  Ile  Val  Ser  Thr  Ala  Glu
               1060                    1065                    1070

Ile  Leu  Phe  Asn  Asp  Ser  Val  Phe  Thr  Leu  Leu  Pro  Gly  Gln  Gly  Ala
          1075                    1080                    1085

Phe  Val  Arg  Ser  Gln  Thr  Glu  Thr  Lys  Val  Glu  Pro  Phe  Glu  Val  Pro
     1090                    1095                    1100

Asn  Pro  Leu  Pro  Leu  Ile  Val  Gly  Ser  Ser  Val  Gly  Gly  Leu  Leu  Leu
1105                    1110                    1115                         1120

Leu  Ala  Leu  Ile  Thr  Ala  Ala  Leu  Tyr  Lys  Leu  Gly  Phe  Phe  Lys  Arg
                    1125                    1130                         1135

Gln  Tyr  Lys  Asp  Met  Met  Ser  Glu  Gly  Gly  Pro  Pro  Gly  Ala  Glu  Pro
               1140                    1145                         1150
```

Gln (2) INFORMATION FOR SEQ ID NO:4:

(i) SEQUENCE CHARACTERISTICS:
        (A) LENGTH: 1163 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Thr Arg Thr Arg Ala Ala Leu Leu Leu Phe Thr Ala Leu Ala Thr
 1               5                  10                  15
Ser Leu Gly Phe Asn Leu Asp Thr Glu Glu Leu Thr Ala Phe Arg Val
            20                  25                  30
Asp Ser Ala Gly Phe Gly Asp Ser Val Val Gln Tyr Ala Asn Ser Trp
        35                  40                  45
Val Val Val Gly Ala Pro Gln Lys Ile Ile Ala Ala Asn Gln Ile Gly
    50                  55                  60
Gly Leu Tyr Gln Cys Gly Tyr Ser Thr Gly Ala Cys Glu Pro Ile Gly
65                  70                  75                  80
Leu Gln Val Pro Pro Glu Ala Val Asn Met Ser Leu Gly Leu Ser Leu
                85                  90                  95
Ala Ser Thr Thr Ser Pro Ser Gln Leu Leu Ala Cys Gly Pro Thr Val
            100                 105                 110
His His Glu Cys Gly Arg Asn Met Tyr Leu Thr Gly Leu Cys Phe Leu
        115                 120                 125
Leu Gly Pro Thr Gln Leu Thr Gln Arg Leu Pro Val Ser Arg Gln Glu
    130                 135                 140
Cys Pro Arg Gln Glu Gln Asp Ile Val Phe Leu Ile Asp Gly Ser Gly
145                 150                 155                 160
Ser Ile Ser Ser Arg Asn Phe Ala Thr Met Met Asn Phe Val Arg Ala
                165                 170                 175
Val Ile Ser Gln Phe Gln Arg Pro Ser Thr Gln Phe Ser Leu Met Gln
            180                 185                 190
Phe Ser Asn Lys Phe Gln Thr His Phe Thr Phe Glu Glu Phe Arg Arg
        195                 200                 205
Thr Ser Asn Pro Leu Ser Leu Leu Ala Ser Val His Gln Leu Gln Gly
    210                 215                 220
Phe Thr Tyr Thr Ala Thr Ala Ile Gln Asn Val Val His Arg Leu Phe
225                 230                 235                 240
His Ala Ser Tyr Gly Ala Arg Arg Asp Ala Ile Lys Ile Leu Ile Val
                245                 250                 255
Ile Thr Asp Gly Lys Lys Glu Gly Asp Ser Leu Asp Tyr Lys Asp Val
            260                 265                 270
Ile Pro Met Ala Asp Ala Ala Gly Ile Ile Arg Tyr Ala Ile Gly Val
        275                 280                 285
Gly Leu Ala Phe Gln Asn Arg Asn Ser Trp Lys Glu Leu Asn Asp Ile
    290                 295                 300
Ala Ser Lys Pro Ser Gln Glu His Ile Phe Lys Val Glu Asp Phe Asp
305                 310                 315                 320
Ala Leu Lys Asp Ile Gln Asn Gln Leu Lys Glu Lys Ile Phe Ala Ile
                325                 330                 335
Glu Gly Thr Glu Thr Ile Ser Ser Ser Ser Phe Glu Leu Glu Met Ala
```

-continued

|  |  |  | 340 |  |  |  | 345 |  |  |  | 350 |  |  |
|---|---|---|---|---|---|---|---|---|---|---|---|---|---|
| Gln | Glu | Gly | Phe | Ser | Ala | Val | Phe | Thr | Pro | Asp | Gly | Pro | Val | Leu | Gly |
|  |  | 355 |  |  |  |  | 360 |  |  |  | 365 |  |  |
| Ala | Val | Gly | Ser | Phe | Thr | Trp | Ser | Gly | Gly | Ala | Phe | Leu | Tyr | Pro | Pro |
| 370 |  |  |  |  |  | 375 |  |  |  |  | 380 |  |  |
| Asn | Met | Ser | Pro | Thr | Phe | Ile | Asn | Met | Ser | Gln | Glu | Asn | Val | Asp | Met |
| 385 |  |  |  |  | 390 |  |  |  |  | 395 |  |  |  |  | 400 |
| Arg | Asp | Ser | Tyr | Leu | Gly | Tyr | Ser | Thr | Glu | Leu | Ala | Leu | Trp | Lys | Gly |
|  |  |  |  | 405 |  |  |  |  | 410 |  |  |  |  | 415 |  |
| Val | Gln | Ser | Leu | Val | Leu | Gly | Ala | Pro | Arg | Tyr | Gln | His | Ile | Gly | Lys |
|  |  |  | 420 |  |  |  |  | 425 |  |  |  |  | 430 |  |  |
| Ala | Val | Ile | Phe | Ile | Gln | Val | Ser | Arg | Gln | Trp | Arg | Met | Lys | Ala | Glu |
|  |  | 435 |  |  |  |  | 440 |  |  |  |  | 445 |  |  |  |
| Val | Ile | Gly | Thr | Gln | Ile | Gly | Ser | Tyr | Phe | Gly | Ala | Ser | Leu | Cys | Ser |
|  |  | 450 |  |  |  |  | 455 |  |  |  |  | 460 |  |  |  |
| Val | Asp | Val | Asp | Thr | Asp | Gly | Ser | Thr | Asp | Leu | Val | Leu | Ile | Gly | Ala |
| 465 |  |  |  |  | 470 |  |  |  |  | 475 |  |  |  |  | 480 |
| Pro | His | Tyr | Tyr | Glu | Gln | Thr | Arg | Gly | Gly | Gln | Val | Ser | Val | Cys | Pro |
|  |  |  |  | 485 |  |  |  |  | 490 |  |  |  |  | 495 |  |
| Leu | Pro | Arg | Gly | Trp | Arg | Arg | Trp | Trp | Cys | Asp | Ala | Val | Leu | Tyr | Gly |
|  |  |  | 500 |  |  |  |  | 505 |  |  |  |  | 510 |  |  |
| Glu | Gln | Gly | His | Pro | Trp | Gly | Arg | Phe | Gly | Ala | Ala | Leu | Thr | Val | Leu |
|  |  | 515 |  |  |  |  | 520 |  |  |  |  | 525 |  |  |  |
| Gly | Asp | Val | Asn | Gly | Asp | Lys | Leu | Thr | Asp | Val | Val | Ile | Gly | Ala | Pro |
|  | 530 |  |  |  |  | 535 |  |  |  |  | 540 |  |  |  |  |
| Gly | Glu | Glu | Glu | Asn | Arg | Gly | Ala | Val | Tyr | Leu | Phe | His | Gly | Val | Leu |
| 545 |  |  |  |  | 550 |  |  |  |  | 555 |  |  |  |  | 560 |
| Gly | Pro | Ser | Ile | Ser | Pro | Ser | His | Ser | Gln | Arg | Ile | Ala | Gly | Ser | Gln |
|  |  |  |  | 565 |  |  |  |  | 570 |  |  |  |  | 575 |  |
| Leu | Ser | Ser | Arg | Leu | Gln | Tyr | Phe | Gly | Gln | Ala | Leu | Ser | Gly | Gly | Gln |
|  |  |  | 580 |  |  |  |  | 585 |  |  |  |  | 590 |  |  |
| Asp | Leu | Thr | Gln | Asp | Gly | Leu | Val | Asp | Leu | Ala | Val | Gly | Ala | Arg | Gly |
|  |  | 595 |  |  |  |  | 600 |  |  |  |  | 605 |  |  |  |
| Gln | Val | Leu | Leu | Leu | Arg | Thr | Arg | Pro | Val | Leu | Trp | Val | Gly | Val | Ser |
|  | 610 |  |  |  |  | 615 |  |  |  |  | 620 |  |  |  |  |
| Met | Gln | Phe | Ile | Pro | Ala | Glu | Ile | Pro | Arg | Ser | Ala | Phe | Glu | Cys | Arg |
| 625 |  |  |  |  | 630 |  |  |  |  | 635 |  |  |  |  | 640 |
| Glu | Gln | Val | Val | Ser | Glu | Gln | Thr | Leu | Val | Gln | Ser | Asn | Ile | Cys | Leu |
|  |  |  |  | 645 |  |  |  |  | 650 |  |  |  |  | 655 |  |
| Tyr | Ile | Asp | Lys | Arg | Ser | Lys | Asn | Leu | Leu | Gly | Ser | Arg | Asp | Leu | Gln |
|  |  |  | 660 |  |  |  |  | 665 |  |  |  |  | 670 |  |  |
| Ser | Ser | Val | Thr | Leu | Asp | Leu | Ala | Leu | Ala | Pro | Gly | Arg | Leu | Ser | Pro |
|  |  | 675 |  |  |  |  | 680 |  |  |  |  | 685 |  |  |  |
| Arg | Ala | Ile | Phe | Gln | Glu | Thr | Lys | Asn | Arg | Ser | Leu | Ser | Arg | Val | Arg |
|  | 690 |  |  |  |  | 695 |  |  |  |  | 700 |  |  |  |  |
| Val | Leu | Gly | Leu | Lys | Ala | His | Cys | Glu | Asn | Phe | Asn | Leu | Leu | Leu | Pro |
| 705 |  |  |  |  | 710 |  |  |  |  | 715 |  |  |  |  | 720 |
| Ser | Cys | Val | Glu | Asp | Ser | Val | Ile | Pro | Ile | Ile | Leu | Arg | Leu | Asn | Phe |
|  |  |  |  | 725 |  |  |  |  | 730 |  |  |  |  | 735 |  |
| Thr | Leu | Val | Gly | Lys | Pro | Leu | Leu | Ala | Phe | Arg | Asn | Leu | Arg | Pro | Met |
|  |  |  | 740 |  |  |  |  | 745 |  |  |  |  | 750 |  |  |
| Leu | Ala | Ala | Leu | Ala | Gln | Arg | Tyr | Phe | Thr | Ala | Ser | Leu | Pro | Phe | Glu |
|  |  | 755 |  |  |  |  | 760 |  |  |  |  | 765 |  |  |  |

```
Lys  Asn  Cys  Gly  Ala  Asp  His  Ile  Cys  Gln  Asp  Asn  Leu  Gly  Ile  Ser
     770                 775                 780
Phe  Ser  Phe  Pro  Gly  Leu  Lys  Ser  Leu  Leu  Val  Gly  Ser  Asn  Leu  Glu
785                 790                 795                 800
Leu  Asn  Ala  Glu  Val  Met  Val  Trp  Asn  Asp  Gly  Glu  Asp  Ser  Tyr  Gly
               805                 810                 815
Thr  Thr  Ile  Thr  Phe  Ser  His  Pro  Ala  Gly  Leu  Ser  Tyr  Arg  Tyr  Val
               820                 825                 830
Ala  Glu  Gly  Gln  Lys  Gln  Gly  Gln  Leu  Arg  Ser  Leu  His  Leu  Thr  Cys
          835                 840                 845
Cys  Ser  Ala  Pro  Val  Gly  Ser  Gln  Gly  Thr  Trp  Ser  Thr  Ser  Cys  Arg
     850                 855                 860
Ile  Asn  His  Leu  Ile  Phe  Arg  Gly  Gly  Ala  Gln  Ile  Thr  Phe  Leu  Ala
865                 870                 875                 880
Thr  Phe  Asp  Val  Ser  Pro  Lys  Ala  Val  Gly  Leu  Asp  Arg  Leu  Leu  Leu
                    885                 890                 895
Ile  Ala  Asn  Val  Ser  Ser  Glu  Asn  Asn  Ile  Pro  Arg  Thr  Ser  Lys  Thr
               900                 905                 910
Ile  Phe  Gln  Leu  Glu  Leu  Pro  Val  Lys  Tyr  Ala  Val  Tyr  Ile  Val  Val
          915                 920                 925
Ser  Ser  His  Glu  Gln  Phe  Thr  Lys  Tyr  Leu  Asn  Phe  Ser  Glu  Ser  Glu
     930                 935                 940
Glu  Lys  Glu  Ser  His  Val  Ala  Met  His  Arg  Tyr  Gln  Val  Asn  Asn  Leu
945                 950                 955                 960
Gly  Gln  Arg  Asp  Leu  Pro  Val  Ser  Ile  Asn  Phe  Trp  Val  Pro  Val  Glu
                    965                 970                 975
Leu  Asn  Gln  Glu  Ala  Val  Trp  Met  Asp  Val  Glu  Val  Ser  His  Pro  Gln
               980                 985                 990
Asn  Pro  Ser  Leu  Arg  Cys  Ser  Ser  Glu  Lys  Ile  Ala  Pro  Pro  Ala  Ser
          995                 1000                1005
Asp  Phe  Leu  Ala  His  Ile  Gln  Lys  Asn  Pro  Val  Leu  Asp  Cys  Ser  Ile
     1010                1015                1020
Ala  Gly  Cys  Leu  Arg  Phe  Arg  Cys  Asp  Val  Pro  Ser  Phe  Ser  Val  Gln
1025                1030                1035                1040
Glu  Glu  Leu  Asp  Phe  Thr  Leu  Lys  Gly  Asn  Leu  Ser  Phe  Gly  Trp  Val
                    1045                1050                1055
Arg  Gln  Ile  Leu  Gln  Lys  Lys  Val  Ser  Val  Val  Ser  Val  Ala  Glu  Ile
               1060                1065                1070
Ile  Phe  Asp  Thr  Ser  Val  Tyr  Ser  Gln  Leu  Pro  Gly  Gln  Glu  Ala  Phe
          1075                1080                1085
Met  Arg  Ala  Gln  Thr  Ile  Thr  Val  Leu  Glu  Lys  Tyr  Lys  Val  His  Asn
     1090                1095                1100
Pro  Ile  Pro  Leu  Ile  Val  Gly  Ser  Ser  Ile  Gly  Gly  Leu  Leu  Leu  Leu
1105                1110                1115                1120
Ala  Leu  Ile  Thr  Ala  Val  Leu  Tyr  Lys  Val  Gly  Phe  Phe  Lys  Arg  Gln
                    1125                1130                1135
Tyr  Lys  Glu  Met  Met  Glu  Glu  Ala  Asn  Gly  Gln  Ile  Ala  Pro  Glu  Asn
               1140                1145                1150
Gly  Thr  Gln  Thr  Pro  Ser  Pro  Pro  Ser  Glu  Lys
          1155                1160
```

( 2 ) INFORMATION FOR SEQ ID NO:5:

( i ) SEQUENCE CHARACTERISTICS:

( A ) LENGTH: 12 amino acids ( B ) TYPE: amino acid
( D ) TOPOLOGY: linear ( i i ) MOLECULE TYPE: peptide ( x i ) SEQUENCE DESCRIPTION: SEQ ID NO:5:

Phe Asn Leu Asp Val Glu Glu Pro Met Val Phe Gln
1               5                   10

( 2 ) INFORMATION FOR SEQ ID NO:6:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA                                    35

( 2 ) INFORMATION FOR SEQ ID NO:7:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA                                   36

( 2 ) INFORMATION FOR SEQ ID NO:8:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCCATGGTC TTCCAA                                   36

( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:9:

TTYAAYYTNG AYGTNGARGA RCC                                                 23

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:10:

TTYAAYYTGG ACGTNGAAGA 20

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TGRAANACCA TNGGYTC 17

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TTGGAAGACC ATNGG YTC 18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATTAACCCTC ACTAAAG 17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AATACGACTC ACTATAG 17

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Val Phe Gln Glu Xaa Gly Ala Gly Phe Gly Gln
1           5                   10

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Leu  Tyr  Asp  Xaa  Val  Ala  Ala  Thr  Gly  Leu  Xaa  Gln  Pro  Ile
 1                  5                        10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Pro  Leu  Glu  Tyr  Xaa  Asp  Val  Ile  Pro  Gln  Ala  Glu
 1                  5                        10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Phe  Gln  Glu  Gly  Phe  Ser  Xaa  Val  Leu  Xaa
 1                  5                        10
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Thr  Ser  Pro  Thr  Phe  Ile  Xaa  Met  Ser  Gln  Glu  Asn  Val  Asp
 1                  5                        10
```

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Leu  Val  Val  Gly  Ala  Pro  Leu  Glu  Val  Val  Ala  Val  Xaa  Gln  Thr  Gly
 1                  5                        10                       15
Arg
```

( 2 ) INFORMATION FOR SEQ ID NO:21:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
1               5

( 2 ) INFORMATION FOR SEQ ID NO:22:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:22:

Phe Gly Glu Gln Phe Ser Glu
1               5

( 2 ) INFORMATION FOR SEQ ID NO:23:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:23:

RAANCCYTCY TGRAAACTYT C                                                    21

( 2 ) INFORMATION FOR SEQ ID NO:24:

( i ) SEQUENCE CHARACTERISTICS:
    ( A ) LENGTH: 1006 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:24:

```
TTCAACCTGG ACGTGGAGGA GCCCATGGTG TTCAAGAGGA TGGAGCTGGC TTTGGACAGA      60
GCGTGGCCCA GCTTGGCGGA TCTAGACTCG TGGTGGGAGC CCCCCTGGAG GTGGTGGCGG     120
TCAACCAAAC AGGAAGGTTG TATGACTGTG TGGCTGCCAC TGGCCTTGTC AACCCATACC     180
CCTGCACACA CCCCCAGATG CTGTGAACAT GTCCCTGGGT CTGTCCCTGT CAGCCGCCGC     240
CAGTCGCCCC TGGCTGCTGG CCTGTGGCCC AACCATGCAC AGAGCCTGTG GGGAGAATAT     300
GTATGCAGAA GGCTTTTGCC TCCTGTTGGA CTCCCATCTG CAGACCATTT GGACAGTACC     360
TGCTGCCCTA CCAGAGTGTC CAAGTCAAGA GATGGACATT GTCTTCCTGA TTGATGGTTC     420
TGGCAGTATG AGCAAAGTGA CTTTAAACAA ATGAAGGATT TGTGAGAGCT GTGATGGGAC     480
AGTTTGAGGG CACCCAAACC CTGTTCTCAC TGATACAGTA TCCCACCTCC CTGAAGATCC     540
ACTTCACCTT CACGCAATTC CAGAGCAGCT GGAACCCTCT GAGCCTGGTG GATCCCATTG     600
TCCAACTGGA CGGCCTGACA TATACAGCCA CGGGCATCCG GAAAGTGGTG GAGGAACTGT     660
TTCATAGTAA GAATGGGGCC CGTAAAAGTG CCAAGAAGAT CCTCATTGTC ATCACAGATG     720
```

| GCAAAAATAC | AAAGACCCCC | TGGAGTACGA | GGACGTATCC | CCAGGCAGAG | AGAGCGGATC | 780 |
| ATCCGCTATG | CCATTGGGGT | GGGAGATGCT | TTCTGGAAAC | CCAGTGCCAA | GCAGGAGCTG | 840 |
| GACAACATTG | GCTCAGAGCC | GGCTCAGGAC | CATGTGTTCA | GGGTGGACAA | CTTTGCAGCA | 900 |
| CTCAGCAGCA | TCCAGGAGCA | GCTGCAGGAG | AAGATCTTTG | CACTCGAAGG | AACCCAGTCG | 960 |
| ACGACAAGTA | GCTCTTTCCA | ACATGAGATG | TTCCAAGAAG | GGTTCA | | 1006 |

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTNTTYCARG ARGAYGG 17

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACTGTCAG GATGCCCGTG 20

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

AGTTACGAAT TCGCCACCAT GGCTCTACGG GTGCTTCTTC TG 42

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AGTTACGAAT TCGCCACCAT GACTCGGACT GTGCTTCTTC TG 42

( 2 ) INFORMATION FOR SEQ ID NO:29:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AGTTACGAAT TCGCCACCAT GACCTTCGGC ACTGTG                36

( 2 ) INFORMATION FOR SEQ ID NO:30:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:30:

TTGCTGACTG CCTGCAGTTC                20

( 2 ) INFORMATION FOR SEQ ID NO:31:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:31:

GTTCTGACGC GTAATGGCAT TGTAGACCTC GTCTTC                36

( 2 ) INFORMATION FOR SEQ ID NO:32:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:32:

ACGTATGCAG GATCCCATCA AGAGATGGAC ATCGCT                36

( 2 ) INFORMATION FOR SEQ ID NO:33:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:33:

ACTGCATGTC TCGAGGCTGA AGCCTTCTTG GGACATC                37

( 2 ) INFORMATION FOR SEQ ID NO:34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:34:

TATAGACTGC TGGGTAGTCC CCAC                24

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

```
TGAAGATTGG GGGTAAATAA CAGA                                        24
```

( 2 ) INFORMATION FOR SEQ ID NO:36:

( i ) SEQUENCE CHARACTERISTICS:
        ( A ) LENGTH: 3528 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3456

( x i ) SEQUENCE DESCRIPTION: SEQ ID NO:36:

```
GGC  TGG  GCC  CTG  GCT  TCC  TGT  CAT  GGG  TCT  AAC  CTG  GAT  GTG  GAG  GAA    48
Gly  Trp  Ala  Leu  Ala  Ser  Cys  His  Gly  Ser  Asn  Leu  Asp  Val  Glu  Glu
 1              5                        10                       15

CCC  ATC  GTG  TTC  AGA  GAG  GAT  GCA  GCC  AGC  TTT  GGA  CAG  ACT  GTG  GTG    96
Pro  Ile  Val  Phe  Arg  Glu  Asp  Ala  Ala  Ser  Phe  Gly  Gln  Thr  Val  Val
               20                        25                       30

CAG  TTT  GGT  GGA  TCT  CGA  CTC  GTG  GTG  GGA  GCC  CCT  CTG  GAG  GCG  GTG   144
Gln  Phe  Gly  Gly  Ser  Arg  Leu  Val  Val  Gly  Ala  Pro  Leu  Glu  Ala  Val
                    35                        40                  45

GCA  GTC  AAC  CAA  ACA  GGA  CGG  TTG  TAT  GAC  TGT  GCA  CCT  GCC  ACT  GGC   192
Ala  Val  Asn  Gln  Thr  Gly  Arg  Leu  Tyr  Asp  Cys  Ala  Pro  Ala  Thr  Gly
          50                        55                  60

ATG  TGC  CAG  CCC  ATC  GTA  CTG  CGC  AGT  CCC  CTA  GAG  GCA  GTG  AAC  ATG   240
Met  Cys  Gln  Pro  Ile  Val  Leu  Arg  Ser  Pro  Leu  Glu  Ala  Val  Asn  Met
 65                      70                       75                          80

TCC  CTG  GGC  CTG  TCT  CTG  GTG  ACT  GCC  ACC  AAT  AAC  GCC  CAG  TTG  CTG   288
Ser  Leu  Gly  Leu  Ser  Leu  Val  Thr  Ala  Thr  Asn  Asn  Ala  Gln  Leu  Leu
                    85                        90                  95

GCT  TGT  GGT  CCA  ACT  GCA  CAG  AGA  GCT  TGT  GTG  AAG  AAC  ATG  TAT  GCG   336
Ala  Cys  Gly  Pro  Thr  Ala  Gln  Arg  Ala  Cys  Val  Lys  Asn  Met  Tyr  Ala
              100                       105                      110

AAA  GGT  TCC  TGC  CTC  CTT  CTC  GGC  TCC  AGC  TTG  CAG  TTC  ATC  CAG  GCA   384
Lys  Gly  Ser  Cys  Leu  Leu  Leu  Gly  Ser  Ser  Leu  Gln  Phe  Ile  Gln  Ala
         115                       120                      125

GTC  CCT  GCC  TCC  ATG  CCA  GAG  TGT  CCA  AGA  CAA  GAG  ATG  GAC  ATT  GCT   432
Val  Pro  Ala  Ser  Met  Pro  Glu  Cys  Pro  Arg  Gln  Glu  Met  Asp  Ile  Ala
     130                      135                      140

TTC  CTG  ATT  GAT  GGT  TCT  GGC  AGC  ATT  AAC  CAA  AGG  GAC  TTT  GCC  CAG   480
Phe  Leu  Ile  Asp  Gly  Ser  Gly  Ser  Ile  Asn  Gln  Arg  Asp  Phe  Ala  Gln
145                      150                      155                     160

ATG  AAG  GAC  TTT  GTC  AAA  GCT  TTG  ATG  GGA  GAG  TTT  GCG  AGC  ACC  AGC   528
Met  Lys  Asp  Phe  Val  Lys  Ala  Leu  Met  Gly  Glu  Phe  Ala  Ser  Thr  Ser
                    165                      170                     175

ACC  TTG  TTC  TCC  CTG  ATG  CAA  TAC  TCG  AAC  ATC  CTG  AAG  ACC  CAT  TTT   576
Thr  Leu  Phe  Ser  Leu  Met  Gln  Tyr  Ser  Asn  Ile  Leu  Lys  Thr  His  Phe
               180                       185                     190
```

| | | | | | | | | | | | | | | | | |
|---|---|---|---|---|---|---|---|---|---|---|---|---|---|---|---|---|
| ACC | TTC | ACT | GAA | TTC | AAG | AAC | ATC | CTG | GAC | CCT | CAG | AGC | CTG | GTG | GAT | 624 |
| Thr | Phe | Thr | Glu | Phe | Lys | Asn | Ile | Leu | Asp | Pro | Gln | Ser | Leu | Val | Asp | |
| | | 195 | | | | | 200 | | | | | 205 | | | | |
| CCC | ATT | GTC | CAG | CTG | CAA | GGC | CTG | ACC | TAC | ACA | GCC | ACA | GGC | ATC | CGG | 672 |
| Pro | Ile | Val | Gln | Leu | Gln | Gly | Leu | Thr | Tyr | Thr | Ala | Thr | Gly | Ile | Arg | |
| | 210 | | | | | 215 | | | | | 220 | | | | | |
| ACA | GTG | ATG | GAA | GAG | CTA | TTT | CAT | AGC | AAG | AAT | GGG | TCC | CGT | AAA | AGT | 720 |
| Thr | Val | Met | Glu | Glu | Leu | Phe | His | Ser | Lys | Asn | Gly | Ser | Arg | Lys | Ser | |
| 225 | | | | | 230 | | | | | 235 | | | | | 240 | |
| GCC | AAG | AAG | ATC | CTC | CTT | GTC | ATC | ACA | GAT | GGG | CAG | AAA | TAC | AGA | GAC | 768 |
| Ala | Lys | Lys | Ile | Leu | Leu | Val | Ile | Thr | Asp | Gly | Gln | Lys | Tyr | Arg | Asp | |
| | | | | 245 | | | | | 250 | | | | | 255 | | |
| CCC | CTG | GAG | TAT | AGT | GAT | GTC | ATT | CCC | GCC | GCA | GAC | AAA | GCT | GGC | ATC | 816 |
| Pro | Leu | Glu | Tyr | Ser | Asp | Val | Ile | Pro | Ala | Ala | Asp | Lys | Ala | Gly | Ile | |
| | | | 260 | | | | | 265 | | | | | 270 | | | |
| ATT | CGT | TAT | GCT | ATT | GGG | GTG | GGA | GAT | GCC | TTC | CAG | GAG | CCC | ACT | GCC | 864 |
| Ile | Arg | Tyr | Ala | Ile | Gly | Val | Gly | Asp | Ala | Phe | Gln | Glu | Pro | Thr | Ala | |
| | | 275 | | | | | 280 | | | | | 285 | | | | |
| CTG | AAG | GAG | CTG | AAC | ACC | ATT | GGC | TCA | GCT | CCC | CCA | CAG | GAC | CAC | GTG | 912 |
| Leu | Lys | Glu | Leu | Asn | Thr | Ile | Gly | Ser | Ala | Pro | Pro | Gln | Asp | His | Val | |
| | 290 | | | | | 295 | | | | | 300 | | | | | |
| TTC | AAG | GTA | GGC | AAC | TTT | GCA | GCA | CTT | CGC | AGC | ATC | CAG | AGG | CAA | CTT | 960 |
| Phe | Lys | Val | Gly | Asn | Phe | Ala | Ala | Leu | Arg | Ser | Ile | Gln | Arg | Gln | Leu | |
| 305 | | | | | 310 | | | | | 315 | | | | | 320 | |
| CAG | GAG | AAA | ATC | TTC | GCC | ATT | GAG | GGA | ACT | CAA | TCA | AGG | TCA | AGT | AGT | 1008 |
| Gln | Glu | Lys | Ile | Phe | Ala | Ile | Glu | Gly | Thr | Gln | Ser | Arg | Ser | Ser | Ser | |
| | | | | 325 | | | | | 330 | | | | | 335 | | |
| TCC | TTT | CAG | CAC | GAG | ATG | TCA | CAA | GAA | GGT | TTC | AGT | TCA | GCT | CTC | ACA | 1056 |
| Ser | Phe | Gln | His | Glu | Met | Ser | Gln | Glu | Gly | Phe | Ser | Ser | Ala | Leu | Thr | |
| | | | 340 | | | | | 345 | | | | | 350 | | | |
| TCG | GAT | GGA | CCC | GTT | CTG | GGG | GCC | GYG | GGA | AGC | TTC | AGC | TGG | TCC | GGA | 1104 |
| Ser | Asp | Gly | Pro | Val | Leu | Gly | Ala | Xaa | Gly | Ser | Phe | Ser | Trp | Ser | Gly | |
| | | 355 | | | | | 360 | | | | | 365 | | | | |
| GGT | GCC | TTC | TTA | TAT | CCC | CCA | AAT | ACG | AGA | CCC | ACC | TTT | ATC | AAC | ATG | 1152 |
| Gly | Ala | Phe | Leu | Tyr | Pro | Pro | Asn | Thr | Arg | Pro | Thr | Phe | Ile | Asn | Met | |
| | 370 | | | | | 375 | | | | | 380 | | | | | |
| TCT | CAG | GAG | AAT | GTG | GAC | ATG | AGA | GAC | TCC | TAC | CTG | GGT | TAC | TCC | ACC | 1200 |
| Ser | Gln | Glu | Asn | Val | Asp | Met | Arg | Asp | Ser | Tyr | Leu | Gly | Tyr | Ser | Thr | |
| 385 | | | | | 390 | | | | | 395 | | | | | 400 | |
| GCA | GTG | GCC | TTT | TGG | AAG | GGG | GTT | CAC | AGC | CTG | ATC | CTG | GGG | GCC | CCG | 1248 |
| Ala | Val | Ala | Phe | Trp | Lys | Gly | Val | His | Ser | Leu | Ile | Leu | Gly | Ala | Pro | |
| | | | | 405 | | | | | 410 | | | | | 415 | | |
| CGT | CAC | CAG | CAC | ACG | GGG | AAG | GTT | GTC | ATC | TTT | ACC | CAG | GAA | GCC | AGG | 1296 |
| Arg | His | Gln | His | Thr | Gly | Lys | Val | Val | Ile | Phe | Thr | Gln | Glu | Ala | Arg | |
| | | | 420 | | | | | 425 | | | | | 430 | | | |
| CAT | TGG | AGG | CCC | AAG | TCT | GAA | GTC | AGA | GGG | ACA | CAG | ATC | GGC | TCC | TAC | 1344 |
| His | Trp | Arg | Pro | Lys | Ser | Glu | Val | Arg | Gly | Thr | Gln | Ile | Gly | Ser | Tyr | |
| | | 435 | | | | | 440 | | | | | 445 | | | | |
| TTC | GGG | GCC | TCT | CTC | TGT | TCT | GTG | GAC | GTG | GAT | AGA | GAT | GGC | AGC | ACY | 1392 |
| Phe | Gly | Ala | Ser | Leu | Cys | Ser | Val | Asp | Val | Asp | Arg | Asp | Gly | Ser | Xaa | |
| | 450 | | | | | 455 | | | | | 460 | | | | | |
| GAC | CTG | GTC | CTG | ATC | GGA | GCC | CCC | CAT | TAC | TAT | GAG | CAG | ACC | CGA | GGG | 1440 |
| Asp | Leu | Val | Leu | Ile | Gly | Ala | Pro | His | Tyr | Tyr | Glu | Gln | Thr | Arg | Gly | |
| 465 | | | | | 470 | | | | | 475 | | | | | 480 | |
| GGG | CAG | GTC | TCA | GTG | TKC | CCC | GTG | CCC | GGT | GTG | AGG | GGC | AGG | TGG | CAG | 1488 |
| Gly | Gln | Val | Ser | Val | Xaa | Pro | Val | Pro | Gly | Val | Arg | Gly | Arg | Trp | Gln | |
| | | | | 485 | | | | | 490 | | | | | 495 | | |
| TGT | GAG | GCC | ACC | CTC | CAC | GGG | GAG | CAG | GRC | CAT | CCT | TGG | GGC | CGC | TTT | 1536 |
| Cys | Glu | Ala | Thr | Leu | His | Gly | Glu | Gln | Xaa | His | Pro | Trp | Gly | Arg | Phe | |
| | | | 500 | | | | | 505 | | | | | 510 | | | |

| | | | | | | | | | | | | | | | | |
|---|---|---|---|---|---|---|---|---|---|---|---|---|---|---|---|---|
| GGG | GTG | GCT | CTG | ACA | GTG | CTG | GGG | GAC | GTA | AAC | GGG | GAC | AAT | CTG | GCA | 1584 |
| Gly | Val | Ala | Leu | Thr | Val | Leu | Gly | Asp | Val | Asn | Gly | Asp | Asn | Leu | Ala | |
| | 515 | | | | 520 | | | | | 525 | | | | | | |
| GAC | GTG | GCT | ATT | GGT | GCC | CCT | GGA | GAG | GAG | GAG | AGC | AGA | GGT | GCT | GTC | 1632 |
| Asp | Val | Ala | Ile | Gly | Ala | Pro | Gly | Glu | Glu | Glu | Ser | Arg | Gly | Ala | Val | |
| 530 | | | | | 535 | | | | | 540 | | | | | | |
| TAC | ATA | TTT | CAT | GGA | GCC | TCG | AGA | CTG | GAG | ATC | ATG | CCC | TCA | CCC | AGC | 1680 |
| Tyr | Ile | Phe | His | Gly | Ala | Ser | Arg | Leu | Glu | Ile | Met | Pro | Ser | Pro | Ser | |
| 545 | | | | | 550 | | | | | 555 | | | | | 560 | |
| CAG | CGG | GTC | ACT | GGC | TCC | CAG | CTC | TCC | CTG | AGA | CTG | CAG | TAT | TTT | GGG | 1728 |
| Gln | Arg | Val | Thr | Gly | Ser | Gln | Leu | Ser | Leu | Arg | Leu | Gln | Tyr | Phe | Gly | |
| | | | | 565 | | | | | 570 | | | | | 575 | | |
| CAG | TCA | TTG | AGT | GGG | GGT | CAG | GAC | CTT | ACA | CAG | GAT | GGC | CTG | GTG | GAC | 1776 |
| Gln | Ser | Leu | Ser | Gly | Gly | Gln | Asp | Leu | Thr | Gln | Asp | Gly | Leu | Val | Asp | |
| | | | 580 | | | | | 585 | | | | | 590 | | | |
| CTG | GCC | GTG | GGA | GCC | CAG | GGG | CAC | GTA | CTG | CTC | AGG | AGT | CTG | CCT | | 1824 |
| Leu | Ala | Val | Gly | Ala | Gln | Gly | His | Val | Leu | Leu | Leu | Arg | Ser | Leu | Pro | |
| | | 595 | | | | | 600 | | | | | 605 | | | | |
| CTG | CTG | AAA | GTG | GAG | CTC | TCC | ATA | AGA | TTC | GCC | CCC | ATG | GAG | GTG | GCA | 1872 |
| Leu | Leu | Lys | Val | Glu | Leu | Ser | Ile | Arg | Phe | Ala | Pro | Met | Glu | Val | Ala | |
| | | 610 | | | | 615 | | | | | 620 | | | | | |
| AAG | GCT | GTG | TAC | CAG | TGC | TGG | GAA | AGG | ACT | CCC | ACT | GTC | CTC | GAA | GCT | 1920 |
| Lys | Ala | Val | Tyr | Gln | Cys | Trp | Glu | Arg | Thr | Pro | Thr | Val | Leu | Glu | Ala | |
| 625 | | | | | 630 | | | | | 635 | | | | | 640 | |
| GGA | GAG | GCC | ACT | GTC | TGT | CTC | ACT | GTC | CAC | AAA | GGC | TCA | CCT | GAC | CTG | 1968 |
| Gly | Glu | Ala | Thr | Val | Cys | Leu | Thr | Val | His | Lys | Gly | Ser | Pro | Asp | Leu | |
| | | | | 645 | | | | | 650 | | | | | 655 | | |
| TTA | GGT | AAT | GTC | CAA | GGC | TCT | GTC | AGG | TAT | GAT | CTG | GCG | TTA | GAT | CCG | 2016 |
| Leu | Gly | Asn | Val | Gln | Gly | Ser | Val | Arg | Tyr | Asp | Leu | Ala | Leu | Asp | Pro | |
| | | | 660 | | | | | 665 | | | | | 670 | | | |
| GGC | CGC | CTG | ATT | TCT | CGT | GCC | ATT | TTT | GAT | GAG | ACT | AAG | AAC | TGC | ACT | 2064 |
| Gly | Arg | Leu | Ile | Ser | Arg | Ala | Ile | Phe | Asp | Glu | Thr | Lys | Asn | Cys | Thr | |
| | | 675 | | | | | 680 | | | | | 685 | | | | |
| TTG | ACG | GGA | AGG | AAG | ACT | CTG | GGG | CTT | GGT | GAT | CAC | TGC | GAA | ACA | GTG | 2112 |
| Leu | Thr | Gly | Arg | Lys | Thr | Leu | Gly | Leu | Gly | Asp | His | Cys | Glu | Thr | Val | |
| | 690 | | | | | 695 | | | | | 700 | | | | | |
| AAG | CTG | CTT | TTG | CCG | GAC | TGT | GTG | GAA | GAT | GCA | GTG | AGC | CCT | ATC | ATC | 2160 |
| Lys | Leu | Leu | Leu | Pro | Asp | Cys | Val | Glu | Asp | Ala | Val | Ser | Pro | Ile | Ile | |
| 705 | | | | | 710 | | | | | 715 | | | | | 720 | |
| CTG | CGC | CTC | AAC | TTT | TCC | CTG | GTG | AGA | GAC | TCT | GCT | TCA | CCC | AGG | AAC | 2208 |
| Leu | Arg | Leu | Asn | Phe | Ser | Leu | Val | Arg | Asp | Ser | Ala | Ser | Pro | Arg | Asn | |
| | | | | 725 | | | | | 730 | | | | | 735 | | |
| CTG | CAT | CCT | GTG | CTG | GCT | GTG | GGC | TCA | CAA | GAC | CAC | ATA | ACT | GCT | TCT | 2256 |
| Leu | His | Pro | Val | Leu | Ala | Val | Gly | Ser | Gln | Asp | His | Ile | Thr | Ala | Ser | |
| | | | 740 | | | | | 745 | | | | | 750 | | | |
| CTG | CCG | TTT | GAG | AAG | AAC | TGT | AAG | CAA | GAA | CTC | CTG | TGT | GAG | GGG | GAC | 2304 |
| Leu | Pro | Phe | Glu | Lys | Asn | Cys | Lys | Gln | Glu | Leu | Leu | Cys | Glu | Gly | Asp | |
| | | 755 | | | | | 760 | | | | | 765 | | | | |
| CTG | GGC | ATC | AGC | TTT | AAC | TTC | TCA | GGC | CTG | CAG | GTC | TTG | GTG | GTG | GGA | 2352 |
| Leu | Gly | Ile | Ser | Phe | Asn | Phe | Ser | Gly | Leu | Gln | Val | Leu | Val | Val | Gly | |
| | 770 | | | | | 775 | | | | | 780 | | | | | |
| GGC | TCC | CCA | GAG | CTC | ACT | GTG | ACA | GTC | ACT | GTG | TGG | AAT | GAG | GGT | GAG | 2400 |
| Gly | Ser | Pro | Glu | Leu | Thr | Val | Thr | Val | Thr | Val | Trp | Asn | Glu | Gly | Glu | |
| 785 | | | | | 790 | | | | | 795 | | | | | 800 | |
| GAC | AGC | TAT | GGA | ACT | TTA | GTC | AAG | TTC | TAC | TAC | CCA | GCA | GGG | CTA | TCT | 2448 |
| Asp | Ser | Tyr | Gly | Thr | Leu | Val | Lys | Phe | Tyr | Tyr | Pro | Ala | Gly | Leu | Ser | |
| | | | | 805 | | | | | 810 | | | | | 815 | | |
| TAC | CGA | CGG | GTA | ACA | GGG | ACT | CAG | CAA | CCT | CAT | CAG | TAC | CCA | CTA | CGC | 2496 |
| Tyr | Arg | Arg | Val | Thr | Gly | Thr | Gln | Gln | Pro | His | Gln | Tyr | Pro | Leu | Arg | |
| | | | 820 | | | | | 825 | | | | | 830 | | | |

```
TTG GCC TGT GAG GCT GAG CCC GCT GCC CAG GAG GAC CTG AGG AGC AGC       2544
Leu Ala Cys Glu Ala Glu Pro Ala Ala Gln Glu Asp Leu Arg Ser Ser
        835             840             845

AGC TGT AGC ATT AAT CAC CCC ATC TTC CGA GAA GGT GCA AAG ACC ACC       2592
Ser Cys Ser Ile Asn His Pro Ile Phe Arg Glu Gly Ala Lys Thr Thr
850             855             860

TTC ATG ATC ACA TTC GAT GTC TCC TAC AAG GCC TTC CTA GGA GAC AGG       2640
Phe Met Ile Thr Phe Asp Val Ser Tyr Lys Ala Phe Leu Gly Asp Arg
865             870             875             880

TTG CTT CTG AGG GCC AAA GCC AGC AGT GAG AAT AAT AAG CCT GAT ACC       2688
Leu Leu Leu Arg Ala Lys Ala Ser Ser Glu Asn Asn Lys Pro Asp Thr
            885             890             895

AAC AAG ACT GCC TTC CAG CTG GAG CTC CCA GTG AAG TAC ACC GTC TAT       2736
Asn Lys Thr Ala Phe Gln Leu Glu Leu Pro Val Lys Tyr Thr Val Tyr
            900             905             910

ACC CTG ATC AGT AGG CAA GAA GAT TCC ACC AAC CAT GTC AAC TTT TCA       2784
Thr Leu Ile Ser Arg Gln Glu Asp Ser Thr Asn His Val Asn Phe Ser
        915             920             925

TCT TCC CAC GGG GGG AGA AGG CAA GAA GCC GCA CAT CGC TAT CGT GTG       2832
Ser Ser His Gly Gly Arg Arg Gln Glu Ala Ala His Arg Tyr Arg Val
        930             935             940

AAT AAC CTG AGT CCA CTG AAG CTG GCC GTC AGA GTT AAC TTC TGG GTC       2880
Asn Asn Leu Ser Pro Leu Lys Leu Ala Val Arg Val Asn Phe Trp Val
945             950             955             960

CCT GTC CTT CTG AAC GGT GTG GCT GTG TGG GAC GTG ACT CTG AGC AGC       2928
Pro Val Leu Leu Asn Gly Val Ala Val Trp Asp Val Thr Leu Ser Ser
            965             970             975

CCA GCA CAG GGT GTC TCC TGC GTG TCC CAG ATG AAA CCT CCT CAG AAT       2976
Pro Ala Gln Gly Val Ser Cys Val Ser Gln Met Lys Pro Pro Gln Asn
            980             985             990

CCC GAC TTT CTG ACC CAG ATT CAG AGA CGT TCT GTG CTG GAC TGC TCC       3024
Pro Asp Phe Leu Thr Gln Ile Gln Arg Arg Ser Val Leu Asp Cys Ser
        995             1000            1005

ATT GCT GAC TGC CTG CAC TCC CGC TGT GAC ATC CCC TCC TTG GAC ATC       3072
Ile Ala Asp Cys Leu His Ser Arg Cys Asp Ile Pro Ser Leu Asp Ile
1010            1015            1020

CAG GAT GAA CTT GAC TTC ATT CTG AGG GGC AAC CTC AGC TTC GGC TGG       3120
Gln Asp Glu Leu Asp Phe Ile Leu Arg Gly Asn Leu Ser Phe Gly Trp
1025            1030            1035            1040

GTC AGT CAG ACA TTG CAG GAA AAG GTG TTG CTT GTG AGT GAG GCT GAA       3168
Val Ser Gln Thr Leu Gln Glu Lys Val Leu Leu Val Ser Glu Ala Glu
            1045            1050            1055

ATC ACT TTC GAC ACA TCT GTG TAC TCC CAG CTG CCA GGA CAG GAG GCA       3216
Ile Thr Phe Asp Thr Ser Val Tyr Ser Gln Leu Pro Gly Gln Glu Ala
            1060            1065            1070

TTT CTG AGA GCC CAG GTG GAG ACA ACG TTA GAA GAA TAC GTG GTC TAT       3264
Phe Leu Arg Ala Gln Val Glu Thr Thr Leu Glu Glu Tyr Val Val Tyr
        1075            1080            1085

GAG CCC ATC TTC CTC GTG GCG GGC AGC TCG GTG GGA GGT CTG CTG TTA       3312
Glu Pro Ile Phe Leu Val Ala Gly Ser Ser Val Gly Gly Leu Leu Leu
        1090            1095            1100

CTG GCT CTC ATC ACA GTG GTA CTG TAC AAG CTT GGC TYC TYC AAA CGT       3360
Leu Ala Leu Ile Thr Val Val Leu Tyr Lys Leu Gly Xaa Xaa Lys Arg
1105            1110            1115            1120

CAG TAC AAA GAA ATG CTG GAC GGC AAG GCT GCA GAT CCT GTC ACA GCC       3408
Gln Tyr Lys Glu Met Leu Asp Gly Lys Ala Ala Asp Pro Val Thr Ala
            1125            1130            1135

GGC CAG GCA GAT TTC GGC TGT GAG ACT CCT CCA TAT CTC
Gly Gln Ala Asp Phe Gly Cys Glu Thr Pro Pro Tyr Leu
        1140            1145
```

-continued

```
                                            GTG  AGC  TAGGAATCCA                3463
                                            Val  Ser
                                            1150
CTCTCCTGCC  TATCTCTGNA  ATGAAGATTG  GTCCTGCCTA  TGAGTCTACT  GGCATGGGAA           3523

CGAGT                                                                            3528
```

( 2 ) INFORMATION FOR SEQ ID NO:37:

( i ) SEQUENCE CHARACTERISTICS:
        ( A ) LENGTH: 1151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Gly  Trp  Ala  Leu  Ala  Ser  Cys  His  Gly  Ser  Asn  Leu  Asp  Val  Glu  Glu
 1                  5                   10                  15

Pro  Ile  Val  Phe  Arg  Glu  Asp  Ala  Ala  Ser  Phe  Gly  Gln  Thr  Val  Val
               20                  25                  30

Gln  Phe  Gly  Gly  Ser  Arg  Leu  Val  Val  Gly  Ala  Pro  Leu  Glu  Ala  Val
          35                  40                  45

Ala  Val  Asn  Gln  Thr  Gly  Arg  Leu  Tyr  Asp  Cys  Ala  Pro  Ala  Thr  Gly
     50                  55                  60

Met  Cys  Gln  Pro  Ile  Val  Leu  Arg  Ser  Pro  Leu  Glu  Ala  Val  Asn  Met
65                  70                  75                  80

Ser  Leu  Gly  Leu  Ser  Leu  Val  Thr  Ala  Thr  Asn  Asn  Ala  Gln  Leu  Leu
               85                  90                  95

Ala  Cys  Gly  Pro  Thr  Ala  Gln  Arg  Ala  Cys  Val  Lys  Asn  Met  Tyr  Ala
               100                 105                 110

Lys  Gly  Ser  Cys  Leu  Leu  Leu  Gly  Ser  Ser  Leu  Gln  Phe  Ile  Gln  Ala
          115                 120                 125

Val  Pro  Ala  Ser  Met  Pro  Glu  Cys  Pro  Arg  Gln  Glu  Met  Asp  Ile  Ala
     130                 135                 140

Phe  Leu  Ile  Asp  Gly  Ser  Gly  Ser  Ile  Asn  Gln  Arg  Asp  Phe  Ala  Gln
145                 150                 155                 160

Met  Lys  Asp  Phe  Val  Lys  Ala  Leu  Met  Gly  Glu  Phe  Ala  Ser  Thr  Ser
               165                 170                 175

Thr  Leu  Phe  Ser  Leu  Met  Gln  Tyr  Ser  Asn  Ile  Leu  Lys  Thr  His  Phe
               180                 185                 190

Thr  Phe  Thr  Glu  Phe  Lys  Asn  Ile  Leu  Asp  Pro  Gln  Ser  Leu  Val  Asp
          195                 200                 205

Pro  Ile  Val  Gln  Leu  Gln  Gly  Leu  Thr  Tyr  Thr  Ala  Thr  Gly  Ile  Arg
     210                 215                 220

Thr  Val  Met  Glu  Glu  Leu  Phe  His  Ser  Lys  Asn  Gly  Ser  Arg  Lys  Ser
225                 230                 235                 240

Ala  Lys  Lys  Ile  Leu  Leu  Val  Ile  Thr  Asp  Gly  Gln  Lys  Tyr  Arg  Asp
               245                 250                 255

Pro  Leu  Glu  Tyr  Ser  Asp  Val  Ile  Pro  Ala  Ala  Asp  Lys  Ala  Gly  Ile
               260                 265                 270

Ile  Arg  Tyr  Ala  Ile  Gly  Val  Gly  Asp  Ala  Phe  Gln  Glu  Pro  Thr  Ala
          275                 280                 285

Leu  Lys  Glu  Leu  Asn  Thr  Ile  Gly  Ser  Ala  Pro  Pro  Gln  Asp  His  Val
     290                 295                 300

Phe  Lys  Val  Gly  Asn  Phe  Ala  Ala  Leu  Arg  Ser  Ile  Gln  Arg  Gln  Leu
305                 310                 315                 320
```

```
Gln  Glu  Lys  Ile  Phe  Ala  Ile  Glu  Gly  Thr  Gln  Ser  Arg  Ser  Ser
               325                      330                     335

Ser  Phe  Gln  His  Glu  Met  Ser  Gln  Glu  Gly  Phe  Ser  Ser  Ala  Leu  Thr
                    340                      345                    350

Ser  Asp  Gly  Pro  Val  Leu  Gly  Ala  Xaa  Gly  Ser  Phe  Trp  Ser  Gly
               355                      360                     365

Gly  Ala  Phe  Leu  Tyr  Pro  Pro  Asn  Thr  Arg  Pro  Thr  Phe  Ile  Asn  Met
     370                      375                     380

Ser  Gln  Glu  Asn  Val  Asp  Met  Arg  Asp  Ser  Tyr  Leu  Gly  Tyr  Ser  Thr
385                      390                      395                          400

Ala  Val  Ala  Phe  Trp  Lys  Gly  Val  His  Ser  Leu  Ile  Leu  Gly  Ala  Pro
                    405                      410                         415

Arg  His  Gln  His  Thr  Gly  Lys  Val  Val  Ile  Phe  Thr  Gln  Glu  Ala  Arg
                    420                      425                    430

His  Trp  Arg  Pro  Lys  Ser  Glu  Val  Arg  Gly  Thr  Gln  Ile  Gly  Ser  Tyr
               435                      440                     445

Phe  Gly  Ala  Ser  Leu  Cys  Ser  Val  Asp  Val  Asp  Arg  Asp  Gly  Ser  Xaa
     450                      455                     460

Asp  Leu  Val  Leu  Ile  Gly  Ala  Pro  His  Tyr  Tyr  Glu  Gln  Thr  Arg  Gly
465                      470                      475                          480

Gly  Gln  Val  Ser  Val  Xaa  Pro  Val  Pro  Gly  Val  Arg  Gly  Arg  Trp  Gln
                    485                      490                         495

Cys  Glu  Ala  Thr  Leu  His  Gly  Glu  Gln  Xaa  His  Pro  Trp  Gly  Arg  Phe
               500                      505                     510

Gly  Val  Ala  Leu  Thr  Val  Leu  Gly  Asp  Val  Asn  Gly  Asp  Asn  Leu  Ala
               515                      520                     525

Asp  Val  Ala  Ile  Gly  Ala  Pro  Gly  Glu  Glu  Ser  Arg  Gly  Ala  Val
     530                      535                     540

Tyr  Ile  Phe  His  Gly  Ala  Ser  Arg  Leu  Glu  Ile  Met  Pro  Ser  Pro  Ser
545                      550                      555                          560

Gln  Arg  Val  Thr  Gly  Ser  Gln  Leu  Ser  Leu  Arg  Leu  Gln  Tyr  Phe  Gly
                    565                      570                         575

Gln  Ser  Leu  Ser  Gly  Gly  Gln  Asp  Leu  Thr  Gln  Asp  Gly  Leu  Val  Asp
               580                      585                     590

Leu  Ala  Val  Gly  Ala  Gln  Gly  His  Val  Leu  Leu  Leu  Arg  Ser  Leu  Pro
          595                      600                     605

Leu  Leu  Lys  Val  Glu  Leu  Ser  Ile  Arg  Phe  Ala  Pro  Met  Glu  Val  Ala
     610                      615                     620

Lys  Ala  Val  Tyr  Gln  Cys  Trp  Glu  Arg  Thr  Pro  Thr  Val  Leu  Glu  Ala
625                      630                      635                          640

Gly  Glu  Ala  Thr  Val  Cys  Leu  Thr  Val  His  Lys  Gly  Ser  Pro  Asp  Leu
               645                      650                     655

Leu  Gly  Asn  Val  Gln  Gly  Ser  Val  Arg  Tyr  Asp  Leu  Ala  Leu  Asp  Pro
               660                      665                     670

Gly  Arg  Leu  Ile  Ser  Arg  Ala  Ile  Phe  Asp  Glu  Thr  Lys  Asn  Cys  Thr
          675                      680                     685

Leu  Thr  Gly  Arg  Lys  Thr  Leu  Gly  Leu  Gly  Asp  His  Cys  Glu  Thr  Val
     690                      695                     700

Lys  Leu  Leu  Leu  Pro  Asp  Cys  Val  Glu  Asp  Ala  Val  Ser  Pro  Ile  Ile
705                      710                      715                          720

Leu  Arg  Leu  Asn  Phe  Ser  Leu  Val  Arg  Asp  Ser  Ala  Ser  Pro  Arg  Asn
                    725                      730                         735

Leu  His  Pro  Val  Leu  Ala  Val  Gly  Ser  Gln  Asp  His  Ile  Thr  Ala  Ser
               740                      745                     750
```

| Leu | Pro | Phe | Glu | Lys | Asn | Cys | Lys | Gln | Glu | Leu | Leu | Cys | Glu | Gly | Asp |
|---|---|---|---|---|---|---|---|---|---|---|---|---|---|---|---|
| | | 755 | | | | | 760 | | | | | 765 | | | |

| Leu | Gly | Ile | Ser | Phe | Asn | Phe | Ser | Gly | Leu | Gln | Val | Leu | Val | Val | Gly |
|---|---|---|---|---|---|---|---|---|---|---|---|---|---|---|---|
| | 770 | | | | | 775 | | | | | 780 | | | | |

| Gly | Ser | Pro | Glu | Leu | Thr | Val | Thr | Val | Thr | Val | Trp | Asn | Glu | Gly | Glu |
|---|---|---|---|---|---|---|---|---|---|---|---|---|---|---|---|
| 785 | | | | | 790 | | | | 795 | | | | | | 800 |

| Asp | Ser | Tyr | Gly | Thr | Leu | Val | Lys | Phe | Tyr | Tyr | Pro | Ala | Gly | Leu | Ser |
|---|---|---|---|---|---|---|---|---|---|---|---|---|---|---|---|
| | | | | 805 | | | | | 810 | | | | | 815 | |

| Tyr | Arg | Arg | Val | Thr | Gly | Thr | Gln | Gln | Pro | His | Gln | Tyr | Pro | Leu | Arg |
|---|---|---|---|---|---|---|---|---|---|---|---|---|---|---|---|
| | | | 820 | | | | | 825 | | | | | 830 | | |

| Leu | Ala | Cys | Glu | Ala | Glu | Pro | Ala | Ala | Gln | Glu | Asp | Leu | Arg | Ser | Ser |
|---|---|---|---|---|---|---|---|---|---|---|---|---|---|---|---|
| | | | 835 | | | | | 840 | | | | | 845 | | |

| Ser | Cys | Ser | Ile | Asn | His | Pro | Ile | Phe | Arg | Glu | Gly | Ala | Lys | Thr | Thr |
|---|---|---|---|---|---|---|---|---|---|---|---|---|---|---|---|
| | 850 | | | | | 855 | | | | | 860 | | | | |

| Phe | Met | Ile | Thr | Phe | Asp | Val | Ser | Tyr | Lys | Ala | Phe | Leu | Gly | Asp | Arg |
|---|---|---|---|---|---|---|---|---|---|---|---|---|---|---|---|
| 865 | | | | | 870 | | | | 875 | | | | | | 880 |

| Leu | Leu | Leu | Arg | Ala | Lys | Ala | Ser | Ser | Glu | Asn | Asn | Lys | Pro | Asp | Thr |
|---|---|---|---|---|---|---|---|---|---|---|---|---|---|---|---|
| | | | | 885 | | | | | 890 | | | | | 895 | |

| Asn | Lys | Thr | Ala | Phe | Gln | Leu | Glu | Leu | Pro | Val | Lys | Tyr | Thr | Val | Tyr |
|---|---|---|---|---|---|---|---|---|---|---|---|---|---|---|---|
| | | | | 900 | | | | | 905 | | | | | 910 | |

| Thr | Leu | Ile | Ser | Arg | Gln | Glu | Asp | Ser | Thr | Asn | His | Val | Asn | Phe | Ser |
|---|---|---|---|---|---|---|---|---|---|---|---|---|---|---|---|
| | | 915 | | | | | 920 | | | | | 925 | | | |

| Ser | Ser | His | Gly | Gly | Arg | Arg | Gln | Glu | Ala | Ala | His | Arg | Tyr | Arg | Val |
|---|---|---|---|---|---|---|---|---|---|---|---|---|---|---|---|
| | 930 | | | | | 935 | | | | | 940 | | | | |

| Asn | Asn | Leu | Ser | Pro | Leu | Lys | Leu | Ala | Val | Arg | Val | Asn | Phe | Trp | Val |
|---|---|---|---|---|---|---|---|---|---|---|---|---|---|---|---|
| 945 | | | | | 950 | | | | | 955 | | | | | 960 |

| Pro | Val | Leu | Leu | Asn | Gly | Val | Ala | Val | Trp | Asp | Val | Thr | Leu | Ser | Ser |
|---|---|---|---|---|---|---|---|---|---|---|---|---|---|---|---|
| | | | | 965 | | | | | 970 | | | | | 975 | |

| Pro | Ala | Gln | Gly | Val | Ser | Cys | Val | Ser | Gln | Met | Lys | Pro | Pro | Gln | Asn |
|---|---|---|---|---|---|---|---|---|---|---|---|---|---|---|---|
| | | | 980 | | | | | 985 | | | | | 990 | | |

| Pro | Asp | Phe | Leu | Thr | Gln | Ile | Gln | Arg | Arg | Ser | Val | Leu | Asp | Cys | Ser |
|---|---|---|---|---|---|---|---|---|---|---|---|---|---|---|---|
| | | 995 | | | | | 1000 | | | | | 1005 | | | |

| Ile | Ala | Asp | Cys | Leu | His | Ser | Arg | Cys | Asp | Ile | Pro | Ser | Leu | Asp | Ile |
|---|---|---|---|---|---|---|---|---|---|---|---|---|---|---|---|
| | | 1010 | | | | | 1015 | | | | | 1020 | | | |

| Gln | Asp | Glu | Leu | Asp | Phe | Ile | Leu | Arg | Gly | Asn | Leu | Ser | Phe | Gly | Trp |
|---|---|---|---|---|---|---|---|---|---|---|---|---|---|---|---|
| 1025 | | | | | 1030 | | | | | 1035 | | | | | 1040 |

| Val | Ser | Gln | Thr | Leu | Gln | Glu | Lys | Val | Leu | Leu | Val | Ser | Glu | Ala | Glu |
|---|---|---|---|---|---|---|---|---|---|---|---|---|---|---|---|
| | | | | 1045 | | | | | 1050 | | | | | 1055 | |

| Ile | Thr | Phe | Asp | Thr | Ser | Val | Tyr | Ser | Gln | Leu | Pro | Gly | Gln | Glu | Ala |
|---|---|---|---|---|---|---|---|---|---|---|---|---|---|---|---|
| | | | | 1060 | | | | | 1065 | | | | | 1070 | |

| Phe | Leu | Arg | Ala | Gln | Val | Glu | Thr | Thr | Leu | Glu | Glu | Tyr | Val | Val | Tyr |
|---|---|---|---|---|---|---|---|---|---|---|---|---|---|---|---|
| | | | 1075 | | | | | 1080 | | | | | 1085 | | |

| Glu | Pro | Ile | Phe | Leu | Val | Ala | Gly | Ser | Ser | Val | Gly | Gly | Leu | Leu | Leu |
|---|---|---|---|---|---|---|---|---|---|---|---|---|---|---|---|
| | | | 1090 | | | | | 1095 | | | | | 1100 | | |

| Leu | Ala | Leu | Ile | Thr | Val | Val | Leu | Tyr | Lys | Leu | Gly | Xaa | Xaa | Lys | Arg |
|---|---|---|---|---|---|---|---|---|---|---|---|---|---|---|---|
| 1105 | | | | | 1110 | | | | | 1115 | | | | | 1120 |

| Gln | Tyr | Lys | Glu | Met | Leu | Asp | Gly | Lys | Ala | Ala | Asp | Pro | Val | Thr | Ala |
|---|---|---|---|---|---|---|---|---|---|---|---|---|---|---|---|
| | | | | 1125 | | | | | 1130 | | | | | 1135 | |

| Gly | Gln | Ala | Asp | Phe | Gly | Cys | Glu | Thr | Pro | Pro | Tyr | Leu | Val | Ser | |
|---|---|---|---|---|---|---|---|---|---|---|---|---|---|---|---|
| | | | 1140 | | | | | 1145 | | | | | 1150 | | |

( 2 ) INFORMATION FOR SEQ ID NO:38:

( i ) SEQUENCE CHARACTERISTICS:

(A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

GTCCAAGCTG TCATGGGCCA G    21

(2) INFORMATION FOR SEQ ID NO:39:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

GTCCAGCAGA CTGAAGAGCA CGG    23

(2) INFORMATION FOR SEQ ID NO:40:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

TGTAAAACGA CGGCCAGT    18

(2) INFORMATION FOR SEQ ID NO:41:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:41:

GGAAACAGCT ATGACCATG    19

(2) INFORMATION FOR SEQ ID NO:42:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:42:

GGACATGTTC ACTGCCTCTA GG    22

(2) INFORMATION FOR SEQ ID NO:43:

(i) SEQUENCE CHARACTERISTICS:
            (A) LENGTH: 25 base pairs
            (B) TYPE: nucleic acid
            (C) STRANDEDNESS: single
            (D) TOPOLOGY: linear ( i i ) MOLECULE TYPE: DNA ( x i ) SEQUENCE DESCRIPTION: SEQ ID NO:43:

GGCGGACAGT CAGACGACTG TCCTG 25

( 2 ) INFORMATION FOR SEQ ID NO:44:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CTGGTTCGGC CCACCTCTGA AGGTTCCAGA ATCGATAG 38

( 2 ) INFORMATION FOR SEQ ID NO:45:

( i ) SEQUENCE CHARACTERISTICS:
        ( A ) LENGTH: 3519 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 52..3519

( x i ) SEQUENCE DESCRIPTION: SEQ ID NO:45:

```
GCTTTCTGAA GGTTCCAGAA TCGATAGTGA ATTCGTGGGC ACTGCTCAGA T ATG GTC           57
                                                          Met Val
                                                            1

CGT GGA GTT GTG ATC CTC CTG TGT GGC TGG GCC CTG GCT TCC TGT CAT          105
Arg Gly Val Val Ile Leu Leu Cys Gly Trp Ala Leu Ala Ser Cys His
          5                  10                  15

GGG TCT AAC CTG GAT GTG GAG AAG CCC GTC GTG TTC AAA GAG GAT GCA          153
Gly Ser Asn Leu Asp Val Glu Lys Pro Val Val Phe Lys Glu Asp Ala
     20                  25                  30

GCC AGC TTC GGA CAG ACT GTG GTG CAG TTT GGT GGA TCT CGA CTC GTG          201
Ala Ser Phe Gly Gln Thr Val Val Gln Phe Gly Gly Ser Arg Leu Val
 35                  40                  45                  50

GTG GGA GCC CCT CTG GAG GCG GTG GCA GTC AAC CAA ACA GGA CAG TCG          249
Val Gly Ala Pro Leu Glu Ala Val Ala Val Asn Gln Thr Gly Gln Ser
                 55                  60                  65

TCT GAC TGT CCG CCT GCC ACT GGC GTG TGC CAG CCC ATC TTA CTG CAC          297
Ser Asp Cys Pro Pro Ala Thr Gly Val Cys Gln Pro Ile Leu Leu His
             70                  75                  80

ATT CCC CTA GAG GCA GTG AAC ATG TCC CTG GGC CTG TCT CTG GTG GCT          345
Ile Pro Leu Glu Ala Val Asn Met Ser Leu Gly Leu Ser Leu Val Ala
         85                  90                  95

GAC ACC AAT AAC TCC CAG TTG CTG GCT TGT GGT CCA ACT GCA CAG AGA          393
Asp Thr Asn Asn Ser Gln Leu Leu Ala Cys Gly Pro Thr Ala Gln Arg
    100                 105                 110

GCT TGT GCA AAG AAC ATG TAT GCA AAA GGT TCC TGC CTC CTT CTG GGC          441
Ala Cys Ala Lys Asn Met Tyr Ala Lys Gly Ser Cys Leu Leu Leu Gly
115                 120                 125                 130

TCC AGC TTG CAG TTC ATC CAG GCA ATC CCT GCT ACC ATG CCA GAG TGT          489
Ser Ser Leu Gln Phe Ile Gln Ala Ile Pro Ala Thr Met Pro Glu Cys
                135                 140                 145

CCA GGA CAA GAG ATG GAC ATT GCT TTC CTG ATT GAT GGC TCC GGC AGC          537
Pro Gly Gln Glu Met Asp Ile Ala Phe Leu Ile Asp Gly Ser Gly Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 150 |     |     |     |     | 155 |     |     |     |     | 160 |     |      |
| ATT | GAT | CAA | AGT | GAC | TTT | ACC | CAG | ATG | AAG | GAC | TTC | GTC | AAA | GCT | TTG | 585  |
| Ile | Asp | Gln | Ser | Asp | Phe | Thr | Gln | Met | Lys | Asp | Phe | Val | Lys | Ala | Leu |      |
|     |     | 165 |     |     |     |     | 170 |     |     |     |     | 175 |     |     |     |      |
| ATG | GGC | CAG | TTG | GCG | AGC | ACC | AGC | ACC | TCG | TTC | TCC | CTG | ATG | CAA | TAC | 633  |
| Met | Gly | Gln | Leu | Ala | Ser | Thr | Ser | Thr | Ser | Phe | Ser | Leu | Met | Gln | Tyr |      |
|     | 180 |     |     |     |     | 185 |     |     |     |     | 190 |     |     |     |     |      |
| TCA | AAC | ATC | CTG | AAG | ACT | CAT | TTT | ACC | TTC | ACG | GAA | TTC | AAG | AGC | AGC | 681  |
| Ser | Asn | Ile | Leu | Lys | Thr | His | Phe | Thr | Phe | Thr | Glu | Phe | Lys | Ser | Ser |      |
| 195 |     |     |     |     | 200 |     |     |     |     | 205 |     |     |     |     | 210 |      |
| CTG | AGC | CCT | CAG | AGC | CTG | GTG | GAT | GCC | ATC | GTC | CAG | CTC | CAA | GGC | CTG | 729  |
| Leu | Ser | Pro | Gln | Ser | Leu | Val | Asp | Ala | Ile | Val | Gln | Leu | Gln | Gly | Leu |      |
|     |     |     |     | 215 |     |     |     |     | 220 |     |     |     |     | 225 |     |      |
| ACG | TAC | ACA | GCC | TCG | GGC | ATC | CAG | AAA | GTG | GTG | AAA | GAG | CTA | TTT | CAT | 777  |
| Thr | Tyr | Thr | Ala | Ser | Gly | Ile | Gln | Lys | Val | Val | Lys | Glu | Leu | Phe | His |      |
|     |     |     | 230 |     |     |     |     | 235 |     |     |     |     | 240 |     |     |      |
| AGC | AAG | AAT | GGG | GCC | CGA | AAA | AGT | GCC | AAG | AAG | ATA | CTA | ATT | GTC | ATC | 825  |
| Ser | Lys | Asn | Gly | Ala | Arg | Lys | Ser | Ala | Lys | Lys | Ile | Leu | Ile | Val | Ile |      |
|     | 245 |     |     |     |     | 250 |     |     |     |     | 255 |     |     |     |     |      |
| ACA | GAT | GGG | CAG | AAA | TTC | AGA | GAC | CCC | CTG | GAG | TAT | AGA | CAT | GTC | ATC | 873  |
| Thr | Asp | Gly | Gln | Lys | Phe | Arg | Asp | Pro | Leu | Glu | Tyr | Arg | His | Val | Ile |      |
| 260 |     |     |     |     | 265 |     |     |     |     | 270 |     |     |     |     |     |      |
| CCT | GAA | GCA | GAG | AAA | GCT | GGG | ATC | ATT | CGC | TAT | GCT | ATA | GGG | GTG | GGA | 921  |
| Pro | Glu | Ala | Glu | Lys | Ala | Gly | Ile | Ile | Arg | Tyr | Ala | Ile | Gly | Val | Gly |      |
| 275 |     |     |     |     | 280 |     |     |     |     | 285 |     |     |     |     | 290 |      |
| GAT | GCC | TTC | CGG | GAA | CCC | ACT | GCC | CTA | CAG | GAG | CTG | AAC | ACC | ATT | GGC | 969  |
| Asp | Ala | Phe | Arg | Glu | Pro | Thr | Ala | Leu | Gln | Glu | Leu | Asn | Thr | Ile | Gly |      |
|     |     |     |     | 295 |     |     |     |     | 300 |     |     |     |     | 305 |     |      |
| TCA | GCT | CCC | TCG | CAG | GAC | CAC | GTG | TTC | AAG | GTG | GGC | AAT | TTT | GTA | GCA | 1017 |
| Ser | Ala | Pro | Ser | Gln | Asp | His | Val | Phe | Lys | Val | Gly | Asn | Phe | Val | Ala |      |
|     |     |     | 310 |     |     |     |     | 315 |     |     |     |     | 320 |     |     |      |
| CTT | CGC | AGC | ATC | CAG | CGG | CAA | ATT | CAG | GAG | AAA | ATC | TTT | GCC | ATT | GAA | 1065 |
| Leu | Arg | Ser | Ile | Gln | Arg | Gln | Ile | Gln | Glu | Lys | Ile | Phe | Ala | Ile | Glu |      |
|     |     | 325 |     |     |     |     | 330 |     |     |     |     | 335 |     |     |     |      |
| GGA | ACC | GAA | TCA | AGG | TCA | AGT | AGT | TCC | TTT | CAG | CAC | GAG | ATG | TCA | CAA | 1113 |
| Gly | Thr | Glu | Ser | Arg | Ser | Ser | Ser | Ser | Phe | Gln | His | Glu | Met | Ser | Gln |      |
| 340 |     |     |     |     | 345 |     |     |     |     | 350 |     |     |     |     |     |      |
| GAA | GGT | TTC | AGC | TCA | GCT | CTC | TCA | ATG | GAT | GGA | CCA | GTT | CTG | GGG | GCT | 1161 |
| Glu | Gly | Phe | Ser | Ser | Ala | Leu | Ser | Met | Asp | Gly | Pro | Val | Leu | Gly | Ala |      |
| 355 |     |     |     |     | 360 |     |     |     |     | 365 |     |     |     |     | 370 |      |
| GTG | GGA | GGC | TTC | AGC | TGG | TCT | GGA | GGT | GCC | TTC | TTG | TAC | CCC | TCA | AAT | 1209 |
| Val | Gly | Gly | Phe | Ser | Trp | Ser | Gly | Gly | Ala | Phe | Leu | Tyr | Pro | Ser | Asn |      |
|     |     |     |     | 375 |     |     |     |     | 380 |     |     |     |     | 385 |     |      |
| ATG | AGA | TCC | ACC | TTC | ATC | AAC | ATG | TCT | CAG | GAG | AAC | GAG | GAT | ATG | AGG | 1257 |
| Met | Arg | Ser | Thr | Phe | Ile | Asn | Met | Ser | Gln | Glu | Asn | Glu | Asp | Met | Arg |      |
|     |     |     | 390 |     |     |     |     | 395 |     |     |     |     | 400 |     |     |      |
| GAC | GCT | TAC | CTG | GGT | TAC | TCC | ACC | GCA | CTG | GCC | TTT | TGG | AAG | GGG | GTC | 1305 |
| Asp | Ala | Tyr | Leu | Gly | Tyr | Ser | Thr | Ala | Leu | Ala | Phe | Trp | Lys | Gly | Val |      |
|     |     | 405 |     |     |     |     | 410 |     |     |     |     | 415 |     |     |     |      |
| CAC | AGC | CTG | ATC | CTG | GGG | GCC | CCT | CGC | CAC | CAG | CAC | ACG | GGG | AAG | GTT | 1353 |
| His | Ser | Leu | Ile | Leu | Gly | Ala | Pro | Arg | His | Gln | His | Thr | Gly | Lys | Val |      |
|     |     | 420 |     |     |     |     | 425 |     |     |     |     | 430 |     |     |     |      |
| GTC | ATC | TTT | ACC | CAG | GAA | TCC | AGG | CAC | TGG | AGG | CCC | AAG | TCT | GAA | GTC | 1401 |
| Val | Ile | Phe | Thr | Gln | Glu | Ser | Arg | His | Trp | Arg | Pro | Lys | Ser | Glu | Val |      |
| 435 |     |     |     |     | 440 |     |     |     |     | 445 |     |     |     |     | 450 |      |
| AGA | GGG | ACA | CAG | ATC | GGC | TCC | TAC | TTT | GGG | GCA | TCT | CTC | TGT | TCT | GTG | 1449 |
| Arg | Gly | Thr | Gln | Ile | Gly | Ser | Tyr | Phe | Gly | Ala | Ser | Leu | Cys | Ser | Val |      |
|     |     |     |     | 455 |     |     |     |     | 460 |     |     |     |     | 465 |     |      |
| GAC | ATG | GAT | AGA | GAT | GGC | AGC | ACT | GAC | CTG | GTC | CTG | ATT | GGA | GTC | CCC | 1497 |
| Asp | Met | Asp | Arg | Asp | Gly | Ser | Thr | Asp | Leu | Val | Leu | Ile | Gly | Val | Pro |      |

-continued

|  |  |  | 470 |  |  |  |  |  | 475 |  |  |  |  | 480 |  |  |
|---|---|---|---|---|---|---|---|---|---|---|---|---|---|---|---|---|
| CAT | TAC | TAT | GAG | CAC | ACC | CGA | GGG | GGG | CAG | GTG | TCG | GTG | TGC | CCC | ATG | 1545 |
| His | Tyr | Tyr 485 | Glu | His | Thr | Arg | Gly 490 | Gly | Gln | Val | Ser 495 | Val | Cys | Pro | Met |  |
| CCT | GGT | GTG | AGG | AGC | AGG | TGG | CAT | TGT | GGG | ACC | ACC | CTC | CAT | GGG | GAG | 1593 |
| Pro | Gly 500 | Val | Arg | Ser | Arg | Trp | His 505 | Cys | Gly | Thr | Thr 510 | Leu | His | Gly | Glu |  |
| CAG | GGC | CAT | CCT | TGG | GGC | CGC | TTT | GGG | GCG | GCT | CTG | ACA | GTG | CTA | GGG | 1641 |
| Gln 515 | Gly | His | Pro | Trp 520 | Gly | Arg | Phe | Gly | Ala | Ala 525 | Leu | Thr | Val | Leu | Gly 530 |  |
| GAC | GTG | AAT | GGG | GAC | AGT | CTG | GCG | GAT | GTG | GCT | ATT | GGT | GCA | CCC | GGA | 1689 |
| Asp | Val | Asn | Gly | Asp | Ser 535 | Leu | Ala | Asp | Val 540 | Ala | Ile | Gly | Ala | Pro 545 | Gly |  |
| GAG | GAG | GAG | AAC | AGA | GGT | GCT | GTC | TAC | ATA | TTT | CAT | GGA | GCC | TCG | AGA | 1737 |
| Glu | Glu | Glu | Asn 550 | Arg | Gly | Ala | Val | Tyr 555 | Ile | Phe | His | Gly | Ala 560 | Ser | Arg |  |
| CAG | GAC | ATC | GCT | CCC | TCG | CCT | AGC | CAG | CGG | GTC | ACT | GGC | TCC | CAG | CTC | 1785 |
| Gln | Asp | Ile 565 | Ala | Pro | Ser | Pro | Ser 570 | Gln | Arg | Val | Thr | Gly 575 | Ser | Gln | Leu |  |
| TTC | CTG | AGG | CTC | CAA | TAT | TTT | GGG | CAG | TCA | TTA | AGT | GGG | GGT | CAG | GAC | 1833 |
| Phe | Leu | Arg 580 | Leu | Gln | Tyr | Phe | Gly 585 | Gln | Ser | Leu | Ser | Gly 590 | Gly | Gln | Asp |  |
| CTT | ACA | CAG | GAT | GGC | CTG | GTG | GAC | CTG | GCC | GTG | GGA | GCC | CAG | GGG | CAC | 1881 |
| Leu 595 | Thr | Gln | Asp | Gly | Leu 600 | Val | Asp | Leu | Ala | Val 605 | Gly | Ala | Gln | Gly | His 610 |  |
| GTG | CTG | CTG | CTT | AGG | AGT | CTG | CCT | TTG | CTG | AAA | GTG | GGG | ATC | TCC | ATT | 1929 |
| Val | Leu | Leu | Leu | Arg 615 | Ser | Leu | Pro | Leu | Leu 620 | Lys | Val | Gly | Ile | Ser 625 | Ile |  |
| AGA | TTT | GCC | CCC | TCA | GAG | GTG | GCA | AAG | ACT | GTG | TAC | CAG | TGC | TGG | GGA | 1977 |
| Arg | Phe | Ala | Pro 630 | Ser | Glu | Val | Ala | Lys 635 | Thr | Val | Tyr | Gln | Cys 640 | Trp | Gly |  |
| AGG | ACT | CCC | ACT | GTC | CTC | GAA | GCT | GGA | GAG | GCC | ACC | GTC | TGT | CTC | ACT | 2025 |
| Arg | Thr | Pro 645 | Thr | Val | Leu | Glu | Ala 650 | Gly | Glu | Ala | Thr | Val 655 | Cys | Leu | Thr |  |
| GTC | CGC | AAA | GGT | TCA | CCT | GAC | CTG | TTA | GGT | GAT | GTC | CAA | AGC | TCT | GTC | 2073 |
| Val | Arg | Lys 660 | Gly | Ser | Pro | Asp | Leu 665 | Leu | Gly | Asp | Val | Gln 670 | Ser | Ser | Val |  |
| AGG | TAT | GAT | CTG | GCG | TTG | GAT | CCG | GGC | CGT | CTG | ATT | TCT | CGT | GCC | ATT | 2121 |
| Arg 675 | Tyr | Asp | Leu | Ala | Leu 680 | Asp | Pro | Gly | Arg | Leu 685 | Ile | Ser | Arg | Ala | Ile 690 |  |
| TTT | GAT | GAG | ACG | AAG | AAC | TGC | ACT | TTG | ACC | CGA | AGG | AAG | ACT | CTG | GGG | 2169 |
| Phe | Asp | Glu | Thr | Lys 695 | Asn | Cys | Thr | Leu | Thr 700 | Arg | Arg | Lys | Thr | Leu 705 | Gly |  |
| CTT | GGT | GAT | CAC | TGC | GAA | ACA | ATG | AAG | CTG | CTT | TTG | CCA | GAC | TGT | GTG | 2217 |
| Leu | Gly | Asp | His 710 | Cys | Glu | Thr | Met | Lys 715 | Leu | Leu | Leu | Pro | Asp 720 | Cys | Val |  |
| GAG | GAT | GCA | GTG | ACC | CCT | ATC | ATC | CTG | CGC | CTT | AAC | TTA | TCC | CTG | GCA | 2265 |
| Glu | Asp | Ala 725 | Val | Thr | Pro | Ile | Ile 730 | Leu | Arg | Leu | Asn | Leu 735 | Ser | Leu | Ala |  |
| GGG | GAC | TCT | GCT | CCA | TCC | AGG | AAC | CTT | CGT | CCT | GTG | CTG | GCT | GTG | GGC | 2313 |
| Gly | Asp | Ser 740 | Ala | Pro | Ser | Arg | Asn 745 | Leu | Arg | Pro | Val | Leu 750 | Ala | Val | Gly |  |
| TCA | CAA | GAC | CAT | GTA | ACA | GCT | TCT | TTC | CCG | TTT | GAG | AAG | AAC | TGT | GAG | 2361 |
| Ser 755 | Gln | Asp | His | Val | Thr 760 | Ala | Ser | Phe | Pro | Phe 765 | Glu | Lys | Asn | Cys | Glu 770 |  |
| GGG | AAC | CTG | GGC | GTC | AGC | TTC | AAC | TTC | TCA | GGC | CTG | CAG | GTC | TTG | GAG | 2409 |
| Gly | Asn | Leu | Gly | Val 775 | Ser | Phe | Asn | Phe | Ser 780 | Gly | Leu | Gln | Val | Leu 785 | Glu |  |
| GTA | GGA | AGC | TCC | CCA | GAG | CTC | ACT | GTG | ACA | GTA | ACA | GTT | TGG | AAT | GAG | 2457 |
| Val | Gly | Ser | Ser | Pro | Glu | Leu | Thr | Val | Thr | Val | Thr | Val | Trp | Asn | Glu |  |

```
                        790                       795                           800
GGT   GAG   GAC   AGC   TAT   GGA   ACC   TTA   ATC   AAG   TTC   TAC   TAC   CCA   GCA   GAG           2505
Gly   Glu   Asp   Ser   Tyr   Gly   Thr   Leu   Ile   Lys   Phe   Tyr   Tyr   Pro   Ala   Glu
            805                       810                       815

CTA   TCT   TAC   CGA   CGG   GTG   ACA   AGA   GCC   CAG   CAA   CCT   CAT   CCG   TAC   CCA           2553
Leu   Ser   Tyr   Arg   Arg   Val   Thr   Arg   Ala   Gln   Gln   Pro   His   Pro   Tyr   Pro
      820                       825                       830

CTA   CGC   CTG   GCA   TGT   GAG   GCT   GAG   CCC   ACG   GGC   CAG   GAG   AGC   CTG   AGG           2601
Leu   Arg   Leu   Ala   Cys   Glu   Ala   Glu   Pro   Thr   Gly   Gln   Glu   Ser   Leu   Arg
835                     840                       845                             850

AGC   AGC   AGC   TGT   AGC   ATC   AAT   CAC   CCC   ATC   TTC   CGA   GAA   GGT   GCC   AAG           2649
Ser   Ser   Ser   Cys   Ser   Ile   Asn   His   Pro   Ile   Phe   Arg   Glu   Gly   Ala   Lys
                        855                       860                             865

GCC   ACC   TTC   ATG   ATC   ACA   TTT   GAT   GTC   TCC   TAC   AAG   GCC   TTC   CTG   GGA           2697
Ala   Thr   Phe   Met   Ile   Thr   Phe   Asp   Val   Ser   Tyr   Lys   Ala   Phe   Leu   Gly
                  870                       875                       880

GAC   AGG   TTG   CTT   CTG   AGG   GCC   AGC   GCA   AGC   AGT   GAG   AAT   AAT   AAG   CCT           2745
Asp   Arg   Leu   Leu   Leu   Arg   Ala   Ser   Ala   Ser   Ser   Glu   Asn   Asn   Lys   Pro
            885                       890                       895

GAA   ACC   AGC   AAG   ACT   GCC   TTC   CAG   CTG   GAG   CTT   CCG   GTG   AAG   TAC   ACG           2793
Glu   Thr   Ser   Lys   Thr   Ala   Phe   Gln   Leu   Glu   Leu   Pro   Val   Lys   Tyr   Thr
900                           905                       910

GTC   TAT   ACC   GTG   ATC   AGT   AGG   CAG   GAA   GAT   TCT   ACC   AAG   CAT   TTC   AAC           2841
Val   Tyr   Thr   Val   Ile   Ser   Arg   Gln   Glu   Asp   Ser   Thr   Lys   His   Phe   Asn
915                     920                       925                             930

TTC   TCA   TCT   TCC   CAC   GGG   GAG   AGA   CAG   AAA   GAG   GCC   GAA   CAT   CGA   TAT           2889
Phe   Ser   Ser   Ser   His   Gly   Glu   Arg   Gln   Lys   Glu   Ala   Glu   His   Arg   Tyr
                        935                       940                             945

CGT   GTG   AAT   AAC   CTG   AGT   CCA   TTG   ACG   CTG   GCC   ATC   AGC   GTT   AAC   TTC           2937
Arg   Val   Asn   Asn   Leu   Ser   Pro   Leu   Thr   Leu   Ala   Ile   Ser   Val   Asn   Phe
                  950                       955                       960

TGG   GTC   CCC   ATC   CTT   CTG   AAT   GGT   GTG   GCC   GTG   TGG   GAT   GTG   ACT   CTG           2985
Trp   Val   Pro   Ile   Leu   Leu   Asn   Gly   Val   Ala   Val   Trp   Asp   Val   Thr   Leu
            965                       970                       975

AGG   AGC   CCA   GCA   CAG   GGT   GTC   TCC   TGT   GTG   TCA   CAG   AGG   GAA   CCT   CCT           3033
Arg   Ser   Pro   Ala   Gln   Gly   Val   Ser   Cys   Val   Ser   Gln   Arg   Glu   Pro   Pro
      980                       985                       990

CAA   CAT   TCC   GAC   CTT   CTG   ACC   CAG   ATC   CAA   GGA   CGC   TCT   GTG   CTG   GAC           3081
Gln   His   Ser   Asp   Leu   Leu   Thr   Gln   Ile   Gln   Gly   Arg   Ser   Val   Leu   Asp
995                           1000                      1005                            1010

TGC   GCC   ATC   GCC   GAC   TGC   CTG   CAC   CTC   CGC   TGT   GAC   ATC   CCC   TCC   TTG           3129
Cys   Ala   Ile   Ala   Asp   Cys   Leu   His   Leu   Arg   Cys   Asp   Ile   Pro   Ser   Leu
                        1015                      1020                            1025

GGC   ACC   CTG   GAT   GAG   CTT   GAC   TTC   ATT   CTG   AAG   GGC   AAC   CTC   AGC   TTC           3177
Gly   Thr   Leu   Asp   Glu   Leu   Asp   Phe   Ile   Leu   Lys   Gly   Asn   Leu   Ser   Phe
                  1030                      1035                      1040

GGC   TGG   ATC   AGT   CAG   ACA   TTG   CAG   AAA   AAG   GTG   TTG   CTC   CTG   AGT   GAG           3225
Gly   Trp   Ile   Ser   Gln   Thr   Leu   Gln   Lys   Lys   Val   Leu   Leu   Leu   Ser   Glu
            1045                      1050                      1055

GCT   GAA   ATC   ACA   TTC   AAC   ACA   TCT   GTG   TAT   TCC   CAG   CTG   CCG   GGA   CAG           3273
Ala   Glu   Ile   Thr   Phe   Asn   Thr   Ser   Val   Tyr   Ser   Gln   Leu   Pro   Gly   Gln
      1060                      1065                      1070

GAG   GCA   TTT   CTG   AGA   GCC   CAG   GTG   TCA   ACG   ATG   CTA   GAA   GAA   TAC   GTG           3321
Glu   Ala   Phe   Leu   Arg   Ala   Gln   Val   Ser   Thr   Met   Leu   Glu   Glu   Tyr   Val
1075                          1080                      1085                            1090

GTC   TAT   GAG   CCC   GTC   TTC   CTC   ATG   GTG   TTC   AGC   TCA   GTG   GGA   GGT   CTG           3369
Val   Tyr   Glu   Pro   Val   Phe   Leu   Met   Val   Phe   Ser   Ser   Val   Gly   Gly   Leu
                        1095                      1100                            1105

CTG   TTA   CTG   GCT   CTC   ATC   ACT   GTG   GCG   CTG   TAC   AAG   CTT   GGC   TTC   TTC           3417
Leu   Leu   Leu   Ala   Leu   Ile   Thr   Val   Ala   Leu   Tyr   Lys   Leu   Gly   Phe   Phe
```

|          |          |          |          |          | 1110     |          |          |          | 1115     |          |          |          | 1120     |          |      |
|----------|----------|----------|----------|----------|----------|----------|----------|----------|----------|----------|----------|----------|----------|----------|------|
| AAA      | CGT      | CAG      | TAT      | AAA      | GAG      | ATG      | CTG      | GAT      | CTA      | CCA      | TCT      | GCA      | GAT      | CCT      | GAC  | 3465 |
| Lys      | Arg      | Gln      | Tyr      | Lys      | Glu      | Met      | Leu      | Asp      | Leu      | Pro      | Ser      | Ala      | Asp      | Pro      | Asp  |      |
|          |          | 1125     |          |          |          |          | 1130     |          |          |          |          | 1135     |          |          |      |      |
| CCA | GCC | GGC | CAG | GCA | GAT | TCC | AAC | CAT | GAG | ACT | CCT | CCA | CAT | CTC | ACG | 3513 |
| Pro | Ala | Gly | Gln | Ala | Asp | Ser | Asn | His | Glu | Thr | Pro | Pro | His | Leu | Thr |  |
|  |  | 1140 |  |  |  | 1145 |  |  |  |  |  | 1150 |  |  |  |  |
| TCC | TAG |  |  |  |  |  |  |  |  |  |  |  |  |  |  | 3519 |
| Ser |  |  |  |  |  |  |  |  |  |  |  |  |  |  |  |  |
| 1155 |  |  |  |  |  |  |  |  |  |  |  |  |  |  |  |  |

( 2 ) INFORMATION FOR SEQ ID NO:46:

( i ) SEQUENCE CHARACTERISTICS:
        ( A ) LENGTH: 1155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

| Met | Val | Arg | Gly | Val | Val | Ile | Leu | Leu | Cys | Gly | Trp | Ala | Leu | Ala | Ser |
|---|---|---|---|---|---|---|---|---|---|---|---|---|---|---|---|
| 1 |  |  |  | 5 |  |  |  |  | 10 |  |  |  |  | 15 |  |
| Cys | His | Gly | Ser | Asn | Leu | Asp | Val | Glu | Lys | Pro | Val | Val | Phe | Lys | Glu |
|  |  |  | 20 |  |  |  |  | 25 |  |  |  |  | 30 |  |  |
| Asp | Ala | Ala | Ser | Phe | Gly | Gln | Thr | Val | Val | Gln | Phe | Gly | Gly | Ser | Arg |
|  |  | 35 |  |  |  |  | 40 |  |  |  |  | 45 |  |  |  |
| Leu | Val | Val | Gly | Ala | Pro | Leu | Glu | Ala | Val | Ala | Val | Asn | Gln | Thr | Gly |
|  | 50 |  |  |  |  | 55 |  |  |  |  | 60 |  |  |  |  |
| Gln | Ser | Ser | Asp | Cys | Pro | Pro | Ala | Thr | Gly | Val | Cys | Gln | Pro | Ile | Leu |
| 65 |  |  |  |  | 70 |  |  |  |  | 75 |  |  |  |  | 80 |
| Leu | His | Ile | Pro | Leu | Glu | Ala | Val | Asn | Met | Ser | Leu | Gly | Leu | Ser | Leu |
|  |  |  |  | 85 |  |  |  |  | 90 |  |  |  |  | 95 |  |
| Val | Ala | Asp | Thr | Asn | Asn | Ser | Gln | Leu | Leu | Ala | Cys | Gly | Pro | Thr | Ala |
|  |  |  | 100 |  |  |  |  | 105 |  |  |  |  | 110 |  |  |
| Gln | Arg | Ala | Cys | Ala | Lys | Asn | Met | Tyr | Ala | Lys | Gly | Ser | Cys | Leu | Leu |
|  |  | 115 |  |  |  |  | 120 |  |  |  |  | 125 |  |  |  |
| Leu | Gly | Ser | Ser | Leu | Gln | Phe | Ile | Gln | Ala | Ile | Pro | Ala | Thr | Met | Pro |
|  | 130 |  |  |  |  | 135 |  |  |  |  | 140 |  |  |  |  |
| Glu | Cys | Pro | Gly | Gln | Glu | Met | Asp | Ile | Ala | Phe | Leu | Ile | Asp | Gly | Ser |
| 145 |  |  |  |  | 150 |  |  |  |  | 155 |  |  |  |  | 160 |
| Gly | Ser | Ile | Asp | Gln | Ser | Asp | Phe | Thr | Gln | Met | Lys | Asp | Phe | Val | Lys |
|  |  |  | 165 |  |  |  |  | 170 |  |  |  |  | 175 |  |  |
| Ala | Leu | Met | Gly | Gln | Leu | Ala | Ser | Thr | Ser | Thr | Ser | Phe | Ser | Leu | Met |
|  |  |  | 180 |  |  |  |  | 185 |  |  |  |  | 190 |  |  |
| Gln | Tyr | Ser | Asn | Ile | Leu | Lys | Thr | His | Phe | Thr | Phe | Thr | Glu | Phe | Lys |
|  |  | 195 |  |  |  |  | 200 |  |  |  |  | 205 |  |  |  |
| Ser | Ser | Leu | Ser | Pro | Gln | Ser | Leu | Val | Asp | Ala | Ile | Val | Gln | Leu | Gln |
|  | 210 |  |  |  |  | 215 |  |  |  |  | 220 |  |  |  |  |
| Gly | Leu | Thr | Tyr | Thr | Ala | Ser | Gly | Ile | Gln | Lys | Val | Val | Lys | Glu | Leu |
| 225 |  |  |  |  | 230 |  |  |  |  | 235 |  |  |  |  | 240 |
| Phe | His | Ser | Lys | Asn | Gly | Ala | Arg | Lys | Ser | Ala | Lys | Lys | Ile | Leu | Ile |
|  |  |  |  | 245 |  |  |  |  | 250 |  |  |  |  | 255 |  |
| Val | Ile | Thr | Asp | Gly | Gln | Lys | Phe | Arg | Asp | Pro | Leu | Glu | Tyr | Arg | His |
|  |  |  | 260 |  |  |  |  | 265 |  |  |  |  | 270 |  |  |
| Val | Ile | Pro | Glu | Ala | Glu | Lys | Ala | Gly | Ile | Ile | Arg | Tyr | Ala | Ile | Gly |
|  |  | 275 |  |  |  |  | 280 |  |  |  |  | 285 |  |  |  |

```
Val Gly Asp Ala Phe Arg Glu Pro Thr Ala Leu Gln Glu Leu Asn Thr
    290             295             300
Ile Gly Ser Ala Pro Ser Gln Asp His Val Phe Lys Val Gly Asn Phe
305             310             315             320
Val Ala Leu Arg Ser Ile Gln Arg Gln Gln Glu Lys Ile Phe Ala
            325             330             335
Ile Glu Gly Thr Glu Ser Arg Ser Ser Ser Phe Gln His Glu Met
            340             345             350
Ser Gln Glu Gly Phe Ser Ser Ala Leu Ser Met Asp Gly Pro Val Leu
            355             360             365
Gly Ala Val Gly Gly Phe Ser Trp Ser Gly Gly Ala Phe Leu Tyr Pro
            370             375             380
Ser Asn Met Arg Ser Thr Phe Ile Asn Met Ser Gln Glu Asn Glu Asp
385             390             395             400
Met Arg Asp Ala Tyr Leu Gly Tyr Ser Thr Ala Leu Ala Phe Trp Lys
                405             410             415
Gly Val His Ser Leu Ile Leu Gly Ala Pro Arg His Gln His Thr Gly
            420             425             430
Lys Val Val Ile Phe Thr Gln Glu Ser Arg His Trp Arg Pro Lys Ser
            435             440             445
Glu Val Arg Gly Thr Gln Ile Gly Ser Tyr Phe Gly Ala Ser Leu Cys
    450             455             460
Ser Val Asp Met Asp Arg Asp Gly Ser Thr Asp Leu Val Leu Ile Gly
465             470             475             480
Val Pro His Tyr Tyr Glu His Thr Arg Gly Gly Gln Val Ser Val Cys
                485             490             495
Pro Met Pro Gly Val Arg Ser Arg Trp His Cys Gly Thr Thr Leu His
            500             505             510
Gly Glu Gln Gly His Pro Trp Gly Arg Phe Gly Ala Ala Leu Thr Val
            515             520             525
Leu Gly Asp Val Asn Gly Asp Ser Leu Ala Asp Val Ala Ile Gly Ala
    530             535             540
Pro Gly Glu Glu Glu Asn Arg Gly Ala Val Tyr Ile Phe His Gly Ala
545             550             555             560
Ser Arg Gln Asp Ile Ala Pro Ser Pro Ser Gln Arg Val Thr Gly Ser
                565             570             575
Gln Leu Phe Leu Arg Leu Gln Tyr Phe Gly Gln Ser Leu Ser Gly Gly
            580             585             590
Gln Asp Leu Thr Gln Asp Gly Leu Val Asp Leu Ala Val Gly Ala Gln
            595             600             605
Gly His Val Leu Leu Leu Arg Ser Leu Pro Leu Leu Lys Val Gly Ile
    610             615             620
Ser Ile Arg Phe Ala Pro Ser Glu Val Ala Lys Thr Val Tyr Gln Cys
625             630             635             640
Trp Gly Arg Thr Pro Thr Val Leu Glu Ala Gly Glu Ala Thr Val Cys
                645             650             655
Leu Thr Val Arg Lys Gly Ser Pro Asp Leu Leu Gly Asp Val Gln Ser
            660             665             670
Ser Val Arg Tyr Asp Leu Ala Leu Asp Pro Gly Arg Leu Ile Ser Arg
            675             680             685
Ala Ile Phe Asp Glu Thr Lys Asn Cys Thr Leu Thr Arg Arg Lys Thr
    690             695             700
Leu Gly Leu Gly Asp His Cys Glu Thr Met Lys Leu Leu Leu Pro Asp
705             710             715             720
```

```
Cys Val Glu Asp Ala Val Thr Pro Ile Ile Leu Arg Leu Asn Leu Ser
            725                 730                 735

Leu Ala Gly Asp Ser Ala Pro Ser Arg Asn Leu Arg Pro Val Leu Ala
            740                 745                 750

Val Gly Ser Gln Asp His Val Thr Ala Ser Phe Pro Phe Glu Lys Asn
            755                 760                 765

Cys Glu Gly Asn Leu Gly Val Ser Phe Asn Phe Ser Gly Leu Gln Val
    770                 775                 780

Leu Glu Val Gly Ser Ser Pro Glu Leu Thr Val Thr Val Thr Val Trp
785                 790                 795                 800

Asn Glu Gly Glu Asp Ser Tyr Gly Thr Leu Ile Lys Phe Tyr Tyr Pro
            805                 810                 815

Ala Glu Leu Ser Tyr Arg Arg Val Thr Arg Ala Gln Gln Pro His Pro
            820                 825                 830

Tyr Pro Leu Arg Leu Ala Cys Glu Ala Glu Pro Thr Gly Gln Glu Ser
            835                 840                 845

Leu Arg Ser Ser Ser Cys Ser Ile Asn His Pro Ile Phe Arg Glu Gly
    850                 855                 860

Ala Lys Ala Thr Phe Met Ile Thr Phe Asp Val Ser Tyr Lys Ala Phe
865                 870                 875                 880

Leu Gly Asp Arg Leu Leu Leu Arg Ala Ala Ser Ser Glu Asn
                    885                 890                 895

Lys Pro Glu Thr Ser Lys Thr Ala Phe Gln Leu Glu Leu Pro Val Lys
            900                 905                 910

Tyr Thr Val Tyr Thr Val Ile Ser Arg Gln Glu Asp Ser Thr Lys His
            915                 920                 925

Phe Asn Phe Ser Ser Ser His Gly Glu Arg Gln Lys Glu Ala Glu His
    930                 935                 940

Arg Tyr Arg Val Asn Asn Leu Ser Pro Leu Thr Leu Ala Ile Ser Val
945                 950                 955                 960

Asn Phe Trp Val Pro Ile Leu Leu Asn Gly Val Ala Val Trp Asp Val
            965                 970                 975

Thr Leu Arg Ser Pro Ala Gln Gly Val Ser Cys Val Ser Gln Arg Glu
            980                 985                 990

Pro Pro Gln His Ser Asp Leu Leu Thr Gln Ile Gln Gly Arg Ser Val
        995                 1000                1005

Leu Asp Cys Ala Ile Ala Asp Cys Leu His Leu Arg Cys Asp Ile Pro
        1010                1015                1020

Ser Leu Gly Thr Leu Asp Glu Leu Asp Phe Ile Leu Lys Gly Asn Leu
1025                1030                1035                1040

Ser Phe Gly Trp Ile Ser Gln Thr Leu Gln Lys Lys Val Leu Leu Leu
                1045                1050                1055

Ser Glu Ala Glu Ile Thr Phe Asn Thr Ser Val Tyr Ser Gln Leu Pro
                1060                1065                1070

Gly Gln Glu Ala Phe Leu Arg Ala Gln Val Ser Thr Met Leu Glu Glu
                1075                1080                1085

Tyr Val Val Tyr Glu Pro Val Phe Leu Met Val Phe Ser Ser Val Gly
        1090                1095                1100

Gly Leu Leu Leu Leu Ala Leu Ile Thr Val Ala Leu Tyr Lys Leu Gly
1105                1110                1115                1120

Phe Phe Lys Arg Gln Tyr Lys Glu Met Leu Asp Leu Pro Ser Ala Asp
                1125                1130                1135

Pro Asp Pro Ala Gly Gln Ala Asp Ser Asn His Glu Thr Pro Pro His
```

| | | |
|---|---|---|
| 1140 | 1145 | 1150 |

Leu Thr Ser
    1155

( 2 ) INFORMATION FOR SEQ ID NO:47:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

AGTTACGGAT CCGGCACCAT GACCTTCGGC ACTGTGATCC TCCTGTGTG    49

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

GCTGGACGAT GGCATCCAC    19

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

GTAGAGTTAC GGATCCGGCA CCAT    24

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

GCAGCCAGCT TCGGACAGAC    20

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CCATGTCCAC AGAACAGAGA G    21

(2) INFORMATION FOR SEQ ID NO:52:

(i) SEQUENCE CHARACTERISTICS:
        (A) LENGTH: 3803 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..3486

(xi) SEQUENCE DESCRIPTION: SEQ ID NO:52:

```
ATG GTC CGT GGA GTT GTG ATC CTC CTG TGT GGC TGG GCC CTG GCT TCC      48
Met Val Arg Gly Val Val Ile Leu Leu Cys Gly Trp Ala Leu Ala Ser
 1               5                  10                  15

TGT CAT GGG TCT AAC CTG GAT GTG GAG AAG CCC GTC GTG TTC AAA GAG      96
Cys His Gly Ser Asn Leu Asp Val Glu Lys Pro Val Val Phe Lys Glu
             20                  25                  30

GAT GCA GCC AGC TTC GGA CAG ACT GTG GTG CAG TTT GGT GGA TCT CGA     144
Asp Ala Ala Ser Phe Gly Gln Thr Val Val Gln Phe Gly Gly Ser Arg
         35                  40                  45

CTC GTG GTG GGA GCC CCT CTG GAG GCG GTG GCA GTC AAC CAA ACA GGA     192
Leu Val Val Gly Ala Pro Leu Glu Ala Val Ala Val Asn Gln Thr Gly
     50                  55                  60

CAG TCG TCT GAC TGT CCG CCT GCC ACT GGC GTG TGC CAG CCC ATC TTA     240
Gln Ser Ser Asp Cys Pro Pro Ala Thr Gly Val Cys Gln Pro Ile Leu
 65                  70                  75                  80

CTG CAC ATT CCC CTA GAG GCA GTG AAC ATG TCC CTG GGC CTG TCT CTG     288
Leu His Ile Pro Leu Glu Ala Val Asn Met Ser Leu Gly Leu Ser Leu
                 85                  90                  95

GTG GCT GAC ACC AAT AAC TCC CAG TTG CTG GCT TGT GGT CCA ACT GCA     336
Val Ala Asp Thr Asn Asn Ser Gln Leu Leu Ala Cys Gly Pro Thr Ala
            100                 105                 110

CAG AGA GCT TGT GCA AAG AAC ATG TAT GCA AAA GGT TCC TGC CTC CTT     384
Gln Arg Ala Cys Ala Lys Asn Met Tyr Ala Lys Gly Ser Cys Leu Leu
        115                 120                 125

CTG GGC TCC AGC TTG CAG TTC ATC CAG GCA ATC CCT GCT ACC ATG CCA     432
Leu Gly Ser Ser Leu Gln Phe Ile Gln Ala Ile Pro Ala Thr Met Pro
    130                 135                 140

GAG TGT CCA GGA CAA GAG ATG GAC ATT GCT TTC CTG ATT GAT GGC TCC     480
Glu Cys Pro Gly Gln Glu Met Asp Ile Ala Phe Leu Ile Asp Gly Ser
145                 150                 155                 160

GGC AGC ATT GAT CAA AGT GAC TTT ACC CAG ATG AAG GAC TTC GTC AAA     528
Gly Ser Ile Asp Gln Ser Asp Phe Thr Gln Met Lys Asp Phe Val Lys
                165                 170                 175

GCT TTG ATG GGC CAG TTG GCG AGC ACC AGC ACC TCG TTC TCC CTG ATG     576
Ala Leu Met Gly Gln Leu Ala Ser Thr Ser Thr Ser Phe Ser Leu Met
            180                 185                 190

CAA TAC TCA AAC ATC CTG AAG ACT CAT TTT ACC TTC ACG GAA TTC AAG     624
Gln Tyr Ser Asn Ile Leu Lys Thr His Phe Thr Phe Thr Glu Phe Lys
        195                 200                 205

AGC AGC CTG AGC CCT CAG AGC CTG GTG GAT GCC ATC GTC CAG CTC CAA     672
Ser Ser Leu Ser Pro Gln Ser Leu Val Asp Ala Ile Val Gln Leu Gln
    210                 215                 220

GGC CTG ACG TAC ACA GCC TCG GGC ATC CAG AAA GTG GTG AAA GAG CTA     720
Gly Leu Thr Tyr Thr Ala Ser Gly Ile Gln Lys Val Val Lys Glu Leu
225                 230                 235                 240

TTT CAT AGC AAG AAT GGG GCC CGA AAA AGT GCC AAG AAG ATA CTA ATT     768
Phe His Ser Lys Asn Gly Ala Arg Lys Ser Ala Lys Lys Ile Leu Ile
                245                 250                 255
```

```
GTC  ATC  ACA  GAT  GGG  CAG  AAA  TTC  AGA  GAC  CCC  CTG  GAG  TAT  AGA  CAT       816
Val  Ile  Thr  Asp  Gly  Gln  Lys  Phe  Arg  Asp  Pro  Leu  Glu  Tyr  Arg  His
          260                      265                          270

GTC  ATC  CCT  GAA  GCA  GAG  AAA  GCT  GGG  ATC  ATT  CGC  TAT  GCT  ATA  GGG       864
Val  Ile  Pro  Glu  Ala  Glu  Lys  Ala  Gly  Ile  Ile  Arg  Tyr  Ala  Ile  Gly
          275                      280                          285

GTG  GGA  GAT  GCC  TTC  CGG  GAA  CCC  ACT  GCC  CTA  CAG  GAG  CTG  AAC  ACC       912
Val  Gly  Asp  Ala  Phe  Arg  Glu  Pro  Thr  Ala  Leu  Gln  Glu  Leu  Asn  Thr
290                           295                          300

ATT  GGC  TCA  GCT  CCC  TCG  CAG  GAC  CAC  GTG  TTC  AAG  GTG  GGC  AAT  TTT       960
Ile  Gly  Ser  Ala  Pro  Ser  Gln  Asp  His  Val  Phe  Lys  Val  Gly  Asn  Phe
305                           310                          315                     320

GTA  GCA  CTT  CGC  AGC  ATC  CAG  CGG  CAA  ATT  CAG  GAG  AAA  ATC  TTT  GCC      1008
Val  Ala  Leu  Arg  Ser  Ile  Gln  Arg  Gln  Ile  Gln  Glu  Lys  Ile  Phe  Ala
                    325                      330                          335

ATT  GAA  GGA  ACC  GAA  TCA  AGG  TCA  AGT  AGT  TCC  TTT  CAG  CAC  GAG  ATG      1056
Ile  Glu  Gly  Thr  Glu  Ser  Arg  Ser  Ser  Ser  Ser  Phe  Gln  His  Glu  Met
               340                      345                          350

TCA  CAA  GAA  GGT  TTC  AGC  TCA  GCT  CTC  TCA  ATG  GAT  GGA  CCA  GTT  CTG      1104
Ser  Gln  Glu  Gly  Phe  Ser  Ser  Ala  Leu  Ser  Met  Asp  Gly  Pro  Val  Leu
          355                      360                          365

GGG  GCT  GTG  GGA  GGC  TTC  AGC  TGG  TCT  GGA  GGT  GCC  TTC  TTG  TAC  CCC      1152
Gly  Ala  Val  Gly  Gly  Phe  Ser  Trp  Ser  Gly  Gly  Ala  Phe  Leu  Tyr  Pro
370                           375                          380

TCA  AAT  ATG  AGA  TCC  ACC  TTC  ATC  AAC  ATG  TCT  CAG  GAG  AAC  GAG  GAT      1200
Ser  Asn  Met  Arg  Ser  Thr  Phe  Ile  Asn  Met  Ser  Gln  Glu  Asn  Glu  Asp
385                           390                          395                     400

ATG  AGG  GAC  GCT  TAC  CTG  GGT  TAC  TCC  ACC  GCA  CTG  GCC  TTT  TGG  AAG      1248
Met  Arg  Asp  Ala  Tyr  Leu  Gly  Tyr  Ser  Thr  Ala  Leu  Ala  Phe  Trp  Lys
                    405                      410                          415

GGG  GTC  CAC  AGC  CTG  ATC  CTG  GGG  GCC  CCT  CGC  CAC  CAG  CAC  ACG  GGG      1296
Gly  Val  His  Ser  Leu  Ile  Leu  Gly  Ala  Pro  Arg  His  Gln  His  Thr  Gly
               420                      425                          430

AAG  GTT  GTC  ATC  TTT  ACC  CAG  GAA  TCC  AGG  CAC  TGG  AGG  CCC  AAG  TCT      1344
Lys  Val  Val  Ile  Phe  Thr  Gln  Glu  Ser  Arg  His  Trp  Arg  Pro  Lys  Ser
          435                      440                          445

GAA  GTC  AGA  GGG  ACA  CAG  ATC  GGC  TCC  TAC  TTT  GGG  GCA  TCT  CTC  TGT      1392
Glu  Val  Arg  Gly  Thr  Gln  Ile  Gly  Ser  Tyr  Phe  Gly  Ala  Ser  Leu  Cys
450                           455                          460

TCT  GTG  GAC  ATG  GAT  AGA  GAT  GGC  AGC  ACT  GAC  CTG  GTC  CTG  ATT  GGA      1440
Ser  Val  Asp  Met  Asp  Arg  Asp  Gly  Ser  Thr  Asp  Leu  Val  Leu  Ile  Gly
465                           470                          475                     480

GTC  CCC  CAT  TAC  TAT  GAG  CAC  ACC  CGA  GGG  GGG  CAG  GTG  TCG  GTG  TGC      1488
Val  Pro  His  Tyr  Tyr  Glu  His  Thr  Arg  Gly  Gly  Gln  Val  Ser  Val  Cys
                    485                      490                          495

CCC  ATG  CCT  GGT  GTG  AGG  AGC  AGG  TGG  CAT  TGT  GGG  ACC  ACC  CTC  CAT      1536
Pro  Met  Pro  Gly  Val  Arg  Ser  Arg  Trp  His  Cys  Gly  Thr  Thr  Leu  His
               500                      505                          510

GGG  GAG  CAG  GGC  CAT  CCT  TGG  GGC  CGC  TTT  GGG  GCG  GCT  CTG  ACA  GTG      1584
Gly  Glu  Gln  Gly  His  Pro  Trp  Gly  Arg  Phe  Gly  Ala  Ala  Leu  Thr  Val
          515                      520                          525

CTA  GGG  GAC  GTG  AAT  GGG  GAC  AGT  CTG  GCG  GAT  GTG  GCT  ATT  GGT  GCA      1632
Leu  Gly  Asp  Val  Asn  Gly  Asp  Ser  Leu  Ala  Asp  Val  Ala  Ile  Gly  Ala
     530                      535                          540

CCC  GGA  GAG  GAG  GAG  AAC  AGA  GGT  GCT  GTC  TAC  ATA  TTT  CAT  GGA  GCC      1680
Pro  Gly  Glu  Glu  Glu  Asn  Arg  Gly  Ala  Val  Tyr  Ile  Phe  His  Gly  Ala
545                           550                          555                     560

TCG  AGA  CAG  GAC  ATC  GCT  CCC  TCG  CCT  AGC  CAG  CGG  GTC  ACT  GGC  TCC      1728
Ser  Arg  Gln  Asp  Ile  Ala  Pro  Ser  Pro  Ser  Gln  Arg  Val  Thr  Gly  Ser
                    565                      570                          575
```

| | | | | | | | | | | | | | | | | |
|---|---|---|---|---|---|---|---|---|---|---|---|---|---|---|---|---|
| CAG | CTC | TTC | CTG | AGG | CTC | CAA | TAT | TTT | GGG | CAG | TCA | TTA | AGT | GGG | GGT | 1776 |
| Gln | Leu | Phe | Leu | Arg | Leu | Gln | Tyr | Phe | Gly | Gln | Ser | Leu | Ser | Gly | Gly | |
| | | | 580 | | | | | 585 | | | | | 590 | | | |
| CAG | GAC | CTT | ACA | CAG | GAT | GGC | CTG | GTG | GAC | CTG | GCC | GTG | GGA | GCC | CAG | 1824 |
| Gln | Asp | Leu | Thr | Gln | Asp | Gly | Leu | Val | Asp | Leu | Ala | Val | Gly | Ala | Gln | |
| | | | 595 | | | | 600 | | | | | 605 | | | | |
| GGG | CAC | GTG | CTG | CTG | CTT | AGG | AGT | CTG | CCT | TTG | CTG | AAA | GTG | GGG | ATC | 1872 |
| Gly | His | Val | Leu | Leu | Leu | Arg | Ser | Leu | Pro | Leu | Leu | Lys | Val | Gly | Ile | |
| | | 610 | | | | | 615 | | | | | 620 | | | | |
| TCC | ATT | AGA | TTT | GCC | CCC | TCA | GAG | GTG | GCA | AAG | ACT | GTG | TAC | CAG | TGC | 1920 |
| Ser | Ile | Arg | Phe | Ala | Pro | Ser | Glu | Val | Ala | Lys | Thr | Val | Tyr | Gln | Cys | |
| 625 | | | | | 630 | | | | | 635 | | | | | 640 | |
| TGG | GGA | AGG | ACT | CCC | ACT | GTC | CTC | GAA | GCT | GGA | GAG | GCC | ACC | GTC | TGT | 1968 |
| Trp | Gly | Arg | Thr | Pro | Thr | Val | Leu | Glu | Ala | Gly | Glu | Ala | Thr | Val | Cys | |
| | | | | 645 | | | | | 650 | | | | | 655 | | |
| CTC | ACT | GTC | CGC | AAA | GGT | TCA | CCT | GAC | CTG | TTA | GGT | GAT | GTC | CAA | AGC | 2016 |
| Leu | Thr | Val | Arg | Lys | Gly | Ser | Pro | Asp | Leu | Leu | Gly | Asp | Val | Gln | Ser | |
| | | | 660 | | | | | 665 | | | | | 670 | | | |
| TCT | GTC | AGG | TAT | GAT | CTG | GCG | TTG | GAT | CCG | GGC | CGT | CTG | ATT | TCT | CGT | 2064 |
| Ser | Val | Arg | Tyr | Asp | Leu | Ala | Leu | Asp | Pro | Gly | Arg | Leu | Ile | Ser | Arg | |
| | | 675 | | | | | 680 | | | | | 685 | | | | |
| GCC | ATT | TTT | GAT | GAG | ACG | AAG | AAC | TGC | ACT | TTG | ACC | CGA | AGG | AAG | ACT | 2112 |
| Ala | Ile | Phe | Asp | Glu | Thr | Lys | Asn | Cys | Thr | Leu | Thr | Arg | Arg | Lys | Thr | |
| 690 | | | | | 695 | | | | | 700 | | | | | | |
| CTG | GGG | CTT | GGT | GAT | CAC | TGC | GAA | ACA | ATG | AAG | CTG | CTT | TTG | CCA | GAC | 2160 |
| Leu | Gly | Leu | Gly | Asp | His | Cys | Glu | Thr | Met | Lys | Leu | Leu | Leu | Pro | Asp | |
| 705 | | | | | 710 | | | | | 715 | | | | | 720 | |
| TGT | GTG | GAG | GAT | GCA | GTG | ACC | CCT | ATC | ATC | CTG | CGC | CTT | AAC | TTA | TCC | 2208 |
| Cys | Val | Glu | Asp | Ala | Val | Thr | Pro | Ile | Ile | Leu | Arg | Leu | Asn | Leu | Ser | |
| | | | | 725 | | | | | 730 | | | | | 735 | | |
| CTG | GCA | GGG | GAC | TCT | GCT | CCA | TCC | AGG | AAC | CTT | CGT | CCT | GTG | CTG | GCT | 2256 |
| Leu | Ala | Gly | Asp | Ser | Ala | Pro | Ser | Arg | Asn | Leu | Arg | Pro | Val | Leu | Ala | |
| | | | 740 | | | | | 745 | | | | | 750 | | | |
| GTG | GGC | TCA | CAA | GAC | CAT | GTA | ACA | GCT | TCT | TTC | CCG | TTT | GAG | AAG | AAC | 2304 |
| Val | Gly | Ser | Gln | Asp | His | Val | Thr | Ala | Ser | Phe | Pro | Phe | Glu | Lys | Asn | |
| | | 755 | | | | | 760 | | | | | 765 | | | | |
| TGT | AAG | CAG | GAG | CTC | CTG | TGT | GAG | GGG | AAC | CTG | GGC | GTC | AGC | TTC | AAC | 2352 |
| Cys | Lys | Gln | Glu | Leu | Leu | Cys | Glu | Gly | Asn | Leu | Gly | Val | Ser | Phe | Asn | |
| | 770 | | | | | 775 | | | | | 780 | | | | | |
| TTC | TCA | GGC | CTG | CAG | GTC | TTG | GAG | GTA | GGA | AGC | TCC | CCA | GAG | CTC | ACT | 2400 |
| Phe | Ser | Gly | Leu | Gln | Val | Leu | Glu | Val | Gly | Ser | Ser | Pro | Glu | Leu | Thr | |
| 785 | | | | | 790 | | | | | 795 | | | | | 800 | |
| GTG | ACA | GTA | ACA | GTT | TGG | AAT | GAG | GGT | GAG | GAC | AGC | TAT | GGA | ACC | TTA | 2448 |
| Val | Thr | Val | Thr | Val | Trp | Asn | Glu | Gly | Glu | Asp | Ser | Tyr | Gly | Thr | Leu | |
| | | | | 805 | | | | | 810 | | | | | 815 | | |
| ATC | AAG | TTC | TAC | TAC | CCA | GCA | GAG | CTA | TCT | TAC | CGA | CGG | GTG | ACA | AGA | 2496 |
| Ile | Lys | Phe | Tyr | Tyr | Pro | Ala | Glu | Leu | Ser | Tyr | Arg | Arg | Val | Thr | Arg | |
| | | | 820 | | | | | 825 | | | | | 830 | | | |
| GCC | CAG | CAA | CCT | CAT | CCG | TAC | CCA | CTA | CGC | CTG | GCA | TGT | GAG | GCT | GAG | 2544 |
| Ala | Gln | Gln | Pro | His | Pro | Tyr | Pro | Leu | Arg | Leu | Ala | Cys | Glu | Ala | Glu | |
| | | 835 | | | | | 840 | | | | | 845 | | | | |
| CCC | ACG | GGC | CAG | GAG | AGC | CTG | AGG | AGC | AGC | AGC | TGT | AGC | ATC | AAT | CAC | 2592 |
| Pro | Thr | Gly | Gln | Glu | Ser | Leu | Arg | Ser | Ser | Ser | Cys | Ser | Ile | Asn | His | |
| | 850 | | | | | 855 | | | | | 860 | | | | | |
| CCC | ATC | TTC | CGA | GAA | GGT | GCC | AAG | GCC | ACC | TTC | ATG | ATC | ACA | TTT | GAT | 2640 |
| Pro | Ile | Phe | Arg | Glu | Gly | Ala | Lys | Ala | Thr | Phe | Met | Ile | Thr | Phe | Asp | |
| 865 | | | | | 870 | | | | | 875 | | | | | 880 | |
| GTC | TCC | TAC | AAG | GCC | TTC | CTG | GGA | GAC | AGG | TTG | CTT | CTG | AGG | GCC | AGC | 2688 |
| Val | Ser | Tyr | Lys | Ala | Phe | Leu | Gly | Asp | Arg | Leu | Leu | Leu | Arg | Ala | Ser | |
| | | | | 885 | | | | | 890 | | | | | 895 | | |

| | | | | | | | | | | | | | | | | |
|---|---|---|---|---|---|---|---|---|---|---|---|---|---|---|---|---|
| GCA | AGC | AGT | GAG | AAT | AAT | AAG | CCT | GAA | ACC | AGC | AAG | ACT | GCC | TTC | CAG | 2736 |
| Ala | Ser | Ser | Glu 900 | Asn | Asn | Lys | Pro | Glu 905 | Thr | Ser | Lys | Thr | Ala 910 | Phe | Gln | |
| CTG | GAG | CTT | CCG | GTG | AAG | TAC | ACG | GTC | TAT | ACC | GTG | ATC | AGT | AGG | CAG | 2784 |
| Leu | Glu | Leu 915 | Pro | Val | Lys | Tyr | Thr | Val 920 | Tyr | Thr | Val | Ile | Ser 925 | Arg | Gln | |
| GAA | GAT | TCT | ACC | AAG | CAT | TTC | AAC | TTC | TCA | TCT | TCC | CAC | GGG | GAG | AGA | 2832 |
| Glu | Asp | Ser | Thr 930 | Lys | His | Phe | Asn | Phe 935 | Ser | Ser | Ser | His | Gly 940 | Glu | Arg | |
| CAG | AAA | GAG | GCC | GAA | CAT | CGA | TAT | CGT | GTG | AAT | AAC | CTG | AGT | CCA | TTG | 2880 |
| Gln | Lys | Glu 945 | Ala | Glu | His | Arg | Tyr 950 | Arg | Val | Asn | Asn | Leu 955 | Ser | Pro | Leu 960 | |
| ACG | CTG | GCC | ATC | AGC | GTT | AAC | TTC | TGG | GTC | CCC | ATC | CTT | CTG | AAT | GGT | 2928 |
| Thr | Leu | Ala | Ile | Ser 965 | Val | Asn | Phe | Trp | Val 970 | Pro | Ile | Leu | Leu | Asn 975 | Gly | |
| GTG | GCC | GTG | TGG | GAT | GTG | ACT | CTG | AGG | AGC | CCA | GCA | CAG | GGT | GTC | TCC | 2976 |
| Val | Ala | Val | Trp 980 | Asp | Val | Thr | Leu | Arg 985 | Ser | Pro | Ala | Gln | Gly 990 | Val | Ser | |
| TGT | GTG | TCA | CAG | AGG | GAA | CCT | CCT | CAA | CAT | TCC | GAC | CTT | CTG | ACC | CAG | 3024 |
| Cys | Val | Ser 995 | Gln | Arg | Glu | Pro | Pro 1000 | Gln | His | Ser | Asp | Leu 1005 | Leu | Thr | Gln | |
| ATC | CAA | GGA | CGC | TCT | GTG | CTG | GAC | TGC | GCC | ATC | GCC | GAC | TGC | CTG | CAC | 3072 |
| Ile | Gln | Gly 1010 | Arg | Ser | Val | Leu | Asp 1015 | Cys | Ala | Ile | Ala | Asp 1020 | Cys | Leu | His | |
| CTC | CGC | TGT | GAC | ATC | CCC | TCC | TTG | GGC | ACC | CTG | GAT | GAG | CTT | GAC | TTC | 3120 |
| Leu 1025 | Arg | Cys | Asp | Ile | Pro 1030 | Ser | Leu | Gly | Thr | Leu 1035 | Asp | Glu | Leu | Asp | Phe 1040 | |
| ATT | CTG | AAG | GGC | AAC | CTC | AGC | TTC | GGC | TGG | ATC | AGT | CAG | ACA | TTG | CAG | 3168 |
| Ile | Leu | Lys | Gly | Asn 1045 | Leu | Ser | Phe | Gly | Trp 1050 | Ile | Ser | Gln | Thr | Leu 1055 | Gln | |
| AAA | AAG | GTG | TTG | CTC | CTG | AGT | GAG | GCT | GAA | ATC | ACA | TTC | AAC | ACA | TCT | 3216 |
| Lys | Lys | Val | Leu 1060 | Leu | Leu | Ser | Glu | Ala 1065 | Glu | Ile | Thr | Phe | Asn 1070 | Thr | Ser | |
| GTG | TAT | TCC | CAG | CTG | CCG | GGA | CAG | GAG | GCA | TTT | CTG | AGA | GCC | CAG | GTG | 3264 |
| Val | Tyr | Ser 1075 | Gln | Leu | Pro | Gly | Gln 1080 | Glu | Ala | Phe | Leu | Arg 1085 | Ala | Gln | Val | |
| TCA | ACG | ATG | CTA | GAA | GAA | TAC | GTG | GTC | TAT | GAG | CCC | GTC | TTC | CTC | ATG | 3312 |
| Ser | Thr | Met 1090 | Leu | Glu | Glu | Tyr | Val 1095 | Val | Tyr | Glu | Pro | Val 1100 | Phe | Leu | Met | |
| GTG | TTC | AGC | TCA | GTG | GGA | GGT | CTG | CTG | TTA | CTG | GCT | CTC | ATC | ACT | GTG | 3360 |
| Val 1105 | Phe | Ser | Ser | Val | Gly 1110 | Gly | Leu | Leu | Leu | Leu 1115 | Ala | Leu | Ile | Thr | Val 1120 | |
| GCG | CTG | TAC | AAG | CTT | GGC | TTC | TTC | AAA | CGT | CAG | TAT | AAA | GAG | ATG | CTG | 3408 |
| Ala | Leu | Tyr | Lys | Leu 1125 | Gly | Phe | Phe | Lys | Arg 1130 | Gln | Tyr | Lys | Glu | Met 1135 | Leu | |
| GAT | CTA | CCA | TCT | GCA | GAT | CCT | GAC | CCA | GCC | GGC | CAG | GCA | GAT | TCC | AAC | 3456 |
| Asp | Leu | Pro | Ser | Ala 1140 | Asp | Pro | Asp | Pro | Ala 1145 | Gly | Gln | Ala | Asp | Ser 1150 | Asn | |
| CAT | GAG | ACT | CCT | CCA | CAT | CTC | ACG | TCC | TAGGAATCTA | CTTTCCTGTA | | | | | | 3503 |
| His | Glu | Thr | Pro 1155 | Pro | His | Leu | Thr | Ser 1160 | | | | | | | | |

| | | | | |
|---|---|---|---|---|
| TATCTCCACA | ATTACGAGAT | TGGTTTTGCT | TTTGCCTATG | AATCTACTGG | CATGGGAACA | 3563 |
| AGTTCTCTTC | AGCTCTGGGC | TAGCCTGGGA | AACTTCCCAG | AAATGATGCC | CTACCTCCTG | 3623 |
| AGCTGGGAGA | TTTTTATGGT | TGCCCATGT | GTCAGATTTC | AGTGCTGATC | CACTTTTTTT | 3683 |
| GCAAGAGCAG | GAATGGGGTC | AGCATAAATT | TACATATGGA | TAAGAACTAA | CACAAGACTG | 3743 |
| AGTAATATGC | TCAATATTCA | ATGTATTGCT | TGTATAAATT | TTTAAAAAAT | AAAATGAAAN | 3803 |

( 2 ) INFORMATION FOR SEQ ID NO:53:

( i ) SEQUENCE CHARACTERISTICS:
    ( A ) LENGTH: 1161 amino acids
    ( B ) TYPE: amino acid
    ( D ) TOPOLOGY: linear ( i i ) MOLECULE TYPE: protein ( x i ) SEQUENCE DESCRIPTION: SEQ ID NO:53:

```
Met  Val  Arg  Gly  Val  Val  Ile  Leu  Leu  Cys  Gly  Trp  Ala  Leu  Ala  Ser
 1              5                        10                       15

Cys  His  Gly  Ser  Asn  Leu  Asp  Val  Glu  Lys  Pro  Val  Val  Phe  Lys  Glu
              20                       25                       30

Asp  Ala  Ala  Ser  Phe  Gly  Gln  Thr  Val  Val  Gln  Phe  Gly  Gly  Ser  Arg
              35                       40                       45

Leu  Val  Val  Gly  Ala  Pro  Leu  Glu  Ala  Val  Ala  Val  Asn  Gln  Thr  Gly
         50                       55                       60

Gln  Ser  Ser  Asp  Cys  Pro  Pro  Ala  Thr  Gly  Val  Cys  Gln  Pro  Ile  Leu
 65                       70                       75                       80

Leu  His  Ile  Pro  Leu  Glu  Ala  Val  Asn  Met  Ser  Leu  Gly  Leu  Ser  Leu
                   85                       90                       95

Val  Ala  Asp  Thr  Asn  Asn  Ser  Gln  Leu  Leu  Ala  Cys  Gly  Pro  Thr  Ala
                  100                      105                      110

Gln  Arg  Ala  Cys  Ala  Lys  Asn  Met  Tyr  Ala  Lys  Gly  Ser  Cys  Leu  Leu
              115                      120                      125

Leu  Gly  Ser  Ser  Leu  Gln  Phe  Ile  Gln  Ala  Ile  Pro  Ala  Thr  Met  Pro
         130                      135                      140

Glu  Cys  Pro  Gly  Gln  Glu  Met  Asp  Ile  Ala  Phe  Leu  Ile  Asp  Gly  Ser
145                      150                      155                      160

Gly  Ser  Ile  Asp  Gln  Ser  Asp  Phe  Thr  Gln  Met  Lys  Asp  Phe  Val  Lys
                   165                      170                      175

Ala  Leu  Met  Gly  Gln  Leu  Ala  Ser  Thr  Ser  Thr  Ser  Phe  Ser  Leu  Met
              180                      185                      190

Gln  Tyr  Ser  Asn  Ile  Leu  Lys  Thr  His  Phe  Thr  Phe  Thr  Glu  Phe  Lys
              195                      200                      205

Ser  Ser  Leu  Ser  Pro  Gln  Ser  Leu  Val  Asp  Ala  Ile  Val  Gln  Leu  Gln
210                      215                      220

Gly  Leu  Thr  Tyr  Thr  Ala  Ser  Gly  Ile  Gln  Lys  Val  Val  Lys  Glu  Leu
225                      230                      235                      240

Phe  His  Ser  Lys  Asn  Gly  Ala  Arg  Lys  Ser  Ala  Lys  Lys  Ile  Leu  Ile
                   245                      250                      255

Val  Ile  Thr  Asp  Gly  Gln  Lys  Phe  Arg  Asp  Pro  Leu  Glu  Tyr  Arg  His
                  260                      265                      270

Val  Ile  Pro  Glu  Ala  Glu  Lys  Ala  Gly  Ile  Ile  Arg  Tyr  Ala  Ile  Gly
              275                      280                      285

Val  Gly  Asp  Ala  Phe  Arg  Glu  Pro  Thr  Ala  Leu  Gln  Glu  Leu  Asn  Thr
         290                      295                      300

Ile  Gly  Ser  Ala  Pro  Ser  Gln  Asp  His  Val  Phe  Lys  Val  Gly  Asn  Phe
305                      310                      315                      320

Val  Ala  Leu  Arg  Ser  Ile  Gln  Arg  Gln  Ile  Gln  Glu  Lys  Ile  Phe  Ala
                   325                      330                      335

Ile  Glu  Gly  Thr  Glu  Ser  Arg  Ser  Ser  Ser  Ser  Phe  Gln  His  Glu  Met
                  340                      345                      350

Ser  Gln  Glu  Gly  Phe  Ser  Ser  Ala  Leu  Ser  Met  Asp  Gly  Pro  Val  Leu
              355                      360                      365
```

| Gly | Ala | Val | Gly | Gly | Phe | Ser | Trp | Ser | Gly | Gly | Ala | Phe | Leu | Tyr | Pro |
|-----|-----|-----|-----|-----|-----|-----|-----|-----|-----|-----|-----|-----|-----|-----|-----|
|     | 370 |     |     |     | 375 |     |     |     |     | 380 |     |     |     |     |     |
| Ser | Asn | Met | Arg | Ser | Thr | Phe | Ile | Asn | Met | Ser | Gln | Glu | Asn | Glu | Asp |
| 385 |     |     |     |     | 390 |     |     |     | 395 |     |     |     |     |     | 400 |
| Met | Arg | Asp | Ala | Tyr | Leu | Gly | Tyr | Ser | Ala | Leu | Ala | Phe | Trp | Lys |
|     |     |     |     | 405 |     |     |     |     | 410 |     |     |     |     | 415 |
| Gly | Val | His | Ser | Leu | Ile | Leu | Gly | Ala | Pro | Arg | His | Gln | His | Thr | Gly |
|     |     |     | 420 |     |     |     |     | 425 |     |     |     |     | 430 |     |     |
| Lys | Val | Val | Ile | Phe | Thr | Gln | Glu | Ser | Arg | His | Trp | Arg | Pro | Lys | Ser |
|     |     | 435 |     |     |     |     | 440 |     |     |     |     | 445 |     |     |     |
| Glu | Val | Arg | Gly | Thr | Gln | Ile | Gly | Ser | Tyr | Phe | Gly | Ala | Ser | Leu | Cys |
|     | 450 |     |     |     |     | 455 |     |     |     |     | 460 |     |     |     |     |
| Ser | Val | Asp | Met | Asp | Arg | Asp | Gly | Ser | Thr | Asp | Leu | Val | Leu | Ile | Gly |
| 465 |     |     |     | 470 |     |     |     |     | 475 |     |     |     |     |     | 480 |
| Val | Pro | His | Tyr | Tyr | Glu | His | Thr | Arg | Gly | Gly | Gln | Val | Ser | Val | Cys |
|     |     |     |     | 485 |     |     |     |     | 490 |     |     |     |     | 495 |     |
| Pro | Met | Pro | Gly | Val | Arg | Ser | Arg | Trp | His | Cys | Gly | Thr | Thr | Leu | His |
|     |     |     | 500 |     |     |     |     | 505 |     |     |     |     | 510 |     |     |
| Gly | Glu | Gln | Gly | His | Pro | Trp | Gly | Arg | Phe | Gly | Ala | Ala | Leu | Thr | Val |
|     |     | 515 |     |     |     |     | 520 |     |     |     |     | 525 |     |     |     |
| Leu | Gly | Asp | Val | Asn | Gly | Asp | Ser | Leu | Ala | Asp | Val | Ala | Ile | Gly | Ala |
|     | 530 |     |     |     |     | 535 |     |     |     |     | 540 |     |     |     |     |
| Pro | Gly | Glu | Glu | Glu | Asn | Arg | Gly | Ala | Val | Tyr | Ile | Phe | His | Gly | Ala |
| 545 |     |     |     |     | 550 |     |     |     |     | 555 |     |     |     |     | 560 |
| Ser | Arg | Gln | Asp | Ile | Ala | Pro | Ser | Pro | Ser | Gln | Arg | Val | Thr | Gly | Ser |
|     |     |     |     | 565 |     |     |     |     | 570 |     |     |     |     | 575 |     |
| Gln | Leu | Phe | Leu | Arg | Leu | Gln | Tyr | Phe | Gly | Gln | Ser | Leu | Ser | Gly | Gly |
|     |     |     | 580 |     |     |     |     | 585 |     |     |     |     | 590 |     |     |
| Gln | Asp | Leu | Thr | Gln | Asp | Gly | Leu | Val | Asp | Leu | Ala | Val | Gly | Ala | Gln |
|     |     | 595 |     |     |     |     | 600 |     |     |     |     | 605 |     |     |     |
| Gly | His | Val | Leu | Leu | Leu | Arg | Ser | Leu | Pro | Leu | Leu | Lys | Val | Gly | Ile |
|     | 610 |     |     |     |     | 615 |     |     |     |     | 620 |     |     |     |     |
| Ser | Ile | Arg | Phe | Ala | Pro | Ser | Glu | Val | Ala | Lys | Thr | Val | Tyr | Gln | Cys |
| 625 |     |     |     |     | 630 |     |     |     |     | 635 |     |     |     |     | 640 |
| Trp | Gly | Arg | Thr | Pro | Thr | Val | Leu | Glu | Ala | Gly | Glu | Ala | Thr | Val | Cys |
|     |     |     |     | 645 |     |     |     |     | 650 |     |     |     |     | 655 |     |
| Leu | Thr | Val | Arg | Lys | Gly | Ser | Pro | Asp | Leu | Leu | Gly | Asp | Val | Gln | Ser |
|     |     |     |     | 660 |     |     |     | 665 |     |     |     |     | 670 |     |     |
| Ser | Val | Arg | Tyr | Asp | Leu | Ala | Leu | Asp | Pro | Gly | Arg | Leu | Ile | Ser | Arg |
|     |     | 675 |     |     |     |     | 680 |     |     |     |     | 685 |     |     |     |
| Ala | Ile | Phe | Asp | Glu | Thr | Lys | Asn | Cys | Thr | Leu | Thr | Arg | Arg | Lys | Thr |
|     |     | 690 |     |     |     |     | 695 |     |     |     |     | 700 |     |     |     |
| Leu | Gly | Leu | Gly | Asp | His | Cys | Glu | Thr | Met | Lys | Leu | Leu | Leu | Pro | Asp |
| 705 |     |     |     |     | 710 |     |     |     |     | 715 |     |     |     |     | 720 |
| Cys | Val | Glu | Asp | Ala | Val | Thr | Pro | Ile | Ile | Leu | Arg | Leu | Asn | Leu | Ser |
|     |     |     |     | 725 |     |     |     |     | 730 |     |     |     |     | 735 |     |
| Leu | Ala | Gly | Asp | Ser | Ala | Pro | Ser | Arg | Asn | Leu | Arg | Pro | Val | Leu | Ala |
|     |     |     | 740 |     |     |     |     | 745 |     |     |     |     | 750 |     |     |
| Val | Gly | Ser | Gln | Asp | His | Val | Thr | Ala | Ser | Phe | Pro | Phe | Glu | Lys | Asn |
|     |     | 755 |     |     |     |     | 760 |     |     |     |     | 765 |     |     |     |
| Cys | Lys | Gln | Glu | Leu | Leu | Cys | Glu | Gly | Asn | Leu | Gly | Val | Ser | Phe | Asn |
|     | 770 |     |     |     |     | 775 |     |     |     |     | 780 |     |     |     |     |
| Phe | Ser | Gly | Leu | Gln | Val | Leu | Glu | Val | Gly | Ser | Ser | Pro | Glu | Leu | Thr |
| 785 |     |     |     |     | 790 |     |     |     |     | 795 |     |     |     |     | 800 |

Val Thr Val Thr Val Trp Asn Glu Gly Glu Asp Ser Tyr Gly Thr Leu
            805                 810                 815
Ile Lys Phe Tyr Tyr Pro Ala Glu Leu Ser Tyr Arg Arg Val Thr Arg
            820                 825                 830
Ala Gln Gln Pro His Pro Tyr Pro Leu Arg Leu Ala Cys Glu Ala Glu
        835                 840                 845
Pro Thr Gly Gln Glu Ser Leu Arg Ser Ser Ser Cys Ser Ile Asn His
    850                 855                 860
Pro Ile Phe Arg Glu Gly Ala Lys Ala Thr Phe Met Ile Thr Phe Asp
865                 870                 875                 880
Val Ser Tyr Lys Ala Phe Leu Gly Asp Arg Leu Leu Leu Arg Ala Ser
                885                 890                 895
Ala Ser Ser Glu Asn Asn Lys Pro Glu Thr Ser Lys Thr Ala Phe Gln
            900                 905                 910
Leu Glu Leu Pro Val Lys Tyr Thr Val Tyr Thr Val Ile Ser Arg Gln
        915                 920                 925
Glu Asp Ser Thr Lys His Phe Asn Phe Ser Ser Ser His Gly Glu Arg
    930                 935                 940
Gln Lys Glu Ala Glu His Arg Tyr Arg Val Asn Asn Leu Ser Pro Leu
945                 950                 955                 960
Thr Leu Ala Ile Ser Val Asn Phe Trp Val Pro Ile Leu Leu Asn Gly
                965                 970                 975
Val Ala Val Trp Asp Val Thr Leu Arg Ser Pro Ala Gln Gly Val Ser
            980                 985                 990
Cys Val Ser Gln Arg Glu Pro Pro Gln His Ser Asp Leu Leu Thr Gln
        995                 1000                1005
Ile Gln Gly Arg Ser Val Leu Asp Cys Ala Ile Ala Asp Cys Leu His
    1010                1015                1020
Leu Arg Cys Asp Ile Pro Ser Leu Gly Thr Leu Asp Glu Leu Asp Phe
1025                1030                1035                1040
Ile Leu Lys Gly Asn Leu Ser Phe Gly Trp Ile Ser Gln Thr Leu Gln
                1045                1050                1055
Lys Lys Val Leu Leu Leu Ser Glu Ala Glu Ile Thr Phe Asn Thr Ser
            1060                1065                1070
Val Tyr Ser Gln Leu Pro Gly Gln Glu Ala Phe Leu Arg Ala Gln Val
        1075                1080                1085
Ser Thr Met Leu Glu Glu Tyr Val Val Tyr Glu Pro Val Phe Leu Met
    1090                1095                1100
Val Phe Ser Ser Val Gly Gly Leu Leu Leu Leu Ala Leu Ile Thr Val
1105                1110                1115                1120
Ala Leu Tyr Lys Leu Gly Phe Phe Lys Arg Gln Tyr Lys Glu Met Leu
                1125                1130                1135
Asp Leu Pro Ser Ala Asp Pro Asp Pro Ala Gly Gln Ala Asp Ser Asn
            1140                1145                1150
His Glu Thr Pro Pro His Leu Thr Ser
    1155                1160

( 2 ) INFORMATION FOR SEQ ID NO:54:

( i ) SEQUENCE CHARACTERISTICS:
      ( A ) LENGTH: 3597 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
  ( A ) NAME/KEY: CDS
  ( B ) LOCATION: 40..3525

( x i ) SEQUENCE DESCRIPTION: SEQ ID NO:54:

```
AGCTTTACAG CTCTCTACTT CTCAGTGCAC TGCTCAGTG ATG GCC GGT GGA GTT              54
                                           Met Ala Gly Gly Val
                                            1               5

GTG ATC CTC CTG TGT GGC TGG GTC CTG GCT TCC TGT CAT GGG TCT AAC            102
Val Ile Leu Leu Cys Gly Trp Val Leu Ala Ser Cys His Gly Ser Asn
             10                  15                  20

CTG GAT GTG GAG GAA CCC ATC GTG TTC AGA GAG GAT GCA GCC AGC TTT            150
Leu Asp Val Glu Glu Pro Ile Val Phe Arg Glu Asp Ala Ala Ser Phe
             25                  30                  35

GGA CAG ACT GTG GTG CAG TTT GGT GGA TCT CGA CTC GTG GTG GGA GCC            198
Gly Gln Thr Val Val Gln Phe Gly Gly Ser Arg Leu Val Val Gly Ala
             40                  45                  50

CCT CTG GAG GCG GTG GCA GTC AAC CAA ACA GGA CGG TTG TAT GAC TGT            246
Pro Leu Glu Ala Val Ala Val Asn Gln Thr Gly Arg Leu Tyr Asp Cys
         55                  60                  65

GCA CCT GCC ACT GGC ATG TGC CAG CCC ATC GTA CTG CGC AGT CCC CTA            294
Ala Pro Ala Thr Gly Met Cys Gln Pro Ile Val Leu Arg Ser Pro Leu
 70              75                  80                      85

GAG GCA GTG AAC ATG TCC CTG GGC CTG TCT CTG GTG ACT GCC ACC AAT            342
Glu Ala Val Asn Met Ser Leu Gly Leu Ser Leu Val Thr Ala Thr Asn
                 90                  95                 100

AAC GCC CAG TTG CTG GCT TGT GGT CCA ACT GCA CAG AGA GCT TGT GTG            390
Asn Ala Gln Leu Leu Ala Cys Gly Pro Thr Ala Gln Arg Ala Cys Val
             105                 110                 115

AAG AAC ATG TAT GCG AAA GGT TCC TGC CTC CTT CTC GGC TCC AGC TTG            438
Lys Asn Met Tyr Ala Lys Gly Ser Cys Leu Leu Leu Gly Ser Ser Leu
         120                 125                 130

CAG TTC ATC CAG GCA GTC CCT GCC TCC ATG CCA GAG TGT CCA AGA CAA            486
Gln Phe Ile Gln Ala Val Pro Ala Ser Met Pro Glu Cys Pro Arg Gln
     135                 140                 145

GAG ATG GAC ATT GCT TTC CTG ATT GAT GGT TCT GGC AGC ATT AAC CAA            534
Glu Met Asp Ile Ala Phe Leu Ile Asp Gly Ser Gly Ser Ile Asn Gln
150              155                 160                 165

AGG GAC TTT GCC CAG ATG AAG GAC TTT GTC AAA GCT TTG ATG GGA GAG            582
Arg Asp Phe Ala Gln Met Lys Asp Phe Val Lys Ala Leu Met Gly Glu
                 170                 175                 180

TTT GCG AGC ACC AGC ACC TTG TTC TCC CTG ATG CAA TAC TCG AAC ATC            630
Phe Ala Ser Thr Ser Thr Leu Phe Ser Leu Met Gln Tyr Ser Asn Ile
             185                 190                 195

CTG AAG ACC CAT TTT ACC TTC ACT GAA TTC AAG AAC ATC CTG GAC CCT            678
Leu Lys Thr His Phe Thr Phe Thr Glu Phe Lys Asn Ile Leu Asp Pro
         200                 205                 210

CAG AGC CTG GTG GAT CCC ATT GTC CAG CTG CAA GGC CTG ACC TAC ACA            726
Gln Ser Leu Val Asp Pro Ile Val Gln Leu Gln Gly Leu Thr Tyr Thr
     215                 220                 225

GCC ACA GGC ATC CGG ACA GTG ATG GAA GAG CTA TTT CAT AGC AAG AAT            774
Ala Thr Gly Ile Arg Thr Val Met Glu Glu Leu Phe His Ser Lys Asn
230              235                 240                 245

GGG TCC CGT AAA AGT GCC AAG AAG ATC CTC CTT GTC ATC ACA GAT GGG            822
Gly Ser Arg Lys Ser Ala Lys Lys Ile Leu Leu Val Ile Thr Asp Gly
                 250                 255                 260

CAG AAA TAC AGA GAC CCC CTG GAG TAT AGT GAT GTC ATT CCC GCC GCA            870
Gln Lys Tyr Arg Asp Pro Leu Glu Tyr Ser Asp Val Ile Pro Ala Ala
             265                 270                 275

GAC AAA GCT GGC ATC ATT CGT TAT GCT ATT GGG GTG GGA GAT GCC TTC            918
```

-continued

```
         Asp  Lys  Ala  Gly  Ile  Ile  Arg  Tyr  Ala  Ile  Gly  Val  Gly  Asp  Ala  Phe
              280                     285                    290

CAG  GAG  CCC  ACT  GCC  CTG  AAG  GAG  CTG  AAC  ACC  ATT  GGC  TCA  GCT  CCC          966
Gln  Glu  Pro  Thr  Ala  Leu  Lys  Glu  Leu  Asn  Thr  Ile  Gly  Ser  Ala  Pro
     295                 300                      305

CCA  CAG  GAC  CAC  GTG  TTC  AAG  GTA  GGC  AAC  TTT  GCA  GCA  CTT  CGC  AGC         1014
Pro  Gln  Asp  His  Val  Phe  Lys  Val  Gly  Asn  Phe  Ala  Ala  Leu  Arg  Ser
310                      315                 320                          325

ATC  CAG  AGG  CAA  CTT  CAG  GAG  AAA  ATC  TTC  GCC  ATT  GAG  GGA  ACT  CAA         1062
Ile  Gln  Arg  Gln  Leu  Gln  Glu  Lys  Ile  Phe  Ala  Ile  Glu  Gly  Thr  Gln
                    330                      335                     340

TCA  AGG  TCA  AGT  AGT  TCC  TTT  CAG  CAC  GAG  ATG  TCA  CAA  GAA  GGT  TTC         1110
Ser  Arg  Ser  Ser  Ser  Ser  Phe  Gln  His  Glu  Met  Ser  Gln  Glu  Gly  Phe
               345                      350                      355

AGT  TCA  GCT  CTC  ACA  TCG  GAT  GGA  CCC  GTT  CTG  GGG  GCC  GTG  GGA  AGC         1158
Ser  Ser  Ala  Leu  Thr  Ser  Asp  Gly  Pro  Val  Leu  Gly  Ala  Val  Gly  Ser
               360                      365                     370

TTC  AGC  TGG  TCC  GGA  GGT  GCC  TTC  TTA  TAT  CCC  CCA  AAT  ACG  AGA  CCC         1206
Phe  Ser  Trp  Ser  Gly  Gly  Ala  Phe  Leu  Tyr  Pro  Pro  Asn  Thr  Arg  Pro
     375                      380                     385

ACC  TTT  ATC  AAC  ATG  TCT  CAG  GAG  AAT  GTG  GAC  ATG  AGA  GAC  TCC  TAC         1254
Thr  Phe  Ile  Asn  Met  Ser  Gln  Glu  Asn  Val  Asp  Met  Arg  Asp  Ser  Tyr
390                      395                     400                          405

CTG  GGT  TAC  TCC  ACC  GCA  GTG  GCC  TTT  TGG  AAG  GGG  GTT  CAC  AGC  CTG         1302
Leu  Gly  Tyr  Ser  Thr  Ala  Val  Ala  Phe  Trp  Lys  Gly  Val  His  Ser  Leu
                    410                      415                     420

ATC  CTG  GGG  GCC  CCG  CGT  CAC  CAG  CAC  ACG  GGG  AAG  GTT  GTC  ATC  TTT         1350
Ile  Leu  Gly  Ala  Pro  Arg  His  Gln  His  Thr  Gly  Lys  Val  Val  Ile  Phe
               425                      430                     435

ACC  CAG  GAA  GCC  AGG  CAT  TGG  AGG  CCC  AAG  TCT  GAA  GTC  AGA  GGG  ACA         1398
Thr  Gln  Glu  Ala  Arg  His  Trp  Arg  Pro  Lys  Ser  Glu  Val  Arg  Gly  Thr
          440                      445                     450

CAG  ATC  GGC  TCC  TAC  TTC  GGG  GCC  TCT  CTC  TGT  TCT  GTG  GAC  GTG  GAT         1446
Gln  Ile  Gly  Ser  Tyr  Phe  Gly  Ala  Ser  Leu  Cys  Ser  Val  Asp  Val  Asp
     455                      460                     465

AGA  GAT  GGC  AGC  ACY  GAC  CTG  GTC  CTG  ATC  GGA  GCC  CCC  CAT  TAC  TAT         1494
Arg  Asp  Gly  Ser  Xaa  Asp  Leu  Val  Leu  Ile  Gly  Ala  Pro  His  Tyr  Tyr
470                      475                     480                          485

GAG  CAG  ACC  CGA  GGG  GGG  CAG  GTC  TCA  GTG  TTC  CCC  GTG  CCC  GGT  GTG         1542
Glu  Gln  Thr  Arg  Gly  Gly  Gln  Val  Ser  Val  Phe  Pro  Val  Pro  Gly  Val
                    490                      495                     500

AGG  GGC  AGG  TGG  CAG  TGT  GAG  GCC  ACC  CTC  CAC  GGG  GAG  CAG  GGC  CAT         1590
Arg  Gly  Arg  Trp  Gln  Cys  Glu  Ala  Thr  Leu  His  Gly  Glu  Gln  Gly  His
               505                      510                     515

CCT  TGG  GGC  CGC  TTT  GGG  GTG  GCT  CTG  ACA  GTG  CTG  GGG  GAC  GTA  AAC         1638
Pro  Trp  Gly  Arg  Phe  Gly  Val  Ala  Leu  Thr  Val  Leu  Gly  Asp  Val  Asn
          520                      525                     530

GGG  GAC  AAT  CTG  GCA  GAC  GTG  GCT  ATT  GGT  GCC  CCT  GGA  GAG  GAG  GAG         1686
Gly  Asp  Asn  Leu  Ala  Asp  Val  Ala  Ile  Gly  Ala  Pro  Gly  Glu  Glu  Glu
     535                     540                      545

AGC  AGA  GGT  GCT  GTC  TAC  ATA  TTT  CAT  GGA  GCC  TCG  AGA  CTG  GAG  ATC         1734
Ser  Arg  Gly  Ala  Val  Tyr  Ile  Phe  His  Gly  Ala  Ser  Arg  Leu  Glu  Ile
550                      555                     560                          565

ATG  CCC  TCA  CCC  AGC  CAG  CGG  GTC  ACT  GGC  TCC  CAG  CTC  TCC  CTG  AGA         1782
Met  Pro  Ser  Pro  Ser  Gln  Arg  Val  Thr  Gly  Ser  Gln  Leu  Ser  Leu  Arg
                    570                      575                     580

CTG  CAG  TAT  TTT  GGG  CAG  TCA  TTG  AGT  GGG  GGT  CAG  GAC  CTT  ACA  CAG         1830
Leu  Gln  Tyr  Phe  Gly  Gln  Ser  Leu  Ser  Gly  Gly  Gln  Asp  Leu  Thr  Gln
               585                      590                     595

GAT  GGC  CTG  GTG  GAC  CTG  GCC  GTG  GGA  GCC  CAG  GGG  CAC  GTA  CTG  CTG         1878
```

```
Asp Gly Leu Val Asp Leu Ala Val Gly Ala Gln Gly His Val Leu Leu
        600             605              610

CTC AGG AGT CTG CCT CTG CTG AAA GTG GAG CTC TCC ATA AGA TTC GCC    1926
Leu Arg Ser Leu Pro Leu Leu Lys Val Glu Leu Ser Ile Arg Phe Ala
    615             620             625

CCC ATG GAG GTG GCA AAG GCT GTG TAC CAG TGC TGG GAA AGG ACT CCC    1974
Pro Met Glu Val Ala Lys Ala Val Tyr Gln Cys Trp Glu Arg Thr Pro
630             635             640                 645

ACT GTC CTC GAA GCT GGA GAG GCC ACT GTC TGT CTC ACT GTC CAC AAA    2022
Thr Val Leu Glu Ala Gly Glu Ala Thr Val Cys Leu Thr Val His Lys
                650             655                 660

GGC TCA CCT GAC CTG TTA GGT AAT GTC CAA GGC TCT GTC AGG TAT GAT    2070
Gly Ser Pro Asp Leu Leu Gly Asn Val Gln Gly Ser Val Arg Tyr Asp
            665             670             675

CTG GCG TTA GAT CCG GGC CGC CTG ATT TCT CGT GCC ATT TTT GAT GAG    2118
Leu Ala Leu Asp Pro Gly Arg Leu Ile Ser Arg Ala Ile Phe Asp Glu
        680             685             690

ACT AAG AAC TGC ACT TTG ACG GGA AGG AAG ACT CTG GGG CTT GGT GAT    2166
Thr Lys Asn Cys Thr Leu Thr Gly Arg Lys Thr Leu Gly Leu Gly Asp
    695             700             705

CAC TGC GAA ACA GTG AAG CTG CTT TTG CCG GAC TGT GTG GAA GAT GCA    2214
His Cys Glu Thr Val Lys Leu Leu Leu Pro Asp Cys Val Glu Asp Ala
710             715             720                 725

GTG AGC CCT ATC ATC CTG CGC CTC AAC TTT TCC CTG GTG AGA GAC TCT    2262
Val Ser Pro Ile Ile Leu Arg Leu Asn Phe Ser Leu Val Arg Asp Ser
                730             735                 740

GCT TCA CCC AGG AAC CTG CAT CCT GTG CTG GCT GTG GGC TCA CAA GAC    2310
Ala Ser Pro Arg Asn Leu His Pro Val Leu Ala Val Gly Ser Gln Asp
            745             750             755

CAC ATA ACT GCT TCT CTG CCG TTT GAG AAG AAC TGT AAG CAA GAA CTC    2358
His Ile Thr Ala Ser Leu Pro Phe Glu Lys Asn Cys Lys Gln Glu Leu
        760             765             770

CTG TGT GAG GGG GAC CTG GGC ATC AGC TTT AAC TTC TCA GGC CTG CAG    2406
Leu Cys Glu Gly Asp Leu Gly Ile Ser Phe Asn Phe Ser Gly Leu Gln
    775             780             785

GTC TTG GTG GTG GGA GGC TCC CCA GAG CTC ACT GTG ACA GTC ACT GTG    2454
Val Leu Val Val Gly Gly Ser Pro Glu Leu Thr Val Thr Val Thr Val
790             795             800                 805

TGG AAT GAG GGT GAG GAC AGC TAT GGA ACT TTA GTC AAG TTC TAC TAC    2502
Trp Asn Glu Gly Glu Asp Ser Tyr Gly Thr Leu Val Lys Phe Tyr Tyr
                810             815                 820

CCA GCA GGG CTA TCT TAC CGA CGG GTA ACA GGG ACT CAG CAA CCT CAT    2550
Pro Ala Gly Leu Ser Tyr Arg Arg Val Thr Gly Thr Gln Gln Pro His
            825             830             835

CAG TAC CCA CTA CGC TTG GCC TGT GAG GCT GAG CCC GCT GCC CAG GAG    2598
Gln Tyr Pro Leu Arg Leu Ala Cys Glu Ala Glu Pro Ala Ala Gln Glu
        840             845             850

GAC CTG AGG AGC AGC AGC TGT AGC ATT AAT CAC CCC ATC TTC CGA GAA    2646
Asp Leu Arg Ser Ser Ser Cys Ser Ile Asn His Pro Ile Phe Arg Glu
    855             860             865

GGT GCA AAG ACC ACC TTC ATG ATC ACA TTC GAT GTC TCC TAC AAG GCC    2694
Gly Ala Lys Thr Thr Phe Met Ile Thr Phe Asp Val Ser Tyr Lys Ala
870             875             880                 885

TTC CTA GGA GAC AGG TTG CTT CTG AGG GCC AAA GCC AGC AGT GAG AAT    2742
Phe Leu Gly Asp Arg Leu Leu Leu Arg Ala Lys Ala Ser Ser Glu Asn
                890             895                 900

AAT AAG CCT GAT ACC AAC AAG ACT GCC TTC CAG CTG GAG CTC CCA GTG    2790
Asn Lys Pro Asp Thr Asn Lys Thr Ala Phe Gln Leu Glu Leu Pro Val
            905             910             915

AAG TAC ACC GTC TAT ACC CTG ATC AGT AGG CAA GAA GAT TCC ACC AAC    2838
```

|     |     |     |     |     |     |     |     |     |     |     |     |     |     |     |
| --- | --- | --- | --- | --- | --- | --- | --- | --- | --- | --- | --- | --- | --- | --- |
| Lys | Tyr | Thr 920 | Val | Tyr | Thr | Leu | Ile | Ser 925 | Arg | Gln | Glu | Asp | Ser 930 | Thr | Asn |

```
CAT  GTC  AAC  TTT  TCA  TCT  TCC  CAC  GGG  GGG  AGA  AGG  CAA  GAA  GCC  GCA      2886
His  Val  Asn  Phe  Ser  Ser  Ser  His  Gly  Gly  Arg  Arg  Gln  Glu  Ala  Ala
     935                      940                     945

CAT  CGC  TAT  CGT  GTG  AAT  AAC  CTG  AGT  CCA  CTG  AAG  CTG  GCC  GTC  AGA      2934
His  Arg  Tyr  Arg  Val  Asn  Asn  Leu  Ser  Pro  Leu  Lys  Leu  Ala  Val  Arg
950                      955                     960                      965

GTT  AAC  TTC  TGG  GTC  CCT  GTC  CTT  CTG  AAC  GGT  GTG  GCT  GTG  TGG  GAC      2982
Val  Asn  Phe  Trp  Val  Pro  Val  Leu  Leu  Asn  Gly  Val  Ala  Val  Trp  Asp
                    970                     975                      980

GTG  ACT  CTG  AGC  AGC  CCA  GCA  CAG  GGT  GTC  TCC  TGC  GTG  TCC  CAG  ATG      3030
Val  Thr  Leu  Ser  Ser  Pro  Ala  Gln  Gly  Val  Ser  Cys  Val  Ser  Gln  Met
               985                      990                     995

AAA  CCT  CCT  CAG  AAT  CCC  GAC  TTT  CTG  ACC  CAG  ATT  CAG  AGA  CGT  TCT      3078
Lys  Pro  Pro  Gln  Asn  Pro  Asp  Phe  Leu  Thr  Gln  Ile  Gln  Arg  Arg  Ser
          1000                     1005                     1010

GTG  CTG  GAC  TGC  TCC  ATT  GCT  GAC  TGC  CTG  CAC  TTC  CGC  TGT  GAC  ATC      3126
Val  Leu  Asp  Cys  Ser  Ile  Ala  Asp  Cys  Leu  His  Phe  Arg  Cys  Asp  Ile
     1015                     1020                     1025

CCC  TCC  TTG  GAC  ATC  CAG  GAT  GAA  CTT  GAC  TTC  ATT  CTG  AGG  GGC  AAC      3174
Pro  Ser  Leu  Asp  Ile  Gln  Asp  Glu  Leu  Asp  Phe  Ile  Leu  Arg  Gly  Asn
1030                     1035                     1040                     1045

CTC  AGC  TTC  GGC  TGG  GTC  AGT  CAG  ACA  TTG  CAG  GAA  AAG  GTG  TTG  CTT      3222
Leu  Ser  Phe  Gly  Trp  Val  Ser  Gln  Thr  Leu  Gln  Glu  Lys  Val  Leu  Leu
                    1050                     1055                     1060

GTG  AGT  GAG  GCT  GAA  ATC  ACT  TTC  GAC  ACA  TCT  GTG  TAC  TCC  CAG  CTG      3270
Val  Ser  Glu  Ala  Glu  Ile  Thr  Phe  Asp  Thr  Ser  Val  Tyr  Ser  Gln  Leu
               1065                     1070                     1075

CCA  GGA  CAG  GAG  GCA  TTT  CTG  AGA  GCC  CAG  GTG  GAG  ACA  ACG  TTA  GAA      3318
Pro  Gly  Gln  Glu  Ala  Phe  Leu  Arg  Ala  Gln  Val  Glu  Thr  Thr  Leu  Glu
          1080                     1085                     1090

GAA  TAC  GTG  GTC  TAT  GAG  CCC  ATC  TTC  CTC  GTG  GCG  GGC  AGC  TCG  GTG      3366
Glu  Tyr  Val  Val  Tyr  Glu  Pro  Ile  Phe  Leu  Val  Ala  Gly  Ser  Ser  Val
     1095                     1100                     1105

GGA  GGT  CTG  CTG  TTA  CTG  GCT  CTC  ATC  ACA  GTG  GTA  CTG  TAC  AAG  CTT      3414
Gly  Gly  Leu  Leu  Leu  Leu  Ala  Leu  Ile  Thr  Val  Val  Leu  Tyr  Lys  Leu
1110                     1115                     1120                     1125

GGC  TTC  TYC  AAA  CGT  CAG  TAC  AAA  GAA  ATG  CTG  GAC  GGC  AAG  GCT  GCA      3462
Gly  Phe  Xaa  Lys  Arg  Gln  Tyr  Lys  Glu  Met  Leu  Asp  Gly  Lys  Ala  Ala
                    1130                     1135                     1140

GAT  CCT  GTC  ACA  GCC  GGC  CAG  GCA  GAT  TTC  GGC  TGT  GAG  ACT  CCT  CCA      3510
Asp  Pro  Val  Thr  Ala  Gly  Gln  Ala  Asp  Phe  Gly  Cys  Glu  Thr  Pro  Pro
               1145                     1150                     1155

TAT  CTC  GTG  AGC  TAGGAATCCA  CTCTCCTGCC  TATCTCTGCA  ATGAAGATTG              3562
Tyr  Leu  Val  Ser
               1160

GTCCTGCCTA  TGAGTCTACT  GGCATGGGAA  CGAGT                                        3597
```

( 2 ) INFORMATION FOR SEQ ID NO:55:

( i ) SEQUENCE CHARACTERISTICS:
            ( A ) LENGTH: 1161 amino acids
            ( B ) TYPE: amino acid
            ( D ) TOPOLOGY: linear ( i i ) MOLECULE TYPE: protein ( x i ) SEQUENCE DESCRIPTION: SEQ ID NO:55:

```
Met  Ala  Gly  Gly  Val  Val  Ile  Leu  Leu  Cys  Gly  Trp  Val  Leu  Ala  Ser
 1              5                    10                      15
```

-continued

| | | | | | | | | | | | | | | |
|---|---|---|---|---|---|---|---|---|---|---|---|---|---|---|
| Cys | His | Gly | Ser | Asn | Leu | Asp | Val | Glu | Glu | Pro | Ile | Val | Phe | Arg | Glu |
| | | | 20 | | | | 25 | | | | | 30 | | | |
| Asp | Ala | Ala | Ser | Phe | Gly | Gln | Thr | Val | Val | Gln | Phe | Gly | Ser | Arg |
| | | | 35 | | | | 40 | | | | | 45 | | |
| Leu | Val | Val | Gly | Ala | Pro | Leu | Glu | Ala | Val | Ala | Val | Asn | Gln | Thr | Gly |
| | | 50 | | | | 55 | | | | | 60 | | | |
| Arg | Leu | Tyr | Asp | Cys | Ala | Pro | Ala | Thr | Gly | Met | Cys | Gln | Pro | Ile | Val |
| 65 | | | | 70 | | | | | 75 | | | | | 80 |
| Leu | Arg | Ser | Pro | Leu | Glu | Ala | Val | Asn | Met | Ser | Leu | Gly | Leu | Ser | Leu |
| | | | | 85 | | | | | 90 | | | | | 95 |
| Val | Thr | Ala | Thr | Asn | Asn | Ala | Gln | Leu | Leu | Ala | Cys | Gly | Pro | Thr | Ala |
| | | | 100 | | | | 105 | | | | | 110 | | |
| Gln | Arg | Ala | Cys | Val | Lys | Asn | Met | Tyr | Ala | Lys | Gly | Ser | Cys | Leu | Leu |
| | | 115 | | | | | 120 | | | | | 125 | | | |
| Leu | Gly | Ser | Ser | Leu | Gln | Phe | Ile | Gln | Ala | Val | Pro | Ala | Ser | Met | Pro |
| | 130 | | | | | 135 | | | | | 140 | | | | |
| Glu | Cys | Pro | Arg | Gln | Glu | Met | Asp | Ile | Ala | Phe | Leu | Ile | Asp | Gly | Ser |
| 145 | | | | | 150 | | | | | 155 | | | | | 160 |
| Gly | Ser | Ile | Asn | Gln | Arg | Asp | Phe | Ala | Gln | Met | Lys | Asp | Phe | Val | Lys |
| | | | | 165 | | | | | 170 | | | | | 175 | |
| Ala | Leu | Met | Gly | Glu | Phe | Ala | Ser | Thr | Ser | Thr | Leu | Phe | Ser | Leu | Met |
| | | | 180 | | | | | 185 | | | | | 190 | | |
| Gln | Tyr | Ser | Asn | Ile | Leu | Lys | Thr | His | Phe | Thr | Phe | Thr | Glu | Phe | Lys |
| | | 195 | | | | | 200 | | | | | 205 | | | |
| Asn | Ile | Leu | Asp | Pro | Gln | Ser | Leu | Val | Asp | Pro | Ile | Val | Gln | Leu | Gln |
| 210 | | | | | | 215 | | | | | 220 | | | | |
| Gly | Leu | Thr | Tyr | Thr | Ala | Thr | Gly | Ile | Arg | Thr | Val | Met | Glu | Glu | Leu |
| 225 | | | | | 230 | | | | | 235 | | | | | 240 |
| Phe | His | Ser | Lys | Asn | Gly | Ser | Arg | Lys | Ser | Ala | Lys | Lys | Ile | Leu | Leu |
| | | | | 245 | | | | | 250 | | | | | 255 | |
| Val | Ile | Thr | Asp | Gly | Gln | Lys | Tyr | Arg | Asp | Pro | Leu | Glu | Tyr | Ser | Asp |
| | | | 260 | | | | | 265 | | | | | 270 | | |
| Val | Ile | Pro | Ala | Ala | Asp | Lys | Ala | Gly | Ile | Ile | Arg | Tyr | Ala | Ile | Gly |
| | | 275 | | | | | 280 | | | | | 285 | | | |
| Val | Gly | Asp | Ala | Phe | Gln | Glu | Pro | Thr | Ala | Leu | Lys | Glu | Leu | Asn | Thr |
| | 290 | | | | | 295 | | | | | 300 | | | | |
| Ile | Gly | Ser | Ala | Pro | Pro | Gln | Asp | His | Val | Phe | Lys | Val | Gly | Asn | Phe |
| 305 | | | | | 310 | | | | | 315 | | | | | 320 |
| Ala | Ala | Leu | Arg | Ser | Ile | Gln | Arg | Gln | Leu | Gln | Glu | Lys | Ile | Phe | Ala |
| | | | | 325 | | | | | 330 | | | | | 335 | |
| Ile | Glu | Gly | Thr | Gln | Ser | Arg | Ser | Ser | Ser | Phe | Gln | His | Glu | Met |
| | | | 340 | | | | | 345 | | | | | 350 | | |
| Ser | Gln | Glu | Gly | Phe | Ser | Ser | Ala | Leu | Thr | Ser | Asp | Gly | Pro | Val | Leu |
| | | 355 | | | | | 360 | | | | | 365 | | | |
| Gly | Ala | Val | Gly | Ser | Phe | Ser | Trp | Ser | Gly | Gly | Ala | Phe | Leu | Tyr | Pro |
| | 370 | | | | | 375 | | | | | 380 | | | | |
| Pro | Asn | Thr | Arg | Pro | Thr | Phe | Ile | Asn | Met | Ser | Gln | Glu | Asn | Val | Asp |
| 385 | | | | | 390 | | | | | 395 | | | | | 400 |
| Met | Arg | Asp | Ser | Tyr | Leu | Gly | Tyr | Ser | Thr | Ala | Val | Ala | Phe | Trp | Lys |
| | | | | 405 | | | | | 410 | | | | | 415 | |
| Gly | Val | His | Ser | Leu | Ile | Leu | Gly | Ala | Pro | Arg | His | Gln | His | Thr | Gly |
| | | | 420 | | | | | 425 | | | | | 430 | | |
| Lys | Val | Val | Ile | Phe | Thr | Gln | Glu | Ala | Arg | His | Trp | Arg | Pro | Lys | Ser |
| | | 435 | | | | | 440 | | | | | 445 | | | |

| | | | | | | | | | | | | | |
|---|---|---|---|---|---|---|---|---|---|---|---|---|---|
| Glu | Val | Arg | Gly | Thr | Gln | Ile | Gly | Ser | Tyr | Phe | Gly | Ala | Ser | Leu | Cys |
| | 450 | | | | 455 | | | | | 460 | | | |
| Ser | Val | Asp | Val | Asp | Arg | Asp | Gly | Ser | Xaa | Asp | Leu | Val | Leu | Ile | Gly |
| 465 | | | | | 470 | | | | | 475 | | | | | 480 |
| Ala | Pro | His | Tyr | Tyr | Glu | Gln | Thr | Arg | Gly | Gln | Val | Ser | Val | Phe |
| | | | | 485 | | | | | 490 | | | | 495 | |
| Pro | Val | Pro | Gly | Val | Arg | Gly | Arg | Trp | Gln | Cys | Glu | Ala | Thr | Leu | His |
| | | | 500 | | | | | 505 | | | | | 510 | | |
| Gly | Glu | Gln | Gly | His | Pro | Trp | Gly | Arg | Phe | Gly | Val | Ala | Leu | Thr | Val |
| | | 515 | | | | 520 | | | | | | 525 | | | |
| Leu | Gly | Asp | Val | Asn | Gly | Asp | Asn | Leu | Ala | Asp | Val | Ala | Ile | Gly | Ala |
| | 530 | | | | | 535 | | | | | 540 | | | | |
| Pro | Gly | Glu | Glu | Glu | Ser | Arg | Gly | Ala | Val | Tyr | Ile | Phe | His | Gly | Ala |
| 545 | | | | | 550 | | | | | 555 | | | | | 560 |
| Ser | Arg | Leu | Glu | Ile | Met | Pro | Ser | Pro | Ser | Gln | Arg | Val | Thr | Gly | Ser |
| | | | | 565 | | | | | 570 | | | | | 575 | |
| Gln | Leu | Ser | Leu | Arg | Leu | Gln | Tyr | Phe | Gly | Gln | Ser | Leu | Ser | Gly | Gly |
| | | | 580 | | | | | 585 | | | | | 590 | | |
| Gln | Asp | Leu | Thr | Gln | Asp | Gly | Leu | Val | Asp | Leu | Ala | Val | Gly | Ala | Gln |
| | | 595 | | | | 600 | | | | | | 605 | | | |
| Gly | His | Val | Leu | Leu | Leu | Arg | Ser | Leu | Pro | Leu | Leu | Lys | Val | Glu | Leu |
| | 610 | | | | | 615 | | | | | 620 | | | | |
| Ser | Ile | Arg | Phe | Ala | Pro | Met | Glu | Val | Ala | Lys | Ala | Val | Tyr | Gln | Cys |
| 625 | | | | | 630 | | | | | 635 | | | | | 640 |
| Trp | Glu | Arg | Thr | Pro | Thr | Val | Leu | Glu | Ala | Gly | Glu | Ala | Thr | Val | Cys |
| | | | | 645 | | | | | 650 | | | | | 655 | |
| Leu | Thr | Val | His | Lys | Gly | Ser | Pro | Asp | Leu | Leu | Gly | Asn | Val | Gln | Gly |
| | | | 660 | | | | | 665 | | | | | 670 | | |
| Ser | Val | Arg | Tyr | Asp | Leu | Ala | Leu | Asp | Pro | Gly | Arg | Leu | Ile | Ser | Arg |
| | | 675 | | | | 680 | | | | | | 685 | | | |
| Ala | Ile | Phe | Asp | Glu | Thr | Lys | Asn | Cys | Thr | Leu | Thr | Gly | Arg | Lys | Thr |
| | | 690 | | | | 695 | | | | | 700 | | | | |
| Leu | Gly | Leu | Gly | Asp | His | Cys | Glu | Thr | Val | Lys | Leu | Leu | Leu | Pro | Asp |
| 705 | | | | | 710 | | | | | 715 | | | | | 720 |
| Cys | Val | Glu | Asp | Ala | Val | Ser | Pro | Ile | Ile | Leu | Arg | Leu | Asn | Phe | Ser |
| | | | | 725 | | | | | 730 | | | | | 735 | |
| Leu | Val | Arg | Asp | Ser | Ala | Ser | Pro | Arg | Asn | Leu | His | Pro | Val | Leu | Ala |
| | | | 740 | | | | | 745 | | | | | 750 | | |
| Val | Gly | Ser | Gln | Asp | His | Ile | Thr | Ala | Ser | Leu | Pro | Phe | Glu | Lys | Asn |
| | | 755 | | | | 760 | | | | | | 765 | | | |
| Cys | Lys | Gln | Glu | Leu | Leu | Cys | Glu | Gly | Asp | Leu | Gly | Ile | Ser | Phe | Asn |
| 770 | | | | | 775 | | | | | 780 | | | | | |
| Phe | Ser | Gly | Leu | Gln | Val | Leu | Val | Val | Gly | Gly | Ser | Pro | Glu | Leu | Thr |
| 785 | | | | | 790 | | | | | 795 | | | | | 800 |
| Val | Thr | Val | Thr | Val | Trp | Asn | Glu | Gly | Glu | Asp | Ser | Tyr | Gly | Thr | Leu |
| | | | | 805 | | | | | 810 | | | | | 815 | |
| Val | Lys | Phe | Tyr | Tyr | Pro | Ala | Gly | Leu | Ser | Tyr | Arg | Arg | Val | Thr | Gly |
| | | | | 820 | | | | | 825 | | | | | 830 | |
| Thr | Gln | Gln | Pro | His | Gln | Tyr | Pro | Leu | Arg | Leu | Ala | Cys | Glu | Ala | Glu |
| | | 835 | | | | 840 | | | | | | 845 | | | |
| Pro | Ala | Ala | Gln | Glu | Asp | Leu | Arg | Ser | Ser | Ser | Cys | Ser | Ile | Asn | His |
| 850 | | | | | 855 | | | | | 860 | | | | | |
| Pro | Ile | Phe | Arg | Glu | Gly | Ala | Lys | Thr | Thr | Phe | Met | Ile | Thr | Phe | Asp |

```
                          865                          870                          875                           880
Val  Ser  Tyr  Lys  Ala  Phe  Leu  Gly  Asp  Arg  Leu  Leu  Leu  Arg  Ala  Lys
                    885                          890                          895

Ala  Ser  Ser  Glu  Asn  Asn  Lys  Pro  Asp  Thr  Asn  Lys  Thr  Ala  Phe  Gln
               900                          905                          910

Leu  Glu  Leu  Pro  Val  Lys  Tyr  Thr  Val  Tyr  Thr  Leu  Ile  Ser  Arg  Gln
          915                          920                          925

Glu  Asp  Ser  Thr  Asn  His  Val  Asn  Phe  Ser  Ser  Ser  His  Gly  Gly  Arg
     930                          935                          940

Arg  Gln  Glu  Ala  Ala  His  Arg  Tyr  Arg  Val  Asn  Asn  Leu  Ser  Pro  Leu
945                          950                          955                           960

Lys  Leu  Ala  Val  Arg  Val  Asn  Phe  Trp  Val  Pro  Val  Leu  Leu  Asn  Gly
               965                          970                          975

Val  Ala  Val  Trp  Asp  Val  Thr  Leu  Ser  Ser  Pro  Ala  Gln  Gly  Val  Ser
               980                          985                          990

Cys  Val  Ser  Gln  Met  Lys  Pro  Pro  Gln  Asn  Pro  Asp  Phe  Leu  Thr  Gln
          995                         1000                         1005

Ile  Gln  Arg  Arg  Ser  Val  Leu  Asp  Cys  Ser  Ile  Ala  Asp  Cys  Leu  His
     1010                         1015                         1020

Phe  Arg  Cys  Asp  Ile  Pro  Ser  Leu  Asp  Ile  Gln  Asp  Glu  Leu  Asp  Phe
1025                         1030                         1035                          1040

Ile  Leu  Arg  Gly  Asn  Leu  Ser  Phe  Gly  Trp  Val  Ser  Gln  Thr  Leu  Gln
                    1045                         1050                         1055

Glu  Lys  Val  Leu  Leu  Val  Ser  Glu  Ala  Glu  Ile  Thr  Phe  Asp  Thr  Ser
                    1060                         1065                         1070

Val  Tyr  Ser  Gln  Leu  Pro  Gly  Gln  Glu  Ala  Phe  Leu  Arg  Ala  Gln  Val
               1075                         1080                         1085

Glu  Thr  Thr  Leu  Glu  Glu  Tyr  Val  Val  Tyr  Glu  Pro  Ile  Phe  Leu  Val
     1090                         1095                         1100

Ala  Gly  Ser  Ser  Val  Gly  Gly  Leu  Leu  Leu  Leu  Ala  Leu  Ile  Thr  Val
1105                         1110                         1115                          1120

Val  Leu  Tyr  Lys  Leu  Gly  Xaa  Xaa  Lys  Arg  Gln  Tyr  Lys  Glu  Met  Leu
                    1125                         1130                         1135

Asp  Gly  Lys  Ala  Ala  Asp  Pro  Val  Thr  Xaa  Gly  Gln  Ala  Asp  Phe  Gly
               1140                         1145                         1150

Cys  Glu  Thr  Pro  Pro  Tyr  Leu  Val  Ser
          1155                         1160
```

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CCTGTCATGG GTCTAACCTG                                                                            20

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AGGTTAGACC CATGACAGG 19

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GGCCTTGCAG CTGGACAATG 20

( 2 ) INFORMATION FOR SEQ ID NO:59:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

CCAAAGCTGG CTGCATCCTC TC 22

( 2 ) INFORMATION FOR SEQ ID NO:60:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

CCGCCTGCCA CTGGCGTGTG C 21

( 2 ) INFORMATION FOR SEQ ID NO:61:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

CCCAGATGAA GGACTTCGTC AA 22

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

GCTGGGATCA TTCGCTATGC 20

( 2 ) INFORMATION FOR SEQ ID NO:63:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

CAATGGATGG ACCAGTTCTG G                        21

( 2 ) INFORMATION FOR SEQ ID NO:64:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

CAGATCGGCT CCTACTTTGG                        20

( 2 ) INFORMATION FOR SEQ ID NO:65:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

CATGGAGCCT CGAGACAGG                         19

( 2 ) INFORMATION FOR SEQ ID NO:66:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

CCACTGTCCT CGAAGCTGGA G                        21

( 2 ) INFORMATION FOR SEQ ID NO:67:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:67:

CTTCGTCCTG TGCTGGCTGT GGGCTC                    26

( 2 ) INFORMATION FOR SEQ ID NO:68:

( i ) SEQUENCE CHARACTERISTICS:

(A) LENGTH: 21 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:68:

CGCCTGGCAT GTGAGGCTGA G        21

(2) INFORMATION FOR SEQ ID NO:69:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:69:

CCGTGATCAG TAGGCAGGAA G        21

(2) INFORMATION FOR SEQ ID NO:70:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:70:

GTCACAGAGG GAACCTCC        18

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:71:

GCTCCTGAGT GAGGCTGAAA TCA        23

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:72:

GAGATGCTGG ATCTACCATC TGC        23

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:73:

CTGAGCTGGG AGATTTTTAT GG 22

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

GTGGATCAGC ACTGAAATCT G 21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

CGTTTGAAGA AGCCAAGCTT G 21

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

CACAGCGGAG GTGCAGGCAG 20

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

CTCACTGCTT GCGCTGGC 18

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

CGGTAAGATA GCTCTGCTGG 20

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

GAGCCCACAG CCAGCACAGG     20

( 2 ) INFORMATION FOR SEQ ID NO:80:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:80:

GATCCAACGC CAGATCATAC C     21

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:81:

CACGGCCAGG TCCACCAGGC     20

( 2 ) INFORMATION FOR SEQ ID NO:82:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:82:

CACGTCCCCT AGCACTGTCA G     21

( 2 ) INFORMATION FOR SEQ ID NO:83:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

TTGACGAAGT CCTTCATCTG GG     22

( 2 ) INFORMATION FOR SEQ ID NO:84:

( i ) SEQUENCE CHARACTERISTICS:

(A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:84:

GAACTGCAAG CTGGAGCCCA G     21

(2) INFORMATION FOR SEQ ID NO:85:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:85:

CTGGATGCTG CGAAGTGCTA C     21

(2) INFORMATION FOR SEQ ID NO:86:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:86:

GCCTTGGAGC TGGACGATGG C     21

(2) INFORMATION FOR SEQ ID NO:87:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:87:

GTAAGATCTC CAGAGTGTCC AAGACAAGAG ATG     33

(2) INFORMATION FOR SEQ ID NO:88:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:88:

CTTCTCGAGT GTGAGAGCTG AACTGAAACC TTC     33

(2) INFORMATION FOR SEQ ID NO:89:

(i) SEQUENCE CHARACTERISTICS:
                (A) LENGTH: 32 base pairs
                (B) TYPE: nucleic acid
                (C) STRANDEDNESS: single
                (D) TOPOLOGY: linear ( i i ) MOLECULE TYPE: DNA ( x i ) SEQUENCE DESCRIPTION: SEQ ID NO:89:

CGCTGTGACG TCAGAGTTGA GTCCAAATAT GG    32

( 2 ) INFORMATION FOR SEQ ID NO:90:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:90:

GGTGACACTA TAGAATAGGG C    21

( 2 ) INFORMATION FOR SEQ ID NO:91:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:91:

AAGCAGGAGCTCCTGTGT    18

( 2 ) INFORMATION FOR SEQ ID NO:92:

( i ) SEQUENCE CHARACTERISTICS:
        ( A ) LENGTH: 852 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 61..852

( x i ) SEQUENCE DESCRIPTION: SEQ ID NO:92:

```
TGATCTCCCT CCAGGCCACT GTTCCCTCTC CACTTCCCCT CACCGCTGCA CTGCTCAGAG         60

ATG  GCC  CTT  GGG  GCT  GTG  GTC  CTC  CTT  GGG  GTC  CTG  GCT  TCT  TAC  CAC      108
Met  Ala  Leu  Gly  Ala  Val  Val  Leu  Leu  Gly  Val  Leu  Ala  Ser  Tyr  His
 1              5                        10                       15

GGA  TTC  AAC  TTG  GAC  GTG  ATG  AGC  GGT  GAT  CTT  CCA  GGA  AGA  CGC  AGC      156
Gly  Phe  Asn  Leu  Asp  Val  Met  Ser  Gly  Asp  Leu  Pro  Gly  Arg  Arg  Ser
             20                       25                       30

GGG  CTT  CGG  GCA  GAG  CGT  GAT  GCA  GTT  TGG  GGA  TCT  CGA  CTC  GTG  GTG      204
Gly  Leu  Arg  Ala  Glu  Arg  Asp  Ala  Val  Trp  Gly  Ser  Arg  Leu  Val  Val
         35                       40                       45

GGA  GCC  CCC  CTG  GCG  GTG  GTG  TCG  GCC  AAC  CAC  ACA  GGA  CGG  CTG  TAC      252
Gly  Ala  Pro  Leu  Ala  Val  Val  Ser  Ala  Asn  His  Thr  Gly  Arg  Leu  Tyr
     50                       55                       60

GAG  TGT  GCG  CCT  GCC  TCC  GGC  ACC  TGC  ACG  CCC  ATT  TTC  CCA  TTC  ATG      300
Glu  Cys  Ala  Pro  Ala  Ser  Gly  Thr  Cys  Thr  Pro  Ile  Phe  Pro  Phe  Met
 65                       70                       75                       80

CCC  CCC  GAA  GCC  GTG  AAC  ATG  TCC  CTG  GGC  CTG  TCC  CTG  GCA  GCC  TCC      348
Pro  Pro  Glu  Ala  Val  Asn  Met  Ser  Leu  Gly  Leu  Ser  Leu  Ala  Ala  Ser
                         85                       90                       95

CCC  AAC  CAT  TCC  CAG  CTG  CTG  GCT  TGT  GGC  CCG  ACC  GTG  CAT  AGA  GCC      396
```

|  |  |  |  |  |  |  |  |  |  |  |  |  |  |  |  |
|---|---|---|---|---|---|---|---|---|---|---|---|---|---|---|---|
| Pro | Asn | His | Ser | Gln | Leu | Leu | Ala | Cys | Gly | Pro | Thr | Val | His | Arg | Ala |
|  |  |  | 100 |  |  |  |  | 105 |  |  |  |  | 110 |  |  |

| TGC | GGG | GAG | GAC | GTG | TAC | GCC | CAG | GGT | TTC | TGT | GTG | CTG | CTG | GAT | GCC | 444 |
|---|---|---|---|---|---|---|---|---|---|---|---|---|---|---|---|---|
| Cys | Gly | Glu | Asp | Val | Tyr | Ala | Gln | Gly | Phe | Cys | Val | Leu | Leu | Asp | Ala |  |
|  |  | 115 |  |  |  |  | 120 |  |  |  |  | 125 |  |  |  |  |

| CAC | GCA | CAG | CCC | ATC | GGG | ACT | GTG | CCA | GCT | GCC | CTG | CCC | GAG | TGC | CCA | 492 |
|---|---|---|---|---|---|---|---|---|---|---|---|---|---|---|---|---|
| His | Ala | Gln | Pro | Ile | Gly | Thr | Val | Pro | Ala | Ala | Leu | Pro | Glu | Cys | Pro |  |
|  | 130 |  |  |  |  | 135 |  |  |  |  | 140 |  |  |  |  |  |

| GAT | CAA | GAG | ATG | GAC | ATT | GTC | TTC | CTG | ATT | GAC | GGC | TCT | GGC | AGC | ATT | 540 |
|---|---|---|---|---|---|---|---|---|---|---|---|---|---|---|---|---|
| Asp | Gln | Glu | Met | Asp | Ile | Val | Phe | Leu | Ile | Asp | Gly | Ser | Gly | Ser | Ile |  |
| 145 |  |  |  |  | 150 |  |  |  |  | 155 |  |  |  |  | 160 |  |

| AGC | TCA | AAT | GAC | TTC | CGC | AAG | ATG | AAG | GAC | TTT | GTC | AGA | GCT | GTG | ATG | 588 |
|---|---|---|---|---|---|---|---|---|---|---|---|---|---|---|---|---|
| Ser | Ser | Asn | Asp | Phe | Arg | Lys | Met | Lys | Asp | Phe | Val | Arg | Ala | Val | Met |  |
|  |  |  |  | 165 |  |  |  |  | 170 |  |  |  |  | 175 |  |  |

| GAC | CAG | TTC | AAG | GAC | ACC | AAC | ACC | CAG | TTC | TCG | CTG | ATG | CAG | TAC | TCC | 636 |
|---|---|---|---|---|---|---|---|---|---|---|---|---|---|---|---|---|
| Asp | Gln | Phe | Lys | Asp | Thr | Asn | Thr | Gln | Phe | Ser | Leu | Met | Gln | Tyr | Ser |  |
|  |  |  | 180 |  |  |  |  | 185 |  |  |  |  | 190 |  |  |  |

| AAT | GTG | CTG | GTG | ACA | CAT | TTC | ACC | TTC | AGC | AGC | TTC | CGG | AAC | AGC | TCC | 684 |
|---|---|---|---|---|---|---|---|---|---|---|---|---|---|---|---|---|
| Asn | Val | Leu | Val | Thr | His | Phe | Thr | Phe | Ser | Ser | Phe | Arg | Asn | Ser | Ser |  |
|  |  | 195 |  |  |  |  | 200 |  |  |  |  | 205 |  |  |  |  |

| AAT | CCT | CAG | GGC | CTA | GTG | GAG | CCC | ATT | GTG | CAG | CTG | ACA | GGC | CTC | ACG | 732 |
|---|---|---|---|---|---|---|---|---|---|---|---|---|---|---|---|---|
| Asn | Pro | Gln | Gly | Leu | Val | Glu | Pro | Ile | Val | Gln | Leu | Thr | Gly | Leu | Thr |  |
|  | 210 |  |  |  |  | 215 |  |  |  |  | 220 |  |  |  |  |  |

| TTC | ACG | GCC | ACA | GGG | ATC | CTG | AAA | GTG | GTG | ACA | GAG | CTG | TTT | CAA | ACC | 780 |
|---|---|---|---|---|---|---|---|---|---|---|---|---|---|---|---|---|
| Phe | Thr | Ala | Thr | Gly | Ile | Leu | Lys | Val | Val | Thr | Glu | Leu | Phe | Gln | Thr |  |
| 225 |  |  |  |  | 230 |  |  |  |  | 235 |  |  |  |  | 240 |  |

| AAG | AAC | GGG | GCC | CGC | GAA | AGT | GCC | AAG | AAG | ATC | CTC | ATC | GTC | ATC | ACA | 828 |
|---|---|---|---|---|---|---|---|---|---|---|---|---|---|---|---|---|
| Lys | Asn | Gly | Ala | Arg | Glu | Ser | Ala | Lys | Lys | Ile | Leu | Ile | Val | Ile | Thr |  |
|  |  |  |  | 245 |  |  |  |  | 250 |  |  |  |  | 255 |  |  |

| GAT | GGG | CAG | AAG | TAC | AAA | GCG | GCA |  |  |  |  |  |  |  |  | 852 |
|---|---|---|---|---|---|---|---|---|---|---|---|---|---|---|---|---|
| Asp | Gly | Gln | Lys | Tyr | Lys | Ala | Ala |  |  |  |  |  |  |  |  |  |
|  | 260 |  |  |  |  |  |  |  |  |  |  |  |  |  |  |  |

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

| Met | Ala | Leu | Gly | Ala | Val | Val | Leu | Leu | Gly | Val | Leu | Ala | Ser | Tyr | His |
|---|---|---|---|---|---|---|---|---|---|---|---|---|---|---|---|
| 1 |  |  |  | 5 |  |  |  |  | 10 |  |  |  |  | 15 |  |

| Gly | Phe | Asn | Leu | Asp | Val | Met | Ser | Gly | Asp | Leu | Pro | Gly | Arg | Arg | Ser |
|---|---|---|---|---|---|---|---|---|---|---|---|---|---|---|---|
|  |  |  | 20 |  |  |  |  | 25 |  |  |  |  | 30 |  |  |

| Gly | Leu | Arg | Ala | Glu | Arg | Asp | Ala | Val | Trp | Gly | Ser | Arg | Leu | Val | Val |
|---|---|---|---|---|---|---|---|---|---|---|---|---|---|---|---|
|  |  | 35 |  |  |  |  | 40 |  |  |  |  | 45 |  |  |  |

| Gly | Ala | Pro | Leu | Ala | Val | Val | Ser | Ala | Asn | His | Thr | Gly | Arg | Leu | Tyr |
|---|---|---|---|---|---|---|---|---|---|---|---|---|---|---|---|
|  | 50 |  |  |  |  | 55 |  |  |  |  | 60 |  |  |  |  |

| Glu | Cys | Ala | Pro | Ala | Ser | Gly | Thr | Cys | Thr | Pro | Ile | Phe | Pro | Phe | Met |
|---|---|---|---|---|---|---|---|---|---|---|---|---|---|---|---|
| 65 |  |  |  |  | 70 |  |  |  |  | 75 |  |  |  |  | 80 |

| Pro | Pro | Glu | Ala | Val | Asn | Met | Ser | Leu | Gly | Leu | Ser | Leu | Ala | Ala | Ser |
|---|---|---|---|---|---|---|---|---|---|---|---|---|---|---|---|
|  |  |  |  | 85 |  |  |  |  | 90 |  |  |  |  | 95 |  |

| Pro | Asn | His | Ser | Gln | Leu | Leu | Ala | Cys | Gly | Pro | Thr | Val | His | Arg | Ala |
|---|---|---|---|---|---|---|---|---|---|---|---|---|---|---|---|
|  |  |  | 100 |  |  |  |  | 105 |  |  |  |  | 110 |  |  |

| Cys | Gly | Glu | Asp | Val | Tyr | Ala | Gln | Gly | Phe | Cys | Val | Leu | Leu | Asp | Ala |
|---|---|---|---|---|---|---|---|---|---|---|---|---|---|---|---|
|  |  | 115 |  |  |  |  | 120 |  |  |  |  | 125 |  |  |  |

| His | Ala | Gln | Pro | Ile | Gly | Thr | Val | Pro | Ala | Ala | Leu | Pro | Glu | Cys | Pro |
|---|---|---|---|---|---|---|---|---|---|---|---|---|---|---|---|

|     |     |     |     |     | 130 |     |     |     |     | 135 |     |     |     |     | 140 |     |     |     |     |
|-----|-----|-----|-----|-----|-----|-----|-----|-----|-----|-----|-----|-----|-----|-----|-----|-----|-----|-----|-----|
| Asp | Gln | Glu | Met | Asp | Ile | Val | Phe | Leu | Ile | Asp | Gly | Ser | Gly | Ser | Ile |
| 145 |     |     |     |     | 150 |     |     |     |     | 155 |     |     |     |     | 160 |
| Ser | Ser | Asn | Asp | Phe | Arg | Lys | Met | Lys | Asp | Phe | Val | Arg | Ala | Val | Met |
|     |     |     |     | 165 |     |     |     |     | 170 |     |     |     |     | 175 |     |
| Asp | Gln | Phe | Lys | Asp | Thr | Asn | Thr | Gln | Phe | Ser | Leu | Met | Gln | Tyr | Ser |
|     |     |     |     | 180 |     |     |     |     | 185 |     |     |     |     | 190 |     |
| Asn | Val | Leu | Val | Thr | His | Phe | Thr | Phe | Ser | Ser | Phe | Arg | Asn | Ser | Ser |
|     |     |     | 195 |     |     |     | 200 |     |     |     |     | 205 |     |     |     |
| Asn | Pro | Gln | Gly | Leu | Val | Glu | Pro | Ile | Val | Gln | Leu | Thr | Gly | Leu | Thr |
|     |     | 210 |     |     |     |     | 215 |     |     |     |     | 220 |     |     |     |
| Phe | Thr | Ala | Thr | Gly | Ile | Leu | Lys | Val | Val | Thr | Glu | Leu | Phe | Gln | Thr |
| 225 |     |     |     |     | 230 |     |     |     |     | 235 |     |     |     |     | 240 |
| Lys | Asn | Gly | Ala | Arg | Glu | Ser | Ala | Lys | Lys | Ile | Leu | Ile | Val | Ile | Thr |
|     |     |     |     | 245 |     |     |     |     | 250 |     |     |     |     | 255 |     |
| Asp | Gly | Gln | Lys | Tyr | Lys | Ala | Ala |
|     |     |     | 260 |

( 2 ) INFORMATION FOR SEQ ID NO:94:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:94:

CTGGTCTGGA GGTGCCTTCC TG        22

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:95:

CCTGAGCAGG AGCACCTGGC C        21

( 2 ) INFORMATION FOR SEQ ID NO:96:

( i ) SEQUENCE CHARACTERISTICS:
        ( A ) LENGTH: 2499 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

| ATGACCTTCG | GCACTGTGCT | TCTTCTGAGT | GTCCTGGCTT | CTTATCATGG | ATTCAACCTG | 60 |
| GATGTGGAGG | AGCCTACGAT | CTTCCAGGAG | GATGCAGGCG | GCTTTGGGCA | GAGCGTGGTG | 120 |
| CAGTTCGGTG | GATCTCGACT | CGTGGTGGGA | GCACCCCTGG | AGGTGGTGGC | GGCCAACCAG | 180 |
| ACGGGACGGC | TGTATGACTG | CGCAGCTGCC | ACCGGCATGT | GCCAGCCCAT | CCCGCTGCAC | 240 |
| ATCCGCCCTG | AGGCCGTGAA | CATGTCCTTG | GGCCTGACCC | TGGCAGCCTC | CACCAACGGC | 300 |
| TCCCGGCTCC | TGGCCTGTGG | CCCGACCCTG | CACAGAGTCT | GTGGGGAGAA | CTCATACTCA | 360 |

```
AAGGGTTCCT  GCCTCCTGCT  GGGCTCGCGC  TGGGAGATCA  TCCAGACAGT  CCCCGACGCC    420

ACGCCAGAGT  GTCCACATCA  AGAGATGGAC  ATCGTCTTCC  TGATTGACGG  CTCTGGAAGC    480

ATTGACCAAA  ATGACTTTAA  CCAGATGAAG  GGCTTTGTCC  AAGCTGTCAT  GGGCCAGTTT    540

GAGGGCACTG  ACACCCTGTT  TGCACTGATG  CAGTACTCAA  ACCTCCTGAA  GATCCACTTC    600

ACCTTCACCC  AATTCCGGAC  CAGCCCGAGC  CAGCAGAGCC  TGGTGGATCC  CATCGTCCAA    660

CTGAAAGGCC  TGACGTTCAC  GGCCACGGGC  ATCCTGACAG  TGGTGACACA  GCTATTTCAT    720

CATAAGAATG  GGGCCCGAAA  AAGTGCCAAG  AAGATCCTCA  TTGTCATCAC  AGATGGGCAG    780

AAGTACAAAG  ACCCCCTGGA  ATACAGTGAT  GTCATCCCCC  AGGCAGAGAA  GGCTGGCATC    840

ATCCGCTACG  CTATCGGGGT  GGGACACGCT  TTCCAGGGAC  CCACTGCCAG  GCAGGAGCTG    900

AATACCATCA  GCTCAGCGCC  TCCGCAGGAC  CACGTGTTCA  AGGTGGACAA  CTTTGCAGCC    960

CTTGGCAGCA  TCCAGAAGCA  GCTGCAGGAG  AAGATCTATG  CAGTTGAGGG  AACCCAGTCC   1020

AGGGCAAGCA  GCTCCTTCCA  GCACGAGATG  TCCCAAGAAG  GCTTCAGCAC  AGCCCTCACA   1080

ATGGATGGCC  TCTTCCTGGG  GGCTGTGGGG  AGCTTTAGCT  GGTCTGGAGG  TGCCTTCCTG   1140

TATCCCCCAA  ATATGAGCCC  CACCTTCATC  AACATGTCTC  AGGAGAATGT  GGACATGAGG   1200

GACTCTTACC  TGGGTTACTC  CACCGAGCTA  GCCCTGTGGA  AGGGGTACA  GAACCTGGTC   1260

CTGGGGGCCC  CCCGCTACCA  GCATACCGGG  AAGGCTGTCA  TCTTCACCCA  GGTGTCCAGG   1320

CAATGGAGGA  AGAAGGCCGA  AGTCACAGGG  ACGCAGATCG  GCTCCTACTT  CGGGGCCTCC   1380

CTCTGCTCCG  TGGATGTGGA  CAGCGATGGC  AGCACCGACC  TGATCCTCAT  TGGGGCCCCC   1440

CATTACTATG  AGCAGACCCG  AGGGGGCCAG  GTGTCCGTGT  GTCCCTTGCC  TAGGGGGAGG   1500

GTGCAGTGGC  AGTGTGACGC  TGTTCTCCGT  GGTGAGCAGG  GCCACCCCTG  GGGCCGCTTT   1560

GGGGCAGCCC  TGACAGTGTT  GGGGGATGTG  AATGAGGACA  AGCTGATAGA  CGTGGCCATT   1620

GGGGCCCCGG  GAGAGCAGGA  GAACCGGGGT  GCTGTCTACC  TGTTTCACGG  AGCCTCAGAA   1680

TCCGGCATCA  GCCCCTCCCA  CAGCCAGCGG  ATTGCCAGCT  CCCAGCTCTC  CCCCAGGCTG   1740

CAGTATTTTG  GGCAGGCGCT  GAGTGGGGGT  CAGGACCTCA  CCCAGGATGG  ACTGATGGAC   1800

CTGGCCGTGG  GGGCCCGGGG  CCAGGTGCTC  CTGCTCAGGA  GTCTGCCGGT  GCTGAAAGTG   1860

GGGGTGGCCA  TGAGATTCAG  CCCTGTGGAG  GTGGCCAAGG  CTGTGTACCG  GTGCTGGGAA   1920

GAGAAGCCCA  GTGCCCTGGA  AGCTGGGGAC  GCCACCGTCT  GTCTCACCAT  CCAGAAAAGC   1980

TCACTGGACC  AGCTAGGTGA  CATCCAAAGC  TCTGTCAGGT  TTGATCTGGC  ACTGGACCCA   2040

GGTCGTCTGA  CTTCTCGTGC  CATTTTCAAT  GAAACCAAGA  ACCCACTTT  GACTCGAAGA   2100

AAAACCCTGG  GACTGGGGAT  TCACTGTGAA  ACCCTGAAGC  TGCTTTTGCC  AGTGAGGACT   2160

TTGGGTTCTG  GGAAGGGGGA  GAGAGGAGGA  GCCCAAGGCT  GGCCTGGAGC  ACCCCCGTTC   2220

TCTGCTGAGC  GAGGTGGGAA  GGGTTAGGAT  GTTGGGGCTG  GAGAGAGGGA  CATTAGGGCA   2280

GGAGAACCTG  GCTCCACGGC  TTGGAGGGAG  CACTGTCAGG  GCAGTGGGGA  GTGGATGCAG   2340

TGGAGGAGGA  CTTGTGGTGG  AGCGTAGAGA  GGACAGCAGG  TTCTTGAAAG  CCTGTTCTCT   2400

CTCAGGATTG  TGTGGAGGAT  GTGGTGAGCC  CCATCATTCT  GCACCTCAAC  TTCTCACTGG   2460

TGAGAGAGCC  CATCCCCTCC  CCCCAGAACC  TGCGTCCTG                            2499
```

( 2 ) INFORMATION FOR SEQ ID NO:97:

( i ) SEQUENCE CHARACTERISTICS:
        ( A ) LENGTH: 3956 base pairs
        ( B ) TYPE: nucleic acid
        ( C ) STRANDEDNESS: single -continued ( D ) TOPOLOGY: linear ( i i ) MOLECULE TYPE: DNA ( x i ) SEQUENCE DESCRIPTION: SEQ ID NO:97:

| | | | | | |
|---|---|---|---|---|---|
| TTTAACTGCA | CCAACTTTAA | AATACGCTAT | TGGAGCTGGA | ATTACCGCGG | CTGCTGGCAC | 60 |
| CAGACTTGCC | CTCCAATGGA | TCCTCGTTAA | AGGATTTAAA | GTGGACTCAT | TCCAATTACA | 120 |
| GGGCCTCGAA | AGAGTCCTGT | ATTGTTATTT | TTCGTCACTA | CCTCCCCGGG | TCGGGAGTGG | 180 |
| GTAATTTGCG | CGCCTGCTGC | CTTCCTTGGA | TGTGGTAGCC | GTTTCTCAGG | CTCCCTCTCC | 240 |
| GGAATCGAAC | CCTGATTCCC | CGTCACCCGT | GGTCACCATG | GTAGGCACGT | GCAGTTCGGT | 300 |
| GGATCTCGAC | TCGTGGTGGG | AGCACCCCTG | GAGGTGGTGG | CGGCCAACCA | GACGGGACGG | 360 |
| CTGTATGACT | GCGCAGCTGC | CACCGGCATG | TGCCAGCCCA | TCCCGCTGCA | CATCCGCCCT | 420 |
| GAGGCCGTGA | ACATGTCCTT | GGGCCTGACC | CTGGCAGCCT | CCACCAACGG | CTCCCGGCTC | 480 |
| CTGGCCTGTG | GCCCGACCCT | GCACAGAGTC | TGTGGGGAGA | ACTCATACTC | AAAGGGTTCC | 540 |
| TGCCTCCTGC | TGGGCTCGCG | CTGGGAGATC | ATCCAGACAG | TCCCCGACGC | CACGCCAGAG | 600 |
| TGTCCACATC | AAGAGATGGA | CATCGTCTTC | CTGATTGACG | GCTCTGGAAG | CATTGACCAA | 660 |
| AATGACTTTA | ACCAGATGAA | GGGCTTTGTC | CAAGCTGTCA | TGGGCCAGTT | TGAGGGCACT | 720 |
| GACACCCTGT | TTGCACTGAT | GCAGTACTCA | AACCTCCTGA | AGATCCACTT | CACCTTCACC | 780 |
| CAATTCCGGA | CCAGCCCGAG | CCAGCAGAGC | CTGGTGGATC | CCATCGTCCA | ACTGAAAGGC | 840 |
| CTGACGTTCA | CGGCCACGGG | CATCCTGACA | GTGGTGACAC | AGCTATTTCA | TCATAAGAAT | 900 |
| GGGGCCCGAA | AAAGTGCCAA | GAAGATCCTC | ATTGTCATCA | CAGATGGGCA | GAAGTACAAA | 960 |
| GACCCCCTGG | AATACAGTGA | TGTCATCCCC | CAGGCAGAGA | AGGCTGGCAT | CATCCGCTAC | 1020 |
| GCTATCGGGG | TGGGACACGC | TTTCCAGGGA | CCCACTGCCA | GGCAGGAGCT | GAATACCATC | 1080 |
| AGCTCAGCGC | CTCCGCAGGA | CCACGTGTTC | AAGGTGGACA | ACTTTGCAGC | CCTTGGCAGC | 1140 |
| ATCCAGAAGC | AGCTGCAGGA | GAAGATCTAT | GCAGTTGAGG | GAACCCAGTC | CAGGGCAAGC | 1200 |
| AGCTCCTTCC | AGCACGAGAT | GTCCCAAGAA | GGCTTCAGCA | CAGCCCTCAC | AATGGATGGC | 1260 |
| CTCTTCCTGG | GGGCTGTGGG | GAGCTTTAGC | TGGTCTGGAG | GTGCCTTCCT | GTATCCCCA | 1320 |
| AATATGAGCC | CCACCTTCAT | CAACATGTCT | CAGGAGAATG | TGGACATGAG | GGACTCTTAC | 1380 |
| CTGGGTTACT | CCACCGAGCT | AGCCCTGTGG | AAGGGGGTAC | AGAACCTGGT | CCTGGGGGCC | 1440 |
| CCCCGCTACC | AGCATACCGG | GAAGGCTGTC | ATCTTCACCC | AGGTGTCCAG | GCAATGGAGG | 1500 |
| AAGAAGGCCG | AAGTCACAGG | GACGCAGATC | GGCTCCTACT | TCGGGGCCTC | CCTCTGCTCC | 1560 |
| GTGGATGTGG | ACAGCGATGG | CAGCACCGAC | CTGATCCTCA | TTGGGGCCCC | CCATTACTAT | 1620 |
| GAGCAGACCC | GAGGGGGCCA | GGTGTCCGTG | TGTCCCTTGC | CTAGGGGGAG | GGTGCAGTGG | 1680 |
| CAGTGTGACG | CTGTTCTCCG | TGGTGAGCAG | GGCCACCCCT | GGGGCCGCTT | TGGGCAGCC | 1740 |
| CTGACAGTGT | TGGGGGATGT | GAATGAGGAC | AAGCTGATAG | ACGTGGCCAT | TGGGGCCCCG | 1800 |
| GGAGAGCAGG | AGAACCGGGG | TGCTGTCTAC | CTGTTTCACG | GAGCCTCAGA | ATCCGGCATC | 1860 |
| AGCCCCTCCC | ACAGCCAGCG | GATTGCCAGC | TCCCAGCTCT | CCCCCAGGCT | GCAGTATTTT | 1920 |
| GGGCAGGCGC | TGAGTGGGGG | TCAGGACCTC | ACCCAGGATG | GACTGATGGA | CCTGGCCGTG | 1980 |
| GGGGCCCGGG | GCCAGGTGCT | CCTGCTCAGG | AGTCTGCCGG | TGCTGAAAGT | GGGGGTGGCC | 2040 |
| ATGAGATTCA | GCCCTGTGGA | GGTGGCCAAG | GCTGTGTACC | GGTGCTGGGA | AGAGAAGCCC | 2100 |
| AGTGCCCTGG | AAGCTGGGGA | CGCCACCGTC | TGTCTCACCA | TCCAGAAAAG | CTCACTGGAC | 2160 |
| CAGCTAGGTG | ACATCCAAAG | CTCTGTCAGG | TTTGATCTGG | CACTGGACCC | AGGTCGTCTG | 2220 |

```
ACTTCTCGTG  CCATTTTCAA  TGAAACCAAG  AACCCCACTT  TGACTCGAAG  AAAAACCCTG   2280
GGACTGGGGA  TTCACTGTGA  AACCCTGAAG  CTGCTTTTGC  CAGATTGTGT  GGAGGATGTG   2340
GTGAGCCCCA  TCATTCTGCA  CCTCAACTTC  TCACTGGTGA  GAGAGCCCAT  CCCCTCCCCC   2400
CAGAACCTGC  GTCCTGTGCT  GGCCGTGGGC  TCACAAGACC  TCTTCACTGC  TTCTCTCCCC   2460
TTCGAGAAGA  ACTGTGGGCA  AGATGGCCTC  TGTGAAGGGG  ACCTGGGTGT  CACCCTCAGC   2520
TTCTCAGGCC  TGCAGACCCT  GACCGTGGGG  AGCTCCCTGG  AGCTCAACGT  GATTGTGACT   2580
GTGTGGAACG  CAGGTGAGGA  TTCCTACGGA  ACCGTGGTCA  GCCTCTACTA  TCCAGCAGGG   2640
CTGTCGCACC  GACGGGTGTC  AGGAGCCCAG  AAGCAGCCCC  ATCAGAGTGC  CCTGCGCCTG   2700
GCATGTGAGA  CAGTGCCCAC  TGAGGATGAG  GGCCTAAGAA  GCAGCCGCTG  CAGTGTCAAC   2760
CACCCCATCT  TCCATGAGGG  CTCTAACGGC  ACCTTCATAG  TCACATTCGA  TGTCTCCTAC   2820
AAGGCCACCC  TGGGAGACAG  GATGCTTATG  AGGGCCAGTG  CAAGCAGTGA  GAACAATAAG   2880
GCTTCAAGCA  GCAAGGCCAC  CTTCCAGCTG  GAGCTCCCGG  TGAAGTATGC  AGTCTACACC   2940
ATGATCAGCA  GGCAGGAAGA  ATCCACCAAG  TACTTCAACT  TTGCAACCTC  CGATGAGAAG   3000
AAAATGAAAG  AGGCTGAGCA  TCGATACCGT  GTGAATAACC  TCAGCCAGCG  AGATCTGGCC   3060
ATCAGCATTA  ACTTCTGGGT  TCCTGTCCTG  CTGAACGGGG  TGGCTGTGTG  GGATGTGGTC   3120
ATGGAGGCCC  CATCTCAGAG  TCTCCCCTGT  GTTCAGAGA   GAAAACCTCC  CCAGCATTCT   3180
GACTTCCTGA  CCCAGATTTC  AAGAAGTCCC  ATGCTGGACT  GCTCCATTGC  TGACTGCCTG   3240
CAGTTCCGCT  GTGACGTCCC  CTCCTTCAGC  GTCCAGGAGG  AGCTGGATTT  CACCCTGAAG   3300
GGCAATCTCA  GTTTCGGCTG  GGTCCGCGAG  ACATTGCAGA  AGAAGGTGTT  GGTCGTGAGT   3360
GTGGCTGAAA  TTACGTTCGA  CACATCCGTG  TACTCCCAGC  TTCCAGGACA  GGAGGCATTT   3420
ATGAGAGCTC  AGATGGAGAT  GGTGCTAGAA  GAAGACGAGG  TCTACAATGC  CATTCCCATC   3480
ATCATGGGCA  GCTCTGTGGG  GGCTCTGCTA  CTGCTGGCGC  TCATCACAGC  CACACTGTAC   3540
AAGCTTGGCT  TCTTCAAACG  CCACTACAAG  GAAATGCTGG  AGGACAAGCC  TGAAGACACT   3600
GCCACATTCA  GTGGGGACGA  TTTCAGCTGT  GTGGCCCCAA  ATGTGCCTTT  GTCCTAATAA   3660
TCCACTTTCC  TGTTTATCTC  TACCACTGTG  GGCTGGACTT  GCTTGCAACC  ATAAATCAAC   3720
TTACATGGAA  ACAACTTCTG  CATAGATCTG  CACTGGCCTA  AGCAACCTAC  CAGGTGCTAA   3780
GCACCTTCTC  GGAGAGATAG  AGATTGTCAA  TGTTTTTACA  TATCTGTCCA  TCTTTTTCAG   3840
CAATGACCCA  CTTTTTACAG  AAGCAGGCAT  GGTGCCAGCA  TAAATTTTCA  TATGCTTAAG   3900
AATTGTCACA  TGAAAAAAAA  AAAAAAAAAA  AAAAAAAAAA  AAAAAAAAAA  CTTTAG       3956
```

( 2 ) INFORMATION FOR SEQ ID NO:98:

( i ) SEQUENCE CHARACTERISTICS:
    ( A ) LENGTH: 3785 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..3486

( x i ) SEQUENCE DESCRIPTION: SEQ ID NO:98:

```
ATG  ACC  TTC  GGC  ACT  GTG  CTT  CTT  CTG  AGT  GTC  CTG  GCT  TCT  TAT  CAT        48
Met  Thr  Phe  Gly  Thr  Val  Leu  Leu  Leu  Ser  Val  Leu  Ala  Ser  Tyr  His
 1                  5                   10                  15

GGA  TTC  AAC  CTG  GAT  GTG  GAG  GAG  CCT  ACG  ATC  TTC  CAG  GAG  GAT  GCA        96
```

|     |     |     |     |     |     |     |     |     |     |     |     |     |     |     |     |
|---|---|---|---|---|---|---|---|---|---|---|---|---|---|---|---|
| Gly | Phe | Asn | Leu | Asp | Val | Glu | Glu | Pro | Thr | Ile | Phe | Gln | Glu | Asp | Ala |
|  |  |  | 20 |  |  |  |  | 25 |  |  |  |  | 30 |  |  |

| GGC | GGC | TTT | GGG | CAG | AGC | GTG | GTG | CAG | TTC | GGT | GGA | TCT | CGA | CTC | GTG | 144 |
|---|---|---|---|---|---|---|---|---|---|---|---|---|---|---|---|---|
| Gly | Gly | Phe | Gly | Gln | Ser | Val | Val | Gln | Phe | Gly | Gly | Ser | Arg | Leu | Val |  |
|  |  |  | 35 |  |  |  | 40 |  |  |  |  | 45 |  |  |  |  |

| GTG | GGA | GCA | CCC | CTG | GAG | GTG | GTG | GCG | GCC | AAC | CAG | ACG | GGA | CGG | CTG | 192 |
|---|---|---|---|---|---|---|---|---|---|---|---|---|---|---|---|---|
| Val | Gly | Ala | Pro | Leu | Glu | Val | Val | Ala | Ala | Asn | Gln | Thr | Gly | Arg | Leu |  |
|  | 50 |  |  |  |  | 55 |  |  |  |  | 60 |  |  |  |  |  |

| TAT | GAC | TGC | GCA | GCT | GCC | ACC | GGC | ATG | TGC | CAG | CCC | ATC | CCG | CTG | CAC | 240 |
|---|---|---|---|---|---|---|---|---|---|---|---|---|---|---|---|---|
| Tyr | Asp | Cys | Ala | Ala | Ala | Thr | Gly | Met | Cys | Gln | Pro | Ile | Pro | Leu | His |  |
| 65 |  |  |  |  | 70 |  |  |  |  | 75 |  |  |  |  | 80 |  |

| ATC | CGC | CCT | GAG | GCC | GTG | AAC | ATG | TCC | TTG | GGC | CTG | ACC | CTG | GCA | GCC | 288 |
|---|---|---|---|---|---|---|---|---|---|---|---|---|---|---|---|---|
| Ile | Arg | Pro | Glu | Ala | Val | Asn | Met | Ser | Leu | Gly | Leu | Thr | Leu | Ala | Ala |  |
|  |  |  |  | 85 |  |  |  |  | 90 |  |  |  |  | 95 |  |  |

| TCC | ACC | AAC | GGC | TCC | CGG | CTC | CTG | GCC | TGT | GGC | CCG | ACC | CTG | CAC | AGA | 336 |
|---|---|---|---|---|---|---|---|---|---|---|---|---|---|---|---|---|
| Ser | Thr | Asn | Gly | Ser | Arg | Leu | Leu | Ala | Cys | Gly | Pro | Thr | Leu | His | Arg |  |
|  |  |  | 100 |  |  |  |  | 105 |  |  |  |  | 110 |  |  |  |

| GTC | TGT | GGG | GAG | AAC | TCA | TAC | TCA | AAG | GGT | TCC | TGC | CTC | CTG | CTG | GGC | 384 |
|---|---|---|---|---|---|---|---|---|---|---|---|---|---|---|---|---|
| Val | Cys | Gly | Glu | Asn | Ser | Tyr | Ser | Lys | Gly | Ser | Cys | Leu | Leu | Leu | Gly |  |
|  |  | 115 |  |  |  |  | 120 |  |  |  |  | 125 |  |  |  |  |

| TCG | CGC | TGG | GAG | ATC | ATC | CAG | ACA | GTC | CCC | GAC | GCC | ACG | CCA | GAG | TGT | 432 |
|---|---|---|---|---|---|---|---|---|---|---|---|---|---|---|---|---|
| Ser | Arg | Trp | Glu | Ile | Ile | Gln | Thr | Val | Pro | Asp | Ala | Thr | Pro | Glu | Cys |  |
|  | 130 |  |  |  |  | 135 |  |  |  |  | 140 |  |  |  |  |  |

| CCA | CAT | CAA | GAG | ATG | GAC | ATC | GTC | TTC | CTG | ATT | GAC | GGC | TCT | GGA | AGC | 480 |
|---|---|---|---|---|---|---|---|---|---|---|---|---|---|---|---|---|
| Pro | His | Gln | Glu | Met | Asp | Ile | Val | Phe | Leu | Ile | Asp | Gly | Ser | Gly | Ser |  |
| 145 |  |  |  | 150 |  |  |  |  | 155 |  |  |  |  | 160 |  |  |

| ATT | GAC | CAA | AAT | GAC | TTT | AAC | CAG | ATG | AAG | GGC | TTT | GTC | CAA | GCT | GTC | 528 |
|---|---|---|---|---|---|---|---|---|---|---|---|---|---|---|---|---|
| Ile | Asp | Gln | Asn | Asp | Phe | Asn | Gln | Met | Lys | Gly | Phe | Val | Gln | Ala | Val |  |
|  |  |  |  | 165 |  |  |  |  | 170 |  |  |  |  | 175 |  |  |

| ATG | GGC | CAG | TTT | GAG | GGC | ACT | GAC | ACC | CTG | TTT | GCA | CTG | ATG | CAG | TAC | 576 |
|---|---|---|---|---|---|---|---|---|---|---|---|---|---|---|---|---|
| Met | Gly | Gln | Phe | Glu | Gly | Thr | Asp | Thr | Leu | Phe | Ala | Leu | Met | Gln | Tyr |  |
|  |  |  | 180 |  |  |  |  | 185 |  |  |  |  | 190 |  |  |  |

| TCA | AAC | CTC | CTG | AAG | ATC | CAC | TTC | ACC | TTC | ACC | CAA | TTC | CGG | ACC | AGC | 624 |
|---|---|---|---|---|---|---|---|---|---|---|---|---|---|---|---|---|
| Ser | Asn | Leu | Leu | Lys | Ile | His | Phe | Thr | Phe | Thr | Gln | Phe | Arg | Thr | Ser |  |
|  |  | 195 |  |  |  |  | 200 |  |  |  |  | 205 |  |  |  |  |

| CCG | AGC | CAG | CAG | AGC | CTG | GTG | GAT | CCC | ATC | GTC | CAA | CTG | AAA | GGC | CTG | 672 |
|---|---|---|---|---|---|---|---|---|---|---|---|---|---|---|---|---|
| Pro | Ser | Gln | Gln | Ser | Leu | Val | Asp | Pro | Ile | Val | Gln | Leu | Lys | Gly | Leu |  |
| 210 |  |  |  |  | 215 |  |  |  |  | 220 |  |  |  |  |  |  |

| ACG | TTC | ACG | GCC | ACG | GGC | ATC | CTG | ACA | GTG | GTG | ACA | CAG | CTA | TTT | CAT | 720 |
|---|---|---|---|---|---|---|---|---|---|---|---|---|---|---|---|---|
| Thr | Phe | Thr | Ala | Thr | Gly | Ile | Leu | Thr | Val | Val | Thr | Gln | Leu | Phe | His |  |
| 225 |  |  |  |  | 230 |  |  |  |  | 235 |  |  |  |  | 240 |  |

| CAT | AAG | AAT | GGG | GCC | CGA | AAA | AGT | GCC | AAG | AAG | ATC | CTC | ATT | GTC | ATC | 768 |
|---|---|---|---|---|---|---|---|---|---|---|---|---|---|---|---|---|
| His | Lys | Asn | Gly | Ala | Arg | Lys | Ser | Ala | Lys | Lys | Ile | Leu | Ile | Val | Ile |  |
|  |  |  |  | 245 |  |  |  |  | 250 |  |  |  |  | 255 |  |  |

| ACA | GAT | GGG | CAG | AAG | TAC | AAA | GAC | CCC | CTG | GAA | TAC | AGT | GAT | GTC | ATC | 816 |
|---|---|---|---|---|---|---|---|---|---|---|---|---|---|---|---|---|
| Thr | Asp | Gly | Gln | Lys | Tyr | Lys | Asp | Pro | Leu | Glu | Tyr | Ser | Asp | Val | Ile |  |
|  |  |  | 260 |  |  |  |  | 265 |  |  |  |  | 270 |  |  |  |

| CCC | CAG | GCA | GAG | AAG | GCT | GGC | ATC | ATC | CGC | TAC | GCT | ATC | GGG | GTG | GGA | 864 |
|---|---|---|---|---|---|---|---|---|---|---|---|---|---|---|---|---|
| Pro | Gln | Ala | Glu | Lys | Ala | Gly | Ile | Ile | Arg | Tyr | Ala | Ile | Gly | Val | Gly |  |
|  |  | 275 |  |  |  |  | 280 |  |  |  |  | 285 |  |  |  |  |

| CAC | GCT | TTC | CAG | GGA | CCC | ACT | GCC | AGG | CAG | GAG | CTG | AAT | ACC | ATC | AGC | 912 |
|---|---|---|---|---|---|---|---|---|---|---|---|---|---|---|---|---|
| His | Ala | Phe | Gln | Gly | Pro | Thr | Ala | Arg | Gln | Glu | Leu | Asn | Thr | Ile | Ser |  |
|  | 290 |  |  |  |  | 295 |  |  |  |  | 300 |  |  |  |  |  |

| TCA | GCG | CCT | CCG | CAG | GAC | CAC | GTG | TTC | AAG | GTG | GAC | AAC | TTT | GCA | GCC | 960 |
|---|---|---|---|---|---|---|---|---|---|---|---|---|---|---|---|---|
| Ser | Ala | Pro | Pro | Gln | Asp | His | Val | Phe | Lys | Val | Asp | Asn | Phe | Ala | Ala |  |
| 305 |  |  |  |  | 310 |  |  |  |  | 315 |  |  |  |  | 320 |  |

| CTT | GGC | AGC | ATC | CAG | AAG | CAG | CTG | CAG | GAG | AAG | ATC | TAT | GCA | GTT | GAG | 1008 |
|---|---|---|---|---|---|---|---|---|---|---|---|---|---|---|---|---|
| Leu | Gly | Ser | Ile | Gln | Lys | Gln | Leu | Gln | Glu | Lys | Ile | Tyr | Ala | Val | Glu |  |
|  |  |  |  | 325 |  |  |  |  | 330 |  |  |  |  | 335 |  |  |

| GGA | ACC | CAG | TCC | AGG | GCA | AGC | AGC | TCC | TTC | CAG | CAC | GAG | ATG | TCC | CAA | 1056 |

-continued

```
Gly Thr Gln Ser Arg Ala Ser Ser Ser Phe Gln His Glu Met Ser Gln
            340                 345                 350

GAA GGC TTC AGC ACA GCC CTC ACA ATG GAT GGC CTC TTC CTG GGG GCT      1104
Glu Gly Phe Ser Thr Ala Leu Thr Met Asp Gly Leu Phe Leu Gly Ala
        355                 360                 365

GTG GGG AGC TTT AGC TGG TCT GGA GGT GCC TTC CTG TAT CCC CCA AAT      1152
Val Gly Ser Phe Ser Trp Ser Gly Gly Ala Phe Leu Tyr Pro Pro Asn
    370                 375                 380

ATG AGC CCC ACC TTC ATC AAC ATG TCT CAG GAG AAT GTG GAC ATG AGG      1200
Met Ser Pro Thr Phe Ile Asn Met Ser Gln Glu Asn Val Asp Met Arg
385                 390                 395                 400

GAC TCT TAC CTG GGT TAC TCC ACC GAG CTA GCC CTG TGG AAG GGG GTA      1248
Asp Ser Tyr Leu Gly Tyr Ser Thr Glu Leu Ala Leu Trp Lys Gly Val
                405                 410                 415

CAG AAC CTG GTC CTG GGG GCC CCC CGC TAC CAG CAT ACC GGG AAG GCT      1296
Gln Asn Leu Val Leu Gly Ala Pro Arg Tyr Gln His Thr Gly Lys Ala
            420                 425                 430

GTC ATC TTC ACC CAG GTG TCC AGG CAA TGG AGG AAG AAG GCC GAA GTC      1344
Val Ile Phe Thr Gln Val Ser Arg Gln Trp Arg Lys Lys Ala Glu Val
        435                 440                 445

ACA GGG ACG CAG ATC GGC TCC TAC TTC GGG GCC TCC CTC TGC TCC GTG      1392
Thr Gly Thr Gln Ile Gly Ser Tyr Phe Gly Ala Ser Leu Cys Ser Val
    450                 455                 460

GAT GTG GAC AGC GAT GGC AGC ACC GAC CTG ATC CTC ATT GGG GCC CCC      1440
Asp Val Asp Ser Asp Gly Ser Thr Asp Leu Ile Leu Ile Gly Ala Pro
465                 470                 475                 480

CAT TAC TAT GAG CAG ACC CGA GGG GGC CAG GTG TCC GTG TGT CCC TTG      1488
His Tyr Tyr Glu Gln Thr Arg Gly Gly Gln Val Ser Val Cys Pro Leu
                485                 490                 495

CCT AGG GGG AGG GTG CAG TGG CAG TGT GAC GCT GTT CTC CGT GGT GAG      1536
Pro Arg Gly Arg Val Gln Trp Gln Cys Asp Ala Val Leu Arg Gly Glu
            500                 505                 510

CAG GGC CAC CCC TGG GGC CGC TTT GGG GCA GCC CTG ACA GTG TTG GGG      1584
Gln Gly His Pro Trp Gly Arg Phe Gly Ala Ala Leu Thr Val Leu Gly
        515                 520                 525

GAT GTG AAT GAG GAC AAG CTG ATA GAC GTG GCC ATT GGG GCC CCG GGA      1632
Asp Val Asn Glu Asp Lys Leu Ile Asp Val Ala Ile Gly Ala Pro Gly
    530                 535                 540

GAG CAG GAG AAC CGG GGT GCT GTC TAC CTG TTT CAC GGA GCC TCA GAA      1680
Glu Gln Glu Asn Arg Gly Ala Val Tyr Leu Phe His Gly Ala Ser Glu
545                 550                 555                 560

TCC GGC ATC AGC CCC TCC CAC AGC CAG CGG ATT GCC AGC TCC CAG CTC      1728
Ser Gly Ile Ser Pro Ser His Ser Gln Arg Ile Ala Ser Ser Gln Leu
                565                 570                 575

TCC CCC AGG CTG CAG TAT TTT GGG CAG GCG CTG AGT GGG GGT CAG GAC      1776
Ser Pro Arg Leu Gln Tyr Phe Gly Gln Ala Leu Ser Gly Gly Gln Asp
            580                 585                 590

CTC ACC CAG GAT GGA CTG ATG GAC CTG GCC GTG GGG GCC CGG GGC CAG      1824
Leu Thr Gln Asp Gly Leu Met Asp Leu Ala Val Gly Ala Arg Gly Gln
        595                 600                 605

GTG CTC CTG CTC AGG AGT CTG CCG GTG CTG AAA GTG GGG GTG GCC ATG      1872
Val Leu Leu Leu Arg Ser Leu Pro Val Leu Lys Val Gly Val Ala Met
    610                 615                 620

AGA TTC AGC CCT GTG GAG GTG GCC AAG GCT GTG TAC CGG TGC TGG GAA      1920
Arg Phe Ser Pro Val Glu Val Ala Lys Ala Val Tyr Arg Cys Trp Glu
625                 630                 635                 640

GAG AAG CCC AGT GCC CTG GAA GCT GGG GAC GCC ACC GTC TGT CTC ACC      1968
Glu Lys Pro Ser Ala Leu Glu Ala Gly Asp Ala Thr Val Cys Leu Thr
                645                 650                 655

ATC CAG AAA AGC TCA CTG GAC CAG CTA GGT GAC ATC CAA AGC TCT GTC      2016
```

```
Ile Gln Lys Ser  Ser Leu Asp Gln  Leu Gly Asp Ile  Gln Ser Ser Val
            660               665                670

AGG TTT GAT CTG  GCA CTG GAC CCA  GGT CGT CTG ACT  TCT CGT GCC ATT        2064
Arg Phe Asp Leu  Ala Leu Asp Pro  Gly Arg Leu Thr  Ser Arg Ala Ile
        675               680                685

TTC AAT GAA ACC  AAG AAC CCC ACT  TTG ACT CGA AGA  AAA ACC CTG GGA        2112
Phe Asn Glu Thr  Lys Asn Pro Thr  Leu Thr Arg Arg  Lys Thr Leu Gly
    690                   695                700

CTG GGG ATT CAC  TGT GAA ACC CTG  AAG CTG CTT TTG  CCA GAT TGT GTG        2160
Leu Gly Ile His  Cys Glu Thr Leu  Lys Leu Leu Leu  Pro Asp Cys Val
705                       710                715                720

GAG GAT GTG GTG  AGC CCC ATC ATT  CTG CAC CTC AAC  TTC TCA CTG GTG        2208
Glu Asp Val Val  Ser Pro Ile Ile  Leu His Leu Asn  Phe Ser Leu Val
                 725                      730                  735

AGA GAG CCC ATC  CCC TCC CCC CAG  AAC CTG CGT CCT  GTG CTG GCC GTG        2256
Arg Glu Pro Ile  Pro Ser Pro Gln  Asn Leu Arg Pro  Val Leu Ala Val
            740                       745                750

GGC TCA CAA GAC  CTC TTC ACT GCT  TCT CTC CCC TTC  GAG AAG AAC TGT        2304
Gly Ser Gln Asp  Leu Phe Thr Ala  Ser Leu Pro Phe  Glu Lys Asn Cys
        755                   760                    765

GGG CAA GAT GGC  CTC TGT GAA GGG  GAC CTG GGT GTC  ACC CTC AGC TTC        2352
Gly Gln Asp Gly  Leu Cys Glu Gly  Asp Leu Gly Val  Thr Leu Ser Phe
    770                       775                780

TCA GGC CTG CAG  ACC CTG ACC GTG  GGG AGC TCC CTG  GAG CTC AAC GTG        2400
Ser Gly Leu Gln  Thr Leu Thr Val  Gly Ser Ser Leu  Glu Leu Asn Val
785                       790                   795                 800

ATT GTG ACT GTG  TGG AAC GCA GGT  GAG GAT TCC TAC  GGA ACC GTG GTC        2448
Ile Val Thr Val  Trp Asn Ala Gly  Glu Asp Ser Tyr  Gly Thr Val Val
                 805                       810                   815

AGC CTC TAC TAT  CCA GCA GGG CTG  TCG CAC CGA CGG  GTG TCA GGA GCC        2496
Ser Leu Tyr Tyr  Pro Ala Gly Leu  Ser His Arg Arg  Val Ser Gly Ala
            820                       825                    830

CAG AAG CAG CCC  CAT CAG AGT GCC  CTG CGC CTG GCA  TGT GAG ACA GTG        2544
Gln Lys Gln Pro  His Gln Ser Ala  Leu Arg Leu Ala  Cys Glu Thr Val
        835                   840                       845

CCC ACT GAG GAT  GAG GGC CTA AGA  AGC AGC CGC TGC  AGT GTC AAC CAC        2592
Pro Thr Glu Asp  Glu Gly Leu Arg  Ser Ser Arg Cys  Ser Val Asn His
    850                       855                   860

CCC ATC TTC CAT  GAG GGC TCT AAC  GGC ACC TTC ATA  GTC ACA TTC GAT        2640
Pro Ile Phe His  Glu Gly Ser Asn  Gly Thr Phe Ile  Val Thr Phe Asp
865                       870                   875                  880

GTC TCC TAC AAG  GCC ACC CTG GGA  GAC AGG ATG CTT  ATG AGG GCC AGT        2688
Val Ser Tyr Lys  Ala Thr Leu Gly  Asp Arg Met Leu  Met Arg Ala Ser
                 885                       890                    895

GCA AGC AGT GAG  AAC AAT AAG GCT  TCA AGC AGC AAG  GCC ACC TTC CAG        2736
Ala Ser Ser Glu  Asn Asn Lys Ala  Ser Ser Ser Lys  Ala Thr Phe Gln
            900                       905                   910

CTG GAG CTC CCG  GTG AAG TAT GCA  GTC TAC ACC ATG  ATC AGC AGG CAG        2784
Leu Glu Leu Pro  Val Lys Tyr Ala  Val Tyr Thr Met  Ile Ser Arg Gln
        915                       920                    925

GAA GAA TCC ACC  AAG TAC TTC AAC  TTT GCA ACC TCC  GAT GAG AAG AAA        2832
Glu Glu Ser Thr  Lys Tyr Phe Asn  Phe Ala Thr Ser  Asp Glu Lys Lys
    930                       935                   940

ATG AAA GAG GCT  GAG CAT CGA TAC  CGT GTG AAT AAC  CTC AGC CAG CGA        2880
Met Lys Glu Ala  Glu His Arg Tyr  Arg Val Asn Asn  Leu Ser Gln Arg
945                       950                    955                 960

GAT CTG GCC ATC  AGC ATT AAC TTC  TGG GTT CCT GTC  CTG CTG AAC GGG        2928
Asp Leu Ala Ile  Ser Ile Asn Phe  Trp Val Pro Val  Leu Leu Asn Gly
                 965                       970                    975

GTG GCT GTG TGG  GAT GTG GTC ATG  GAG GCC CCA TCT  CAG AGT CTC CCC        2976
```

|  |  |  |  |  |  |  |  |  |  |  |  |  |  |  |  |
|---|---|---|---|---|---|---|---|---|---|---|---|---|---|---|---|
| Val | Ala | Val | Trp | Asp | Val | Val | Met | Glu | Ala | Pro | Ser | Gln | Ser | Leu | Pro |
|  |  |  | 980 |  |  |  | 985 |  |  |  |  |  | 990 |  |  |

| TGT | GTT | TCA | GAG | AGA | AAA | CCT | CCC | CAG | CAT | TCT | GAC | TTC | CTG | ACC | CAG | 3024 |
|---|---|---|---|---|---|---|---|---|---|---|---|---|---|---|---|---|
| Cys | Val | Ser | Glu | Arg | Lys | Pro | Pro | Gln | His | Ser | Asp | Phe | Leu | Thr | Gln |  |
|  |  | 995 |  |  |  |  | 1000 |  |  |  |  |  | 1005 |  |  |  |

| ATT | TCA | AGA | AGT | CCC | ATG | CTG | GAC | TGC | TCC | ATT | GCT | GAC | TGC | CTG | CAG | 3072 |
|---|---|---|---|---|---|---|---|---|---|---|---|---|---|---|---|---|
| Ile | Ser | Arg | Ser | Pro | Met | Leu | Asp | Cys | Ser | Ile | Ala | Asp | Cys | Leu | Gln |  |
|  | 1010 |  |  |  |  | 1015 |  |  |  |  | 1020 |  |  |  |  |  |

| TTC | CGC | TGT | GAC | GTC | CCC | TCC | TTC | AGC | GTC | CAG | GAG | GAG | CTG | GAT | TTC | 3120 |
|---|---|---|---|---|---|---|---|---|---|---|---|---|---|---|---|---|
| Phe | Arg | Cys | Asp | Val | Pro | Ser | Phe | Ser | Val | Gln | Glu | Glu | Leu | Asp | Phe |  |
| 1025 |  |  |  |  | 1030 |  |  |  |  | 1035 |  |  |  |  | 1040 |  |

| ACC | CTG | AAG | GGC | AAT | CTC | AGT | TTC | GGC | TGG | GTC | CGC | GAG | ACA | TTG | CAG | 3168 |
|---|---|---|---|---|---|---|---|---|---|---|---|---|---|---|---|---|
| Thr | Leu | Lys | Gly | Asn | Leu | Ser | Phe | Gly | Trp | Val | Arg | Glu | Thr | Leu | Gln |  |
|  |  |  |  | 1045 |  |  |  |  | 1050 |  |  |  |  | 1055 |  |  |

| AAG | AAG | GTG | TTG | GTC | GTG | AGT | GTG | GCT | GAA | ATT | ACG | TTC | GAC | ACA | TCC | 3216 |
|---|---|---|---|---|---|---|---|---|---|---|---|---|---|---|---|---|
| Lys | Lys | Val | Leu | Val | Val | Ser | Val | Ala | Glu | Ile | Thr | Phe | Asp | Thr | Ser |  |
|  |  |  |  | 1060 |  |  |  |  | 1065 |  |  |  |  | 1070 |  |  |

| GTG | TAC | TCC | CAG | CTT | CCA | GGA | CAG | GAG | GCA | TTT | ATG | AGA | GCT | CAG | ATG | 3264 |
|---|---|---|---|---|---|---|---|---|---|---|---|---|---|---|---|---|
| Val | Tyr | Ser | Gln | Leu | Pro | Gly | Gln | Glu | Ala | Phe | Met | Arg | Ala | Gln | Met |  |
|  |  | 1075 |  |  |  |  | 1080 |  |  |  |  | 1085 |  |  |  |  |

| GAG | ATG | GTG | CTA | GAA | GAA | GAC | GAG | GTC | TAC | AAT | GCC | ATT | CCC | ATC | ATC | 3312 |
|---|---|---|---|---|---|---|---|---|---|---|---|---|---|---|---|---|
| Glu | Met | Val | Leu | Glu | Glu | Asp | Glu | Val | Tyr | Asn | Ala | Ile | Pro | Ile | Ile |  |
|  | 1090 |  |  |  |  | 1095 |  |  |  |  | 1100 |  |  |  |  |  |

| ATG | GGC | AGC | TCT | GTG | GGG | GCT | CTG | CTA | CTG | CTG | GCG | CTC | ATC | ACA | GCC | 3360 |
|---|---|---|---|---|---|---|---|---|---|---|---|---|---|---|---|---|
| Met | Gly | Ser | Ser | Val | Gly | Ala | Leu | Leu | Leu | Leu | Ala | Leu | Ile | Thr | Ala |  |
| 1105 |  |  |  |  | 1110 |  |  |  |  | 1115 |  |  |  |  | 1120 |  |

| ACA | CTG | TAC | AAG | CTT | GGC | TTC | TTC | AAA | CGC | CAC | TAC | AAG | GAA | ATG | CTG | 3408 |
|---|---|---|---|---|---|---|---|---|---|---|---|---|---|---|---|---|
| Thr | Leu | Tyr | Lys | Leu | Gly | Phe | Phe | Lys | Arg | His | Tyr | Lys | Glu | Met | Leu |  |
|  |  |  |  | 1125 |  |  |  |  | 1130 |  |  |  |  | 1135 |  |  |

| GAG | GAC | AAG | CCT | GAA | GAC | ACT | GCC | ACA | TTC | AGT | GGG | GAC | GAT | TTC | AGC | 3456 |
|---|---|---|---|---|---|---|---|---|---|---|---|---|---|---|---|---|
| Glu | Asp | Lys | Pro | Glu | Asp | Thr | Ala | Thr | Phe | Ser | Gly | Asp | Asp | Phe | Ser |  |
|  |  |  | 1140 |  |  |  |  | 1145 |  |  |  |  | 1150 |  |  |  |

| TGT | GTG | GCC | CCA | AAT | GTG | CCT | TTG | TCC | TAATAATCCA | CTTTCCTGTT | 3503 |
|---|---|---|---|---|---|---|---|---|---|---|---|
| Cys | Val | Ala | Pro | Asn | Val | Pro | Leu | Ser |  |  |  |
|  |  | 1155 |  |  |  |  | 1160 |  |  |  |  |

| TATCTCTACC | ACTGTGGGCT | GGACTTGCTT | GCAACCATAA | ATCAACTTAC | ATGGAAACAA | 3563 |
|---|---|---|---|---|---|---|
| CTTCTGCATA | GATCTGCACT | GGCCTAAGCA | ACCTACCAGG | TGCTAAGCAC | CTTCTCGGAG | 3623 |
| AGATAGAGAT | TGTCAATGTT | TTTACATATC | TGTCCATCTT | TTTCAGCAAT | GACCCACTTT | 3683 |
| TTACAGAAGC | AGGCATGGTG | CCAGCATAAA | TTTTCATATG | CTTAAGAATT | GTCACATGAA | 3743 |
| AAAAAAAAAA | AAAAAAAAA | AAAAAAAAA | AAAAACTTT | AG |  | 3785 |

( 2 ) INFORMATION FOR SEQ ID NO:99:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

| Met | Thr | Phe | Gly | Thr | Val | Leu | Leu | Leu | Ser | Val | Leu | Ala | Ser | Tyr | His |
|---|---|---|---|---|---|---|---|---|---|---|---|---|---|---|---|
| 1 |  |  |  | 5 |  |  |  |  | 10 |  |  |  |  | 15 |  |

| Gly | Phe | Asn | Leu | Asp | Val | Glu | Glu | Pro | Thr | Ile | Phe | Gln | Glu | Asp | Ala |
|---|---|---|---|---|---|---|---|---|---|---|---|---|---|---|---|
|  |  |  | 20 |  |  |  |  | 25 |  |  |  |  | 30 |  |  |

| Gly | Gly | Phe | Gly | Gln | Ser | Val | Val | Gln | Phe | Gly | Gly | Ser | Arg | Leu | Val |
|---|---|---|---|---|---|---|---|---|---|---|---|---|---|---|---|
|  |  | 35 |  |  |  |  | 40 |  |  |  |  | 45 |  |  |  |

| Val | Gly | Ala | Pro | Leu | Glu | Val | Val | Ala | Ala | Asn | Gln | Thr | Gly | Arg | Leu |
|---|---|---|---|---|---|---|---|---|---|---|---|---|---|---|---|
|  | 50 |  |  |  |  | 55 |  |  |  |  | 60 |  |  |  |  |

| | | | | | | | | | | | | | | | |
|---|---|---|---|---|---|---|---|---|---|---|---|---|---|---|---|
| Tyr | Asp | Cys | Ala | Ala | Ala | Thr | Gly | Met | Cys | Gln | Pro | Ile | Pro | Leu | His |
| 65 | | | | | 70 | | | | 75 | | | | | | 80 |
| Ile | Arg | Pro | Glu | Ala | Val | Asn | Met | Ser | Leu | Gly | Leu | Thr | Leu | Ala | Ala |
| | | | | 85 | | | | | 90 | | | | | 95 | |
| Ser | Thr | Asn | Gly | Ser | Arg | Leu | Leu | Ala | Cys | Gly | Pro | Thr | Leu | His | Arg |
| | | | 100 | | | | | 105 | | | | | 110 | | |
| Val | Cys | Gly | Glu | Asn | Ser | Tyr | Ser | Lys | Gly | Ser | Cys | Leu | Leu | Leu | Gly |
| | | 115 | | | | | 120 | | | | | 125 | | | |
| Ser | Arg | Trp | Glu | Ile | Ile | Gln | Thr | Val | Pro | Asp | Ala | Thr | Pro | Glu | Cys |
| | 130 | | | | | 135 | | | | | 140 | | | | |
| Pro | His | Gln | Glu | Met | Asp | Ile | Val | Phe | Leu | Ile | Asp | Gly | Ser | Gly | Ser |
| 145 | | | | | 150 | | | | | 155 | | | | | 160 |
| Ile | Asp | Gln | Asn | Asp | Phe | Asn | Gln | Met | Lys | Gly | Phe | Val | Gln | Ala | Val |
| | | | | 165 | | | | | 170 | | | | | 175 | |
| Met | Gly | Gln | Phe | Glu | Gly | Thr | Asp | Thr | Leu | Phe | Ala | Leu | Met | Gln | Tyr |
| | | | 180 | | | | | 185 | | | | | 190 | | |
| Ser | Asn | Leu | Leu | Lys | Ile | His | Phe | Thr | Phe | Thr | Gln | Phe | Arg | Thr | Ser |
| | | | 195 | | | | | 200 | | | | | 205 | | |
| Pro | Ser | Gln | Gln | Ser | Leu | Val | Asp | Pro | Ile | Val | Gln | Leu | Lys | Gly | Leu |
| | 210 | | | | | 215 | | | | | 220 | | | | |
| Thr | Phe | Thr | Ala | Thr | Gly | Ile | Leu | Thr | Val | Val | Thr | Gln | Leu | Phe | His |
| 225 | | | | | 230 | | | | | 235 | | | | | 240 |
| His | Lys | Asn | Gly | Ala | Arg | Lys | Ser | Ala | Lys | Lys | Ile | Leu | Ile | Val | Ile |
| | | | | 245 | | | | | 250 | | | | | 255 | |
| Thr | Asp | Gly | Gln | Lys | Tyr | Lys | Asp | Pro | Leu | Glu | Tyr | Ser | Asp | Val | Ile |
| | | | 260 | | | | | 265 | | | | | 270 | | |
| Pro | Gln | Ala | Glu | Lys | Ala | Gly | Ile | Ile | Arg | Tyr | Ala | Ile | Gly | Val | Gly |
| | | 275 | | | | | 280 | | | | | 285 | | | |
| His | Ala | Phe | Gln | Gly | Pro | Thr | Ala | Arg | Gln | Glu | Leu | Asn | Thr | Ile | Ser |
| | 290 | | | | | 295 | | | | | 300 | | | | |
| Ser | Ala | Pro | Pro | Gln | Asp | His | Val | Phe | Lys | Val | Asp | Asn | Phe | Ala | Ala |
| 305 | | | | | 310 | | | | | 315 | | | | | 320 |
| Leu | Gly | Ser | Ile | Gln | Lys | Gln | Leu | Gln | Glu | Lys | Ile | Tyr | Ala | Val | Glu |
| | | | | 325 | | | | | 330 | | | | | 335 | |
| Gly | Thr | Gln | Ser | Arg | Ala | Ser | Ser | Ser | Phe | Gln | His | Glu | Met | Ser | Gln |
| | | | 340 | | | | | 345 | | | | | 350 | | |
| Glu | Gly | Phe | Ser | Thr | Ala | Leu | Thr | Met | Asp | Gly | Leu | Phe | Leu | Gly | Ala |
| | | 355 | | | | | 360 | | | | | 365 | | | |
| Val | Gly | Ser | Phe | Ser | Trp | Ser | Gly | Gly | Ala | Phe | Leu | Tyr | Pro | Pro | Asn |
| | 370 | | | | | 375 | | | | | 380 | | | | |
| Met | Ser | Pro | Thr | Phe | Ile | Asn | Met | Ser | Gln | Glu | Asn | Val | Asp | Met | Arg |
| 385 | | | | | 390 | | | | | 395 | | | | | 400 |
| Asp | Ser | Tyr | Leu | Gly | Tyr | Ser | Thr | Glu | Leu | Ala | Leu | Trp | Lys | Gly | Val |
| | | | | 405 | | | | | 410 | | | | | 415 | |
| Gln | Asn | Leu | Val | Leu | Gly | Ala | Pro | Arg | Tyr | Gln | His | Thr | Gly | Lys | Ala |
| | | | 420 | | | | | 425 | | | | | 430 | | |
| Val | Ile | Phe | Thr | Gln | Val | Ser | Arg | Gln | Trp | Arg | Lys | Lys | Ala | Glu | Val |
| | | 435 | | | | | 440 | | | | | 445 | | | |
| Thr | Gly | Thr | Gln | Ile | Gly | Ser | Tyr | Phe | Gly | Ala | Ser | Leu | Cys | Ser | Val |
| | 450 | | | | | 455 | | | | | 460 | | | | |
| Asp | Val | Asp | Ser | Asp | Gly | Ser | Thr | Asp | Leu | Ile | Leu | Ile | Gly | Ala | Pro |
| 465 | | | | | 470 | | | | | 475 | | | | | 480 |
| His | Tyr | Tyr | Glu | Gln | Thr | Arg | Gly | Gly | Gln | Val | Ser | Val | Cys | Pro | Leu |

-continued

|   |   |   | 485 |   |   |   |   | 490 |   |   |   |   | 495 |   |
|---|---|---|---|---|---|---|---|---|---|---|---|---|---|---|
| Pro | Arg | Gly | Arg | Val | Gln | Trp | Gln | Cys | Asp | Ala | Val | Leu | Arg | Gly | Glu |
|     |     |     | 500 |     |     |     |     | 505 |     |     |     |     | 510 |     |     |
| Gln | Gly | His | Pro | Trp | Gly | Arg | Phe | Gly | Ala | Ala | Leu | Thr | Val | Leu | Gly |
|     |     | 515 |     |     |     | 520 |     |     |     |     |     | 525 |     |     |     |
| Asp | Val | Asn | Glu | Asp | Lys | Leu | Ile | Asp | Val | Ala | Ile | Gly | Ala | Pro | Gly |
|     | 530 |     |     |     | 535 |     |     |     |     |     | 540 |     |     |     |     |
| Glu | Gln | Glu | Asn | Arg | Gly | Ala | Val | Tyr | Leu | Phe | His | Gly | Ala | Ser | Glu |
| 545 |     |     |     |     | 550 |     |     |     |     | 555 |     |     |     |     | 560 |
| Ser | Gly | Ile | Ser | Pro | Ser | His | Ser | Gln | Arg | Ile | Ala | Ser | Ser | Gln | Leu |
|     |     |     |     | 565 |     |     |     |     | 570 |     |     |     |     | 575 |     |
| Ser | Pro | Arg | Leu | Gln | Tyr | Phe | Gly | Gln | Ala | Leu | Ser | Gly | Gly | Gln | Asp |
|     |     |     | 580 |     |     |     |     | 585 |     |     |     |     | 590 |     |     |
| Leu | Thr | Gln | Asp | Gly | Leu | Met | Asp | Leu | Ala | Val | Gly | Ala | Arg | Gly | Gln |
|     |     | 595 |     |     |     |     | 600 |     |     |     |     | 605 |     |     |     |
| Val | Leu | Leu | Leu | Arg | Ser | Leu | Pro | Val | Leu | Lys | Val | Gly | Val | Ala | Met |
|     |     | 610 |     |     |     |     | 615 |     |     |     |     | 620 |     |     |     |
| Arg | Phe | Ser | Pro | Val | Glu | Val | Ala | Lys | Ala | Val | Tyr | Arg | Cys | Trp | Glu |
| 625 |     |     |     |     | 630 |     |     |     |     | 635 |     |     |     |     | 640 |
| Glu | Lys | Pro | Ser | Ala | Leu | Glu | Ala | Gly | Asp | Ala | Thr | Val | Cys | Leu | Thr |
|     |     |     |     | 645 |     |     |     |     | 650 |     |     |     |     | 655 |     |
| Ile | Gln | Lys | Ser | Ser | Leu | Asp | Gln | Leu | Gly | Asp | Ile | Gln | Ser | Ser | Val |
|     |     |     | 660 |     |     |     |     | 665 |     |     |     |     | 670 |     |     |
| Arg | Phe | Asp | Leu | Ala | Leu | Asp | Pro | Gly | Arg | Leu | Thr | Ser | Arg | Ala | Ile |
|     |     | 675 |     |     |     |     | 680 |     |     |     |     | 685 |     |     |     |
| Phe | Asn | Glu | Thr | Lys | Asn | Pro | Thr | Leu | Thr | Arg | Arg | Lys | Thr | Leu | Gly |
|     | 690 |     |     |     |     | 695 |     |     |     |     | 700 |     |     |     |     |
| Leu | Gly | Ile | His | Cys | Glu | Thr | Leu | Lys | Leu | Leu | Leu | Pro | Asp | Cys | Val |
| 705 |     |     |     |     | 710 |     |     |     |     | 715 |     |     |     |     | 720 |
| Glu | Asp | Val | Val | Ser | Pro | Ile | Ile | Leu | His | Leu | Asn | Phe | Ser | Leu | Val |
|     |     |     |     | 725 |     |     |     |     | 730 |     |     |     |     | 735 |     |
| Arg | Glu | Pro | Ile | Pro | Ser | Pro | Gln | Asn | Leu | Arg | Pro | Val | Leu | Ala | Val |
|     |     |     | 740 |     |     |     |     | 745 |     |     |     |     | 750 |     |     |
| Gly | Ser | Gln | Asp | Leu | Phe | Thr | Ala | Ser | Leu | Pro | Phe | Glu | Lys | Asn | Cys |
|     |     | 755 |     |     |     |     | 760 |     |     |     |     | 765 |     |     |     |
| Gly | Gln | Asp | Gly | Leu | Cys | Glu | Gly | Asp | Leu | Gly | Val | Thr | Leu | Ser | Phe |
| 770 |     |     |     |     | 775 |     |     |     |     | 780 |     |     |     |     |     |
| Ser | Gly | Leu | Gln | Thr | Leu | Thr | Val | Gly | Ser | Ser | Leu | Glu | Leu | Asn | Val |
| 785 |     |     |     |     | 790 |     |     |     |     | 795 |     |     |     |     | 800 |
| Ile | Val | Thr | Val | Trp | Asn | Ala | Gly | Glu | Asp | Ser | Tyr | Gly | Thr | Val | Val |
|     |     |     |     | 805 |     |     |     |     | 810 |     |     |     |     | 815 |     |
| Ser | Leu | Tyr | Tyr | Pro | Ala | Gly | Leu | Ser | His | Arg | Arg | Val | Ser | Gly | Ala |
|     |     |     |     | 820 |     |     |     | 825 |     |     |     |     | 830 |     |     |
| Gln | Lys | Gln | Pro | His | Gln | Ser | Ala | Leu | Arg | Leu | Ala | Cys | Glu | Thr | Val |
|     |     |     | 835 |     |     |     |     | 840 |     |     |     |     | 845 |     |     |
| Pro | Thr | Glu | Asp | Glu | Gly | Leu | Arg | Ser | Ser | Arg | Cys | Ser | Val | Asn | His |
|     |     | 850 |     |     |     |     | 855 |     |     |     |     | 860 |     |     |     |
| Pro | Ile | Phe | His | Glu | Gly | Ser | Asn | Gly | Thr | Phe | Ile | Val | Thr | Phe | Asp |
| 865 |     |     |     |     | 870 |     |     |     |     | 875 |     |     |     |     | 880 |
| Val | Ser | Tyr | Lys | Ala | Thr | Leu | Gly | Asp | Arg | Met | Leu | Met | Arg | Ala | Ser |
|     |     |     |     | 885 |     |     |     |     | 890 |     |     |     |     | 895 |     |
| Ala | Ser | Ser | Glu | Asn | Asn | Lys | Ala | Ser | Ser | Ser | Lys | Ala | Thr | Phe | Gln |
|     |     |     | 900 |     |     |     |     | 905 |     |     |     |     | 910 |     |     |

| | | | | | | | | | | | | | | |
|---|---|---|---|---|---|---|---|---|---|---|---|---|---|---|
| Leu | Glu | Leu | Pro | Val | Lys | Tyr | Ala | Val | Tyr | Thr | Met | Ile | Ser | Arg | Gln |
| | | 915 | | | | 920 | | | | | 925 | | | | |
| Glu | Glu | Ser | Thr | Lys | Tyr | Phe | Asn | Phe | Ala | Thr | Ser | Asp | Glu | Lys | Lys |
| | | 930 | | | | 935 | | | | | 940 | | | | |
| Met | Lys | Glu | Ala | Glu | His | Arg | Tyr | Arg | Val | Asn | Leu | Ser | Gln | Arg |
| 945 | | | | | 950 | | | | | 955 | | | | 960 |
| Asp | Leu | Ala | Ile | Ser | Ile | Asn | Phe | Trp | Val | Pro | Val | Leu | Leu | Asn | Gly |
| | | | | 965 | | | | | 970 | | | | | 975 | |
| Val | Ala | Val | Trp | Asp | Val | Val | Met | Glu | Ala | Pro | Ser | Gln | Ser | Leu | Pro |
| | | | 980 | | | | | 985 | | | | | 990 | | |
| Cys | Val | Ser | Glu | Arg | Lys | Pro | Pro | Gln | His | Ser | Asp | Phe | Leu | Thr | Gln |
| | | 995 | | | | | 1000 | | | | | 1005 | | | |
| Ile | Ser | Arg | Ser | Pro | Met | Leu | Asp | Cys | Ser | Ile | Ala | Asp | Cys | Leu | Gln |
| | 1010 | | | | | 1015 | | | | | 1020 | | | | |
| Phe | Arg | Cys | Asp | Val | Pro | Ser | Phe | Ser | Val | Gln | Glu | Glu | Leu | Asp | Phe |
| 1025 | | | | | 1030 | | | | | 1035 | | | | | 1040 |
| Thr | Leu | Lys | Gly | Asn | Leu | Ser | Phe | Gly | Trp | Val | Arg | Glu | Thr | Leu | Gln |
| | | | | 1045 | | | | | 1050 | | | | | 1055 | |
| Lys | Lys | Val | Leu | Val | Val | Ser | Val | Ala | Glu | Ile | Thr | Phe | Asp | Thr | Ser |
| | | | 1060 | | | | | 1065 | | | | | 1070 | | |
| Val | Tyr | Ser | Gln | Leu | Pro | Gly | Gln | Glu | Ala | Phe | Met | Arg | Ala | Gln | Met |
| | | 1075 | | | | | 1080 | | | | | 1085 | | | |
| Glu | Met | Val | Leu | Glu | Glu | Asp | Glu | Val | Tyr | Asn | Ala | Ile | Pro | Ile | Ile |
| | 1090 | | | | | 1095 | | | | | 1100 | | | | |
| Met | Gly | Ser | Ser | Val | Gly | Ala | Leu | Leu | Leu | Leu | Ala | Leu | Ile | Thr | Ala |
| 1105 | | | | | 1110 | | | | | 1115 | | | | | 1120 |
| Thr | Leu | Tyr | Lys | Leu | Gly | Phe | Phe | Lys | Arg | His | Tyr | Lys | Glu | Met | Leu |
| | | | | 1125 | | | | | 1130 | | | | | 1135 | |
| Glu | Asp | Lys | Pro | Glu | Asp | Thr | Ala | Thr | Phe | Ser | Gly | Asp | Asp | Phe | Ser |
| | | | 1140 | | | | | 1145 | | | | | 1150 | | |
| Cys | Val | Ala | Pro | Asn | Val | Pro | Leu | Ser | | | | | | | |
| | | | 1155 | | | | 1160 | | | | | | | | |

( 2 ) INFORMATION FOR SEQ ID NO:100:

( i ) SEQUENCE CHARACTERISTICS:
        ( A ) LENGTH: 1318 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 17..1255

( x i ) SEQUENCE DESCRIPTION: SEQ ID NO:100:

```
AATTCGGCAC GAGCTT GGG GCT GTG GTC CTC CTT GGG GTC CTG GCT TCT              49
               Gly Ala Val Val Leu Leu Gly Val Leu Ala Ser
                1               5                        10

TAC CAC GGA TTC AAC TTG GAC GTG GAT GAG CCG GTG ATC TTC CAG GAA            97
Tyr His Gly Phe Asn Leu Asp Val Asp Glu Pro Val Ile Phe Gln Glu
            15                  20                  25

GAC GCA GCG GGC TTC GGG CAG AGC GTG ATG CAG TTT GGA GGA TCT CGA            145
Asp Ala Ala Gly Phe Gly Gln Ser Val Met Gln Phe Gly Gly Ser Arg
        30                  35                  40

CTC GTG GTG GGA GCC CCC CTG GCG GTG GTG TCG GCC AAC CAC ACA GGA            193
Leu Val Val Gly Ala Pro Leu Ala Val Val Ser Ala Asn His Thr Gly
        45                  50                  55
```

| | | | | | | | | | | | | | | | | |
|---|---|---|---|---|---|---|---|---|---|---|---|---|---|---|---|---|
| CGG | CTG | TAC | GAG | TGT | GCG | CCT | GCC | TCC | GGC | ACC | TGC | ACG | CCC | ATT | TTC | 241 |
| Arg | Leu | Tyr | Glu | Cys | Ala | Pro | Ala | Ser | Gly | Thr | Cys | Thr | Pro | Ile | Phe | |
| 60 | | | | | 65 | | | | | 70 | | | | | 75 | |
| CCA | TTC | ATG | CCC | CCC | GAA | GCC | GTG | AAC | ATG | TCC | CTG | GGC | CTG | TCC | CTG | 289 |
| Pro | Phe | Met | Pro | Pro | Glu | Ala | Val | Asn | Met | Ser | Leu | Gly | Leu | Ser | Leu | |
| | | | | 80 | | | | | 85 | | | | | 90 | | |
| GCA | GCC | TCC | CCC | AAC | CAT | TCC | CAG | CTG | CTG | GCT | TGT | GGC | CCG | ACC | GTG | 337 |
| Ala | Ala | Ser | Pro | Asn | His | Ser | Gln | Leu | Leu | Ala | Cys | Gly | Pro | Thr | Val | |
| | | | | 95 | | | | | 100 | | | | | 105 | | |
| CAT | AGA | GCC | TGC | GGG | GAG | GAC | GTG | TAC | GCC | CAG | GGT | TTC | TGT | GTG | CTG | 385 |
| His | Arg | Ala | Cys | Gly | Glu | Asp | Val | Tyr | Ala | Gln | Gly | Phe | Cys | Val | Leu | |
| | | | 110 | | | | | 115 | | | | | 120 | | | |
| CTG | GAT | GCC | CAC | GCA | CAG | CCC | ATC | GGG | ACT | GTG | CCA | GCT | GCC | CTG | CCC | 433 |
| Leu | Asp | Ala | His | Ala | Gln | Pro | Ile | Gly | Thr | Val | Pro | Ala | Ala | Leu | Pro | |
| | | 125 | | | | | 130 | | | | | 135 | | | | |
| GAG | TGC | CCA | GAT | CAA | GAG | ATG | GAC | ATT | GTC | TTC | CTG | ATT | GAC | GGC | TCT | 481 |
| Glu | Cys | Pro | Asp | Gln | Glu | Met | Asp | Ile | Val | Phe | Leu | Ile | Asp | Gly | Ser | |
| 140 | | | | | 145 | | | | | 150 | | | | | 155 | |
| GGC | AGC | ATT | AGC | TCA | AAT | GAC | TTC | CGC | AAG | ATG | AAG | GAC | TTT | GTC | AGA | 529 |
| Gly | Ser | Ile | Ser | Ser | Asn | Asp | Phe | Arg | Lys | Met | Lys | Asp | Phe | Val | Arg | |
| | | | | 160 | | | | | 165 | | | | | 170 | | |
| GCT | GTG | ATG | GAC | CAG | TTC | AAG | GAC | ACC | AAC | ACC | CAG | TTC | TCG | CTG | ATG | 577 |
| Ala | Val | Met | Asp | Gln | Phe | Lys | Asp | Thr | Asn | Thr | Gln | Phe | Ser | Leu | Met | |
| | | | 175 | | | | | 180 | | | | | 185 | | | |
| CAG | TAC | TCC | AAT | GTG | CTG | GTG | ACA | CAT | TTC | ACC | TTC | AGC | AGC | TTC | CGG | 625 |
| Gln | Tyr | Ser | Asn | Val | Leu | Val | Thr | His | Phe | Thr | Phe | Ser | Ser | Phe | Arg | |
| | | 190 | | | | | 195 | | | | | 200 | | | | |
| AAC | AGC | TCC | AAT | CCT | CAG | GGC | CTA | GTG | GAG | CCC | ATT | GTG | CAG | CTG | ACA | 673 |
| Asn | Ser | Ser | Asn | Pro | Gln | Gly | Leu | Val | Glu | Pro | Ile | Val | Gln | Leu | Thr | |
| | | 205 | | | | | 210 | | | | | 215 | | | | |
| GGC | CTC | ACG | TTC | ACG | GCC | ACA | GGG | ATC | CTG | AAA | GTG | GTG | ACA | GAG | CTG | 721 |
| Gly | Leu | Thr | Phe | Thr | Ala | Thr | Gly | Ile | Leu | Lys | Val | Val | Thr | Glu | Leu | |
| 220 | | | | | 225 | | | | | 230 | | | | | 235 | |
| TTT | CAA | ACC | AAG | AAC | GGG | GCC | CGC | GAA | AGT | GCC | AAG | AAG | ATC | CTC | ATC | 769 |
| Phe | Gln | Thr | Lys | Asn | Gly | Ala | Arg | Glu | Ser | Ala | Lys | Lys | Ile | Leu | Ile | |
| | | | | 240 | | | | | 245 | | | | | 250 | | |
| GTC | ATC | ACA | GAT | GGG | CAG | AAG | TAC | AAA | GAC | CCC | CTG | CAC | TAC | AGT | GCT | 817 |
| Val | Ile | Thr | Asp | Gly | Gln | Lys | Tyr | Lys | Asp | Pro | Leu | His | Tyr | Ser | Ala | |
| | | | 255 | | | | | 260 | | | | | 265 | | | |
| GTC | ATC | CCA | CAG | GCA | GAG | CAG | GCG | GGC | ATC | ATC | CGC | TAC | GCC | ATC | GGG | 865 |
| Val | Ile | Pro | Gln | Ala | Glu | Gln | Ala | Gly | Ile | Ile | Arg | Tyr | Ala | Ile | Gly | |
| | | 270 | | | | | 275 | | | | | 280 | | | | |
| GTG | GGG | GAC | GCG | TTC | CAG | AAA | CCC | ACA | GCC | AGG | CAG | GAG | CTG | GAC | ACC | 913 |
| Val | Gly | Asp | Ala | Phe | Gln | Lys | Pro | Thr | Ala | Arg | Gln | Glu | Leu | Asp | Thr | |
| | 285 | | | | | 290 | | | | | 295 | | | | | |
| ATC | GCC | TCC | GAG | CCG | CCC | GAC | GCC | CAC | GTG | TTC | CAG | GTG | GAC | AAT | TTC | 961 |
| Ile | Ala | Ser | Glu | Pro | Pro | Asp | Ala | His | Val | Phe | Gln | Val | Asp | Asn | Phe | |
| 300 | | | | | 305 | | | | | 310 | | | | | 315 | |
| TCA | GCA | CTC | AGC | AGC | ATC | CAA | AAG | CAG | CTG | TAT | GAC | AGG | ATC | TTT | GCC | 1009 |
| Ser | Ala | Leu | Ser | Ser | Ile | Gln | Lys | Gln | Leu | Tyr | Asp | Arg | Ile | Phe | Ala | |
| | | | | 320 | | | | | 325 | | | | | 330 | | |
| GTC | GAG | GGA | ACC | CTG | TCA | TCG | GCA | AGC | ACC | TCC | TTC | CAG | CAT | GAG | ATG | 1057 |
| Val | Glu | Gly | Thr | Leu | Ser | Ser | Ala | Ser | Thr | Ser | Phe | Gln | His | Glu | Met | |
| | | | 335 | | | | | 340 | | | | | 345 | | | |
| TCC | CAA | GAG | GGC | TTC | AGC | TCA | CTT | CTC | ACC | ACG | GAA | GGA | CCG | GTG | CTG | 1105 |
| Ser | Gln | Glu | Gly | Phe | Ser | Ser | Leu | Leu | Thr | Thr | Glu | Gly | Pro | Val | Leu | |
| | | 350 | | | | | 355 | | | | | 360 | | | | |
| GGG | GCT | GTG | GGC | AGC | TTC | GAT | TGG | TCC | GGG | GGT | GCT | TTC | CTG | TAC | CCC | 1153 |
| Gly | Ala | Val | Gly | Ser | Phe | Asp | Trp | Ser | Gly | Gly | Ala | Phe | Leu | Tyr | Pro | |
| 365 | | | | | | 370 | | | | | | 375 | | | | |

```
CCC  GGC  GGG  AGC  CCC  ACC  TTC  ATC  AAC  ATG  TCT  CAG  CAG  AAC  GTG  GAC       1201
Pro  Gly  Gly  Ser  Pro  Thr  Phe  Ile  Asn  Met  Ser  Gln  Gln  Asn  Val  Asp
380                      385                      390                      395

ATG  AGG  GAC  TCC  TAC  CTG  GGT  GAG  GAA  GGG  GTG  GGG  GTG  GGG  ACA  GGT       1249
Met  Arg  Asp  Ser  Tyr  Leu  Gly  Glu  Glu  Gly  Val  Gly  Val  Gly  Thr  Gly
                         400                      405                      410

GGG  AGC  TGAGGCTTGG  GGTGGGGTGG  GGCTGGGCTG  GGAGGGGAGG  GAAGAGGAGG                  1305
Gly  Ser
GGAGAGGCAA  AGA                                                                       1318
```

( 2 ) INFORMATION FOR SEQ ID NO:101:

( i ) SEQUENCE CHARACTERISTICS:
        ( A ) LENGTH: 413 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

```
Gly  Ala  Val  Val  Leu  Leu  Gly  Val  Leu  Ala  Ser  Tyr  His  Gly  Phe  Asn
 1              5                        10                       15

Leu  Asp  Val  Asp  Glu  Pro  Val  Ile  Phe  Gln  Glu  Asp  Ala  Ala  Gly  Phe
               20                        25                       30

Gly  Gln  Ser  Val  Met  Gln  Phe  Gly  Gly  Ser  Arg  Leu  Val  Val  Gly  Ala
          35                        40                       45

Pro  Leu  Ala  Val  Val  Ser  Ala  Asn  His  Thr  Gly  Arg  Leu  Tyr  Glu  Cys
          50                        55                       60

Ala  Pro  Ala  Ser  Gly  Thr  Cys  Thr  Pro  Ile  Phe  Pro  Phe  Met  Pro  Pro
 65                       70                        75                       80

Glu  Ala  Val  Asn  Met  Ser  Leu  Gly  Leu  Ser  Leu  Ala  Ala  Ser  Pro  Asn
                    85                        90                       95

His  Ser  Gln  Leu  Leu  Ala  Cys  Gly  Pro  Thr  Val  His  Arg  Ala  Cys  Gly
                    100                       105                      110

Glu  Asp  Val  Tyr  Ala  Gln  Gly  Phe  Cys  Val  Leu  Leu  Asp  Ala  His  Ala
               115                       120                      125

Gln  Pro  Ile  Gly  Thr  Val  Pro  Ala  Ala  Leu  Pro  Glu  Cys  Pro  Asp  Gln
          130                       135                      140

Glu  Met  Asp  Ile  Val  Phe  Leu  Ile  Asp  Gly  Ser  Gly  Ser  Ile  Ser  Ser
145                           150                      155                      160

Asn  Asp  Phe  Arg  Lys  Met  Lys  Asp  Phe  Val  Arg  Ala  Val  Met  Asp  Gln
                    165                       170                      175

Phe  Lys  Asp  Thr  Asn  Thr  Gln  Phe  Ser  Leu  Met  Gln  Tyr  Ser  Asn  Val
               180                       185                      190

Leu  Val  Thr  His  Phe  Thr  Phe  Ser  Ser  Phe  Arg  Asn  Ser  Ser  Asn  Pro
          195                       200                      205

Gln  Gly  Leu  Val  Glu  Pro  Ile  Val  Gln  Leu  Thr  Gly  Leu  Thr  Phe  Thr
          210                       215                      220

Ala  Thr  Gly  Ile  Leu  Lys  Val  Val  Thr  Glu  Leu  Phe  Gln  Thr  Lys  Asn
225                      230                       235                      240

Gly  Ala  Arg  Glu  Ser  Ala  Lys  Lys  Ile  Leu  Ile  Val  Ile  Thr  Asp  Gly
                    245                       250                      255

Gln  Lys  Tyr  Lys  Asp  Pro  Leu  His  Tyr  Ser  Ala  Val  Ile  Pro  Gln  Ala
               260                       265                      270

Glu  Gln  Ala  Gly  Ile  Ile  Arg  Tyr  Ala  Ile  Gly  Val  Gly  Asp  Ala  Phe
          275                       280                      285

Gln  Lys  Pro  Thr  Ala  Arg  Gln  Glu  Leu  Asp  Thr  Ile  Ala  Ser  Glu  Pro
```

|  |  |  |  | 290 |  |  |  |  | 295 |  |  |  |  | 300 |  |  |
|---|---|---|---|---|---|---|---|---|---|---|---|---|---|---|---|---|
| Pro | Asp | Ala | His | Val | Phe | Gln | Val | Asp | Asn | Phe | Ser | Ala | Leu | Ser | Ser |  |
| 305 |  |  |  | 310 |  |  |  |  | 315 |  |  |  |  |  | 320 |  |
| Ile | Gln | Lys | Gln | Leu | Tyr | Asp | Arg | Ile | Phe | Ala | Val | Glu | Gly | Thr | Leu |  |
|  |  |  |  | 325 |  |  |  |  | 330 |  |  |  |  | 335 |  |  |
| Ser | Ser | Ala | Ser | Thr | Ser | Phe | Gln | His | Glu | Met | Ser | Gln | Glu | Gly | Phe |  |
|  |  |  | 340 |  |  |  |  | 345 |  |  |  |  | 350 |  |  |  |
| Ser | Ser | Leu | Leu | Thr | Thr | Glu | Gly | Pro | Val | Leu | Gly | Ala | Val | Gly | Ser |  |
|  |  | 355 |  |  |  |  | 360 |  |  |  |  | 365 |  |  |  |  |
| Phe | Asp | Trp | Ser | Gly | Gly | Ala | Phe | Leu | Tyr | Pro | Pro | Gly | Gly | Ser | Pro |  |
|  | 370 |  |  |  |  | 375 |  |  |  |  | 380 |  |  |  |  |  |
| Thr | Phe | Ile | Asn | Met | Ser | Gln | Gln | Asn | Val | Asp | Met | Arg | Asp | Ser | Tyr |  |
| 385 |  |  |  |  | 390 |  |  |  |  | 395 |  |  |  |  | 400 |  |
| Leu | Gly | Glu | Glu | Gly | Val | Gly | Val | Gly | Thr | Gly | Gly | Ser |  |  |  |  |
|  |  |  |  | 405 |  |  |  |  | 410 |  |  |  |  |  |  |  |

( 2 ) INFORMATION FOR SEQ ID NO:102:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1482

( x i ) SEQUENCE DESCRIPTION: SEQ ID NO:102:

| GAT | GTC | CAG | AGC | TCC | ATC | AGC | TAT | GAT | CTG | GCA | CTG | GAC | CCA | GGC | CGC | 48 |
|---|---|---|---|---|---|---|---|---|---|---|---|---|---|---|---|---|
| Asp | Val | Gln | Ser | Ser | Ile | Ser | Tyr | Asp | Leu | Ala | Leu | Asp | Pro | Gly | Arg |  |
| 1 |  |  |  | 5 |  |  |  |  | 10 |  |  |  |  | 15 |  |  |
| CTG | GTC | TCT | CGG | GCC | ATT | TTT | CAA | GAG | ACC | CAG | AAC | CAG | ACT | TTA | ACT | 96 |
| Leu | Val | Ser | Arg | Ala | Ile | Phe | Gln | Glu | Thr | Gln | Asn | Gln | Thr | Leu | Thr |  |
|  |  |  | 20 |  |  |  |  | 25 |  |  |  |  | 30 |  |  |  |
| CGA | AGG | AAG | ACC | CTG | GGG | CTG | GGG | CGT | CAC | TGT | GAA | ACC | ATG | AGG | CTA | 144 |
| Arg | Arg | Lys | Thr | Leu | Gly | Leu | Gly | Arg | His | Cys | Glu | Thr | Met | Arg | Leu |  |
|  |  | 35 |  |  |  |  | 40 |  |  |  |  | 45 |  |  |  |  |
| CTT | TTG | CCA | GAC | TGC | GTA | GAG | GAC | GTG | GTG | AAC | CCC | ATC | GTC | CTG | CAC | 192 |
| Leu | Leu | Pro | Asp | Cys | Val | Glu | Asp | Val | Val | Asn | Pro | Ile | Val | Leu | His |  |
|  | 50 |  |  |  |  | 55 |  |  |  |  | 60 |  |  |  |  |  |
| CTC | AAC | TTC | TCC | CTG | GAG | GGA | CAG | CCA | ATC | CTC | TCA | TCC | CAG | AAT | CTG | 240 |
| Leu | Asn | Phe | Ser | Leu | Glu | Gly | Gln | Pro | Ile | Leu | Ser | Ser | Gln | Asn | Leu |  |
| 65 |  |  |  |  | 70 |  |  |  |  | 75 |  |  |  |  | 80 |  |
| CGC | CCT | GTG | CTG | GCC | ACG | GGC | TCG | CAG | GAC | CAC | TTC | ATT | GCC | TCC | CTC | 288 |
| Arg | Pro | Val | Leu | Ala | Thr | Gly | Ser | Gln | Asp | His | Phe | Ile | Ala | Ser | Leu |  |
|  |  |  |  | 85 |  |  |  |  | 90 |  |  |  |  | 95 |  |  |
| CCC | TTT | GAG | AAG | AAC | TGC | GGA | CAA | GAT | CGC | CTG | TGT | GAG | GGG | GAC | CTG | 336 |
| Pro | Phe | Glu | Lys | Asn | Cys | Gly | Gln | Asp | Arg | Leu | Cys | Glu | Gly | Asp | Leu |  |
|  |  |  | 100 |  |  |  |  | 105 |  |  |  |  | 110 |  |  |  |
| AGC | ATC | AGC | TTC | AAC | TTC | TCG | GGC | TTG | AAT | ACC | CTG | CTG | GTG | GGG | CTC | 384 |
| Ser | Ile | Ser | Phe | Asn | Phe | Ser | Gly | Leu | Asn | Thr | Leu | Leu | Val | Gly | Leu |  |
|  |  | 115 |  |  |  |  | 120 |  |  |  |  | 125 |  |  |  |  |
| TCC | CTG | GAG | CTC | ACA | GTG | ACA | GTG | ACC | GTG | CGG | AAT | GAG | GGC | GAG | GAC | 432 |
| Ser | Leu | Glu | Leu | Thr | Val | Thr | Val | Thr | Val | Arg | Asn | Glu | Gly | Glu | Asp |  |
|  | 130 |  |  |  |  | 135 |  |  |  |  | 140 |  |  |  |  |  |
| TCC | TAT | GGG | ACC | GCC | ATC | ACC | CTC | TAC | TAC | CCA | GCA | GGG | CTA | TCC | TAC | 480 |
| Ser | Tyr | Gly | Thr | Ala | Ile | Thr | Leu | Tyr | Tyr | Pro | Ala | Gly | Leu | Ser | Tyr |  |
| 145 |  |  |  |  | 150 |  |  |  |  | 155 |  |  |  |  | 160 |  |

| | | | | | | | | | | | | | | | | |
|---|---|---|---|---|---|---|---|---|---|---|---|---|---|---|---|---|
| AGG | CGG | GTG | TCG | GGC | CAG | ACA | CAA | CCC | TGG | CAG | CGC | CCC | CTG | CAC | CTC | 528 |
| Arg | Arg | Val | Ser | Gly 165 | Gln | Thr | Gln | Pro | Trp 170 | Gln | Arg | Pro | Leu | His 175 | Leu | |
| GCA | TGT | GAG | GCT | GTA | CCT | ACC | GAG | AGC | GAG | GGC | TTG | AGG | AGT | ACC | AGC | 576 |
| Ala | Cys | Glu | Ala 180 | Val | Pro | Thr | Glu | Ser 185 | Glu | Gly | Leu | Arg | Ser 190 | Thr | Ser | |
| TGC | AGC | GTC | AAC | CAC | CCC | ATC | TTC | CAA | GGG | GGT | GCT | CAG | GGC | ACT | TTC | 624 |
| Cys | Ser | Val 195 | Asn | His | Pro | Ile | Phe 200 | Gln | Gly | Gly | Ala | Gln 205 | Gly | Thr | Phe | |
| GTA | GTC | AAG | TTC | GAT | GTC | TCC | TCC | AAG | GCC | AGC | CTG | GGT | GAC | AGG | TTG | 672 |
| Val | Val 210 | Lys | Phe | Asp | Val | Ser 215 | Ser | Lys | Ala | Ser | Leu 220 | Gly | Asp | Arg | Leu | |
| CTC | ATG | GGG | GCC | AGT | GCC | AGC | AGT | GAG | AAT | AAT | AAG | CCT | GCG | AGC | AAC | 720 |
| Leu 225 | Met | Gly | Ala | Ser 230 | Ala | Ser | Ser | Glu | Asn 235 | Asn | Lys | Pro | Ala | Ser 240 | Asn | |
| AAG | ACC | TCC | TTT | GAG | CTG | GAA | CTG | CCA | GTG | AAA | TAC | GCT | GTC | TAC | ATG | 768 |
| Lys | Thr | Ser | Phe | Glu 245 | Leu | Glu | Leu | Pro | Val 250 | Lys | Tyr | Ala | Val | Tyr 255 | Met | |
| ATG | ATC | ACA | AGG | CAC | GAA | GGC | TCC | ACC | AGG | TTC | TTC | AAC | TTT | TCC | ACT | 816 |
| Met | Ile | Thr | Arg 260 | His | Glu | Gly | Ser | Thr 265 | Arg | Phe | Phe | Asn | Phe 270 | Ser | Thr | |
| TCC | GCT | GAG | AAG | AGC | AGC | AAA | GAG | GCC | GAG | CAC | CGC | TAT | CGG | GTG | AAC | 864 |
| Ser | Ala | Glu 275 | Lys | Ser | Ser | Lys | Glu 280 | Ala | Glu | His | Arg | Tyr 285 | Arg | Val | Asn | |
| AAC | CTG | AGT | CTG | CGA | GAT | GTG | GCC | GTC | AGC | GTG | GAC | TTC | TGG | GCC | CCC | 912 |
| Asn | Leu 290 | Ser | Leu | Arg | Asp | Val 295 | Ala | Val | Ser | Val | Asp 300 | Phe | Trp | Ala | Pro | |
| GTG | CAG | CTG | AAC | GGA | GCA | GCT | GTG | TGG | GAC | GTG | GCG | GTG | GAG | GCC | CCT | 960 |
| Val 305 | Gln | Leu | Asn | Gly | Ala 310 | Ala | Val | Trp | Asp | Val 315 | Ala | Val | Glu | Ala | Pro 320 | |
| GCC | CAG | AGC | CTG | CCC | TGT | GCG | CGG | GAG | AGG | GAA | CCT | CCG | AGG | ACC | TCT | 1008 |
| Ala | Gln | Ser | Leu | Pro 325 | Cys | Ala | Arg | Glu | Arg 330 | Glu | Pro | Pro | Arg | Thr 335 | Ser | |
| GAC | CTG | AGC | CGG | GTC | CCG | GGG | AGT | CCC | GTG | CTG | GAC | TGC | AGC | GTT | GCG | 1056 |
| Asp | Leu | Ser | Arg 340 | Val | Pro | Gly | Ser | Pro 345 | Val | Leu | Asp | Cys | Ser 350 | Val | Ala | |
| CAC | TGC | CTG | AGG | TTC | CGC | TGC | CAC | ATC | CCC | TCC | TTC | AGC | GCC | AAG | GAG | 1104 |
| His | Cys | Leu 355 | Arg | Phe | Arg | Cys | His 360 | Ile | Pro | Ser | Phe | Ser 365 | Ala | Lys | Glu | |
| GAG | CTC | CAC | TTC | ACC | CTG | AAG | GGC | AAC | CTC | AGC | TTC | GCC | TGG | GTC | AGC | 1152 |
| Glu | Leu | His 370 | Phe | Thr | Leu | Lys 375 | Gly | Asn | Leu | Ser | Phe 380 | Ala | Trp | Val | Ser | |
| CAG | ATG | CTG | CAA | AAG | AAG | GTG | TCG | GTG | GTG | AGT | GTG | GCC | GAG | ATC | ACC | 1200 |
| Gln | Met | Leu 385 | Gln | Lys | Lys | Val 390 | Ser | Val | Val | Ser | Val 395 | Ala | Glu | Ile | Thr 400 | |
| TTC | AAC | AGG | GCC | GTG | TAC | TCC | CAA | GTT | CCG | GGC | GAG | GAG | CCC | TTT | ATG | 1248 |
| Phe | Asn | Arg | Ala | Val 405 | Tyr | Ser | Gln | Val | Pro 410 | Gly | Glu | Glu | Pro | Phe 415 | Met | |
| AGA | GCC | CAG | GTG | GAG | ACG | GTG | CTG | GAG | GAG | TAT | GAG | GAG | CAC | GAC | CCC | 1296 |
| Arg | Ala | Gln | Val 420 | Glu | Thr | Val | Leu | Glu 425 | Glu | Tyr | Glu | Glu | His 430 | Asp | Pro | |
| GTC | CCC | CTG | GTG | GTG | GGC | AGC | TGT | GTG | GGC | GGC | CTG | CTG | CTG | CTG | GCT | 1344 |
| Val | Pro | Leu 435 | Val | Val | Gly | Ser | Cys 440 | Val | Gly | Gly | Leu | Leu 445 | Leu | Leu | Ala | |
| CTC | ATC | TCA | GCC | ACC | CTG | TAC | AAG | CTT | GGC | TTC | TTC | AAG | CGC | CGG | TAC | 1392 |
| Leu | Ile | Ser | Ala | Thr 455 | Leu | Tyr | Lys | Leu | Gly 460 | Phe | Phe | Lys | Arg | Arg | Tyr | |
| AAG | GAG | ATG | CTG | GGC | GAG | AAA | CCG | GGA | GAC | GCG | GCC | ACC | TTC | CCC | GGG | 1440 |
| Lys | Glu | Met | Leu | Gly 470 | Glu | Lys | Pro | Gly | Asp 475 | Ala | Ala | Thr | Phe | Pro 480 | Gly | |

-continued

| GAG | GAC | GCC | AGC | TGC | GGG | GCT | TCA | GAT | TTG | CCT | TTG | TCC | CAG | | 1482 |
|-----|-----|-----|-----|-----|-----|-----|-----|-----|-----|-----|-----|-----|-----|---|------|
| Glu | Asp | Ala | Ser | Cys | Gly | Ala | Ser | Asp | Leu | Pro | Leu | Ser | Gln | | |
|     |     |     |     | 485 |     |     |     | 490 |     |     |     |     |     | | |

TG                                                                                                                1484

(2) INFORMATION FOR SEQ ID NO:103:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:103:

| Asp | Val | Gln | Ser | Ser | Ile | Ser | Tyr | Asp | Leu | Ala | Leu | Asp | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     |     | 15  |

| Leu | Val | Ser | Arg | Ala | Ile | Phe | Gln | Glu | Thr | Gln | Asn | Gln | Thr | Leu | Thr |
|-----|-----|-----|-----|-----|-----|-----|-----|-----|-----|-----|-----|-----|-----|-----|-----|
|     |     |     | 20  |     |     |     |     |     | 25  |     |     |     |     | 30  |     |

| Arg | Arg | Lys | Thr | Leu | Gly | Leu | Gly | Arg | His | Cys | Glu | Thr | Met | Arg | Leu |
|-----|-----|-----|-----|-----|-----|-----|-----|-----|-----|-----|-----|-----|-----|-----|-----|
|     |     |     | 35  |     |     |     |     | 40  |     |     |     | 45  |     |     |     |

| Leu | Leu | Pro | Asp | Cys | Val | Glu | Asp | Val | Val | Asn | Pro | Ile | Val | Leu | His |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Asn | Phe | Ser | Leu | Glu | Gly | Gln | Pro | Ile | Leu | Ser | Ser | Gln | Asn | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Pro | Val | Leu | Ala | Thr | Gly | Ser | Gln | Asp | His | Phe | Ile | Ala | Ser | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Pro | Phe | Glu | Lys | Asn | Cys | Gly | Gln | Asp | Arg | Leu | Cys | Glu | Gly | Asp | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Ile | Ser | Phe | Asn | Phe | Ser | Gly | Leu | Asn | Thr | Leu | Leu | Val | Gly | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Leu | Glu | Leu | Thr | Val | Thr | Val | Thr | Val | Arg | Asn | Glu | Gly | Glu | Asp |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Tyr | Gly | Thr | Ala | Ile | Thr | Leu | Tyr | Tyr | Pro | Ala | Gly | Leu | Ser | Tyr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Arg | Arg | Val | Ser | Gly | Gln | Thr | Gln | Pro | Trp | Gln | Arg | Pro | Leu | His | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Cys | Glu | Ala | Val | Pro | Thr | Glu | Ser | Glu | Gly | Leu | Arg | Ser | Thr | Ser |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Cys | Ser | Val | Asn | His | Pro | Ile | Phe | Gln | Gly | Gly | Ala | Gln | Gly | Thr | Phe |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Val | Val | Lys | Phe | Asp | Val | Ser | Ser | Lys | Ala | Ser | Leu | Gly | Asp | Arg | Leu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Leu | Met | Gly | Ala | Ser | Ala | Ser | Ser | Glu | Asn | Asn | Lys | Pro | Ala | Ser | Asn |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Lys | Thr | Ser | Phe | Glu | Leu | Glu | Leu | Pro | Val | Lys | Tyr | Ala | Val | Tyr | Met |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Met | Ile | Thr | Arg | His | Glu | Gly | Ser | Thr | Arg | Phe | Phe | Asn | Phe | Ser | Thr |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ser | Ala | Glu | Lys | Ser | Ser | Lys | Glu | Ala | Glu | His | Arg | Tyr | Arg | Val | Asn |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Leu | Ser | Leu | Arg | Asp | Val | Ala | Val | Ser | Val | Asp | Phe | Trp | Ala | Pro |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Val | Gln | Leu | Asn | Gly | Ala | Ala | Val | Trp | Asp | Val | Ala | Val | Glu | Ala | Pro |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Ala | Gln | Ser | Leu | Pro | Cys | Ala | Arg | Glu | Arg | Glu | Pro | Pro | Arg | Thr | Ser |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

-continued

```
Asp  Leu  Ser  Arg  Val  Pro  Gly  Ser  Pro  Val  Leu  Asp  Cys  Ser  Val  Ala
               340            345                           350

His  Cys  Leu  Arg  Phe  Arg  Cys  His  Ile  Pro  Ser  Phe  Ser  Ala  Lys  Glu
          355                      360                      365

Glu  Leu  His  Phe  Thr  Leu  Lys  Gly  Asn  Leu  Ser  Phe  Ala  Trp  Val  Ser
     370                 375                      380

Gln  Met  Leu  Gln  Lys  Lys  Val  Ser  Val  Val  Ser  Val  Ala  Glu  Ile  Thr
385                      390                      395                           400

Phe  Asn  Arg  Ala  Val  Tyr  Ser  Gln  Val  Pro  Gly  Glu  Glu  Pro  Phe  Met
               405                      410                           415

Arg  Ala  Gln  Val  Glu  Thr  Val  Leu  Glu  Glu  Tyr  Glu  Glu  His  Asp  Pro
               420                 425                           430

Val  Pro  Leu  Val  Val  Gly  Ser  Cys  Val  Gly  Gly  Leu  Leu  Leu  Leu  Ala
          435                      440                      445

Leu  Ile  Ser  Ala  Thr  Leu  Tyr  Lys  Leu  Gly  Phe  Phe  Lys  Arg  Arg  Tyr
     450                      455                 460

Lys  Glu  Met  Leu  Gly  Glu  Lys  Pro  Gly  Asp  Ala  Ala  Thr  Phe  Pro  Gly
465                      470                 475                           480

Glu  Asp  Ala  Ser  Cys  Gly  Ala  Ser  Asp  Leu  Pro  Leu  Ser  Gln
               485                      490
```